US006210654B1

(12) United States Patent
Ihle et al.

(10) Patent No.: US 6,210,654 B1
(45) Date of Patent: Apr. 3, 2001

(54) JAK KINASES AND REGULATION OF CYTOKINE SIGNAL TRANSDUCTION

(75) Inventors: James Ihle; Bruce A. Witthuhn; Frederick W. Quelle, all of Memphis, TN (US); Ollie Silvennoinen, Helsinki (FI)

(73) Assignee: St. Jude Children's Hospital, Memphis, TN (US)

(*) Notice: Subject to any disclaimer, the term of this patent is extended or adjusted under 35 U.S.C. 154(b) by 0 days.

(21) Appl. No.: 08/946,994

(22) Filed: Oct. 8, 1997

Related U.S. Application Data

(60) Division of application No. 08/665,574, filed on Jun. 18, 1996, which is a continuation-in-part of application No. 08/097,997, filed on Jul. 29, 1993, now Pat. No. 5,728,536.

(51) Int. Cl.$^7$ ................................................. A61K 49/00
(52) U.S. Cl. ........................ 424/9.2; 424/9.1; 424/94.1; 424/94.5; 435/21; 514/2; 514/21
(58) Field of Search ........................ 435/7.1, 7.2, 7.4, 435/7.92, 21; 436/518; 424/9.1, 94.1, 94.5, 9.2; 514/2, 21

(56) References Cited

U.S. PATENT DOCUMENTS 5,190,931  3/1993  Inouye et al. ........................ 435/91

FOREIGN PATENT DOCUMENTS

WO 92/10519  6/1992  (WO).

OTHER PUBLICATIONS

Argetsinger, L.S. et al., "Identification of JAK2 as a Growth Hormone Receptor–Associated Tyrosine Kinase," *Cell* 74:237–244 (Jul. 1993).
Bartholomew, C. and J.N. Ihle, "Retroviral Insertions 90 Kilobases Proximal to the Evi–1 Myeloid Transforming Gene Activate Transcription from the Normal Promoter," *Mol. Cell. Biol.* 11(4):1820–1828 (1991).
Bird, T.A. et al., "Evidence that MAP (Mitogen–Activated Protein) Kinase Activation May Be a Necessary but not Sufficient Signal for a Restricted Subset of Responses in IL–1 Treated Epidermal Cells," *Cytokine* 4(6):429–440 (Nov. 1993).
Campbell, G.S. et al., "Evidence for Involvement of the Growth Hormone Receptor–associated Tyrosine Kinase in Actions of Growth Hormone," *J. Biol. Chem.* 268(10):7427–7434 (Apr. 1993).
Carroll, M.P. et al., "Erythropoietin Induces Raf–1 Activation and Raf–1 is Required for Erythropoietin–mediated Proliferation," *J. Biol. Chem.* 266(23):14964–14969 (1991).
Carroll, M.P. et al., "Interleukin–3 and Granulocyte–Macrophage Colony–stimulating Factor Mediate Rapid Phosphorylation and Activation of Cytosolic c–raf," *J. Biol. Chem.* 265(32):19812–19817 (1990).

Cleveland, J.L. et al., "Tyrosine Kinase Oncogenes Abrogate Interleukin–3 Dependence of Murine Myeloid Cells through Signaling Pathways Involving c–myc: Conditional Regulation of c–myc Transcription by Temperature–Sensitive v–abl," *Mol. Cell. Biol.* 9(12):5685–5695 (1989).
Dusanter–Fourt, I. et al., "Erythropoietin Induces the Tyrosine Phosphorylation of Its Own Receptor in Human Erythropoietin–responsive Cells," *J. Biol. Chem.* 267(15):10670–10675 (May 1992).
Edgington, S.M., "Molecular Crosstalk: Will virology and growth–factor research aid cytokine drug discovery?" *Bio/Technol.* 11:465–468 (Apr. 1993).
Firmbach–Kraft, I. et al., "tyk2, prototype of a novel class of non–receptor tyrosine kinase genes," *Oncogene* 5:1329–1336 (1990).
Fu, X.–Y., "A Transcription Factor with SH2 and SH3 Domains is Directly Activated by an Interferon α–Induced Cytoplasmic Protein Tyrosine Kinase(s)," *Cell* 70:323–335 (Jul. 1992).
Fu, X.–Y. et al., "The proteins of ISGF–3, the interferon α–induced transcriptional activator, define a gene family involved in signal transduction," *Proc. Natl. Acad. Sci. USA* 89:7840–7843 (Aug. 1992).
Fung, M.R. et al., "A Tyrosine Kinase Physically Associates With the β–Subunit of the Human IL–2 Receptor," *J. Immunol.* 147(4):1253–1260 (1991).
Gilmour, K.C. and N. C. Reich, "Receptor to nucleus signaling by prolactin and interleukin 2 via activation of latent DNA–binding factors," *Proc. Natl. Acad. Sci. USA* 91:6850–6854 (Jul. 1994).
Hanks, S.K. et al., "The Protein Kinase Family: Conserved Features and Deduced Phylogeny of the Catalytic Domains," *Science* 241:42–52 (1988).
Harpur, A.G. et al., "JAK2, a third member of the JAK family of protein tyrosine kinases," *Oncogene* 7:1347–1353 (Jul. 1992).
Howard, O.M.Z. et al., "Characterization of a class 3 tyrosine kinase," *Oncogene* 7:895–900 (May 1992).
Hunter, T., "A Thousand and One Protein Kinases," *Cell* 50:823–829 (1987).
Hunter, T., "Cytokine Connections," *Nature* 366:114–116 (Nov. 1993).
Ihle, J.N., "Interleukin–3 and Hematopoiesis," in: *Interleukins: Molecular Biology and Immunology*, Kishimoto, T., ed., Karger, Basel, pp. 65–106 (1992).

(List continued on next page.)

*Primary Examiner*—Jeffrey Stucker
(74) *Attorney, Agent, or Firm*—Sterne, Kessler, Goldstein & Fox P.L.L.C.

(57) ABSTRACT

Provided are methods for regulating the cellular response to cytokines by inhibiting or enhancing of at least one Jak kinase activity which mediates the response; assays for identifying inhibitors of Jak kinase activity or cytokine-induced Jak kinase activation useful in the methods of the invention are also provided; antibodies raised against peptide fragments of at least one epitope specific for a Jak kinase without interfering with kinase activity; polypeptides for Jak kinases; and nucleic acid encoding therefor.

6 Claims, 33 Drawing Sheets

OTHER PUBLICATIONS

Ihle, J.N. and D. Askew, "Origins and Properties of Hematopoietic Growth Factor–Dependent Cell Lines," *Int. J. Cell. Cloning* 7(2):68–91 (1989).

Ihle, J.N., "Cytokine receptor signalling," *Nature* 377:591–594 (Oct. 1995).

Ip, N.Y. et al., "CNTF and LIF Act on Neuronal Cells via Shared Signaling Pathways That Involve the IL–6 Signal Transducing Receptor Component gp130," *Cell* 69:1121–1132 (Jun. 1992).

Isfort, R.J. et al., "Interleukin 3 binds to a 140–kDa phosphotyrosine–containing cell surface protein," *Proc. Natl. Acad. Sci. USA* 85:7982–7986 (1988).

Kappel, C.A. et al., "Regulating gene expression in transgenic animals," *Curr. Opin. Biotech.* 3:548–553 (1992).

Koch, C.A. et al., "SH2 and SH3 Domains: Elements That Control Interactions of Cytoplasmic Signaling Proteins," *Science* 252:668–674 (1991).

Linnekin, D. et al., "Association of the erythropoietin receptor with protein tyrosine kinase activity," *Proc. Natl. Acad. Sci. USA* 89:6237–6241 (Jul. 1992).

Linnekin, D. and W.L. Farrar, "Signal transduction of human interleukin 3 and granulocyte–macrophage colony–stimulating factor through serine and tyrosine phosphorylation," *J. Biochem.* 271:317–324 (1990).

Mano, H. et al., "Expression of a novel form of Tec kinase in hematopoietic cells and mapping of the gene to chromosome 5 near Kit," *Oncogene* 8:417–424 (Feb. 1993).

Manthorpe, M. et al., "Cholinergic Neuronotrophic Factors: Fractionation Properties of an Extract from Selected Chick Embryonic Eye Tissues," *J. Neurochem.* 34(1):69–75 (1980).

Metcalf, D., "The molecular control of cell division, differentiation commitment and maturation in haemopoietic cells," *Nature* 339:27–30 (1989).

Miura, O. et al., "Inactivation of Erythropoietin Receptor Function by Point Mutations in a Region Having Homology with Other Cytokine Receptors," *Mol. Cell. Biol.* 13(3):1788–1795 (Mar. 1993).

Miura, O. et al., "Induction of Tyrosine Phosphorylation by the Erythropoietin Receptor Correlates with Mitogenesis," *Mol. Cell. Biol.* 11(10):4895–4902 (1991).

Miyajima, A. et al., "Cytokine Receptors and Signal Transduction," *Annu. Rev. Immunol.* 10:295–331 (Apr. 1992).

Morla, A.O. et al., "Hematopoietic Growth Factors Activate the Tyrosine Phosphorylation of Distinct Sets of Proteins in Interleukin–3–Dependent Murine Cell Lines," *Mol. Cell. Biol.* 8(5):2214–2218 (1988).

Müller, M. et al., "The protein tyrosine kinase JAK1 complements defects in interferonα/β and –γ signal transduction," *Nature* 366:129–135 (Nov. 1993).

Ohtsuka, M. et al., "Ligand–Induced Phosphorylation of the Colony–Stimulating Factor 1 Receptor Can Occur through an Intermolecular Reaction That Triggers Receptor Down Modulation," *Mol. Cell. Biol.* 10(4):1664–1671 (1990).

Partanen, J. et al., "Putative tyrosine kinases expressed in K–562 human Leukemia cells," *Proc. Natl. Acad. Sci. USA* 87:8913–8917 (1990).

Pellegrini, S. and C. Schindler, "Early events in signaling by interferons," *TIBS* 18:338–342 (Sep. 1993).

Pellegrini, S. et al., "Use of a Selectable Marker Regulated by Alpha Interferon To Obtain Mutations in the Signaling Pathway," *Mol. Cell. Biol.* 9(11):4605–4612 (1989).

Pritchard, M.A. et al., "Two members of the JAK family of protein tyrosine kinases map to Chromosome 1p31.3 and 9p24," *Mammalian Genome* 3:36–38 (Feb. 1992).

Quelle, F.W. et al., "Interleukin 3, Granulocyte–Macrophage Colony–stimulating Factor, and Transfected Erythropoietin Receptors Mediate Tyrosine Phosphorylation of a Common Cytosolic Protein (pp100) in FDC–ER Cells," *J. Biol. Chem.* 267(24):17055–17060 (Aug. 1992).

Quelle, F.W. and D.M. Wojchowski, "Proliferative Action of Erythropoietin is Associated with Rapid Protein Tyrosine Phosphorylation in Responsive B6SUt.EP Cells," *J. Biol. Chem.* 266(1):609–614 (1991).

Riordan, M.L. and J.C. Martin, "Oligonucleotide–based therapeutics," *Nature* 350:442–443 (Apr. 1991).

Schindler, C. et al., "Interferon–Dependent Tyrosine Phosphorylation of a Latent Cytoplasmic Transcription Factor," *Science* 257:809–813 (Aug. 1992).

Schindler, C. et al., "Proteins of transcription factor ISGF–3: One gene encodes the 91– and 84–kDa ISGF–3 proteins that are activated by interferon α," *Proc. Natl. Acad. Sci. USA* 89:7836–7839 (Aug. 1992).

Shohat, O. et al., "Inhibition of Cell Growth Mediated by Plasmids Encoding p53 Anti–Sense," *Oncogene* 1:277–283 (1987).

Shuai, K. et al., "Activation of Transcription by IFN–γ: Tyrosine Phosphorylation of a 91–kD DNA Binding Protein," *Science* 258:1808–1812 (Dec. 1992).

Silvennoinen, O. et al., "Structure of the murine Jak2 protein–tyrosine kinase and its role in interleukin 3 signal transduction," *Proc. Natl. Acad. Sci. USA* 90:8429–8433 (Sep. 1993).

Sorensen, P. et al., "Interleukin–3 Stimulates the Tyrosine Phosphorylation of the 140–Kilodalton Interleukin–3 Receptor," *J. Biol. Chem.* 264(32):19253–19258 (1989).

Spangler, R. et al., "Erythropoietin Increases c–myc mRNA by a Protein Kinase C–dependent Pathway," *J. Biol. Chem.* 266(2):681–684 (1991).

Stahl, N. et al., "Cross–linking Identifies Leukemia Inhibitory Factor–binding Protein as a Ciliary Neurotrophic Factor Receptor Component," *J. Biol. Chem.* 268(11):7628–7631 (Apr. 1993).

Takahashi, T. and T. Shirasawa, "Molecular Cloning of Rat JAK3, a Novel Member of the JAK Family of Protein Tyrosine Kinases," *FEBS Letts.* 342:124–128 (1994).

Torigoe, T. et al., "Interleukin–3 Regulates the Activity of the LYN Protein–Tyrosine Kinase in Myeloid–Committed Leukemic Cell Lines," *Blood* 80(3):617–624 (Aug. 1992).

Turner, B. et al., "Interleukin 2 induces tyrosine phosphorylation and activation of p72–74 Raf–1 kinase in a T–cell line," *Proc. Natl. Acad. Sci. USA* 88:1227–1231 (1991).

Ullrich, A. and J. Schlessinger, "Signal Transduction by Receptors with Tyrosine Kinase Activity," *Cell* 61:203–212 (1990).

Velasquez, L. et al., "A Protein Kinase in the Interferon α/β Signaling Pathway," *Cell* 70:313–322 (Jul. 1992).

Wang, X. et al., "Growth Hormone–promoted Tyrosyl Phosphorylation of a 121–kDa Growth Hormone Receptor–associated Protein," *J. Biol. Chem.* 268(5):3573–3579 (Feb. 1993).

Wang, Y. and G.M. Fuller, "Phosphorylation and Internalization of gp130 Occur After IL–6 Activation of JAK2 Kinase in Hepatocytes," *Molecular Biology of the Cell* 5:819–828 (Jul. 1994).

Wilks, A.F., "Two putative protein–tyrosine kinases identified by application of the polymerase chain reaction," *Proc. Natl. Acad. Sci. USA 86*: 1603–1607 (1989).

Wilks, A.F., "Structure and Function of the Protein Tyrosine Kinases," *Prog. Growth Factor Res. 2*:97–111 (1990).

Wilks, A.F., "Cloning Members of Protein–Tyrosine Kinase Family Using Polymerase Chain Reaction," *Meth. Enzymol. 200*:533–546 (1991).

Wilks, A.F. et al., "Two Novel Protein–Tyrosine Kinases, Each with a Second Phosphotransferase–Related Catalytic Domain, Define a New Class of Protein Kinase," *Mol. Cell. Biol. 11*(4):2057–2065 (1991).

Wilks, A.F. and A.G. Harpur, "Cytokine Signal Transduction and the JAK Family of Protein Tyrosine Kinase," *BioEssays 16*(5):313–320 (May 1994).

Witthuhn, B.A. et al., "JAK2 Associated with the Erythropoietin Receptor and Is Tyrosine Phosphorylated and Activated following Stimulation with Erythropoietin," *Cell 74*:227–236 (Jul. 1993).

Witthuhn, B.A. et al., "Involvement of the Jak–3 Janus kinase in signalling by interleukins 2 and 4 in lymphoid and myelooid cells," *Nature 370*:153–157 (Jul. 1994).

Yarden, Y. and A. Ullrich, "Growth Factor Receptor Tyrosine Kinases," *Ann. Rev. Biochem. 57*:443–478 (1988).

Yoshimura, A. and H.F. Lodish, "In vitro Phosphorylation of the Erythropoietin Receptor and an Associated Protein," *Mol. Cell. Biol. 12*:706–715 (Feb. 1992).

Yoshimura, A. et al., "Point mutation in the exoplasmic domain of the erythropoietin receptor resulting in hormone–independent activation and tumorigenicity," *Nature 348*:647–649 (1990).

```
CGGGGGAACA AGATGTGAAC TGTTTTCCCT CCCCAGAAGA AGAGGCCCTT TTTTTCCCTC        60

CCGCGAAGGC CAATGTTCTG AAAAAAGCTC TAG ATG GGA ATG GCC TGC CTT ACA       114
                                    Met Gly Met Ala Cys Leu Thr
                                     1                   5

ATG ACA GAA ATG GAG GCA ACC TCC ACA TCT CCT GTA CAT CAG AAT GGT        162
Met Thr Glu Met Glu Ala Thr Ser Thr Ser Pro Val His Gln Asn Gly
         10              15                  20

GAT ATT CCT GGA AGT GCT AAT TCT GTG AAG CAG ATA GAG CCA GTC CTT        210
Asp Ile Pro Gly Ser Ala Asn Ser Val Lys Gln Ile Glu Pro Val Leu
     25              30                  35

CAA GTG TAT CTG TAC CAT TCT CTT GGG CAA GCT GAA GGA GAG TAT CTG        258
Gln Val Tyr Leu Tyr His Ser Leu Gly Gln Ala Glu Gly Glu Tyr Leu
 40              45                  50                  55

AAG TTT CCA AGT GGA GAG TAT GTT GCA GAA GAA ATT TGT GTG GCT GCT        306
Lys Phe Pro Ser Gly Glu Tyr Val Ala Glu Glu Ile Cys Val Ala Ala
                 60                  65                  70

TCT AAA GCT TGT GGT ATT ACG CCT GTG TAT CAT AAT ATG TTT GCG TTA        354
Ser Lys Ala Cys Gly Ile Thr Pro Val Tyr His Asn Met Phe Ala Leu
             75                  80                  85

ATG AGT GAA ACC GAA AGG ATC TGG TAC CCA CCC AAT CAT GTC TTC CAC        402
Met Ser Glu Thr Glu Arg Ile Trp Tyr Pro Pro Asn His Val Phe His
         90                  95                 100

ATA GAC GAG TCA ACC AGG CAT GAC ATA CTC TAC AGG ATA AGG TTC TAC        450
Ile Asp Glu Ser Thr Arg His Asp Ile Leu Tyr Arg Ile Arg Phe Tyr
        105                 110                 115

TTC CCT CAT TGG TAC TGT AGT GGC AGC AGC AGA ACC TAC AGA TAC GGA        498
Phe Pro His Trp Tyr Cys Ser Gly Ser Ser Arg Thr Tyr Arg Tyr Gly
120                 125                 130                 135
                                    >
GTG TCC CGT GGG GCT GAA GCT CCT CTG CTT GAT GAC TTT GTC ATG TCT        546
Val Ser Arg Gly Ala Glu Ala Pro Leu Leu Asp Asp Phe Val Met Ser
                140                 145                 150
```

FIG.1A

```
                cc  c
TAC CTT TTT GCT CAG TGG CGG CAT GAT TTT GTT CAC GGA TGG ATA AAA      594
Tyr Leu Phe Ala Gln Trp Arg His Asp Phe Val His Gly Trp Ile Lys
        S   P                 160             165
            155

GTA CCT GTG ACT CAT GAA ACT CAG GAA GAG TGT CTT GGG ATG GCC GTG      642
Val Pro Val Thr His Glu Thr Gln Glu Glu Cys Leu Gly Met Ala Val
        170             175             180

TTA GAC ATG ATG AGA ATA GCT AAG GAG AAA GAC CAG ACT CCA CTG GCT      690
Leu Asp Met Met Arg Ile Ala Lys Glu Lys Asp Gln Thr Pro Leu Ala
        185             190             195

GTC TAT AAC TCT GTC AGC TAC AAG ACA TTC TTA CCA AAG TGC GTT CGA      738
Val Tyr Asn Ser Val Ser Tyr Lys Thr Phe Leu Pro Lys Cys Val Arg
200             205             210             215

GCG AAG ATC CAA GAC TAT CAC ATT TTA ACC CGG AAG CGA ATC AGG TAC      786
Ala Lys Ile Gln Asp Tyr His Ile Leu Thr Arg Lys Arg Ile Arg Tyr
                220             225             230

AGA TTT CGC AGA TTC ATT CAG CAA TTC AGT CAA TGT AAA GCC ACT GCC      834
Arg Phe Arg Arg Phe Ile Gln Gln Phe Ser Gln Cys Lys Ala Thr Ala
            235             240             245

AGG AAC CTA AAA CTT AAG TAT CTT ATA AAC CTG GAA ACC CTG CAG TCT      882
Arg Asn Leu Lys Leu Lys Tyr Leu Ile Asn Leu Glu Thr Leu Gln Ser
        250             255             260

GCC TTC TAC ACA GAA CAG TTT GAA GTA AAA GAA TCT GCA AGA GGT CCT      930
Ala Phe Tyr Thr Glu Gln Phe Glu Val Lys Glu Ser Ala Arg Gly Pro
265             270             275

TCA GGT GAG GAG ATT TTT GCA ACC ATT ATA ATA ACT GGA AAC GGT GGA      978
Ser Gly Glu Glu Ile Phe Ala Thr Ile Ile Ile Thr Gly Asn Gly Gly
280             285             290             295

ATT CAG TGG TCA AGA GGG AAA CAT AAG GAA AGT GAG ACA CTG ACA GAA     1026
Ile Gln Trp Ser Arg Gly Lys His Lys Glu Ser Glu Thr Leu Thr Glu
                300             305             310
```

FIG.1B

```
CAG GAC GTA CAG TTA TAT TGT GAT TTC CCT GAT ATT ATT GAT GTC AGT          1074
Gln Asp Val Gln Leu Tyr Cys Asp Phe Pro Asp Ile Ile Asp Val Ser
            315                 320                 325
                        t           c       g       g   c
ATT AAG CAA GCA AAC CAG GAA TGC TCA AAT GAA AGT AGA ATT GTA ACT          1122
Ile Lys Gln Ala Asn Gln Glu Cys Ser Asn Glu Ser Arg Ile Val Thr
        330                 335     T       340 V
        c   g   g   c   g   g   c
GTC CAT AAA CAA GAT GGT AAA GTT TTG GAG ATA GAA CTT AGC TCA TTA          1170
Val His Lys Gln Asp Gly Lys Val Leu Glu Ile Glu Leu Ser Ser Leu
        345                 350             355
                            t       g
AAA GAA GCC TTG TCA TTC GTG TCA TTA ATT GAC GGG TAT TAC AGA CTA          1218
Lys Glu Ala Leu Ser Phe Val Ser Leu Ile Asp Gly Tyr Tyr Arg Leu
360                 365                 370                 375
                g                   t               t       c
ACT GCG GAT GCG CAC CAT TAC CTC TGC AAA GAG GTG GCT CCC CCA GCT          1266
Thr Ala Asp Ala His His Tyr Leu Cys Lys Glu Val Ala Pro Pro Ala
                    380                 385                 390
    t   g                           t               t
GTG CTC GAG AAC ATA CAC AGC AAC TGC CAC GGC CCA ATA TCA ATG GAT          1314
Val Leu Glu Asn Ile His Ser Asn Cys His Gly Pro Ile Ser Met Asp
            395                 400                 405
            c                       a   a                   g
TTT GCC ATT AGC AAA CTA AAG AAG GCG GGT AAC CAG ACT GGA CTA TAT          1362
Phe Ala Ile Ser Lys Leu Lys Lys Ala Gly Asn Gln Thr Gly Leu Tyr
        410                 415                 420
    g   t   t                                   c
GTG CTA CGA TGC AGC CCT AAG GAC TTC AAC AAA TAC TTT CTG ACC TTT          1410
Val Leu Arg Cys Ser Pro Lys Asp Phe Asn Lys Tyr Phe Leu Thr Phe
        425                 430                 435
c                       t                               g
GCT GTT GAG CGA GAA AAT GTC ATT GAA TAT AAA CAC TGT TTG ATT ACG          1458
Ala Val Glu Arg Glu Asn Val Ile Glu Tyr Lys His Cys Leu Ile Thr
440                 445                 450                 455
                        g                   t
AAG AAT GAG AAT GGA GAA TAC AAC CTC AGC GGG ACT AAG AGG AAC TTC          1506
Lys Asn Glu Asn Gly Glu Tyr Asn Leu Ser Gly Thr Lys Arg Asn Phe
                    460                 465                 470
```

FIG.1C

```
                          gt
AGT AAC CTT AAG GAC CTT TTG AAT TGC TAC CAG ATG GAA ACT GTG CGC    1554
Ser Asn Leu Lys Asp Leu Leu Asn Cys Tyr Gln Met Glu Thr Val Arg
     S      475             480             485
                                   c             t  t        g
TCA GAC AGT ATC ATC TTC CAG TTT ACC AAA TGC TGC CCC CCA AAG CCA    1602
Ser Asp Ser Ile Ile Phe Gln Phe Thr Lys Cys Cys Pro Pro Lys Pro
         490             495             500
                            t                        g
AAA GAT AAA TCA AAC CTT CTC GTC TTC AGA ACA AAT GGT ATT TCT GAT    1650
Lys Asp Lys Ser Asn Leu Leu Val Phe Arg Thr Asn Gly Ile Ser Asp
     505             510             515        V
             C
GTT CAG ATC TCA CCA ACA TTA CAG AGG CAT AAT AAT GTG AAT CAA ATG    1698
Val Gln Ile Ser Pro Thr Leu Gln Arg His Asn Asn Val Asn Gln Met
520      L       525             530             535
                                 g                        c
GTG TTT CAC AAA ATC AGG AAT GAA GAT TTA ATA TTT AAT GAA AGT CTT    1746
Val Phe His Lys Ile Arg Asn Glu Asp Leu Ile Phe Asn Glu Ser Leu
             540             545             550
         c                  a
GGC CAA GGT ACT TTT ACA AAA ATT TTT AAA GGT GTA AGA AGA GAA GTT    1794
Gly Gln Gly Thr Phe Thr Lys Ile Phe Lys Gly Val Arg Arg Glu Val
             555             560             565
             g       g   c
GGA GAT TAT GGT CAA CTG CAC AAA ACG GAA GTT CTT TTG AAA GTC CTA    1842
Gly Asp Tyr Gly Gln Leu His Lys Thr Glu Val Leu Leu Lys Val Leu
             570         K               580
                         575
         a                                       t
GAT AAA GCA CAT AGG AAC TAT TCA GAG TCT TTC TTC GAA GCA GCA AGC    1890
Asp Lys Ala His Arg Asn Tyr Ser Glu Ser Phe Phe Glu Ala Ala Ser
     585             590             595
                                             a       a
ATG ATG AGT CAG CTT TCT CAC AAG CAT TTG GTT TTG AAT TAT GGT GTC    1938
Met Met Ser Gln Leu Ser His Lys His Leu Val Leu Asn Tyr Gly Val
600             605             610             615
                         t           g
TGT GTC TGT GGA GAG GAG AAC ATT CTG GTT CAA GAA TTT GTA AAA TTT    1986
Cys Val Cys Gly Glu Glu Asn Ile Leu Val Gln Glu Phe Val Lys Phe
             620             625             630
```

FIG.1D

```
                                                    t
GGA TCA CTG GAT ACA TAC CTG AAG AAG AAC AAA AAT TCC ATA AAT ATA          2034
Gly Ser Leu Asp Thr Tyr Leu Lys Lys Asn Lys Asn Ser Ile Asn Ile
            635                 640                 645
                g                                       c   c
TTA TGG AAA CTT GGA GTG GCT AAG CAG TTG GCA TGG GCC ATG CAT TTT          2082
Leu Trp Lys Leu Gly Val Ala Lys Gln Leu Ala Trp Ala Met His Phe
        650                 655                 660

CTA GAA GAA AAA TCC CTT ATT CAT GGG AAT GTG TGT GCT AAA AAT ATC          2130
Leu Glu Glu Lys Ser Leu Ile His Gly Asn Val Cys Ala Lys Asn Ile
    665                 670                 675

CTG CTT ATC AGA GAA GAA GAC AGG AGA ACG GGG AAC CCA CCT TTC ATC          2178
Leu Leu Ile Arg Glu Glu Asp Arg Arg Thr Gly Asn Pro Pro Phe Ile
680                 685                 690                 695

AAA CTT AGT GAT CCT GGC ATT AGC ATT ACA GTT CTA CCG AAG GAC ATT          2226
Lys Leu Ser Asp Pro Gly Ile Ser Ile Thr Val Leu Pro Lys Asp Ile
                700                 705                 710
                            a       g
CTT CAG GAG AGA ATA CCA TGG GTA CCT CCT GAA TGC ATT GAG AAT CCT          2274
Leu Gln Glu Arg Ile Pro Trp Val Pro Pro Glu Cys Ile Glu Asn Pro
            715 T               720                 725
    a   c
AAA AAT CTC AAT CTG GCA ACA GAC AAG TGG AGC TTC GGG ACC ACT CTG          2322
Lys Asn Leu Asn Leu Ala Thr Asp Lys Trp Ser Phe Gly Thr Thr Leu
        730 T               735                 740

TGG GAG ATC TGC AGT GGA GGA GAT AAG CCC CTG AGT GCT CTG GAT TCT          2370
Trp Glu Ile Cys Ser Gly Gly Asp Lys Pro Leu Ser Ala Leu Asp Ser
    745                 750                 755

CAA AGA AAG CTG CAG TTC TAT GAA GAT AAG CAT CAG CTT CCT GCA CCC          2418
Gln Arg Lys Leu Gln Phe Tyr Glu Asp Lys His Gln Leu Pro Ala Pro
760                 765                 770                 775
```

FIG.1E

```
                                          9
AAG TGG ACA GAG TTA GCA AAC CTT ATA AAT AAT TGC ATG GAC TAT GAG        2466
Lys Trp Thr Glu Leu Ala Asn Leu Ile Asn Asn Cys Met Asp Tyr Glu
                    780             785             790

CCA GAT TTC AGG CCT GCT TTC AGA GCT GTC ATC CGT GAT CTT AAC AGC        2514
Pro Asp Phe Arg Pro Ala Phe Arg Ala Val Ile Arg Asp Leu Asn Ser
                795             800             805

CTG TTT ACT CCA GAT TAT GAA CTA CTA ACA GAA AAT GAC ATG CTA CCA        2562
Leu Phe Thr Pro Asp Tyr Glu Leu Leu Thr Glu Asn Asp Met Leu Pro
            810             815             820

AAC ATG AGA ATA GGT GCC CTA GGG TTT TCT GGT GCT TTT GAA GAC AGG        2610
Asn Met Arg Ile Gly Ala Leu Gly Phe Ser Gly Ala Phe Glu Asp Arg
            825             830             835

GAC CCT ACA CAG TTT GAA GAG AGA CAC TTG AAG TTT CTA CAG CAG CTT        2658
Asp Pro Thr Gln Phe Glu Glu Arg His Leu Lys Phe Leu Gln Gln Leu
840             845             850             855

GGC AAA GGT AAC TTC GGG AGT GTG GAG ATG TGC CGC TAT GAC CCG CTG        2706
Gly Lys Gly Asn Phe Gly Ser Val Glu Met Cys Arg Tyr Asp Pro Leu
                860             865             870

CAG GAC AAC ACT GGC GAG GTG GTC GCT GTG AAG AAA CTC CAG CAC AGC        2754
Gln Asp Asn Thr Gly Glu Val Val Ala Val Lys Lys Leu Gln His Ser
                875             880             885

ACT GAA GAG CAC CTC CGA GAC TTT GAG AGG GAG ATC GAG ATC CTG AAA        2802
Thr Glu Glu His Leu Arg Asp Phe Glu Arg Glu Ile Glu Ile Leu Lys
            890             895             900

TCC TTG CAG CAT GAC AAC ATC GTC AAG TAC AAG GGA GTG TGC TAC AGT        2850
Ser Leu Gln His Asp Asn Ile Val Lys Tyr Lys Gly Val Cys Tyr Ser
            905             910             915

GCG GGT CGG CGC AAC CTA AGA TTA ATT ATG GAA TAT TTA CCA TAT GGA        2898
Ala Gly Arg Arg Asn Leu Arg Leu Ile Met Glu Tyr Leu Pro Tyr Gly
920             925             930             935
```

FIG.1F

```
AGT TTA CGA GAC TAT CTC CAA AAA CAT AAA GAA CGG ATA GAT CAC AAA        2946
Ser Leu Arg Asp Tyr Leu Gln Lys His Lys Glu Arg Ile Asp His Lys
            940             945             950

AAA CTT CTT CAA TAC ACA TCT CAG ATA TGC AAG GGC ATG GAA TAT CTT        2994
Lys Leu Leu Gln Tyr Thr Ser Gln Ile Cys Lys Gly Met Glu Tyr Leu
            955             960             965

GGT ACA AAA AGG TAT ATC CAC AGG GAC CTG GCA ACA AGG AAC ATA TTG        3042
Gly Thr Lys Arg Tyr Ile His Arg Asp Leu Ala Thr Arg Asn Ile Leu
            970             975             980

GTG GAA AAT GAG AAC AGG GTT AAA ATA GGA GAC TTC GGA TTA ACC AAA        3090
Val Glu Asn Glu Asn Arg Val Lys Ile Gly Asp Phe Gly Leu Thr Lys
            985             990             995

GTC TTG CCG CAG GAC AAA GAA TAC TAC AAA GTA AAG GAG CCA GGG GAA        3138
Val Leu Pro Gln Asp Lys Glu Tyr Tyr Lys Val Lys Glu Pro Gly Glu
1000            1005            1010            1015

AGC CCC ATA TTC TGG TAC GCA CCT GAA TCC TTG ACG GAG AGC AAG TTT        3186
Ser Pro Ile Phe Trp Tyr Ala Pro Glu Ser Leu Thr Glu Ser Lys Phe
            1020            1025            1030

TCT GTG GCC TCA GAT GTG TGG AGC TTT GGA GTG GTT CTA TAC GAA CTT        3234
Ser Val Ala Ser Asp Val Trp Ser Phe Gly Val Val Leu Tyr Glu Leu
            1035            1040            1045

TTC ACA TAC ATC GAG AAG AGT AAA AGT CCA CCC GTG GAA TTT ATG CGA        3282
Phe Thr Tyr Ile Glu Lys Ser Lys Ser Pro Pro Val Glu Phe Met Arg
            1050            1055            1060

ATG ATT GGC AAT GAT AAA CAA GGG CAA ATG ATT GTG TTC CAT TTG ATA        3330
Met Ile Gly Asn Asp Lys Gln Gly Gln Met Ile Val Phe His Leu Ile
            1065            1070            1075

GAG CTA CTG AAG AGC AAC GGA AGA TTG CCA AGG CCA GAA GGA TGC CCA        3378
Glu Leu Leu Lys Ser Asn Gly Arg Leu Pro Arg Pro Glu Gly Cys Pro
1080            1085            1090            1095
```

FIG.1G

```
GAT GAG ATT TAT GTG ATC ATG ACA GAG TGC TGG AAC AAC AAT GTG AGC        3426
Asp Glu Ile Tyr Val Ile Met Thr Glu Cys Trp Asn Asn Asn Val Ser
            1100                1105                1110
                                    c
CAG CGT CCC TCC TTC AGG GAC CTT TCG TTC GGG TGG ATC AAA TCC GGG        3474
Gln Arg Pro Ser Phe Arg Asp Leu Ser Phe Gly Trp Ile Lys Ser Gly
            1115                1120                1125

ACA GTA TAGCTGCGTG AAAGAGATGG CCTTCACTCA GAGACCAAGC AGACTTCCAG         3530
Thr Val c
AACCAGAACA AAGCTCTGTA GCCTTGTGTC TACACATCCT TATCATGATG CTAGCTAGGC      3590
  (a) (a)              (a)
AGAAGAAACT GTGACGCCGT CTGCTCAAAG CTTTGCTTC                             3629
```

FIG.1H

Human JAK1

| | | |
|---|---|---|
| ATG GCT TTC TGT GCT AAA ATG AGG AGC TCC AAG AAG ACT GAG GTG AAC | 123 | |
| Met Ala Phe Cys Ala Lys Met Arg Ser Ser Lys Lys Thr Glu Val Asn | 16 | |
| CTG GAG GCC CCT GAG CCA GGG GTG GAA GTG ATC TTC TAT CTG TCG GAC | 171 | |
| Leu Glu Ala Pro Glu Pro Gly Val Glu Val Ile Phe Tyr Leu Ser Asp | 32 | |
| AGG GAG CCC CTC CGG CTG GGC AGT GGA GAG TAC ACA GCA GAG GAA CTG | 219 | |
| Arg Glu Pro Leu Arg Leu Gly Ser Gly Glu Tyr Thr Ala Glu Glu Leu | 48 | |
| TGC ATC AGG GCT GCA CAG GCA TGC CGT ATC TCT CCT CTT TGT CAC AAC | 267 | |
| Cys Ile Arg Ala Ala Gln Ala Cys Arg Ile Ser Pro Leu Cys His Asn | 64 | |
| CTC TTT GCC CTG TAT GAC GAG AAC ACC AAG CTC TGG TAT GCT CCA AAT | 315 | |
| Leu Phe Ala Leu Tyr Asp Glu Asn Thr Lys Leu Trp Tyr Ala Pro Asn | 80 | |
| CGC ACC ATC ACC GTT GAT GAC AAG ATG TCC CTC CGG CTC CAC TAC CGG | 363 | |
| Arg Thr Ile Thr Val Asp Asp Lys Met Ser Leu Arg Leu His Tyr Arg | 96 | |
| ATG AGG TTC TAT TTC ACC AAT TGG CAT GGA ACC AAC GAC AAT GAG CAG | 411 | |
| Met Arg Phe Tyr Phe Thr Asn Trp His Gly Thr Asn Asp Asn Glu Gln | 112 | |
| TCA GTG TGG CGT CAT TCT CCA AAG AAG CAG AAA AAT GGC TAC GAG AAA | 459 | |
| Ser Val Trp Arg His Ser Pro Lys Lys Gln Lys Asn Gly Tyr Glu Lys | 128 | |
| AAA AAG ATT CCA GAT GCA ACC CCT CTC CTT GAT GCC AGC TCA CTG GAG | 507 | |
| Lys Lys Ile Pro Asp Ala Thr Pro Leu Leu Asp Ala Ser Ser Leu Glu | 144 | |
| TAT CTG TTT GCT CAG GGA CAG TAT GAT TTG GTG AAA TGC CTG GCT CCT | 555 | |
| Tyr Leu Phe Ala Gln Gly Gln Tyr Asp Leu Val Lys Cys Leu Ala Pro | 160 | |
| ATT CGA GAC CCC AAG ACC GAG CAG GAT GGA CAT GAT ATT GAG AAC GAG | 603 | |
| Ile Arg Asp Pro Lys Thr Glu Gln Asp Gly His Asp Ile Glu Asn Glu | 176 | |
| TGT CTA GGG ATG GCT GTC CTG GCC ATC TCA CAC TAT GCC ATG ATG AAG | 651 | |
| Cys Leu Gly Met Ala Val Leu Ala Ile Ser His Tyr Ala Met Met Lys | 192 | |
| AAG ATG CAG TTG CCA GAA CTG CCC AAG GAC ATC AGC TAC AAG CGA TAT | 699 | |
| Lys Met Gln Leu Pro Glu Leu Pro Lys Asp Ile Ser Tyr Lys Arg Tyr | 208 | |
| ATT CCA GAA ACA TTG AAT AAG TCC ATC AGA CAG AGG AAC CTT CTC ACC | 747 | |
| Ile Pro Glu Thr Leu Asn Lys Ser Ile Arg Gln Arg Asn Leu Leu Thr | 224 | |
| AGG ATG CGG ATA AAT AAT GTT TTC AAG GAT TTC CTA AAG GAA TTT AAC | 795 | |
| Arg Met Arg Ile Asn Asn Val Phe Lys Asp Phe Leu Lys Glu Phe Asn | 240 | |
| AAC AAG ACC ATT TGT GAC AGC AGC GTG TCC ACG CAT GAC CTG AAG GTG | 843 | |
| Asn Lys Thr Ile Cys Asp Ser Ser Val Ser Thr His Asp Leu Lys Val | 256 | |
| AAA TAC TTG GCT ACC TTG GAA ACT TTG ACA AAA CAT TAC GGT GCT GAA | 891 | |
| Lys Tyr Leu Ala Thr Leu Glu Thr Leu Thr Lys His Tyr Gly Ala Glu | 272 | FIG.2A |

| | | |
|---|---|---|
| ATA TTT GAG ACT TCC ATG TTA CTG ATT TCA TCA GAA AAT GAG ATG AAT | 939 | |
| Ile Phe Glu Thr Ser Met Leu Leu Ile Ser Ser Glu Asn Glu Met Asn | 288 | |
| TGG TTT CAT TCG AAT GAC GGT GGA AAC GTT CTC TAC TAC GAA GTG ATG | 987 | |
| Trp Phe His Ser Asn Asp Gly Gly Asn Val Leu Tyr Tyr Glu Val Met | 304 | |
| GTG ACT GGG AAT CTT GGA ATC CAG TGG AGG CAT AAA CCA AAT GTT GTT | 1035 | |
| Val Thr Gly Asn Leu Gly Ile Gln Trp Arg His Lys Pro Asn Val Val | 320 | |
| TCT GTT GAA AAG GAA AAA AAT AAA CTG AAG CGG AAA AAA CTG GAA AAT | 1083 | |
| Ser Val Glu Lys Glu Lys Asn Lys Leu Lys Arg Lys Lys Leu Glu Asn | 336 | |
| AAA GAC AAG AAG GAT GAG GAG AAA AAC AAG ATC CGG GAA GAG TGG AAC | 1131 | |
| Lys Asp Lys Lys Asp Glu Glu Lys Asn Lys Ile Arg Glu Glu Trp Asn | 352 | |
| AAT TTT TCA TTC TTC CCT GAA ATC ACT CAC ATT GTA ATA AAG GAG TCT | 1179 | |
| Asn Phe Ser Phe Phe Pro Glu Ile Thr His Ile Val Ile Lys Glu Ser | 368 | |
| GTG GTC AGC ATT AAC AAG CAG GAC AAC AAG AAA ATG GAA CTG AAG CTC | 1227 | |
| Val Val Ser Ile Asn Lys Gln Asp Asn Lys Lys Met Glu Leu Lys Leu | 384 | |
| TCT TCC CAC GAG GAG GCC TTG TCC TTT GTG TCC CTG GTA GAT GGC TAC | 1275 | |
| Ser Ser His Glu Glu Ala Leu Ser Phe Val Ser Leu Val Asp Gly Tyr | 400 | |
| TTC CGG CTC ACA GCA GAT GCC CAT CAT TAC CTC TGC ACC GAC GTG GCC | 1323 | |
| Phe Arg Leu Thr Ala Asp Ala His His Tyr Leu Cys Thr Asp Val Ala | 416 | |
| CCC CCG TTG ATC GTC CAC AAC ATA CAG AAT GGC TGT CAT GGT CCA ATC | 1371 | |
| Pro Pro Leu Ile Val His Asn Ile Gln Asn Gly Cys His Gly Pro Ile | 432 | |
| TGT ACA GAA TAC GCC ATC AAT AAA TTG CGG CAA GAA GGA AGC GAG GAG | 1419 | |
| Cys Thr Glu Tyr Ala Ile Asn Lys Leu Arg Gln Glu Gly Ser Glu Glu | 448 | |
| GGG ATG TAC GTG CTG AGG TGG AGC TGC ACC GAC TTT GAC AAC ATC CTC | 1467 | |
| Gly Met Tyr Val Leu Arg Trp Ser Cys Thr Asp Phe Asp Asn Ile Leu | 464 | |
| ATG ACC GTC ACC TGC TTT GAG AAG TCT GAG CAG GTG CAG GGT GCC CAG | 1515 | |
| Met Thr Val Thr Cys Phe Glu Lys Ser Glu Gln Val Gln Gly Ala Gln | 480 | |
| AAG CAG TTC AAG AAC TTT CAG ATC GAG GTG CAG AAG GGC CGC TAC AGT | 1563 | |
| Lys Gln Phe Lys Asn Phe Gln Ile Glu Val Gln Lys Gly Arg Tyr Ser | 496 | |
| CTG CAC GGT TCG GAC CGC AGC TTC CCC AGC TTG GGA GAC CTC ATG AGC | 1611 | |
| Leu His Gly Ser Asp Arg Ser Phe Pro Ser Leu Gly Asp Leu Met Ser | 512 | |
| CAC CTC AAG AAG CAG ATC CTG CGC ACG GAT AAC ATC AGC TTC ATG CTA | 1659 | |
| His Leu Lys Lys Gln Ile Leu Arg Thr Asp Asn Ile Ser Phe Met Leu | 528 | |
| AAA CGC TGC TGC CAG CCC AAG CCC CGA GAA ATC TCC AAC CTG CTG GTG | 1707 | |
| Lys Arg Cys Cys Gln Pro Lys Pro Arg Glu Ile Ser Asn Leu Leu Val | 544 | |
| GCT ACT AAG AAA GCC CAG GAG TGG CAG CCC GTC TAC CCC ATG AGC CAG | 1755 | |
| Ala Thr Lys Lys Ala Gln Glu Trp Gln Pro Val Tyr Pro Met Ser Gln | 560 | |

FIG.2B

```
CTG AGT TTC GAT CGG ATC CTC AAG AAG GAT CTG GTG CAG GGC GAG CAC    1803
Leu Ser Phe Asp Arg Ile Leu Lys Lys Asp Leu Val Gln Gly Glu His     576

CTT GGG AGA GGC ACG AGA ACA CAC ATC TAT TCT GGG ACC CTG ATG GAT    1851
Leu Gly Arg Gly Thr Arg Thr His Ile Tyr Ser Gly Thr Leu Met Asp     592

TAC AAG GAT GAC GAA GGA ACT TCT GAA GAG AAG AAG ATA AAA GTG ATC    1899
Tyr Lys Asp Asp Glu Gly Thr Ser Glu Glu Lys Lys Ile Lys Val Ile     608

CTC AAA GTC TTA GAC CCC AGC CAC AGG GAT ATT TCC CTG GCC TTC TTC    1947
Leu Lys Val Leu Asp Pro Ser His Arg Asp Ile Ser Leu Ala Phe Phe     624

GAG GCA GCC AGC ATG ATG AGA CAG GTC TCC CAC AAA CAC ATC GTG TAC    1995
Glu Ala Ala Ser Met Met Arg Gln Val Ser His Lys His Ile Val Tyr     640

CTC TAT GGC GTC TGT GTC CGC GAC GTG GAG AAT ATC ATG GTG GAA GAG    2043
Leu Tyr Gly Val Cys Val Arg Asp Val Glu Asn Ile Met Val Glu Glu     656

TTT GTG GAA GGG GGT CCT CTG GAT CTC TTC ATG CAC CGG AAA AGT GAT    2091
Phe Val Glu Gly Gly Pro Leu Asp Leu Phe Met His Arg Lys Ser Asp     672

GTC CTT ACC ACA CCA TGG AAA TTC AAA GTT GCC AAA CAG CTG GCC AGT    2139
Val Leu Thr Thr Pro Trp Lys Phe Lys Val Ala Lys Gln Leu Ala Ser     688

GCC CTG AGC TAC TTG GAG GAT AAA GAC CTG GTC CAT GGA AAT GTG TGT    2187
Ala Leu Ser Tyr Leu Glu Asp Lys Asp Leu Val His Gly Asn Val Cys     704

ACT AAA AAC CTC CTC CTG GCC CGT GAG GGA ATC GAC AGT GAG TGT GGC    2235
Thr Lys Asn Leu Leu Leu Ala Arg Glu Gly Ile Asp Ser Glu Cys Gly     720

CCA TTC ATC AAG CTC AGT GAC CCC GGC ATC CCC ATT ACG GTG CTG TCT    2283
Pro Phe Ile Lys Leu Ser Asp Pro Gly Ile Pro Ile Thr Val Leu Ser     736

AGG CAA GAA TGC ATT GAA CGA ATC CCA TGG ATT GCT CCT GAG TGT GTT    2331
Arg Gln Glu Cys Ile Glu Arg Ile Pro Trp Ile Ala Pro Glu Cys Val     752

GAG GAC TCC AAG AAC CTG AGT GTG GCT GCT GAC AAG TGG AGC TTT GGA    2379
Glu Asp Ser Lys Asn Leu Ser Val Ala Ala Asp Lys Trp Ser Phe Gly     768

ACC ACG CTC TGG GAA ATC TGC TAC AAT GGC GAG ATC CCC TTG AAA GAC    2427
Thr Thr Leu Trp Glu Ile Cys Tyr Asn Gly Glu Ile Pro Leu Lys Asp     784

AAG ACG CTG ATT GAG AAA GAG AGA TTC TAT GAA AGC CGG TGC AGG CCA    2475
Lys Thr Leu Ile Glu Lys Glu Arg Phe Tyr Glu Ser Arg Cys Arg Pro     800

GTG ACA CCA TCA TGT AAG GAG CTG GCT GAC CTC ATG ACC CGC TGC ATG    2523
Val Thr Pro Ser Cys Lys Glu Leu Ala Asp Leu Met Thr Arg Cys Met     816

AAC TAT GAC CCC AAT CAG AGG CCT TTC TTC CGA GCC ATC ATG AGA GAC    2571
Asn Tyr Asp Pro Asn Gln Arg Pro Phe Phe Arg Ala Ile Met Arg Asp     832

ATT AAT AAG CTT GAA GAG CAG AAT CCA GAT ATT GTT TCC AGA AAA AAA    2619
Ile Asn Lys Leu Glu Glu Gln Asn Pro Asp Ile Val Ser Arg Lys Lys     848
```

FIG.2C

```
AAC CAG CCA ACT GAA GTG GAC CCC ACA CAT TTT GAG AAG CGC TTC CTA    2667
Asn Gln Pro Thr Glu Val Asp Pro Thr His Phe Glu Lys Arg Phe Leu    864

AAG AGG ATC CGT GAC TTG GGA GAG GGC CAC TTT GGG AAG GTT GAG CTC    2715
Lys Arg Ile Arg Asp Leu Gly Glu Gly His Phe Gly Lys Val Glu Leu    880

TGC AGG TAT GAC CCC GAA GAC AAT ACA GGG GAG CAG GTG GCT GTT AAA    2763
Cys Arg Tyr Asp Pro Glu Asp Asn Thr Gly Glu Gln Val Ala Val Lys    896

TCT CTG AAG CCT GAG AGT GGA GGT AAC CAC ATA GCT GAT CTG AAA AAG    2811
Ser Leu Lys Pro Glu Ser Gly Gly Asn His Ile Ala Asp Leu Lys Lys    912

GAA ATC GAG ATC TTA AGG AAC CTC TAT CAT GAG AAC ATT GTG AAG TAC    2859
Glu Ile Glu Ile Leu Arg Asn Leu Tyr His Glu Asn Ile Val Lys Tyr    928

AAA GGA ATC TGC ACA GAA GAC GGA GGA AAT GGT ATT AAG CTC ATC ATG    2907
Lys Gly Ile Cys Thr Glu Asp Gly Gly Asn Gly Ile Lys Leu Ile Met    944

GAA TTT CTG CCT TCG GGA AGC CTT AAG GAA TAT CTT CCA AAG AAT AAG    2955
Glu Phe Leu Pro Ser Gly Ser Leu Lys Glu Tyr Leu Pro Lys Asn Lys    960

AAC AAA ATA AAC CTC AAA CAG CAG CTA AAA TAT GCC GTT CAG ATT TGT    3003
Asn Lys Ile Asn Leu Lys Gln Gln Leu Lys Tyr Ala Val Gln Ile Cys    976

AAG GGG ATG GAC TAT TTG GGT TCT CGG CAA TAC GTT CAC CGG GAC TTG    3051
Lys Gly Met Asp Tyr Leu Gly Ser Arg Gln Tyr Val His Arg Asp Leu    992

GCA GCA AGA AAT GTC CTT GTT GAG AGT GAA CAC CAA GTG AAA ATT GGA    3099
Ala Ala Arg Asn Val Leu Val Glu Ser Glu His Gln Val Lys Ile Gly    1008

GAC TTC GGT TTA ACC AAA GCA ATT GAA ACC GAT AAG GAG TAT TAC ACC    3147
Asp Phe Gly Leu Thr Lys Ala Ile Glu Thr Asp Lys Glu Tyr Tyr Thr    1024

GTC AAG GAT GAC CGG GAC AGC CCT GTG TTT TGG TAT GCT CCA GAA TGT    3195
Val Lys Asp Asp Arg Asp Ser Pro Val Phe Trp Tyr Ala Pro Glu Cys    1040

TTA ATG CAA TCT AAA TTT TAT ATT GCC TCT GAC GTC TGG TCT TTT GGA    3243
Leu Met Gln Ser Lys Phe Tyr Ile Ala Ser Asp Val Trp Ser Phe Gly    1056

GTC ACT CTG CAT GAG CTG CTG ACT TAC TGT GAT TCA GAT TCT AGT CCC    3291
Val Thr Leu His Glu Leu Leu Thr Tyr Cys Asp Ser Asp Ser Ser Pro    1072

ATG GCT TTG TTC CTG AAA ATG ATA GGC CCA ACC CAT GGC CAG ATG ACA    3339
Met Ala Leu Phe Leu Lys Met Ile Gly Pro Thr His Gly Gln Met Thr    1088

GTC ACA AGA CTT GTG AAT ACG TTA AAA GAA GGA AAA CGC CTG CCG TGC    3387
Val Thr Arg Leu Val Asn Thr Leu Lys Glu Gly Lys Arg Leu Pro Cys    1104

CCA CCT AAC TGT CCA GAT GAG GTT TAT CAG CTT ATG AGA AAA TGC TGG    3435
Pro Pro Asn Cys Pro Asp Glu Val Tyr Gln Leu Met Arg Lys Cys Trp    1120

GAA TTC CAA CCA TCC AAT CGG ACA AGC TTT CAG AAC CTT ATT GAA GGA    3483
Glu Phe Gln Pro Ser Asn Arg Thr Ser Phe Gln Asn Leu Ile Glu Gly    1136

TTT GAA GCA CTT TTA AAA TAA                                        3504
Phe Glu Ala Leu Leu Lys  *                                         1143
```

FIG.2D

Human TYK2

| | |
|---|---|
| ATG CCT CTG CGC CAC TGG GGG ATG GCC AGG GGC AGT AAG CCC GTT GGG | 354 |
| Met Pro Leu Arg His Trp Gly Met Ala Arg Gly Ser Lys Pro Val Gly | 16 |
| GAT GGA GCC CAG CCC ATG GCT GCC ATG GGA GGC CTG AAG GTG CTT CTG | 402 |
| Asp Gly Ala Gln Pro Met Ala Ala Met Gly Gly Leu Lys Val Leu Leu | 32 |
| CAC TGG GCT GGT CCA GGC GGC GGG GAG CCC TGG GTC ACT TTC AGT GAG | 450 |
| His Trp Ala Gly Pro Gly Gly Gly Glu Pro Trp Val Thr Phe Ser Glu | 48 |
| TCA TCG CTG ACA GCT GAG GAA GTC TGC ATC CAC ATT GCA CAT AAA GTT | 498 |
| Ser Ser Leu Thr Ala Glu Glu Val Cys Ile His Ile Ala His Lys Val | 64 |
| GGT ATC ACT CCT CCT TGC TTC AAT CTC TTT GCC CTC TTC GAT GCT CAG | 546 |
| Gly Ile Thr Pro Pro Cys Phe Asn Leu Phe Ala Leu Phe Asp Ala Gln | 80 |
| GCC CAA GTC TGG TTG CCC CCA AAC CAC ATC CTA GAG ATC CCC AGA GAT | 594 |
| Ala Gln Val Trp Leu Pro Pro Asn His Ile Leu Glu Ile Pro Arg Asp | 96 |
| GCA AGC CTG ATG CTA TAT TTC CGC ATA AGG TTT TAT TTC CGG AAC TGG | 642 |
| Ala Ser Leu Met Leu Tyr Phe Arg Ile Arg Phe Tyr Phe Arg Asn Trp | 112 |
| CAT GGC ATG AAT CCT CGG GAA CCG GCT GTG TAC CGT TGT GGG CCC CCA | 690 |
| His Gly Met Asn Pro Arg Glu Pro Ala Val Tyr Arg Cys Gly Pro Pro | 128 |
| GGA ACC GAG GCA TCC TCA GAT CAG ACA GCA CAG GGG ATG CAA CTC CTG | 738 |
| Gly Thr Glu Ala Ser Ser Asp Gln Thr Ala Gln Gly Met Gln Leu Leu | 144 |
| GAC CCA GCC TCA TTT GAG TAC CTC TTT GAG CAG GGC AAG CAT GAG TTT | 786 |
| Asp Pro Ala Ser Phe Glu Tyr Leu Phe Glu Gln Gly Lys His Glu Phe | 160 |
| GTG AAT GAC GTG GCA TCA CTG TGG GAG CTG TCG ACC GAG GAG GAG ATC | 834 |
| Val Asn Asp Val Ala Ser Leu Trp Glu Leu Ser Thr Glu Glu Glu Ile | 176 |
| CAC CAC TTT AAG AAT GAG AGC CTG GGC ATG GCC TTT CTG CAC CTC TGT | 882 |
| His His Phe Lys Asn Glu Ser Leu Gly Met Ala Phe Leu His Leu Cys | 192 |
| CAC CTC GCT CTC CGC CAT GGC ATC CCC CTG GAG GAG GTG GCC AAG AAG | 930 |
| His Leu Ala Leu Arg His Gly Ile Pro Leu Glu Glu Val Ala Lys Lys | 208 |
| ACC AGC TTC AAG GAC TGC ATC CCG CGC TCC TTC CGC CGG CAT ATC CGG | 978 |
| Thr Ser Phe Lys Asp Cys Ile Pro Arg Ser Phe Arg Arg His Ile Arg | 224 |
| CAG CAC AGC GCC CTG ACC CGG CTG CGC CTT CGG AAC GTC TTC CGC AGG | 1026 |
| Gln His Ser Ala Leu Thr Arg Leu Arg Leu Arg Asn Val Phe Arg Arg | 240 |
| TTC CTG CGG GAC TTC CAG CCG GGC CGA CTC TCC CAG CAG ATG GTC ATG | 1074 |
| Phe Leu Arg Asp Phe Gln Pro Gly Arg Leu Ser Gln Gln Met Val Met | 256 |
| GTC AAA TAC CTA GCC ACA CTC GAG CGG CTG GCA CCC CGC TTC GGC ACA | 1122 |
| Val Lys Tyr Leu Ala Thr Leu Glu Arg Leu Ala Pro Arg Phe Gly Thr | 272 |

FIG.3A

```
GAG CGT GTG CCC GTG TGC CAC CTG AGG CTG CTG GCC CAG GCC GAG GGG      1170
Glu Arg Val Pro Val Cys His Leu Arg Leu Leu Ala Gln Ala Glu Gly       288

GAG CCC TGC TAC ATC CGG GAC AGT GGG GTG GCC CCT ACA GAC CCT GGC      1218
Glu Pro Cys Tyr Ile Arg Asp Ser Gly Val Ala Pro Thr Asp Pro Gly       304

CCT GAG TCT GCT GCT GGG CCC CCA ACC CAC GAG GTG CTG GTG ACA GGC      1266
Pro Glu Ser Ala Ala Gly Pro Pro Thr His Glu Val Leu Val Thr Gly       320

ACT GGT GGC ATC CAG TGG TGG CCA GTA GAG GAG GAG GTG AAC AAG GAG      1314
Thr Gly Gly Ile Gln Trp Trp Pro Val Glu Glu Glu Val Asn Lys Glu       336

GAG GGT TCT AGT GGC AGC AGT GGC AGG AAC CCC CAA GCC AGC CTG TTT      1362
Glu Gly Ser Ser Gly Ser Ser Gly Arg Asn Pro Gln Ala Ser Leu Phe       352

GGG AAG AAG GCC AAG GCT CAC AAG GCA TTC GGC CAG CCG GCA GAC AGG      1410
Gly Lys Lys Ala Lys Ala His Lys Ala Phe Gly Gln Pro Ala Asp Arg       368

CCG CGG GAG CCA CTG TGG GCC TAC TTC TGT GAC TTC CGG GAC ATC ACC      1458
Pro Arg Glu Pro Leu Trp Ala Tyr Phe Cys Asp Phe Arg Asp Ile Thr       384

CAC GTG GTG CTG AAA GAG CAC TGT GTC AGC ATC CGG CAG GAC AAC          1506
His Val Val Leu Lys Glu His Cys Val Ser Ile His Arg Gln Asp Asn       400

AAG TGC CTG GAG CTG AGC TTG CCT TCC CGG GCT GCG GCG CTG TCC TTC      1554
Lys Cys Leu Glu Leu Ser Leu Pro Ser Arg Ala Ala Ala Leu Ser Phe       416

GTG TCG CTG GTG GAC GGC TAT TTC CGC CTG ACG GCC GAC TCC AGC CAC      1602
Val Ser Leu Val Asp Gly Tyr Phe Arg Leu Thr Ala Asp Ser Ser His       432

TAC CTG TGC CAC GAG GTG GCT CCC CCA CGG CTG GTG ATG AGC ATC CGG      1650
Tyr Leu Cys His Glu Val Ala Pro Pro Arg Leu Val Met Ser Ile Arg       448

GAT GGG ATC CAC GGA CCC CTG CTG GAG CCA TTT GTG CAG GCC AAG CTG      1698
Asp Gly Ile His Gly Pro Leu Leu Glu Pro Phe Val Gln Ala Lys Leu       464

CGG CCC GAG GAC GGC CTG TAC CTC ATT CAC TGG AGC ACC AGC CAC CCC      1746
Arg Pro Glu Asp Gly Leu Tyr Leu Ile His Trp Ser Thr Ser His Pro       480

TAC CGC CTG ATC CTC ACA GTG GCC CAG CGT AGC CAG GCA CCA GAC GGC      1794
Tyr Arg Leu Ile Leu Thr Val Ala Gln Arg Ser Gln Ala Pro Asp Gly       496

ATG CAG AGC TTG CGG CTC CGA AAG TTC CCC ATT GAG CAG CAG GAC GGG      1842
Met Gln Ser Leu Arg Leu Arg Lys Phe Pro Ile Glu Gln Gln Asp Gly       512

GCC TTC GTG CTG GAG GGC TGG GGC CGG TCC TTC CCC AGC GTT CGG GAA      1890
Ala Phe Val Leu Glu Gly Trp Gly Arg Ser Phe Pro Ser Val Arg Glu       528

CTT GGG GCT GCC TTG CAG GGC TGC TTG CTG AGG GCC GGG GAT GAC TGC      1938
Leu Gly Ala Ala Leu Gln Gly Cys Leu Leu Arg Ala Gly Asp Asp Cys       544

TTC TCT CTG CGT CGC TGT TGC CTG CCC CAA CCA GGA GAA ACC TCC AAT      1986
Phe Ser Leu Arg Arg Cys Cys Leu Pro Gln Pro Gly Glu Thr Ser Asn       560
```

FIG.3B

| | |
|---|---|
| CTC ATC ATC ATG CGG GGG GCT CGG GCC AGC CCC AGG ACA CTC AAC CTC<br>Leu Ile Ile Met Arg Gly Ala Arg Ala Ser Pro Arg Thr Leu Asn Leu | 2034<br>576 |
| AGC CAG CTC AGC TTC CAC CGG GTT GAC CAG AAG GAG ATC ACC CAG CTG<br>Ser Gln Leu Ser Phe His Arg Val Asp Gln Lys Glu Ile Thr Gln Leu | 2082<br>592 |
| TCC CAC TTG GGC CAG GGC ACA AGG ACC AAC GTG TAT GAG GGC CGC CTG<br>Ser His Leu Gly Gln Gly Thr Arg Thr Asn Val Tyr Glu Gly Arg Leu | 2130<br>608 |
| CGA GTG GAG GGC AGC GGG GAC CCT GAG GAG GGC AAG ATG GAT GAC GAG<br>Arg Val Glu Gly Ser Gly Asp Pro Glu Glu Gly Lys Met Asp Asp Glu | 2178<br>624 |
| GAC CCC CTC GTG CCT GGC AGG GAC CGT GGG CAG GAG CTA CGA GTG GTG<br>Asp Pro Leu Val Pro Gly Arg Asp Arg Gly Gln Glu Leu Arg Val Val | 2226<br>640 |
| CTC AAA GTG CTG GAC CCT AGT CAC CAT GAC ATC GCC CTG GCC TTC TAC<br>Leu Lys Val Leu Asp Pro Ser His His Asp Ile Ala Leu Ala Phe Tyr | 2274<br>656 |
| GAG ACA GCC AGC CTC ATG AGC CAG GTC TCC CAC ACG CAC CTG GCC TTC<br>Glu Thr Ala Ser Leu Met Ser Gln Val Ser His Thr His Leu Ala Phe | 2322<br>672 |
| GTG CAT GGC GTC TGT GTG CGC GGC CCT GAA AAT AGC ATG GTG ACA GAG<br>Val His Gly Val Cys Val Arg Gly Pro Glu Asn Ser Met Val Thr Glu | 2370<br>688 |
| TAC GTG GAG CAC GGA CCC CTG GAT GTG TGG CTG CGG AGG GAG CGG GGC<br>Tyr Val Glu His Gly Pro Leu Asp Val Trp Leu Arg Arg Glu Arg Gly | 2418<br>704 |
| CAT GTG CCC ATG GCT TGG AAG ATG GTG GTG GCC CAG CAG CTG GCC AGC<br>His Val Pro Met Ala Trp Lys Met Val Val Ala Gln Gln Leu Ala Ser | 2466<br>720 |
| GCC CTC AGC TAC CTG GAG AAC AAG AAC CTG GTT CAT GGT AAT GTG TGT<br>Ala Leu Ser Tyr Leu Glu Asn Lys Asn Leu Val His Gly Asn Val Cys | 2514<br>736 |
| GGC CGG AAC ATC CTG CTG GCC CGG CTG GGG TTG GCA GAG GGC ACC AGC<br>Gly Arg Asn Ile Leu Leu Ala Arg Leu Gly Leu Ala Glu Gly Thr Ser | 2562<br>752 |
| CCC TTC ATC AAG CTG AGT GAT CCT GGC GTG GGC CTG GGC GCC CTC TCC<br>Pro Phe Ile Lys Leu Ser Asp Pro Gly Val Gly Leu Gly Ala Leu Ser | 2610<br>768 |
| AGG GAG GAG CGG GTG GAG AGG ATC CCC TGG CTG GCC CCC GAA TGC CTA<br>Arg Glu Glu Arg Val Glu Arg Ile Pro Trp Leu Ala Pro Glu Cys Leu | 2658<br>784 |
| CCA GGT GGG GCC AAC AGC CTA AGC ACC GCC ATG GAC AAG TGG GGG TTT<br>Pro Gly Gly Ala Asn Ser Leu Ser Thr Ala Met Asp Lys Trp Gly Phe | 2706<br>800 |
| GGC GCC ACC CTC CTG GAG ATC TGC TTT GAC GGA GAG GCC CCT CTG CAG<br>Gly Ala Thr Leu Leu Glu Ile Cys Phe Asp Gly Glu Ala Pro Leu Gln | 2754<br>816 |
| AGC CGC AGT CCC TCC GAG AAG GAG CAT TTC TAC CAG AGG CAG CAC CGG<br>Ser Arg Ser Pro Ser Glu Lys Glu His Phe Tyr Gln Arg Gln His Arg | 2802<br>832 |
| CTG CCC GAG CCC TCC TGC CCA CAG CTG GCC ACA CTC ACC AGC CAG TGT<br>Leu Pro Glu Pro Ser Cys Pro Gln Leu Ala Thr Leu Thr Ser Gln Cys | 2850<br>848 |

FIG.3C

```
CTG ACC TAT GAG CCA ACC CAG AGG CCA TCA TTC CGC ACC ATC CTG CGT     2898
Leu Thr Tyr Glu Pro Thr Gln Arg Pro Ser Phe Arg Thr Ile Leu Arg      864

GAC CTC ACC CGC GTG CAG CCC CAC AAT CTT GCT GAC GTC TTG ACT GTG     2946
Asp Leu Thr Arg Val Gln Pro His Asn Leu Ala Asp Val Leu Thr Val      880

AAC CGG GAC TCA CCG GCC GTC GGA CCT ACT ACT TTC CAC AAG CGC TAT     2994
Asn Arg Asp Ser Pro Ala Val Gly Pro Thr Thr Phe His Lys Arg Tyr      896

TTG AAA AAG ATC CGA GAT CTG GGC GAG GGT CAC TTC GGC AAG GTC AGC     3042
Leu Lys Lys Ile Arg Asp Leu Gly Glu Gly His Phe Gly Lys Val Ser      912

TTG TAC TGC TAC GAT CCG ACC AAC GAC GGC ACT GGC GAG ATG GTG GCG     3090
Leu Tyr Cys Tyr Asp Pro Thr Asn Asp Gly Thr Gly Glu Met Val Ala      928

GTG AAA GCC CTC AAG GCA GAC TGC GGC CCC CAG CAC CGC TCG GGC TGG     3138
Val Lys Ala Leu Lys Ala Asp Cys Gly Pro Gln His Arg Ser Gly Trp      944

AAG CAG GAG ATT GAC ATT CTG CGC ACG CTC TAC CAC GAG CAC ATC ATC     3186
Lys Gln Glu Ile Asp Ile Leu Arg Thr Leu Tyr His Glu His Ile Ile      960

AAG TAC AAG GGC TGC TGC GAG GAC CAA GGC GAG AAG TCG CTG CAG CTG     3234
Lys Tyr Lys Gly Cys Cys Glu Asp Gln Gly Glu Lys Ser Leu Gln Leu      976

GTC ATG GAG TAC GTG CCC CTG GGC AGC CTC CGA GAC TAC CTG CCC CGG     3282
Val Met Glu Tyr Val Pro Leu Gly Ser Leu Arg Asp Tyr Leu Pro Arg      992

CAC AGC ATC GGG CTG GCC CAG CTG CTC TTC GCC CAG CAG ATC TGC         3330
His Ser Ile Gly Leu Ala Gln Leu Leu Leu Phe Ala Gln Gln Ile Cys     1008

GAG GGC ATG GCC TAT CTG CAC GCG CAC GAC TAC ATC CAC CGA GAC CTA     3378
Glu Gly Met Ala Tyr Leu His Ala His Asp Tyr Ile His Arg Asp Leu     1024

GCC GCG CGC AAC GTG CTG CTG GAC AAC GAC AGG CTG GTC AAG ATC GGG     3426
Ala Ala Arg Asn Val Leu Leu Asp Asn Asp Arg Leu Val Lys Ile Gly     1040

GAC TTT GGC CTA GCC AAG GCC GTG CCC GAA GGC CAC GAG TAC TAC CGC     3474
Asp Phe Gly Leu Ala Lys Ala Val Pro Glu Gly His Glu Tyr Tyr Arg     1056

GTG CGC GAG GAT GGG GAC AGC CCC GTG TTC TGG TAT GCC CCA GAG TGC     3522
Val Arg Glu Asp Gly Asp Ser Pro Val Phe Trp Tyr Ala Pro Glu Cys     1072

CTG AAG GAG TAT AAG TTC TAC TAT GCG TCA GAT GTC TGG TCC TTC GGG     3570
Leu Lys Glu Tyr Lys Phe Tyr Tyr Ala Ser Asp Val Trp Ser Phe Gly     1088

GTG ACC CTG TAT GAG CTG CTG ACG CAC TGT GAC TCC AGC CAG AGC CCC     3618
Val Thr Leu Tyr Glu Leu Leu Thr His Cys Asp Ser Ser Gln Ser Pro     1104

CCC ACG AAA TTC CTT GAG CTC ATA GGC ATT GCT CAG GGT CAG ATG ACA     3666
Pro Thr Lys Phe Leu Glu Leu Ile Gly Ile Ala Gln Gly Gln Met Thr     1120

GTT CTG AGA CTC ACT GAG TTG CTG GAA CGA GGG GAG AGG CTG CCA CGG     3714
Val Leu Arg Leu Thr Glu Leu Leu Glu Arg Gly Glu Arg Leu Pro Arg     1136
```

FIG.3D

| | |
|---|---|
| CCC GAC AAA TGT CCC TGT GAG GTC TAT CAT CTC ATG AAG AAC TGC TGG | 3762 |
| Pro Asp Lys Cys Pro Cys Glu Val Tyr His Leu Met Lys Asn Cys Trp | 1152 |
| | |
| GAG ACA GAG GCG TCC TTT CGC CCA ACC TTC GAG AAC CTC ATA CCC ATT | 3810 |
| Glu Thr Glu Ala Ser Phe Arg Pro Thr Phe Glu Asn Leu Ile Pro Ile | 1168 |
| | |
| CTG AAG ACA GTC CAT GAG AAG TAC CAA GGC CAG GCC CCT TCA GTG TTC | 3858 |
| Leu Lys Thr Val His Glu Lys Tyr Gln Gly Gln Ala Pro Ser Val Phe | 1184 |
| | |
| AGC GTG TGC | 3867 |
| Ser Val Cys | 1187 |

FIG.3E

```
pileup.msf(Jak1)   ..MQYLNIKE   DCNAMAFCAK   MRSFKKTEVK   QVVP.EPGVE   VTFYLLDREP
pileup.msf(Tyk2)   MPLRHWGMAR   GSKPVG....   .......DGAQ  PMAA.MGGLK   VLLHWAGPGG
pileup.msf(Jak2)   MGMACLTMTE   MEATSTSPVH   QNGDIPGSAN   SVKQIEPVLQ   VYLYHSLGQA
       Consensus   M-M--L-M-E   ----------   ----------   -V---EPGL-   V-LY------ pileup.msf(Jak1)   ....LRLGSG   EYTAEELCIR   AAQECSISPL   CHNLFALYDE   STKLWYAPNR
pileup.msf(Tyk2)   GEPWTFSES    SLTAEEVCIH   IAHKVGITPP   CFNLFALFDA   QAQVWLPPNH
pileup.msf(Jak2)   EGEYLKFPSG   EYVAEEICVA   ASKACGITPV   YHNMFALMSE   TERIWYPPNH
       Consensus   ----L-FSG    EYTAEE-CI-   AA--CGITP-   CHNLFAL-DE   ----WYPPNH pileup.mfs(Jak1)   IITVDDKTSL   RLHYRMRFYF   TNWHGTNDNE   QSVWRHSPKK   QKNGYEKKRV
pileup.msf(Tyk2)   ILEIPRDASL   MLYFRIRFYF   RNWHGMNPRE   PAVYRCGPPG   TEASSD..QT
pileup.msf(Jak2)   VFHIDESTRH   DILYRIRFYF   PHWY......   ......CSGSS  RTYRYGVSRG
       Consensus   I--ID--TSL   -L-YRIRFYF   -NWHG-N--E   --V-RCSP--   ----Y---R- pileup.msf(Jak1)   PEATPLLDAS   SLEYLFAQGQ   YDLIKFLAPI   RDPKTEQDGH   DIENECLGMA
pileup.msf(Tyk2)   AQGMQLLDPA   SFEYLFEQGK   HEFVNDVASL   WELSTEEEIH   HFKNESLGMA
pileup.msf(Jak2)   AEA.PLLDDF   VMSYLFAQWR   HDFVHGWIKV   .......PVTH  ETQEECLGMA
       Consensus   AEA-PLLD--   S-EYLFAQG-   HDFV---A--   ----TE---H   ---NECLGMA pileup.msf(Jak1)   VLAISHYAMM   KKMQLPELPK   DISYKRYIPE   TLNKSIRQRN   LLTRMRINNV
pileup.msf(Tyk2)   FLHLCHLALR   HGIPLEEVAK   KTSFKDCIPR   SFRRHIRQHS   ALTRLRLRNV
pileup.msf(Jak2)   VLDMMRIAKE   KDQTPLAVYN   SVSYKTFLPK   CVRAKIQDYH   ILTRKRIRYR
       Consensus   VL---H-A--   K--L-EV-K    --SYK--IP-   -R--IRQ--    -LTR-RIRNV
```

FIG. 5A

```
pileup.msf(Jak1)    FKDFLKEFNN   KTICDSSVST   HDLKVKYLAT   LETLTKHYGA   EIFETSMLLI
pileup.msf(Tyk2)    FRRFLRDFQ.   ...PGRLSQ    QWMVKYLAT    LERLAPRFGT   ERVPVCHLRL
pileup.msf(Jak2)    FRRFIQQF..   ...SQCKATA   RNLKLKYLIN   LETLQSAFYT   EQFEV.....
       Consensus    FRRFL--F--   -------S--   --LKVKYLAT   LETL---FGT   E-FEV--L-- pileup.msf(Jak1)    SSENELSRCH   SNDS......   .......GNV   LYEVMVTGNL   GIQWRQXPNV
pileup.msf(Tyk2)    LAQAEGEPCY   IRDSGVAPTD   PGPESAAGPP   THEVLVTGTG   GIQWPVEEE
pileup.msf(Jak2)    ..........   ...KE.....   SARGPSQEEI   FATIIITGNG   GIQWS.....
       Consensus    ----E----C   ---DS-----   -------G--   --EV-VTGNG   GIQWS----- pileup.msf(Jak1)    VPVEKE....   ....KNKLK    RKKLEYNKHK   KDDERNKLRE   EWNNFSYFPE
pileup.msf(Tyk2)    VNKEEGSSGS   SGRNPQASLF   GKKAKAHKAF   GQPADRPREP   LWAYFCDFRD
pileup.msf(Jak2)    ..........   ..........   .....RGK     HKESETLTEQ   DVQLYCDFPD
       Consensus    V--E------   --------L-   -KK----K-K   ------E---   -W--FCDFPD pileup.msf(Jak1)    ITHIVIKE..   .......SVV   SINKQDNKNM   ELKLSSREEA   LSFVSLVDGY
pileup.msf(Tyk2)    ITHVVLKE..   .......HCV   SIHRQDNKCL   ELSLPSRAAA   LSFVSLVDGY
pileup.msf(Jak2)    IIDVSIKQAN   QECSNESRIV   TVHKQDGKVL   EIELSSLKEA   LSFVSLIDGY
       Consensus    ITHVVIKE--   --------V   SIHKQDNK-L   EL-LSSR-EA   LSFVSLVDGY pileup.msf(Jak1)    FRLTADAHHY   LCTDVAPPLI   VHNIQNGCHG   PICTEYAINK   LRQEGSEEGM
pileup.msf(Tyk2)    FRLTADSSHY   LCHEVAPPRL   VMSIRDGIHG   PLLEPFVQAK   LR...PEDGL
pileup.msf(Jak2)    YRLTADAHHY   LCKEVAPPAV   LENIHSNCHG   PTSMDFAISK   LKKAGNQTGL
       Consensus    FRLTADAHHY   LC-EVAPP--   V-NI--GCHG   PI---FAI-L   LR-G-E-GL
```

FIG.5B

```
pileup.msf(Jak1)   YVLRWSCTDF   DNILMTVTCG   EKSEVLGGQK   ..QFNFQIE   VQKFRYSLHG
pileup.msf(Tyk2)   YLIHWSTSHP   YRLILTVA..   QRSQAPDGMQ   SLRLRKFPIE   QQDGAFVLEG
pileup.msf(Jak2)   YVLRCSPKDF   NKYFLTFA.V   ERENVIEYKH   CLITKN....   .ENGEYNLSG
Consensus          YVLRWS--DF   ----LTVA--   ERS-V--G--   -L--KNF-IE   -Q-G-Y-L-G pileup.msf(Jak1)   SMDHFPSLRD   LMNHLKKQIL   RTDNISFVLK   RCCQPKPREI   SNLLV.....
pileup.msf(Tyk2)   WGRSFPSVRE   LGAALQGCLL   RAGDDCFSLR   RCCLPQPGET   SNLIT.....
pileup.msf(Jak2)   TKRNFSNLKD   LLNCYQMETV   RSDSIIFQFT   KCCPPKPKDK   SNLLVFRTNG
Consensus          --R-FPSLRD   L-N-LQ---L   R-D-I-F-L-   RCC-PKP-E-   SNLLV----- pileup.msf(Jak1)   ..ATKKAQEW   QPVYSMSQLS   FDRILKKDII   QGEHLGRGTR   THIYSGTLL.
pileup.msf(Tyk2)   ...MRGARAS   PRTLNLSQLS   FHRVDQKEIT   QLSHLGQGTR   TNVYEGRLRV
pileup.msf(Jak2)   ISDVQISPTL   QRHNNVNQMV   FHKIRNEDLI   FNESLGQGTF   TKIFKGVRRE
Consensus          -------A--   QR--N-SQLS   FHRI--KDII   Q-EHLGQGTR   T-IY-G-LRpileup.msf(Jak1)   .........D   YKDEEGIAEE   K....KIKVI   LKVLDPSHRD   ISLAFFEAAS
pileup.msf(Tyk2)   EGSGDPEEGK   MDDEDPLVPG   RDRGQELRVV   LKVLDPSHHD   IALAFYETAS
pileup.msf(Jak2)   ..........   ......VGD   YGQLHKTEVL   LKVLDKAHRN   YSESFFEAAS
Consensus          -------A--   --DE----V-   -----K--V-   LKVLDPSHRD   ISLAFFEAAS pileup.msf(Jak1)   MMRQVSHKHI   VYLYGVCVRD   VENIMWEEFV   EGGPLDLFMH   RKSDALTTPW
pileup.msf(Tyk2)   LMSQVSHTHL   AFVHGVCVRG   PENIMVTEYV   EHGPLDVWLR   RERGHVPMAW
pileup.msf(Jak2)   MMSQLSHKHL   VLNYGVCVCG   EENILVQEFV   KFGSLDTYLK   KNKNSINILW
Consensus          MMSQVSHKHL   V--YGVCVRG   -ENIMV-EFV   E-GPLD--L-   R-------W

FIG.5C
```

```
pileup.msf(Jak1)    KFKVAKQLAS    ALSYLEDKDL    VHGNVCTKNL    LLAR.EGIDS    DIGPFIKSLD
pileup.msf(Tykw)    KMVVAQQLAS    ALSYLENKNL    VHGNVCGRNI    LLAR.LGLAE    GTSPFIKLSD
pileup.msf(Jak2)    KLGVAKQLAW    AMHFLEEKSL    IHGNVCAKNI    LLIREEDRRT    GNPPFIKLSD
Consensus           K--VAKQLAS    ALSYLE-L-L    VHGNVC-KNI    LLAR-EG---    G--PFIKLSD pileup.msf(Jak1)    PGIPVSVLTR    QECIERIPWI    APECVEDSKN    .LSVAADKWS    FGTTLWEICY
pileuplmsf(Tyk2)    PGVGLGALSR    EERVERIPWL    APECLPGGAN    SLSTAMDKWG    FGATLLEICF
pileup.msf(Jak2)    PGISITVLPK    DILQERIPWV    PPECIENPKN    .LNLATDKWS    FGTTLWEICS
Consensus           PGI---VL-R    -E--ERIPW-    APEC-E--KN    -LS-A-DKWS    FGTTLWEICpileup.msf(Jak1)    NGEIPLKDKT    LIEKERFYES    RCRPVTPSCK    ELADLMTRCM    NYDPNQRPFF
pileup.msf(Tyk2)    DGEAPLQSRS    PSEKEHFYQR    APECLPGGAN    QLATLTSQCL    FGATLLEICF
pileup.msf(Jak2)    GGDKPLSALD    SQRKLQFYED    KHQLPAPKWT    ELANLINNCM    FGTTLWEICS
Consensus           -GE-PL----    --EKE-FYE-    --HRLP-PSC-   ELA-L---CM    -YEP-QRP-F pileup.msf(Jak1)    RAIMRDINKL    ..........E   EQN.PDI...    .VSEKQPTTE    VDPTHFEKRF
pileup.msf(Tyk2)    RTILRDLTRL    ..........Q   PHNLADV...    .LTVNPDSPA    SDPTVFHKRY
pileup.msf(Jak2)    RAVIRDLNSL    FTPDYELLTE    NDMLPNMRIG    ALGFSGAFED    RDPTQFEERH
Consensus           RAI-RDLN-L    ----------E   --NLPD----    -L--------   -DPT-FEKRpileup.msf(Jak1)    LKKRIRDLGEG   HFGKVELCRY    DPECDNTGEQ    VAVKSLKPES    GGNHIADLKK
pileup.msf(Tyk2)    LKKIRDLGEG    HFGKVSLYCY    DPTNDGTGEM    VAVKALKADC    GPQHRSGWKQ
pileup.msf(Jak2)    LKFLQQLGKG    NFGSVEMCRY    DPLQDNTGEV    VAVKKLQ.HS    TEEHLRDFER
Consensus           LK-IRDLGEG    HFGKVELCRY    DP--DNTGE-    VAVK-LK--S    G--H--D-K-
```

FIG. 5D

```
pileup.msf(Jak1)   EIEILRNLYH   ENIVKYKGIC   MEDGGNGIKL   IMEFLPSGSL   KEYLPKNKNK
pileup.msf(Tyk2)   EIDILRTLYH   EHIIKYKGCC   EDQGEKSLQL   VMEYVPLGSL   RDYLP..RHS
pileup.msf(Jak2)   EIEILKSLQH   DNVKYKGVCQ   YSAGRRNLRL   IMEYLPYGSL   RDYLQKHKER
       Consensus   EIEILR-LYH   ENIVKYKG-C   ---G---L-L   IMEYLP-GSL   RDYLPK-K-- pileup.msf(Jak1)   INLKQQLKYA   IQICKGMDYL   GSRQYVHRDL   AARNVLVESE   HQVKIGDFGL
pileup.msf(Tyk2)   IGLAQLLLFA   QQICECMAYL   HAQHYIHRDL   AARNVLLDND   RLVKIGDFGL
pileup.msf(Jak2)   IDHKKLLQYT   SQICKGMEYL   GTKRYIHRDL   ATRNILVENE   NRVKIGDFGL
       Consensus   I-LKQLL-YA   -QICKGM-YL   G---YIHRDL   AARNVLVENE   --VKIGDFGL pileup.msf(Jak1)   TKAIETDKEY   YTVKDDRDSP   VFWYAPECLI   QCKFYIASDV   WSFGVTLHEL
pileup.msf(Tyk2)   AKAVPEGHEY   YRVREDGDSP   VFWYAPECLK   EYKFYYASDV   WSFGVTLYEL
pileup.msf(Jak2)   TKVLPQDKEY   YKVKEPGESP   IFWYAPESLT   ESKFSVASDV   WSFGVVLYEL
       Consensus   TAK-P-DKEY   Y--VKEDGDSP  VFWYAPECL-   ESKFSVASDV   WSFGVVLYEL pileup.msf(Jak1)   LTYCDSDFSP   MALFLKMIGP   T.HGQMTVTR   LVNTLKEGKR   LPCPPNCPDE
pileup.msf(Tyk2)   LTHCDSSQSP   PTKFLELIGI   A.QGQMTVLR   LTELLERGER   LPRPDKCPCE
pileup.msf(Jak2)   FTYIEKSKSP   PVEFMRMIGN   DKQGQMIVFH   LIELLSKNGR   LPRPEGCPDE
       Consensus   LTYCDSS-SP   P--FL-MIG-   --QGQMTV-R   L-ELLK-G-R   LPRP--CPDE pileup.msf(Jak1)   VYQLMRKCWE   FQPSNRTTFQ   NLIEGFEALL   K.........   FSVC*
pileup.msf(Tyk2)   VYHLMKNCWE   TEASFRPTFE   NLIPILKTVH   EKYQGQAPSV   .....
pileup.msf(Jak2)   IYVIMTECWN   NNVSQRPSFR   DLSFGWIKSG   TVI.......   -----
       Consensus   VY-LM--CWE   ---S-RPTF-   NLI-G-----   ----------   -----
```

```
            1                11               21               31               41               51               61               71               81               91
JAK3    M...............APPSEETPLIPQRSCSLSSSEAGALHVLLPPRGPGPPQRLSFSFGDYLAEDLCVRAAKACGILPVYHSLFALATEDFSCWFPPSH
JAK2    MGMACLTMTEMEATSTSPVHQNGDIPGSANSVKQIEPVLQVYLYHSLGQAEGEYLKFPSGEYVAEEICVAASKACGITPVYHNMFALMSETERIWYPPNH
JAK1    MQYLNIKEDCNAMAFCAKMRSFKKTEVKQVVPEP..GVEVTFYLLDR...EP..LRLGSGEYTAEELCIRAAQECSISPLCHNLFALYDESTKLWYAPNR
TYK2    MPLRHW.........GMARGSKPVGDGAQPMAAMGGLKVLLHWAGPGGGEP.WVTFSESSLTAEEVCIHIAHKVGITPPCFNLFALFDAQAQVWLPPNH
CON     M.......................G..EP..L.F..G.Y.AEE.C..AA..CGI.P..HNLFAL..E...W.PPNH 101              111              121              131              141              151              161              171              181              191
JAK3    IFCIEDVDTQVLVYRLRFYFPDWF.............GLETCHRFGLRKDLTS..AILDLHVLEHLFAQHRSDLVSGRLPV.......GLSMKEQGEFLSLA
JAK2    VFHIDESTRHDILYRIRFYFPHWY..........CSGSSRTYRGVSRGAEA.PLLDDFVMSYLFAQMRHDFVHGWIKV......PVTHETQEECLGMA
JAK1    IITVDDKTSLRLHYRMRFYFTNWHGTNDNEQSVWRHSPKKQNGYEKKRVPEATPLLDASSLEYLFAQGQYDLIKFLAPIRDPKTEQDGHDIENECLGMA
TYK2    ILEIPRDASLMLYFRIRFYFRNWHGMNPREPAVYRCGPPGTEASSDQT..AQGMQLLDPASFEYLFEQGKHEFVNDVASLWELSTEEIHHFKNESLGMA
CON     I..I......L.YR.RFYF..W.........................LLD.....EYLFAQ...D.V..........H...E.LGMA 201              211              221              231              241              251              261              271              281              291
JAK3    VLDLAQMAREQAQRPGELLKTVSYKACLPPSLRDVIQGQNFVTRRRIR...RTVVLALLP...CGRLPGRPYALMAKYILDLERLHPAATTETFRV......
JAK2    VLDMMRIAKEKDQTPLAVYNSVSYKTFLPKCVRAKIQDYHILTRKRIRYRFRRF IQQFSQ..CKATARN...LKLKYLINLETLQSAFYTEQFEV......
JAK1    VLAISHYAMMKKMQLPELPKDISYKRYIPETLNKSIRQRNLLTRMRINNVFKDFLKEFNNKTICDSSVSTH.DLKVKYLATLETLTKHYGAEIFETS..M
TYK2    FLHLCHLALRHGIPLEEVAKKTSFKDCIPRSFRRHIRQHSALTRLRLRNVFRRFLRDFQP......GRLSQQ.MVMVKYLATLERLAPRFGTERVPVCHLR
CON     VL.........A......E..K.SYK...P..R.I....LTR.RIR...F...C..........L..KYL..LE.L......TE.F.V......

301              311              321              331              341              351              361              371              381              391
JAK3    ...........GL....PGAQEEPGL....LRVAGDNGIPW....................................SS...ND.ELF.....QT...........FCDFP
JAK2    ............KESARGPSGEEIFAT....IIITGNGGIQW..........................SRGKHKESETLTEQDVQL...............YCDFP
JAK1    LLISSENELSRCHSND.........SGNVLYEVMVTGNLGIQWRQKPNVVPVEKEKN..........KLKRKKLEYNKHKKDDERNKLREE..WNNFSYFP
TYK2    LLAQAEGEPCYIRDSGVAPTDPGPESAAGPPTHEVLVTGTGGIQWMPVEEEVNKEEGSSGSGRNPQASLFGKKAKAHKAFGQPADRPREPLWAYFCDFR
CON     ....................................P......................................VTG.GGIQW..........................S.....................................FCDFP 401              411              421              431              441              451              461              471              481              491
JAK3    EIVDVSINQAPRVGPAGEHRLVTVTRMDGHILEAEFPGLPEALSFVALVDGYFRLICDSRHYFCKEVAPPRLLEEEADVCHGPITLDFAIHKLKAAGSLP
JAK2    DIDVSIKQANQ.ECSNESRIVTVHKQDDGKVLEIELSSLKEALSFVSLIDGYYRLTADAHHYLCKEVAPPAVLENIHSNCHGPISMDFAISKLKAGNQT
JAK1    EITHIVIKE........SVVSINKQDNKNMELKLSSREEALSFVSLVDGYFRLTADSSHYLCHEVAPPRLVMSIRDGIHGPLLEPFVQAKLR...PED
TYK2    DITHVLKE........HCVSIHRQDNKCLELSLPSRAAALSFVSLVDGYFRLTAD..K.LE..L.S..EALSFVSLDGYFRLTAD..HYLC.EVAPP......
CON     ..I.V.IK.............V....QD..K.LE...L.S..EALSFVSLDGYFRLTAD..HYLC.EVAPP.......I....CHGPI..FAI.KL...G...
```

FIG.6B

```
             901         911         921         931         941         951         961         971         981         991
JAK3   RRPSFRAILRDLNGLITSDYELLSDPTPGIPSPRDELCVAGAQLYACQDPAIFEERHLKYISLLGKGNFGSVELCRYDPLGDNTGPLVAVKQLQ.HSVPD
JAK2   FRPAFRAVIRDLNSLFTPDYELLTENDM.LPNMRIGALGF.SGAFEDRDPTQFEERHLKFLQQLGKGNFGSVEMCRYDPLQDNTGEVVAVKKLQ.HSTEE
JAK1   QRPFFRAIMRDINKLEEQN.PDIVSEKQP.........TTEVDPTHFEKRFLKRIRDLGEGHFGKVELCRYDPEGDNTGEQVAVKSLKPESGGN
TYK2   QRPSFRTILRDLTRVQPHNLADVLTVNRDSP........A.VGPTTFHKRYLKKIRDLGEGHFGKVSLYCYDPTNDGTGEMVAVKALKADCGPQ
CON    .RP.FRAI.RDLN.L..........P................PT.FE.R.LK.I..LG.G.FG.VELCRYDP..DNTGE.VAVK.L...S...

1001        1011        1021        1031        1041        1051        1061        1071        1081        1091
JAK3   QQRDFQREIQILKALHSDFIVKYRGVSYGPGRQSLRLVMEYLPSGCLRDLLQRHRG.LHTDRLLLFAWQICKGMEYLGARRCVHRDLAARNILVESEAHV
JAK2   HLRDFEREIEILKSLQHDNIVKYKGVCYSAGRRNLRLIMEYLPYGSLRDYLQKHKERIDHKKLLQYTSQICKGMEYLGTKRYIHRDLATRNILVENENRV
JAK1   HIADLKKEIEILRNLYHENIVKYKGICMEDGGNGIKLIMEFLPSGSLKEYLRNGKGSLRDYLPRHS...IGLAQLLLFAQQICEGMAYLHAHDYIHRDLAARNVLLDNDRLV
TYK2   HRSGWKQEIDILRTLYHEHIIKYKGCCEDGGEKSLQLVMEYVPLGSLRDYLPRHS...IGLAQLLLFAQQICEGMAYLHAHDYIHRDLAARNVLLDNDRLV
CON    H..D...EI.IL..L.H..IVKYKG.C....G....L.L.MEYLP.GSLRDYL.H...I....LL..A.QICKGM.YLG....Y.HRDLAARN.LVE.E..V 1101        1111        1121        1131        1141        1151        1161        1171        1181        1191
JAK3   KIADFGLAKILLPLGKDYYVVREPGQSPIFWYAPESLSDNIFSRQSDVWSFGVVLYELFTYCDKSCSPSAEFLRMMGPEREGPPLC.RLLELLAEGRRLPP
JAK2   KIGDFGLTKVLPQDKEYYKVKEPGESPIFWYAPESLTESKFSVASDVWSFGVVLYELFTYIEKSKSPPVEFMRMIGNDKQGQMIVFHLIELLKSNGRLPR
JAK1   KIGDFGLTKAIETDKEYYTVKDDRDSPVFWYAPECLIQCKFYIASDVWSFGVTLHELLTYCDSDSFPMALFLKMIGPT.HGQMTVRLVNTLKEGKRLPC
TYK2   KIGDFGLAKAVPEGHEYYRVREDGDSPVFWYAPECLKEYKFYYASDVWSFGVTLYELLTHCDSSQSPPTKFLELIGIA.QQQMTVLRLTELLERGERLPR
CON    KIGDFGL.K..P..KEYY.V.E.G.SP.FWYAPE.L...KF..ASDVWSFGV.LYEL.TYCD.S.SP...FL.MIG....GQM.V.RL.ELL..G.RLP.

1201        1211        1221        1231        1241
JAK3   PPTCPTEVQOELMQLCWAPEPHDRPAFATLSPQLDPLW.RG........RPG*
JAK2   PEGCPDEIYVIMTECWNNNVSQRPSFRDLSFG....WIKS.........GTV*
JAK1   PPNCPDEVYQLMRKCWEFQPSNRTITFQNLIEGFEALLK*
TYK2   PDKCPCEVYHLMKNCWETEASFRPTFENLIPILKTVHEKYQGQAPSVFSVC*
CON    P..CP.EVY.LM..CW....S.RP.F..L..........................

FIG.6C
```

JAK KINASES AND REGULATION OF CYTOKINE SIGNAL TRANSDUCTION

This application is a division of application Ser. No. 08/665,574, filed Jun. 18, 1996, which is a CIP of Ser. No. 08/097,997, filed Jul. 29, 1993, now U.S. Pat. No. 5,728,536.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds under Grant No. RO1 DK42932 from the National Institute of Diabetes and Digestive and Kidney Diseases; Grant No. P30 CA21765 from the National Cancer Institute Center Support (CORE); Grant No. RO1 DK42932 from the National Institute of Diabetes and Kidney Diseases; and Grant No. CA58223 from the National Cancer Institute Specialized Program of Research Excellence in Breast Cancer (SPORE) The U.S. Government has certain rights in this invention.

BACKGROUND OF THE INVENTION

1. Field of the Invention

The present invention relates generally to the Jak family of kinases and their role in the cellular response to the binding of cytokines to their respective receptors. The invention relates more specifically to the cytoki-induced activation of at least one member of a Jak kinase family, to the identification of interactions between specific cytokines and members of the Jak kinase family, and to compounds, compositions and methods relating to the regulation of this interaction.

2. Description of the Background Art

The growth, differentiation and function of eukaryotic cells is regulated in large part by extracellular factors, referred to generally as cytokines herein. These cytokines induce cellular responses by binding to their respective receptors. The receptors for cytokines fall into two major families, the cytokine receptor superfamily and the tyrosine kinase receptor superfamily.

Receptors belonging to the tyrosine kinase receptor superfamily are characterized by the presence of an identifiable cytoplasmic tyrosine kinase domain involved in the transduction of the cytokine-receptor binding signal. Members of this receptor family have been further classified into three structural subgroups (Yarden et al., *Ann. Rev. Biochem.* 57: 443–478 (1988). Members of the first subgroup are characterized as monomeric with two cysteine rich sequence repeat regions within their extracellular domains and include, e.g., the receptor for epidermal growth factor (EGF) and TGF-α (see, e.g., Ullrich et al., *Nature* 309: 418–425 (1984)). Members of the second subgroup are characterized as functioning as heterotetramers and include the receptors for insulin (Ullrich, supra, (1985); Ebina et al., *Cell* 40: 747–758 (1985)) and insulin-like growth factor-1 (IGF-1) (Ullrich et al., *EMBO J.* 5:2503–2512 (1986)). Members of the third subgroup are characterized by the presence of conserved repeat structures and the interruption of their catalytic domains by long (77–107 amino acids) insertion sequences. This third subgroup includes, e.g., receptors for platelet-derived growth factor (PDGF-R) (Yarden et al., *Nature* 323: 226–232 (1986)) and the colony stimulating growth factor (CSF-1) (Sherr et al., *Cell* 41: 665–676 (1985)).

Receptors belonging to the cytokine receptor superfamily are characterized by the presence of four positionally conserved cysteines and a WSXWS (SEQ ID No. 1) motif in the extracellular domain. The family is also characterized by variably sized cytoplasmic domains that show very limited sequence similarity and which do not contain identifiable motifs that might indicate the signal transducing mechanisms. Members of the cytokine receptor superfamily include the hematopoietic growth factor receptors, receptors for growth hormone, the prolactin receptor, ciliary neurotrophic factor and others (Bazan, *Science* 257:41014 413 (1992)). The receptors for interferon, although more distantly related, have been speculated to have evolved from a progenitor common to this receptor superfamily.

In spite of the lack of catalytic domains, considerable evidence suggests that signal transduction of members of the cytokine receptor superfamily involves tyrosine phosphorylation (Miyajima et al., *Annu. Rev. Immnunol.* 10:295–331 (1992); Metcalf, *Nature* 339:27–30 (1989)). There is also some evidence that members of this receptor superfamily may utilize common tyrosine phosphorylation pathways for signal transduction. Specifically, binding of hematopoietic growth factors to their respective receptors have been found to induce comparable patterns of tyrosine phosphorylation (Ihle, in *Interleukins: Molecular Biology and Immunology*, Kishimoto, ed., Karger, Basel, pp. 65–106 (1992)).

While it is widely appreciated that cytokine receptors from both families described above play a key role in cellular growth regulation, little is known about the biochemical cascades triggered by the binding of cytokines to these receptors. An understanding of the steps involved in the transduction of the cytokine signal through these receptors would be useful for identifying molecules which play a critical role in signal transduction and which can serve as targets for regulating the activity of these cytokines.

A model for the study of receptor signal transduction has been developed for the erythropoietin receptor (EPOR), one of the hematopoietic growth factor receptors and a member of the cytokine receptor superfamily. Introduction of the EPOR into interleukin-3 (IL-3) dependent cell lines confers on the cells the ability to proliferate in response to EPO (D'Andrea et al., *Cell* 57:277–285 (1989); Miura et al., *Mol. Cell Biol.* 11:4895–4902 (1991)). In transfected cells, EPO induces the expression of a series of immediate early genes including c-myc, c-fos, c-pim-1 and egr-1 (Miura et al., *Mol. Cell. Biol.* 13:1788–1795 (1993)). In addition, EPO induces the rapid tyrosine phosphorylation of a series of cellular substrates (Linnekin et al., *Proc. Natl. Acad. Sci. USA* 89:6237–6241 (1992); Dusanter-Fourt et al., *J. Biol. Chem.* 267:10670–10675 (1992); Quelle and Wojchowski, *J. Biol. Chem.* 266:609–614 (1991); Miura et al., *Mol. Cell Biol.* 11:4895–4902 (1991); Yoshimura and Lodish, *Mol. Cell. Biol.* 12:706–715 (1992); Damen et al., *Blood* 80:1923–1932 (1992)), suggesting that EPOR may function by coupling ligand binding to the activation of a protein tyrosine kinase.

Although the importance of protein tyrosine phosphorylation for biological activities associated with EPO-EPOR binding has been clearly demonstrated, very little has been known concerning the kinases that might be involved. The rapid induction of tyrosine phosphorylation of the carboxyl region of EPOR (Miura et al., *Mol. Cell Biol.* 11:4895–4902 (1991); Yoshimura and Lodish, *Mol. Cell. Biol.* 12:706–715 (1992); Dusanter-Fourt et al., *J. Biol. Chem.* 267:10670–10675 (1992)) suggests that the receptor is closely associated with a kinase, either constitutively or following ligand binding. One study Yoshimura and Lodish, *Mol. Cell. Biol.* 12:706–715 (1992)) identified a non-glycosylated protein of 130 kDa that could be cross-linked with the receptor and which was tyrosine phosphorylated either in vivo or in in vitro kinase assays as assessed by its ability to be detected by an anti-phosphotyrosine antibody. Whether the 130 kDa protein was a kinase could not be determined. Recent studies (Linnekin et al., *Proc. Natl. Acad. Sci. USA* 89:6237–6241 (1992)) also identified a 97 kDa substrate of tyrosine phosphorylation which could be radiolabeled with an azido derivative of ATP, suggesting that it was a kinase. Whether the 130 kDa or 97 Kda potential kinases are previously characterized kinases was not determined.

Tyrosine phosphorylation has also been observed in response to the cytokine interferon gamma (IFNγ). Recent studies (Shuai et al., *Science* 259:1808–1812 (1992)) have demonstrated that IFNγ induces tyrosine phosphorylation of a 91 kDa protein, and that this 91 kDa protein migrates to the nucleus and binds a γ-activated site.

Tyrosine phosphorylation has further been associated with the response to the cytokine growth hormone (GH). Studies in 3T3-F442A cells showing rapid GH-dependent tyrosyl phosphorylation of multiple proteins, tyrosyl phosphorylation of microtubule-associated protein kinases, and stimulation of microtubule-associated protein kinase activity, as well as the inhibition of these actions by inhibitors of growth hormone receptor (GHR)-associated tyrosine kinase (Campbell et al., *J. Biol. Chem.* 268:7427–7434 (1993)), suggest a central role for a GHR-associated tyrosine kinase activity in signaling by GH. In addition, the presence of a tyrosine kinase activity in a complex with GH receptor (GHR) prepared from GH-treated fibroblasts has been reported (Carter-Su. et al., *J. Biol. Chem.* 264:18654–18661 (1989); Stred et al., Endocrinol. 130: 1626–1636 (1992); Wang et al., *J. Biol. Chem.* 267: 17390–17396 (1992)). More recently, a nonreceptor tyrosyl phosphorylated 122 kd protein was identified in a kinase-active GH-GHR preparation (Wang et al., *J. Biol. Chem.* 268:3573–3579 (1993)).

To identify the spectrum of protein tyrosine kinases that are expressed in IL-3-dependent cells which might be involved in signal transduction, polymerase chain reactions (PCR) have been done with degenerative oligonucleotides to conserved protein tyrosine kinase domains (Wilks, *Methods Enzymol.* 200:533–546 (1991)). Using this approach and Northern blot analysis, IL-3 dependent cells have been shown to express the genes for a number of protein tyrosine kinases including lyn, Tec, c-fes, Jak1 and Jak2 (Mano et al., *Oncogene* 8:417–424 (1993)). Whether these tyrosine kinases, or other as yet unidentified tyrosine kinases, are involved in cytokine signal transduction is largely unknown.

The potential involvement of lyn kinase in signal transduction was indicated by a recent studies that indicated that IL-3 stimulation increased lyn kinase activity in immune precipitates (Torigoe et al., *Blood* 80:617–624 (1992)).

Two of the other tyrosine kinases expressed in IL-3-dependent cells, Jak1 and Jak2, belong to the Jak family of kinases. The Jak (Janus kinase; alternatively referred to as just another kinase) family of kinases were initially detected in PCR amplification of tyrosine kinase domains in hematopoietic cells (Wilks, *Proc. Natl. Acad. Sci. USA* 86:1603–1607 (1989)). These studies identified two closely related genes (FD17 and FD22; later termed Jak2 and Jak1) from which the major PCR amplification products were derived. The complete structure of the human Jak1 gene has been reported (Wilks et al., *Mol. Cell. Biol.* 11:2057–2065 (1991)) and, recently, a partial sequence of the murine Jak2 gene was published (Harpur et al., *Oncogene* 7:1347–1353 (1992)). Independently a third member of the family (Tyk2) was isolated by screening a cDNA library with a tyrosine kinase domain probe from the c-fms gene (Firmbach-Kraft et al., *Oncogene* 5:1329–1336 (1990)). The family is characterized by the presence of two kinase domains, one of which is a carboxyl domain that has all the hallmarks of protein kinases. The second domain is immediately amino terminal and bears all the hallmarks of a protein kinase but differs significantly from both the protein tyrosine and serine/threonine kinases. Amino terminal to the kinase domains, there are no SH2 and SH3 domains that characterize most of the non-receptor tyrosine kinases. However, there is extensive similarity in this region among the Jak family members and a number of homology domains have been defined (Harpur et al., *Oncogene* 7:1347–1353 (1992)).

A link between one member of the Jak family of kinases and the signal transduction of interferon alpha (IFNα) has been recently reported (Velazquez et al., *Cell* 70:313–322 (1992); Fu, *Cell* 70:323–335 (1992); Schindler et al., *Science* 257:809–813 (1992)). Using a genetic approach, the Tyk2 gene was cloned by its ability to functionally reconstitute the cellular response to IFNα in a mutant human cell line that was unresponsive to IFNα. No other link between Tyk2, or any other member of the Jak kinase family, and the signal transduction of any cytokine other than IFNα has been reported.

Ciliary neurotrophic factor (CNTF), as its name implies, is a protein that is specifically required for the survival of embryonic chick ciliary ganglion neurons in vitro (Manthorpe et al., *J. Neurochem.* 34:69–75 (1980)). CNTF has been cloned and synthesized in eukaryotic as well as bacterial expression systems, as described in International Application No. PCT/US90/05241, filed Sep. 14, 1990 by Sendtner et al., incorporated by reference in its entirety herein.

Over the past decade, a number of biological effects have been ascribed to CNTF in addition to its ability to support the survival of ciliary ganglion neurons. CNTF is believed to induce the differentiation of bipotential glial progenitor cells in the perinatal rat optic nerve and brain (Hughes et al., *Nature* 335:70–73 (1988)). Furthermore, it has been observed to promote the survival of embryonic chick dorsal root ganglion sensory neurons (Skaper and Varon, *Brain Res.* 389:39–46 (1986)).

Several novel activities of CNTF have also been discovered, including its ability to support the survival and differentiation of motor neurons and hippocampal neurons, and to increase the rate of hippocampal astrocyte proliferation (International Application No. PCT/US 90/05241, supra).

The CNTF receptor (CNTFR or CNTFRα) has been cloned and expressed in eukaryotic cells, as described in International Application No. PCT/US91/03896, filed Jun. 3, 1991, incorporated herein by reference in its entirety.

The sequence of CNTFR reveals that, unlike most receptors which contain an extracellular domain, a hydrophobic transmembrane domain, and a cytoplasmic domain, CNTFR does not appear to have a cytoplasmic domain. Additionally, the transmembrane hydrophobic domain is proteolytically processed, with the mature form of CNTFR becoming anchored to the cell surface by an unconventional linkage, referred to as a glycophosphatidyl inositol (GPI) linkage (Id.). GPI-linked proteins such as CNTFR may be released from the cell surface through cleavage of the GPI anchor by the enzyme phosphatidylinositol-specific phospholipase C. Of other known receptor sequences, CNTFR is related to a number of receptors, referred to herein as the CNTF/IL-6/

LIF receptor family, including IL-6, LIF, G-CSF and oncostatin M (OSM) (Bazan, *Neuron* 7:197–208 (1991); Rose and Bruce, *Proc. Natl. Acad. Sci.* 88:8641–8645, (1991)), but appears to be most closely related to the sequence of the receptor for IL-6. However, IL-6 has not been shown to be a GPI-linked protein (e.g., Taga et al., *Cell* 51:573–581 (1989); Hibi et al., *Cell* 63:1149–1157 (1989)).

The cloning, sequencing and expression of the CNTF receptor (CNTFR) led to the discovery that CNTFR and CNTF may for a complex that interacts with a membrane bound, signal transducing component, thus suggesting therapeutic activity of a soluble CNTF/CNTFR receptor complex.

One such signal transducing component involved in high affinity binding of CNTF and the subsequent functional response of the cell has been identified as gp130, a β component common to the IL-6, OSM, LIF family of receptors (Fukunaga et al., *EMBO J.* 10:2855–2865 (1991); Gearing et al., *EMBO J.* 10:2839–2848 (1991); Gearing et al., *Science* 255:1434–1437 (1992); Ip et al., *Cell* 69:1121–1132 (1991)). A further β component identified as being involved in binding and signal transduction in response to LIF (LIFRβ) appears to be the same or similar to a β component necessary for response to CNTF. (As a consequence of the identification of β components necessary for binding and signal transduction of CNTF, what was originally generally termed CNTFR is currently referred to as CNTFRα).

IL-6 is a pleiotropic cytokine which acts on a wide variety of cells, exerting growth promotion and inhibition and specific gene expression sometimes accompanied by cellular differentiation; it has been implicated as being involved in several diseases including inflammation, autoimmunities and lymphoid malignancies (Kishimoto et al., *Science* 258:593 (1992)). LIF, G-CSF and OSM are all broadly acting factors that, despite having unique growth-regulating activities, share several common actions with IL-6 during hemopoiesis as well as in other processes. For example, all can inhibit the proliferation and induce the differentiation of the murine myeloid leukemia cell line, M1 (Rose and Bruce, *Proc. Natl. Acad. Sci.* 88:8641–8645 (1991)). LIF and OSM induced tyrosine phosphorylations and gene activation in neuronal cells which are indistinguishable from responses induced by CNTF (Ip et al., *Cell* 69:1121–1132 (1992)).

Although the events surrounding CNTF binding and receptor activation have recently been elucidated (Davis et al., *Science* 253:59–63 (1991); Ip et al., *Cell* 69:1121–1132 (1992); Stahl et al., *Cell* 74:587–590 (1993); Davis et al., *Science* 260:1805–1018 (1993)), the mechanism by which signal transduction is initiated inside the cell is more poorly understood. Like the other distantly related receptors for the extended cytokine family—which includes Interleukin (IL)-3, IL-5, GM-CSF, G-CSF, EPO, GH, and the interferons ((Bazan, J. F., *Proc. Natl. Acad. Sci. USA* 87:6934–6938 (1990); Bazan, J. F., *Neuron* 7:197–208 (1991))—the CNTF receptor β subunits gp130 and LIFRβ do not have protein tyrosine kinase domains in their cytoplasmic regions (Hibi et al., *Cell* 63:1149–115 (1990); Gearing et al., *EMBO J.* 10:2839–2848 (1991)). In spite of this, CNTF-induced dimerization of the β subunits somehow result in the rapid accumulation of a set of tyrosine phosphorylated proteins called the CLIPs (Ip et al., *Cell* 69:1121–1132 (1992)).

Although, as described above, two of the more prominent CLIPs were identified as the β subunits themselves, most of the others have yet to be characterized. The activation of cytoplasmic tyrosine kinase(s) appears to be essential for CNTF action since inhibitors that block the tyrosine phosphorylations also block subsequent downstream events such as gene inductions (Ip et al., *Cell* 69:1121–1132 (1992)).

A possible clue to the identity of the cytoplasmic tyrosine kinase(s) activated by the CNTF family of factors came from the finding that other distantly related cytokines resulted in the activation of the Jak/Tyk family of kinases (Firmbach-Kraft et al., *Oncogene* 5:1329–1336 (1990); Wilks et al., *Mol. Cell. Biol.* 11:2057–2065 (1991); Harpur et al., *Oncogene* 7:1347–1353 (1992)). This family of non-receptor cytoplasmic protein tyrosine kinases consists of 3 known members—Jak1, Jak2, and Tyk2—which are all equally related to each other and share the unusual feature of having two potential kinase domains and no Src homology 2 (SH2) domains. Elegant studies involving complementation of a genetic defect in a cell line unresponsive to IFNa resulted in the identification of Tyk2 as a required component of the IFNα signaling cascade ((Velasquez et al., *Cell* 70:313–322 (1992)). More recently, the receptors for cytokines such as EPO, GM-CSF, and GH were shown to associate with and activate Jak2 (Argetsinger et al., *Cell* 74:237–244 (1993); Silvennoinen et al., *Proc. Natl. Acad. Sci. USA* (1993, in press); Witthuhn et al., *Cell* 74:227–236 (1993)). The kinase was shown to bind to the membrane proximal cytoplasmic region of the receptor, and mutations of this region that prevented Jak2 binding also resulted in the loss of EPO induced proliferation, suggesting that Jak2 plays a critical role in EPO signaling. Jak1 has not been reported to be significantly activated by any of these receptor systems.

The identification of hemopoietic factors that share receptor components with CNTF would enable the utilization of CNTF and its specific receptor components for activation of targeted cells that are normally responsive to such hemopoietic factors.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention is based in part upon the discovery that the cellular response to several cytokines, particularly those cytokines which function by binding to members of the cytokine receptor superfamily, is mediated by the activation (i.e. phosphorylation) of a member of the Jak kinase family. According to the present invention, Jak kinases mediate cytokine activity through their tyrosine phosphorylation (i.e. activation) in response to cytokine-receptor binding.

The present invention is also directed to methods for regulating cytokines whose activity is mediated by the activation of a Jak kinase.

The present invention provides methods for inhibiting the cellular response to cytokines whose activity is mediated by activation of at least one Jak kinase activity.

The present invention also provides methods for treating disease conditions caused by an excessive response to a cytokine whose activity is mediated by the activation of a Jak kinase, such as cytokine induced excessive proliferation of eukaryotic cells.

The present invention also provides assays for identifying compositions capable of inhibiting the biological response of a eukaryotic cell to a cytokine whose activity is mediated by the activation of a Jak kinase.

The present invention also provides methods for enhancing the biological response of a eukaryotic cell to a cytokine whose activity is mediated by the activation of a Jak kinase activity.

The present invention further provides antibodies useful for detecting and extracting a particular Jak protein without interfering with its kinase activity.

Particular cytokines are also provided by the present invention whose activity is mediated by at least one Jak kinase.

The present invention is also based on the elucidation of the complete DNA and amino acid sequence for particular Jak kinases, as described herein. Accordingly, the present invention also furnishes oligonucleotide probe sequences, and gene sequences coding, for the Jak kinases, expression vehicles containing the gene sequence capable of expressing a portion of, or a full-length sequence of, a Jak kinase, and hosts transformed therewith.

Other utilities, features, embodiments and methods of the present invention will be apparent to skilled artisans from the following detailed description and non-limiting examples relating to the present invention.

BRIEF DESCRIPTION OF THE DRAWINGS

FIGS. 1A–1H. The nucleotide sequence of the Jak2 open reading frame and flanking non-coding regions is shown (SEQ ID No. 8). The single letter amino acid sequence is shown below (SEQ ID No. 9). Nucleotide and amino acid sequence information from the published partial Jak2 cDNA sequence (Haipur et al., *Oncogene* 7:1347–1353 (1992)) is shown above and below the sequences provided where that information is different. The ATG codons are indicated (*) The arrow (>) above nucleotide 522 designates the 5' end of the reported Jak2 sequence. The arrow (^) at nucleotide position 2226 indicates the location of a 7 amino acid insert, detected in previous studies (Harpur, supra, (1992)). The nucleotides in parenthesis in the 3' non-coding region were present in the previous studies (Harpur, supra (1992)) and not detected in our studies.

FIGS. 2A–2D. The published amino acid (SEQ ID No. 11) and DNA coding sequence (SEQ ID No. 10) for human Jak1 kinase is shown (Wilks et al., *Mol. Cell. Biol.* 11: 2057–2065 (1991)). Nucleotide numbering is retained from the published sequence, with the coding sequence beginning at nucleotide 76 and ending at nucleotide 3504.

FIGS. 3A–3E. The published amino acid (SEQ ID No. 13) and DNA coding sequence (SEQ ID No. 12) for human Tyk2 kinase is shown (Firmbach-Kraft et al., *Oncogene* 5: 1329–1336 (1990)). Nucleotide numbering is retained from the published sequence, with the coding sequence beginning at nucleotide 307 and ending at nucleotide 3867.

FIGS. 5A–5E. An alignment of the amino acid sequences of Jak1 (line 1; SEQ ID NO: 14)), Tyk2 (line 2; SEQ ID NO: 13), and Jak2 (line 3; SEQ ID NO:9)), along with the consensus sequence (line 4) generated using the Intelligenetics computer program "Pileup" is shown (Plurality=2.00; Threshold=1.00; AveWeight=1.00; AveMatch=0.54; AvMisMatch=-0.4).

FIGS. 6A–6C. Amino acid sequence comparisons of the Jak family kinases. The amino sequences of murine Jak1 (SEQ ID NO: 14) with additional N-terminal amino acid sequence-MQYLNIKEDCNA (SEQ ID NO: 16) (O. Silvennoinen, J. H. Ihle, unpublished data), murine Jak2 (SEQ ID NO: 11) (Silvennoinen, *Proc. Natl. Acad. Sci. USA* 90:8429–8433 (1993)) and human Tyk2 (SEQ ID NO: 13) (Firmbach-Kraft, et al., *Oncogene* 5:1329–1336 (1990)) are compared with the murine Jak3 (SEQ ID NO: 17) sequence. Alignments were initially made by computer analysis with an intelligenetics program and were subsequently aligned by inspection. Gaps were introduced to optimize alignment. The consensus alignment indicates positioning in which 3 or 4 of the sequences have an identical amino acid. PCR amplification with degenerate kinase domain primers, and cDNA from primary breast cancer tissue was used to identify novel kinases as previously described (Cance et al., *Int. J. Cancer* 54:571–577 (1993)). The PCR fragment (TK5) was used to screen a mouse pre-B cell cDNA library (Schatz et al., *Cell* 59:1035–1048 (1989)) by standard techniques. Four cDNA clones were obtained, one of which was near the size of the transcript detected by Northern blots. The nucleotide sequence was determined by dideoxynucleotide, chain termination sequencing (Sanger et al., *Proc. Natl. Acad. Sci. USA* 74:5463–5467 (1977)) in both directions.

FIG. 7A: cDNAs for murine Jak1, Jak2 and Jak3 and human Tyk2 were transcribed and translated in vitro utilizing the Promega (Madison, Wis.) TNT T3 coupled reticulocyte system and labeled with ($^{35}$S) methionine as previously described (Silvennoinen, et al., *Proc. Natl. Acad. Sci. USA* 90:8429–8433 (1993)). The reaction products were subsequently resolved by SDS-PAGE and the proteins detected by autoradiography. FIG. 7B: Characterization of antisera against Jaks. The ($^{35}$S) labeled Jak3 protein from the in vitro translation reactions with a preimmune serum (lane 1), an antipeptide antiserum against Jak3 (lane 2), the antiserum against Jak3 in the presence of excess peptide (100 µg/ml) to which the antiserum was raised (lane 3) or an irrelevant peptide (lane 4). The antipeptide antiserum was raised against the peptide AKLLPLDKDYYVVREPG (SEQ ID NO: 15) derived from a region of the kinase domain of Jak3 by previously described techniques (Silvennoinen, *Proc. Natl. Acad. Sci. USA* 90:8429–8433 (1993)). The cross-reactive, antipeptide antiserum was made against a synthetic peptide derived from Tyk2 (SPSEKEHFYQAQHRLPEPS (SEQ ID NO:7).

FIG. 9A: CTLL cells were deprived of growth factors for 14 hr and were either left unstimulated (lanes 1, 4, 7 and 10), were stimulated with 100 U/ml with IL-2 (Cetus) for 10 min (lanes 2, 5, 8 and 11) or were stimulated with 100 ng/ml of IL4 (R&D) for 10 min (lanes 3, 6, 9 and 12). Extracts were prepared as previously described (Witthuhn et al., *Cell*:227–236 (1993)) and used for immunoprecipitation with the indicated antisera. The immunoprecipitates were resolved by SDS-PAGE, electrophoretically transferred to nitrocellulose and the membranes were probed with the 4G10 monoclonal antibody (UBI) against phosphotyrosine. FIG. 9B: CTLL cells were deprived of growth factors for 14 hr and were either unstimulated (lane 1), stimulated with IL-2 (lane 2) or stimulated with IL-4 (lane 3) as above. Extracts were prepared and used for immunoprecipitation with the Jak3/Jak1 cross-reactive antipeptide antiserum against Tyk2. The immunoprecipitates were used in in vitro kinase assays as previously described (Witthuhn et al., *Cell*:227–236 (1993)) and the products resolved by SDS-PAGE and visualized by autoradiography. FIG. 9C: 32Dc13 cells transfected with the human IL-2 β receptor chain (32D/IL2Rβ) were deprived of IL-2 for 14 hr and either not stimulated (lanes 1 and 4) or stimulated with 100 U/ml of IL-2 (lanes 2 and 5) or 10 U/ml of I1–3 and 6). Extracts were made, resolved by SDS-PAGE and transferred to filters as above. The filters were probed with the 4G10 monoclonal antibody for phosphotyrosine. FIG. 9D: CTLL cells transfected with the EPO receptor were deprived of IL-2 for 14 hr and were either left unstimulated (lanes 1 and 5), were stimulated with 100 U/ml of IL-2 (lanes 2 and 6), 100 ng/ml of IL-4) or 10 U/ml of EPO (lanes 4 and 7). Extracts were prepared and blots obtained as above and probed with the 4G10 monoclonal antibody against phosphotyrosine. The positions of migration of standards are shown on the left. Cells were harvested and extracts prepared in 0.1% triton as previously described (Witthuhn et al., *Cell*:227–236 (1993)). Cell extracts from 2×10⁷ cells were used for immunoprecipitations with the designated antisera and the complexes collected with protein A SEPHAROSE. The immunoprecipitates were subjected to SDS-PAGE and electrophoretically transferred to nitrocellulose filters. Filters were probed with the 4G10 monoclonal antibody (Upstate Biologicals Inc.) against phosphotyrosine. Detection was done by enhanced chemiluminescence, ECL (Amersham) and exposure to film. The conditions for the in vitro kinase assays are as previously described (Witthuhn et al., *Cell*:227–236 (1993)).

DETAILED DESCRIPTION OF THE INVENTION

Figure 4:
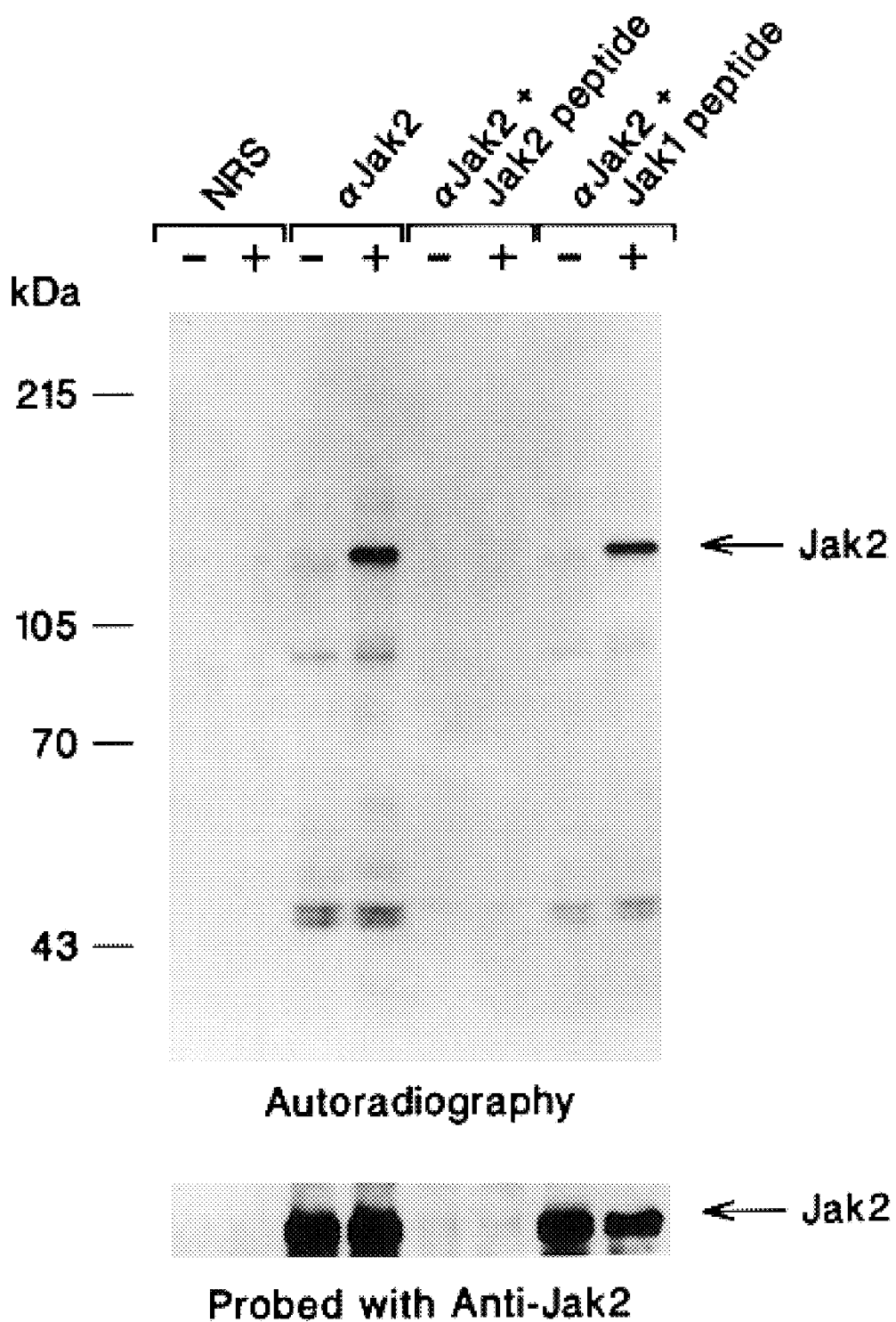
FIG. 4. DA-3 cells were removed from growth factors and were either unstimulated (−) or stimulated (+) with IL-3 for 10 min as described in Materials and Methods. Cell extracts were then immunoprecipitated with normal rabbit serum (NRS) or the antipeptide antiserum specific for Jak2 in the absence of competing peptide (αJak2) or in the presence of the peptide (30 µg/ml) to which the antiserum was raised (αJak2+Jak2 peptide) or in the presence of an equivalent amount of the peptide that corresponds to the comparable region of Jak1 (αJak2+Jak1 peptide). The immunoprecipitates were used for in vitro kinase assays as described in Methods and Materials (Example 1). The products of the reactions were resolved by SDS-PAGE, transferred to nitrocellulose and detected by autoradiography (top panel). The blots were subsequently probed with the antiserum against Jak2 (bottom panel).

The present invention is in part directed to novel methods for regulating the cellular response to cytokines. These methods are based upon the general role of a Jak family of kinases in the cellular response to cytokines.

By "cytokine" is meant any polypeptide secreted by cells that affects the function, such as survival, mitosis, differentiation or metabolism, of other cells. Examples of cytokines include, but are not limited to, peptide hormones and growth factors.

By "cellular response to a cytokine" or "cytokine activity" is meant the general biological effect upon a eukatyotic cell or cell population which ultimately results from the association of a particular cytokine with its cellular receptor and typically involves the modification of gene expression within the cell. The invention relates to cytokine activity which is mediated by the activation of a Jak kinase. Examples of such activity include, but are not limited to, the proliferation and differentiation of hematopoietic progenitor cells in response to interleukin-3 (IL-3), the proliferation and differentiation of erythroid lineage cells in response to erythropoietin (EPO), somatic cell growth in response to growth hormone (GH), and other similar responses as known in the art, and/or as taught herein.

The methods taught by the invention apply to any cytokine whose activity is mediated by a member of the Jak kinase family, which includes, but is not limited to, Jak1, Jak2, Jak3 and Tyk2. Cytokines of this type include those which function by binding to members of the cytokine receptor superfamily, and also those which function by binding to members of the tyrosine kinase receptor superfamily. More specifically, these cytokines include, but are not limited to, at least one selected from the group consisting of interleukin-3 (IL-3), interleukin 2 (IL-2), interleukin 4 (IL-4), interleukin 5 (IL-5), interleukin 6 (IL-6), interleukin 7 (IL-7), interleukin 9 (IL-9), interleukin 11 (IL-11), oncostatin M (OSM), leukemia inhibitory factor (LIF), granulocyte-macrophage specific colony stimulating factor (GM-CSF), erythropoietin (EPO), granulocyte colony stimulating factor (G-CSF), interferon-γ (IFN-γ), prolactin hormone and growth hormone.

According to the invention, Jak kinases mediate cytokine activity through their tyrosine phosphorylation (i.e. activation) in response to cytokine-receptor binding. Thus, cytokines susceptible to the methods of regulation provided by the present invention may be identified on the basis of their ability to cause the tyrosine phosphorylation (i.e. activation) of one or more members of the Jak kinase family. Tyrosine phosphorylation of a Jak kinase in a cell following cytokine stimulation may be detected, for example, by assaying for its ability to bind antiphosphotyrosine monoclonal antibody; only tyrosine phosphorylated Jak kinases will bind this type of antibody. Alternatively, in vitro kinase assays as described below may be used to determine the state of activation (tyrosine phosphorylation) of a Jak kinase in a cell following cytokine stimulation.

Jak Kinase Peptides (JKP). A Jak kinase peptide (JKP), according to the present invention, can refer to any subset of a Jak kinase (JK) having JK activity. A peptide fragment according to the present invention can be prepared by proteolytic digestion of the intact molecule or a fragment thereof, by chemical peptide synthesis methods well-known in the art, by recombinant DNA methods discussed in more detail below, and/or by any other method capable of producing a JKP and having a conformation similar to an active portion of JK and having Jak kinase activity, according to known Jak activity as screening assays, e.g., as described herein. The minimum peptide sequence to have activity is based on the smallest unit containing or comprising a particular region, consensus sequence, or repeating unit thereof of a JK having Jak kinase activity, i.e., ability to be phosphorylated at least one tyrosine by at least one cytokine.

Accordingly, a JKP of the present invention alternatively includes polypeptides having a portion of a JK amino acid sequence which substantially corresponds to at least one 15 to 400 amino acid fragment and/or consensus sequence of a known Jak kinase or group of JKs, wherein the JKP has homology of at least 80%, such as 80–99% homology, or any range or value therein, while maintaining Jak kinase biological activity, wherein a JKP of the present invention is not naturally occurring or is naturally occurring but is in a purified or isolated form which does not occur in nature. Preferably, a JKP of the present invention substantially corresponds to a Jak kinase domain of particular Jak kinase, or group of Jak kinases, as a consensus sequence, such as between Jak1 and Jak2.

Percent homology may be determined, for example, by comparing sequence information using the GAP computer program, version 6.0, available from the University of Wisconsin Genetics Computer Group (UWGCG). The GAP program utilizes the alignment method of Needleman and Wunsch (*J. Mol. Biol.* 48:443 (1970), as revised by Smith and Waterman (*Adv. Appl. Math.* 2:482 (1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) and the weighted comparison matrix of Gribskov and Burgess, *Nucl. Acids Res.* 14:6745 (1986), as described by Schwartz and Dayhoff, eds., ATLAS OF PROTEIN SEQUENCE AND STRUCTURE, National Biomedical Research Foundation, pp. 353–358 (1979); (2) a penalty of 3.0 for each gap and an additional 0.10 penalty for each symbol in each gap; and (3) no penalty for end gaps.

Figure 6B:
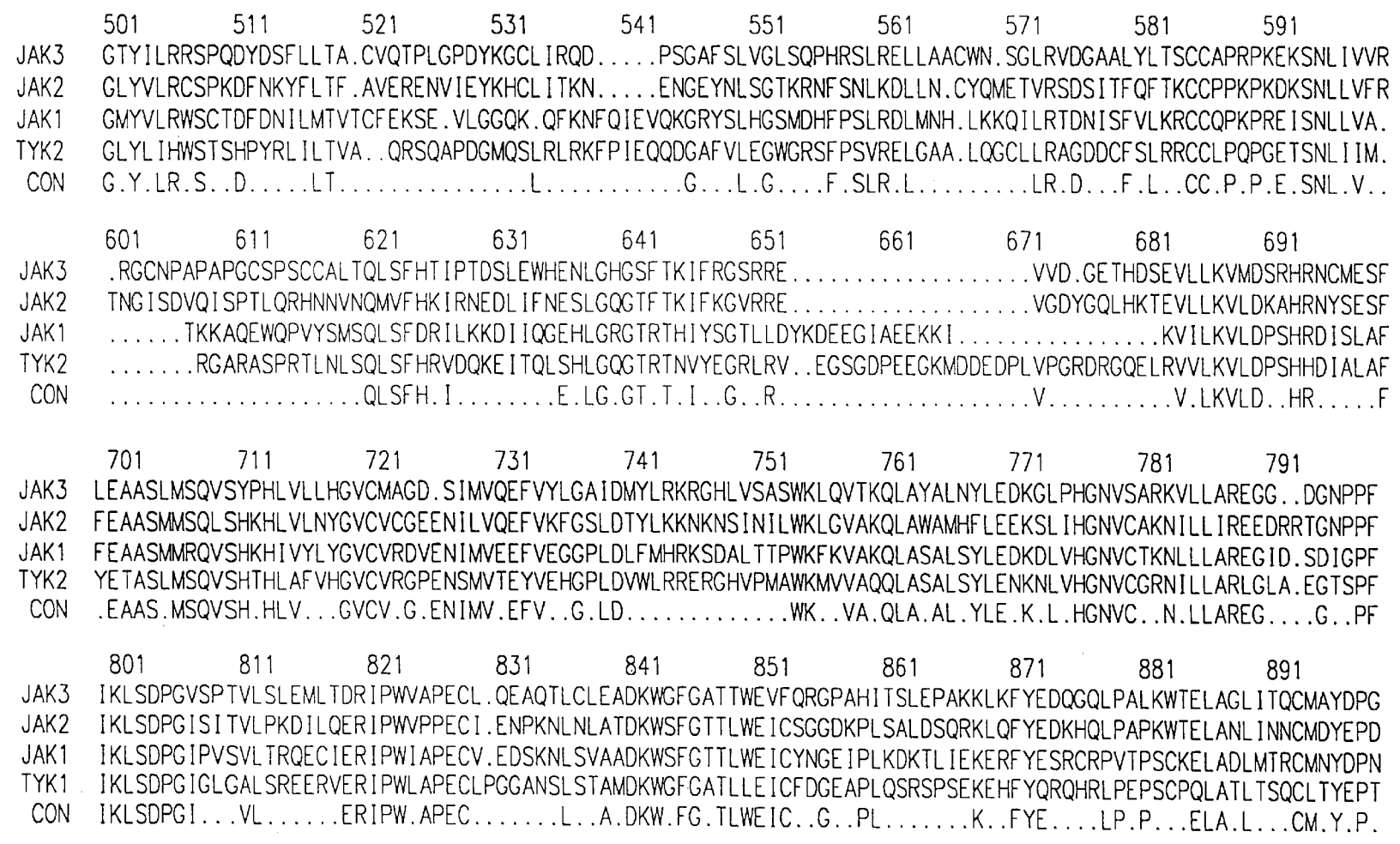

In a preferred embodiment, the peptide of the present invention corresponds to an active portion of a sequence of FIG. 6.

A peptide of at least about 5–335 amino acids (or any range or value therein) that has the basic structure of the active portion of a JK can, in one embodiment, be characterized as having 80–99% homology (or any range or value therein) to the above JK sequences, which peptide can have JK activity and is contemplated within the scope of the present invention. Thus, one of ordinary skill in the art, given the teachings and guidance presented in the present specification, will know how to substitute other amino acid residues in other positions of a JK to obtain a JKP, including substituted, deletional or insertional variants.

A JKP of the present invention also includes a variant wherein at least one amino acid residue in the polypeptide has been conservatively replaced, inserted or deleted by at least one different amino acid.

An amino acid or nucleic acid sequence of a JKP of the present invention is said to "substantially correspond" to another amino acid or nucleic acid sequence respectively, if the sequence of amino acids or nucleic acid in both molecules provides polypeptides having biological activity that is substantially similar, qualitatively or quantitatively, to the corresponding fragment of at least one JK domain having JK activity. Such "substantially corresponding" JKP sequences include conservative amino acid or nucleotide substitutions, or degenerate nucleotide codon substitutions wherein individual amino acid or nucleotide substitutions are well known in the art.

Accordingly, JKPs of the present invention, or nucleic acid encoding therefor, include a finite set of substantially corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., *Principles of Protein Structure*, Springer-Verlag, New York, 1978, and Creighton, T. E., *Proteins: Structure and Molecular Properties*, W. H. Freeman & Co., San Francisco, 1983, which are hereby incorporated by reference. For a presentation of nucleotide sequence substitutions, such as codon preferences, see Ausubel et al., eds, *Current Protocols in Molecular Biology*, Greene Publishing Assoc., New York, N.Y. (1987, 1988, 1989, 1990, 1991, 1992, 1993, 1994) at §§A.1.1–A.1.24, and Sambrook et al, *Molecular Cloning*: A Laboratory Manual, Second Edition, Cold Spring Harbor Press, Cold Spring Harbor, N.Y. (1989), at Appendices C and D.

Amino Acid Substitutions of a Native JK for a JKP. Conservative substitutions of a JKP of the present invention includes a variant wherein at least one amino acid residue in the polypeptide has been conservatively replaced, inserted or deleted by at least one different amino acid.

Such substitutions preferably are made in accordance with the following list as presented in Table 1, which substitutions can be determined by routine experimentation to provide modified structural and functional properties of a synthesized polypeptide molecule, while maintaining JK biological activity, as determined by known JK activity assays. In the context of the present invention, the term JKP or "substantially corresponding to" includes such substitutions.

TABLE 1

| Original Residue | Exemplary Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Accordingly, based on the above examples of specific substitutions, alternative substitutions can be made by routine experimentation, to provide alternative JKPs of the present invention, e.g., by making one or more conservative substitutions of JK fragments which provide JK activity.

Alternatively, another group of substitutions of JKPs of the present invention are those in which at least one amino acid residue in the protein molecule has been removed and a different residue inserted in its place according to the following Table 2. The types of substitutions which can be made in the protein or peptide molecule of the present invention can be based on analysis of the frequencies of amino acid changes between a homologous protein of different species, such as those presented in Table 1–2 of Schulz et al., infra. Based on such an analysis, alternative conservative substitutions are defined herein as exchanges within one of the following five groups:

TABLE 2

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

The three amino acid residues in parentheses above have special roles in protein architecture. Gly is the only residue lacking any side chain and thus imparts flexibility to the chain. This however tends to promote the formation of secondary structure other than a-helical. Pro, because of its unusual geometry, tightly constrains the chain. It generally tends to promote β-turn-like structures, although in some cases Cys can be capable of participating in disulfide bond formation which is important in protein folding. Note that Schulz et al. would merge Groups 1 and 2, above. Note also that Tyr, because of its hydrogen bonding potential, has significant kinship with Ser, and Thr, etc.

Conservative amino acid substitutions, included in the term "substantially corresponding" or "corresponding", according to the present invention, e.g., as presented above, are well known in the art and would be expected to maintain biological and structural properties of the polypeptide after amino acid. substitution. Most deletions and insertions, and substitutions according to the present invention are those which do not produce radical changes in the characteristics of the protein or peptide molecule. "Characteristics" is defined in a non-inclusive manner to define both changes in secondary structure, e.g. α-helix or β-sheet, as well as changes in physiological activity, e.g. in receptor binding assays.

However, when the exact effect of the substitution, deletion, or insertion is to be confirmed, one skilled in the art will appreciate that the effect of the substitution or substitutions will be evaluated by routine JK activity screening assays, either immunoassays or bioassays, to confirm biological activity, such as, but not limited to, Jak kinase.

Amino acid sequence insertions as included in JKP variant can also include amino and/or carboxyl-terminal fusions of from one residue to polypeptides of essentially unrestricted length, as well as intrasequence insertions of single or multiple amino acid residues. Intrasequence insertions can range generally from about 1 to 10 residues, more preferably 1 to 5. An example of a terminal insertion includes a fusion of a signal sequence, whether heterologous or homologous to the host cell, to a JKP to facilitate secretion from recombinant bacterial hosts.

One additional group of variants according to the present invention is those in which at least one amino acid residue in the peptide molecule, and preferably, only one, has been removed and a different residue inserted in its place.

For a detailed description of protein chemistry and structure, see Schulz et al., *Principles of Protein Structure*, Springer-Verlag, New York, 1978; Ausubel, infra, which are hereby incorporated by reference.

Most deletions and insertions, and substitutions of JKPs according to the present invention are those which maintain or improve the Jak kinase characteristics of the peptide molecule. However, when it is difficult to predict the exact effect of the substitution, deletion, or insertion in advance of doing so, one skilled in the art will appreciate that the effect will be evaluated by routine screening assays. For example, a variant made by site-specific mutagenesis of the peptide molecule-encoding nucleic acid and expression of the variant JKP in cell culture or, alternatively, by chemical synthesis, can be tested for Jak kinase activity (e.g., as is known or as described herein). The activity of the cell lysate or purified peptide variant can be screened in a suitable screening assay for the desired characteristic, for example Jak kinase activity in any of the several assays.

Modifications of peptide properties, such as redox or thermal stability, hydrophobicity, susceptibility to proteolytic degradation or the tendency to aggregate with carriers or into multimers, can also be assayed by methods well known to the ordinarily skilled artisan.

Also included in the scope of the invention are salts of the JKPs of the invention. As used herein, the term "salts" refers to both salts of carboxyl groups and to acid addition salts of amino groups of the protein or peptide molecule.

Amino acid sequence variants of a JKP of the present invention can also be prepared by mutations in the DNA. Such variants include, for example, deletions from, or insertions or substitutions of, residues within the amino acid sequence. Any combination of deletion, insertion, and substitution can also be made to arrive at the final construct, provided that the final construct possesses some Jak kinase activity. Preferably improved Jak kinase activity is found over that of the non-variant peptide. Obviously, mutations that will be made in the DNA encoding the variant must not place the sequence out of reading frame and preferably will not create complementary regions that could produce secondary mRNA structure (see, e.g., EP Patent Application Publication No. 75,444; Ausubel, infra; Sambrook, infra).

At the genetic level, these variants ordinarily are prepared by site-directed mutagenesis of nucleotides in the DNA encoding a JKP, thereby producing DNA encoding the variant, and thereafter expressing the DNA in recombinant cell culture. The variants typically exhibit the same qualitative biological activity as the naturally occurring JK (see, e.g., Ausubel, infra; Sambrook, infra).

Knowledge of the three-dimensional structures of proteins is crucial in understanding how they function. The three-dimensional structures of more than 400 proteins are currently available in the protein structure database (in contrast to around 200,000 known protein and peptide sequences in sequence databases, e.g., Genbank, Chemical Abstracts REGISTRY, etc.). Analysis of these structures shows that they fall into recognizable classes or motifs. It is possible to model the three-dimensional structure of protein based on homology to a related protein of known structure. Examples are known where two proteins that have relatively low sequence homology, but are found to have almost identical three dimensional structure. Such homologous variants are also included in JKPs of the present invention.

Once a Jak kinase structure or characteristics have been determined using the above analysis, JKPs can be recombinantly or synthetically produced, or optionally purified, to provide commercially useful amounts of JKPs for use in diagnostic or research applications, according to known method steps (see, e.g., Ausubel, infra, and Sambrook, infra, which references are herein entirely incorporated by reference).

Methods for Inhibiting Cytokine Activity Dependent Upon Jak Kinases

According to the invention, the activity of a cytokine may be inhibited by inhibiting the activity of the Jak kinase which mediates that cytokine's effect upon the cell.

One way of inhibiting Jak kinase activity within the scope of the present invention is by inhibiting Jak gene expression. Expression of Jak kinases may be inhibited using antisense molecules or ribozymes.

Antisense molecules and their use for inhibiting gene expression are well known in the art (see, for example, Cohen, J., *Oligodeoxyibonucleotides, Antisense Inhibitors of Gene Expression*, CRC Press (1989); Toole, WO 92/10590). Antisense molecules useful for inhibiting the expression of a Jak kinase contain nucleic acid sequences complementary to, and capable of binding to, the mRNA and/or DNA gene sequence of the Jak kinase desired to be inhibited. Such antisense molecules may be provided to the cell via genetic expression using DNA encoding the antisense molecule as taught by U.S. Pat. No. 5,190,931, issued Mar. 2, 1993 to Inoue, M. (incorporated by reference herein in its entirety). Alternatively, antisense molecules of the invention may be made synthetically and then provided to the cell. Synthetic antisense molecules contemplated by the invention include oligonucleotide derivatives known in the art which have improved biological activity compared to unmodified oligonucleotides (see, e.g., Cohen, J., supra; U.S. Pat. No. 5,023,243, issued Jun. 11, 1991 to Tullis, R. H. and incorporated by reference herein in its entirety).

Ribozymes and their use for inhibiting gene expression are also well known in the art (see, e.g., Cech et al., *J. Biol. Chem.* 267: 17479–17482 (1992); Hampel et al., *Biochemistry* 28: 4929–4933 (1989); Haseloff et al., *Nature* 334: 585–591 (1988); Eckstein et al., WO 92/07065; and U.S. Pat. No. 5,168,053 issued to Altman et al. and incorporated by reference herein in its entirety). Like antisense molecules, ribozymes contain target sequences complementary to the mRNA of the genes whose expression they are designed to inhibit. Ribozymes useful for inhibiting the expression of a Jak kinase may be designed by incorporating target sequences into the basic ribozyme structure which are complementary to the mRNA sequence of the Jak kinase desired to be inhibited. Ribozymes targeting a Jak kinase may be synthesized using commercially available reagents (Applied Biosystems) or they may be genetically expressed from DNA encoding them.

As will be recognized by the skilled artisan, antisense and ribozyme molecules may be designed to inhibit a specific member of the Jak kinase family by targeting sequences unique to that member. Alternatively, antisense and ribozyme molecules may be designed to inhibit more than one Jak kinase by targeting sequences shared by the Jak members desired to be inhibited.

Jak kinase activity may also be inhibited through the use of compounds or peptides which inhibit the ability of the Jak protein to function as a kinase. Such inhibitors include, but are not limited to, drugs, anti-Jak kinase antibody, Jak kinase agonists and antagonists, trans-dominant mutants of Jak kinase, and general inhibitors of tyrosine kinase activity such as GENESTEIN. These inhibitors may have a general inhibitory effect upon all Jak kinases or they may possess a more specific inhibitory effect upon a specific member or subset of the Jak kinase family.

The term "antibody", as used herein, refers both to monoclonal antibodies which are a substantially homogeneous population and to polyclonal antibodies which are heterogeneous populations. Such antibodies may be of any immunoglobulin class including IgG, IgM, IgE, IgA, IgD and any subclass thereof. The term "antibody", as used herein, is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less nonspecific tissue binding than an intact antibody (Wahl et al., *J. Nucl. Med.* 24:316–325 (1983)). Such fragments are typically produced by proteolytic cleavage, using enzymes such as papain (to produce Fab fragments) or pepsin (to produce F(ab')$_2$ fragments). See, generally, Kohler and Milstein, Nature 256:495–497 (1975); U.S. Pat. No. 4,376,110; Ausubel et al, eds., CURRENT PROTOCOLS IN MOLECULAR BIOLOGY, Greene Publishing Assoc. and Wiley Interscience, N.Y., (1987, 1992, 1993, 1994); and Harlow and Lane ANTIBODIES: A LABORATORY MANUAL Cold Spring Harbor Laboratory (1988); Colligan et al., eds., *Current Protocols in Immunology*, Greene Publishing Assoc. and Wiley Interscience, N.Y., (1992, 1993), the contents of which references are entirely incorporated herein by reference. Such antibodies may be of any immunoglobulin class including IgG, IgM, IgE, IgA, GILD and any subclass thereof.

Both monoclonal and polyclonal antibodies to Jak kinase may be made according to methods well known in the art (see, e.g., Harlow, supra; Colligan, supra; Ausubel, supra, at §§11.4.2–11.13.4). Antibodies may be generated against Jak kinase protein produced recombinantly or isolated from cells and tissues where the Jak kinase naturally occurs. Antibodies may be generated against the entire Jak kinase protein or, more preferably, antibodies are generated against peptide subfragments representing functional domains of the Jak kinase protein required for its cytokine-induced tyrosine kinase activity. Antibodies for specifically inhibiting a particular Jak kinase may be generated against peptide fragments unique to that Jak kinase. Alternatively, antibodies for generally inhibiting more than one member of the Jak kinase family may be generated against peptide fragments shared by the Jak kinases desired to be inhibited.

Another method for inhibiting Jak kinase activity taught by the invention is through the use of inhibitors of the cytokine-dependent activation of the Jak kinase. Prior to cytokine stimulation, cellular Jak kinase is present in an inactivated state. Inhibitors of Jak kinase activation may be identified by their ability to inhibit the conversion of the Jak kinase into its catalytically active state, which can be detected by in vitro kinase assay as described below and in the Examples.

As discovered by the present inventors, Jak kinases are activated by their cytokine-induced tyrosine phosphorylation. Accordingly, inhibitors may also be identified according to the invention as those compounds or peptides which block or significantly reduce the cytokine-induced tyrosine phosphorylation of the Jak kinase into its catalytically active form. The state of tyrosine phosphorylation of a Jak kinase following cytokine stimulation may be assayed, for example, by the ability of the Jak kinase to be detected with an antiphosphotyrosine monoclonal antibody.

Activation of a Jak kinase by a particular cytokine may require the physical association of the Jak kinase with the receptor for that cytokine (see Example 2). According to the invention, peptide antagonists mimicking those portions of the Jak kinase or cytokine receptor involved in this association are useful as inhibitors of Jak kinase activation. These peptides are contemplated by the invention to act as inhibitors by associating with either the cytokine receptor (for the Jak kinase peptides) or the Jak kinase (for the cytokine receptor peptides), thus blocking the association of the Jak kinase with the cytokine receptor.

In particular, the invention teaches that Jak2 activation by EPO requires the physical association of Jak2 with the EPO receptor (EPOR) and that this association requires a membrane proximal region of EPOR that is essential for mitogenesis. According to the invention, peptide antagonists mimicking this membrane proximal region and capable of blocking the EPOR-Jak2 interaction are useful as inhibitors of Jak2 activation by EPO.

Assays for Inhibitors of Jak kinase activity

The present invention also provides screening assays for identifying inhibitors of Jak kinase activity useful in the methods described herein above.

Jak tyrosine kinase activity can be assayed in vitro by combining catalytically active Jak kinase, a Jak phosphorylation substrate(s), and ATP with the phosphorous at the γ position detectably labelled with, for example, a radiolabel such as $^{32}P$. In this assay, the Jak kinase catalyzes the transfer of the labelled phosphorous from ATP to the substrate and Jak kinase activity is detected by the generation of substrate containing detectably labelled phosphorous (i.e. labelled substrate). Inhibitors of Jak kinase activity are identified as those compounds or peptides which, when incorporated into the assay, significantly reduce or eliminate the generation of labelled substrate.

Catalytically active Jak kinase for use in this assay may be obtained from a variety of sources. Preferably, a catalytically active Jak kinase is obtained from insect cells transformed with a baculovirus vector capable of expressing the Jak kinase at high levels. Jak2 kinase produced in this way has been found to be catalytically active and useful in in vitro kinase assays. It is expected that other Jak kinases produced in large amounts in insect cells in a similar manner will also be catalytically active.

A catalytically active Jak kinase may also be obtained from cells carrying mutations which result in constitutive activation of the Jak kinase. For example, an EPOR mutation known as $R^{199}$ to C results in constitutive activation of the EPOR (Yoshimura et al., Nature 348:647–649 (1990)). In cells expressing this mutation, in the absence of EPO, Jak2 kinase is constitutively tyrosine phosphorylated and possesses in vitro kinase activity.

Catalytically active forms of each Jak kinase may also be obtained from cells stimulated with a cytokine which causes their activation. For example, catalytically active Jak2 kinase may be obtained from cells stimulated with EPO, growth hormone, IL-3, and other cytokines, while catalytically active Tyk2 may be obtained from cells stimulated with IFNα.

Any phosphorylation substrate of the Jak kinase whose activity is being determined may be used in the assay. For a Jak kinase which possesses autophosphorylation activity, a preferred substrate is the Jak kinase itself, or a subfragment thereof containing the autophosphorylation site. Tyrosine kinases such as the Jak kinases generally tend to possess autophosphorylation activity (see, for example, Hanks, S. K. et al., Science 241: 42–52 (1988). Moreover, autophosphorylation activity for Jak2 has been established and the autophosphorylation site has been found to reside on a peptide fragment containing amino acids 1000–1015 of Jak2 (see FIGS. 1A–1H; the sequence is VLPQD-KEYYKVKEPG (SEQ ID No. 2)). Similar peptides fragments exist in the Jak1 protein at amino acids 1015–1029 (see FIGS. 2A–2D; the sequence is AIETDKEYYTVKDDR (SEQ ID NO:3)) and in the Tyk2 protein at amino acids 1047–1061 (see FIG. 3; the sequence is AVPEGHEYYRVREDG (SEQ ID NO:4)). Based on structural and functional similarities among the Jak kinases, as well as functional similarities among tyrosine kinases in general, it is expected that the other members of the Jak kinase family also possess autophosphorylation activity.

The present invention also provides an assay for inhibitors of cytoline-induced activation of a Jak kinase. Cytokine-induced activation of a Jak kinase can be assayed by preparing Jak kinase extracts from cells following cytokine induction and assaying the extracts for in vitro kinase activity as described herein. Inhibitors of cytokine-induced activation of a Jak kinase are identified as those compounds or peptides which, when present in the cells before and/or during cytokine induction, significantly reduce or eliminate the in vitro kinase activity detected in the Jak kinase extracts prepared from the cells following cytokine induction.

The present invention also provides an assay for inhibitors of Jak kinase-cytokine receptor interactions which are potential inhibitors of cytokine-induced Jak kinase activation. For those cytokine receptors which are phosphorylated by an activated Jak kinase, the Jak kinase-cytokine receptor interaction may be detected using the in vitro kinase assay described above by incorporating the cytokine receptor into the assay as the phosphorylation substrate. For example, phosphorylation of the erythropoietin receptor (EPOR) by Jak2 kinase may be detected using this assay. Inhibitors of the Jak kinase-cytokine receptor interactions are identified as those compounds or peptides which, when incorporated into this assay, significantly reduce or eliminate the generation of phosphorylated (labelled) cytokine receptor protein.

Cytokine receptor protein is preferably obtained for use in this assay by production and purification from a recombinant host suitable for such purposes as described herein for the production of Jak kinases. A preferable host is insect cells transformed with a baculovirus vector capable of expressing cytokine receptor at high levels. Alternatively, cytokine receptor protein may be isolated from natural sources.

Methods for Enhancing Cytokine Activity Dependent Upon Jak kinases

In those situations where the biological response of a cell to a cytokine is deficient due to insufficient amounts of a Jak kinase, the present invention provides for enhancing this response by increasing the levels of the Jak kinase in the cell (see Example 4). This situation could be due to mutations which reduce the amount of the Jak kinase produced by the cell to sub-normal levels. This situation could also be due to mutations which reduce the rate or degree of cytokine-induced Jak activation such that the level of Jak kinase produced by the cell does not provide sufficient levels of activated Jak kinase following cytokine induction.

The levels of Jak kinase may be increased in a cell by adding Jak kinase protein to the cell, or by introducing a vector into the cell capable of expressing the Jak kinase. Vectors and methods for the expression of Jak2 are provided below. As will be readily apparent to one of skill in the art, these methods may also be applied to the production and expression of other members of the Jak kinase family.

Therapeutic Applications Of The Methods For Regulating Cytokine Activity

It is also contemplated by the invention that methods provided for regulating Jak kinase activity as described above may be applied to treating disease conditions caused by an abnormal cellular response to a cytokine whose activity is mediated by the activation of a Jak kinase. Thus disease conditions caused by an excessive cellular response to a cytokine whose activity is mediated by the activation of a Jak kinase may be treated by inhibiting Jak kinase activity. In particular, disease conditions caused by excessive proliferation of eukaryotic cells may be treated by inhibiting Jak kinase activity where this excessive proliferation occurs in response to a cytokine whose activity is mediated by the activation of a Jak kinase. Such disease conditions are caused by genetically acquired mutations or spontaneously acquired mutations.

For example, erythrocytosis is a genetically acquired disease that involves excess proliferation of erythrocytes from progenitor cells. The overproduction is dependent upon erythropoietin (EPO) and is caused by a mutation in the EPO receptor (EPOR) that results in the abnormal regulation of Jak2 kinase activity through EPO-EPOR binding. Comparable mutations may also occur spontaneously and give rise to this disease condition. In addition, analogous disease conditions may occur in other cell lineages that are regulated through a Jak kinase mediated cytokine response.

Alternatively, disease conditions caused by a deficient cellular response, or nonresponsiveness, to a cytokine whose activity is mediated by the activation of a Jak kinase may be treated by enhancing Jak kinase activity.

It is contemplated by the invention that administration of the compositions as described herein capable of inhibiting Jak kinase activity, including antisense molecules, ribozymes, Jak antibodies, antagonists, etc. may be accomplished by any of the methods known to the skilled artisan. For example, administration may be by parenteral, subcutaneous, intravenous, intramuscular, intra-peritoneal, or transdermal routes, administered in a pharmaceutically acceptable carrier by any means recognized as suitable by the skilled artisan.

It is understood that the dosage of a pharmaceutical compound or composition of the present invention administered in vivo or in vitro will be dependent upon the age, sex, health, and weight of the recipient, kind of concurrent treatment, if any, frequency of treatment, and the nature of the pharmaceutical effect desired. The ranges of effective doses provided herein are not intended to be limiting and represent preferred dose ranges. The most preferred dosage will be tailored to the individual subject, as is understood and determinable by one skilled in the relevant arts. See, e.g., Berkow et al., eds., *The Merck Manual,* 16th edition, Merck and Co., Rahway, N.J. (1992); Goodman et al., eds., *Goodman and Gilman's The Pharmacological Basis of Therapeutics,* 8th edition, Pergamon Press, Inc., Elmsford, N.Y. (1990); *Avery's Drug Treatment: Principles and Practice of Clinical Pharmacology and Therapeutics,* 3rd edition, ADIS Press, LTD., Williams and Wilkins, Baltimore, Md. (1987); Ebadi, *Pharmacology,* Little, Brown and Co., Boston (1985); Osol et al., eds., *Remington's Pharmaceutical Sciences,* 17th edition, Mack Publishing Co., Easton, Pa. (1990); Katzung, *Basic and Clinical Pharmacology,* Appleton and Lange, Norwalk, Conn., (1992), which references are entirely incorporated herein by reference.

The total dose required for each treatment can be administered by multiple doses or in a single dose. The diagnostic/pharmaceutical compound or composition can be administered alone or in conjunction with other diagnostics and/or pharmaceuticals directed to the pathology, or directed to other symptoms of the pathology.

Effective amounts of a diagnostic/pharmaceutical compound or composition of the present invention are from about 0.001 µg/kg to about 10 mg/kg body weight, administered at intervals of 4–72 hours, for a period of 2 hours to 5 years, and/or any range or value therein, such as 0.000001–0.0001, 0.0001–0.01, 0.01–1.0, 1–10, 10–50 and 50–100, 0.000001–0.00001, 0.00001–0.0001, 0.0001–0.001, 0.001–0.01, 0.01–0.1, 0.1–1.0, 1.0–10 and 5–10 mg/kg, at intervals of 1–2, 2–4, 4–6, 6–8, 8–10, 10–12, 12–14, 14–16, 16–18, 18–20, 20–22, 22–24, 24–26, 26–28, 28–30, 30–32, 32–34, 34–36, 36–40, 40–44, 44–48, 48–52, 52–56, 56–60, 60–64, 64–68, 68–72 hours, for a period of 1, 2, 4, 6, 8, 10, 12, 14, 16, 18, 20, 22, 24, 26, 28, 30, 32, 34, 36, 38, 40, 42, 44, 46, 48, 50, 60, 70, 80, 90, 100 days, or 1, 2, 4, 6, 8, 10, 12, 14, 16, 18, 20, 24, 28, 32, 36, 40, 44, 48, 52 and/or more weeks, and/or 1, 2, 3, 4, 5, 6, 8, 10, 12, 14, 16, 18, 20, 22, 24, 30, 36, 40, 50, and/or 60 years, or any range or value therein.

The recipients of administration of compounds and/or compositions of the present invention can be any vertebrate animal, such as mammals, birds, bony fish, frogs and toads. Among mammals, the preferred recipients are mammals of the Orders Primata (including humans, apes and monkeys), Arteriodactyla (including horses, goats, cows, sheep, pigs), Rodenta (including mice, rats, rabbits, and hamsters), and Carnivora (including cats, and dogs). Among birds, the preferred recipients are turkeys, chickens and other members of the same order. The most preferred recipients are humans.

Antibodies Capable of Binding To Specific Jak Proteins Without Interfering With Kinase Activity The present invention also provides antibodies useful for detecting and extracting specific Jak kinases from eukaryotic cells without disrupting their kinase activity. These antibodies are generated against a peptide fragment representing a portion of the Jak hinge region between domains 1 and 2 that is different for each Jak kinase. Peptides useful for generating such antibodies are derived from amino acids 758–776 of Jak2 (FIGS. 1A–1H; the sequence is DSQRKLQFYED-KHQLPAPK (SEQ ID NO:5)), amino acids 786–804 of Jak1 (FIGS. 2A–2D; the sequence is TLIEKERFYESRCR-PVTPS (SEQ ID NO:6)), and amino acids 819–837 of Tyk2 (FIG. 3; the sequence is SPSEKEHFYQRQHRLPEPS (SEQ ID NO:7)). According to the invention antibodies generated against these peptides can specifically bind to and recognize the Jak protein from which the peptide antigen was derived without interfering with kinase activity.

Through the application of standard immunoprecipitation techniques, these antibodies can be used to obtain cell extracts containing a specific Jak protein for use in the in vitro kinase assay. Such a use is demonstrated for antibody generated against the hinge region of Jak2 kinase in Examples 1–3 and 5.

Jak Genes and Proteins

According to the present invention, the cDNA sequences and corresponding amino acid sequences of Jak kinases are provided, such as Jak3 and murine Jak2 kinase. The nucleotide sequence of a full-length Jak2 cDNA is provided in FIG. 1 (SEQ ID NO:8) and contains an open reading frame (ORF) of 3387 bp encoding the Jak2 protein, which is 1129 amino acids long and has a calculated molecular weight of 130 kDa. The 5' end of the Jak2 cDNA in FIG. 1 has three stop codons before the first ATG. Although the first ATG does not fulfill the Kozak consensus flanking sequences, it is immediately followed by an ATG codon in the typical translation initiation environment (Kozak, M., *Nucl. Acids Res.* 15:8125–8148 (1987)). The 5' end does not contain an obvious signal peptide. The compiled size of the 3' untranslated region of the Jak2 clones is 0.9 kb which corresponds to a 4.4 kb transcript.

Jak3 cDNA was 3.8 kb and contained a long open reading frame encoding a protein with 1099 amino acids and a size of 122.6 kDa The sequence (FIG. 6) is highly related to other Jaks and was termed Jak3.

Known method steps for synthesizing oligonucleotides probes useful for cloning and expressing DNA encoding a Jak kinase of the present invention, based on the teaching and guidance presented herein, are disclosed by, e.g., Ausubel, infra; Sambrook, infra; and Wu et al., *Prog. Nucl. Acid. Res. Molec. Biol.* 21:101–141 (1978), which references are entirely incorporated herein by reference.

A suitable oligonucleotide, or set of oligonucleotides, which is capable of encoding (or which is complementary to a sequence encoding) a Jak fragment is identified as above, synthesized, and hybridized by means well known in the art, against a DNA or, more preferably, a cDNA preparation derived from cells having Jak genes and/or which are capable of expressing a Jak kinase. Single stranded oligonucleotide probes complementary to a Jak activity encoding sequence can be synthesized using method steps (see, e.g., Ausubel, infra; Sambrook, infra).

Such a labeled, detectable probe can be used by known procedures for screening a genomic or cDNA library as described above, or as a basis for synthesizing PCR probes for amplifying a cDNA generated from an isolated RNA encoding a Jak nucleic acid or amino acid sequence. As a further non-limiting example, transformants can be selected for expression by a host cell of a Jak kinase by use of selection media appropriate to the vector used, RNA analysis or by the use of antibodies specific for a target protein as a Jak kinase used in a method according to the present invention.

A target, detectably labeled probe of this sort can be a fragment of an oligonucleotide that is complementary to a polynucleotide encoding a Jak kinase. Alternatively, a synthetic oligonucleotide can be used as a Jak probe which is preferably at least about 10 nucleotides in length (such as 10, 15, 16, 17, 18, 19, 20, 21, 22, 23, 24, 25, 26, 27, 28, 29, 30, 35, 40, 45, 50, 60, 70, 80, 90, 100, or more, or any combination or range therein, in increments of 1 nucleotide), in order to be specific for a target a nucleic acid to be detected, amplified or expressed. The probe can correspond to such lengths of a DNA or RNA encoding a Jak, such as a sequence corresponding to a portion of SEQ ID NO: 1 or a Jak1, Jak2, Jak3 or trk1 sequence presented FIG. 6, wherein the probe sequence is selected according to the host cell containing the DNA, e.g., as presented in Table A1.4 of Ausubel, infra. Jak kinase encoding nucleic acids of the present invention can include 15–1500, such as 15–1009, 15–1006, 30–600, and 90–1500 nucleotides, or any range or value therein, substantially complementary to a portion of a sequence presented in FIG. 6, wherein the codons can be substituted by codons encoding the same or conservatively substituted amino acids, as well known in the art.

Culturing of the host and induction of protein expression can be induced by methods known per se. A nucleic acid sequence encoding a Jak kinase of the present invention can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Known techniques for such manipulations are disclosed, e.g., by Ausubel, infra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression of a Jak kinase or peptide having Jak activity in recoverable amounts. The precise nature of the regulatory regions needed for gene expression can vary from organism to organism, as is well known in the analogous art. See, e.g., Sambrook, infra; Ausubel, infra.

The process for genetically engineering Jak2 kinase, according to the invention, is facilitated through the cloning of DNA encoding a Jak kinase and through the expression of such sequences. DNA encoding a Jak kinase may be derived from a variety of sources according to the invention, including genomic DNA, cDNA, synthetic DNA, and combinations thereof.

Genomic DNA may or may not include naturally occurring introns. Moreover, such genomic DNA may be obtained in association with the 5' promoter region of a Jak gene sequence. The 5' promoter region may be retained and employed for expression of a Jak in those host cells which recognize the expression signals present in this promoter region.

Genomic DNA or cDNA, which does not contain introns, may be obtained in several ways. Genomic DNA can be extracted and purified from suitable cells by means well known in the art. Alternatively, messenger RNA (mRNA) may be isolated from a cell which produces a Jak kinase and used to prepare cDNA by means well known in the art. Such suitable DNA preparations are enzymatically cleaved, or randomly sheared, and ligated into recombinant vectors to form either a genomic or cDNA sequence library (see Ausubel, F. M. et al., *Current Protocols in Molecular Biology*, published by Current Protocols, §§5.0.3–5.10.2 (1987, 1992, 1993, 1994)). Such libraries can then be screened for hybridization with nucleic acid probes based upon a Jak gene sequence provided in FIG. 1 (SEQ ID NO:8) or FIG. 6, in order to identify and isolate cloned Jak encoding sequences (see Ausubel, F. M. et al. supra, §§6.0.3–6.6.1). The members of the library identified by this screen are then analyzed to determine the extent and nature of the Jak sequences they contain.

In lieu of the above-described recombinant methods, a gene sequence encoding Jak kinase can be prepared synthetically according to methods well known in the art (see Ausubel, F. M. et aL, supra, §§2.11.1–2.11.18).

The cloned Jak encoding sequences, obtained through the methods described above, may be operably linked to an expression vector and introduced into a bacterial or eukaryotic cell to produce a Jak kinase. Techniques for such manipulations are well known in the art and are disclosed in Ausubel, F. M. et al., supra, at §§3.0.3–3.16.11.

A DNA is said to be "capable of expressing" a polypeptide if it contains nucleotide sequences which contain transcriptional and translational regulatory information and such sequences are "operably linked" to nucleotide sequences encoding the polypeptide. An operable linkage is a linkage in which the regulatory DNA sequences and the DNA coding sequence sought to be expressed are connected in such a way as to permit expression of the coding sequence. The precise nature of the regulatory regions needed for gene expression may vary from organism to organism, but shall generally include a promoter region which, in prokaryotes, contains both the promoter (which directs the initiation of RNA transcription) as well as the DNA sequences which, when transcribed into RNA, will signal the initiation of translation of the coding sequence. Such regions will normally include those 5'-non-coding sequences involved with initiation of transcription and translation, such as the TATA box, capping sequence, CAAT sequence, and the like.

If desired, the non-coding region 3' to the gene sequence coding for the Jak2 kinase may be obtained by the above-described methods. This region may be retained for its regulatory sequences, such as transcriptional termination and polyadenylation signals. Thus by retaining the 3'-region naturally contiguous to the DNA sequence coding for a Jak kinase, these regulatory regions may be provided. Where the regulatory signals are not satisfactorily functional in the expression host cell, then a 3' region functional in the host cell may be substituted.

To express a Jak kinase in a prokaryotic cell (such as, for example, *E. coli, B. subtilis*, Pseudomonas, Streptomyces, etc.), it is necessary to operably link the Jak kinase encoding sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, etc. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen, I., et al., *J. Bacteriol.* 162:176–182 (1985)) and the σ-28-specific promoters of *B. subtilis* (Gilman, M. Z., et al., *Gene sequence* 324:11–20 (1984)), the promoters of the bacteriophages of Bacillus (Gryczan, T. J., In: *The Molecular Biology of the Bacilli*, Academic Press, Inc., N.Y. (1982)), and Streptomyces promoters (Ward, J. M., et al., *Mol. Gen. Genet.* 203:468–478 (1986)). Prokaryotic promoters are reviewed by Glick, B. R., *J. Ind. Microbiol.* 1:277–282 (1987); Cenatiempo, Y., *Biochimie* 68:505–516 (1986); and Gottesman, S., *Ann. Rev. Genet.* 18:415–442 (1984).

Proper expression in a prokaryotic cell also requires the presence of a ribosome binding site upstream of the gene sequence-encoding sequence. Such ribosome binding sites are disclosed, for example, by Gold, L., et al., *Ann. Rev. Microbiol.* 35:365–404 (1981).

Preferred eukaryotic hosts include yeast, fungi, insect cells, mammalian cells either in vivo, or in tissue culture. Mammalian cells which may be useful as hosts include, but are not limited to, COS cells and cells or cell lines derived from fibroblasts, myeloid leukemias, or normal hematopoietic tissues.

For a mammalian host, several possible vector systems are available for the expression of the Jak kinase. A wide variety of transcriptional and translational regulatory sequences may be employed, depending upon the nature of the host. The transcriptional and translational regulatory signals may be derived from viral sources, such as adenovirus, bovine papilloma virus, Simian virus, or the like, where the regulatory signals are associated with a particular gene sequence which has a high level of expression. Alternatively, promoters from mammalian expression products, such as actin, collagen, myosin, etc., may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation. See, e.g., Ausubel et al., infra, at §§1.5, 1.10, 7.1, 7.3, 8.1, 9.6, 9.7, 13.4, 16.2, 16.6, and 16.8–16.11. Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species.

A preferred host for production of catalytically active Jak kinases is insect cells, for example the Drosophila larvae. Using insect cells as hosts, the Drosophila alcohol dehydrogenase promoter can be used (Rubin, G. M., *Science* 240:1453–1459 (1988)). Alternatively, baculovirus vectors can be engineered to express large amounts of Jak kinase in insects cells (see, for example, Ausubel, F. M. et al., *Current Protocols in Molecular Biology*, published by Current Protocols, §§16.8.1–16.11.7 (1987, 1993, 1994); Jasny, B. R., *Science* 238:1653 (1987); Miller, D. W., et al., in *Genetic Engineering* (1986), Setlow, J. K., et al., eds., *Plenum*, Vol. 8, pp. 277–297). Expression of Jak kinase in insect cells from baculovirus vectors produces activated Jak kinase which may be used in screening assays for inhibitors of Jak kinase activity as described above.

As discussed above, expression of the Jak kinase in eukaryotic hosts requires the use of eukaryotic regulatory regions. Such regions will, in general, include a promoter region sufficient to direct the initiation of RNA synthesis. Preferred eukaryotic promoters include the promoter of the mouse metallothionein I gene sequence (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature (London)* 290:304–310 (1981)); the yeast gal4 gene sequence promoter (Johnston, S. A., et al., *Proc. Natl. Acad. Sci. (USA)* 79:6971–6975 (1982); Silver, P. A., et al., *Proc. Natl. Acad. Sci. (USA)* 81:5951–5955 (1984)); and the 9–27 gene promoter (Reid, L. E., et al., *Proc. Natl. Acad. Sci. USA* 86:840–844 (1989); Ausubel, infra; Lewin, *Genes III*, John Wiley & Sons, publishers, New York, N.Y. (1990); Sambrook et al., Molecular Cloning: A Laboratory Manual, Second edition, Cold Spring Harbor Laboratory, Cold Spring Harbor, N.Y. (1989)).

As is widely known, translation of eukaryotic mRNA is initiated at the codon which encodes the first methionine. For this reason, it is preferable to ensure that the linkage between a eukaryotic promoter and a DNA sequence which encodes the Jak kinase does not contain any intervening codons which are capable of encoding a methionine (i.e., AUG). The presence of such codons results either in a formation of a fusion protein (if the AUG codon is in the same reading frame as the Jak kinase encoding DNA sequence) or a frame-shift mutation (if the AUG codon is not in the same reading frame as the Jak kinase encoding sequence).

The Jak kinase encoding sequence and an operably linked promoter may be introduced into a recipient prokaryotic or eukaryotic cell either as part of a non-replicating DNA (or RNA) molecule, which may either be a linear molecule or, more preferably, a closed covalent circular molecule. Since such molecules are incapable of autonomous replication, the expression of the Jak kinase may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototropy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, H., *Molec. Cel. Biol.* 3:280 (1983); Ausubel, infra; Sambrook, infra.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, πVX. Such plasmids are, for example, disclosed by Sambrook, infra). Bacillus plasmids include pC194, pC221, pT127, etc. Such plasmids are disclosed by Gryczan, T. (In: *The Molecular Biology of the Bacilli*, Academic Press, N.Y. (1982), pp. 307–329). Suitable Streptomyces plasmids include pIJ101 (Kendall, K. J., et al., *J. Bacteriol.* 169:4177–4183 (1987)), and streptomyces bacteriophages such as ΦC31 (Chater, K. F., et al;, In: *Sixth International Snyposium on Actinomycetales Biology*, Akademiai Kaido, Budapest, Hungary (1986), pp. 45–54). Pseudomonas plasmids are reviewed by John, J. F., et al. (*Rev. Infect. Dis.* 8:693–704 (1986)), and Izaki, K. (*Jpn. J. Bacteriol* 33:729–742 (1978)).

Preferred eukaryotic plasmids include BPV, vaccinia, SV40, 2-micron circle, etc., or their derivatives. Such plasmids are well known in the art (Botstein, D., et al., *Miami Wntr. Symp.* 19:265–274 (1982); Broach, J. R., In: *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982); Bollon, D. P., et al., *J. Clin. Hematol. Oncol.* 10:39–48 (1980); Maniatis, T., In: *Cell Biology: A Comprehensive Treatise*, Vol. 3, *Gene sequence Expression*, Academic Press, N.Y., pp. 563–608 (1980)).

Once the vector or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphate-precipitation, direct microinjection, etc. After the introduction of the vector, recipient cells are grown in a selective medium, which selects for the growth of vector-containing cells. Expression of the cloned gene sequence(s) results in the production of the Jak kinase.

Expressed Jak kinase may be isolated and purified as described herein, using conventional methods such as extraction, precipitation, immunoprecipitation, chromatography, affinity chromatography, electrophoresis, or the like.

Having now generally described the invention, the same will be more readily understood through reference to the following example which is provided by way of illustration, and is not intended to be limiting of the present invention.

EXAMPLES

Example 1
Structure of the Murine Jak2 Protein Tyrosine Kinase and Its Role In IL-3 Signal Transduction
Summary Interleukin 3 (IL-3) regulates the proliferation and differentiation of a variety of hematopoietic cells including early progenitors and cells committed to various lineages. The receptor for IL-3 consists of α and β subunits that together are required for the expression of a high affinity receptor. The IL-3 receptor chains are members of the cytokine receptor family and contain cytoplasmic domains that lack identifiable kinase catalytic domains. However, IL-3 binding rapidly induces tyrosine phosphorylation of the β chain of the receptor as well as a number of cellular proteins. To investigate the potential role of the Jak family of protein tyrosine kinases in IL-3 signal transduction, we have obtained full-length CDNA clones for murine Jak1 and Jak2 and prepared antiserum against the predicted proteins. Using antisera against Jak2 we demonstrate that IL-3 stimulation results in the rapid and specific tyrosine phosphorylation of Jak2 and activates its in vitro kinase activity. These results support the hypothesis that Jak2 couples IL-3 binding to tyrosine phosphorylation and ultimately to the biological responses mediated by IL-3.
Introduction Hematopoiesis is regulated through the interaction of a variety of growth factors with their cognate receptors (Metcalf, D., *Nature* 339:27–30 (1989); Clark and Kamen, *Science* 236:1229–1237 (1987)). Among the known hematopoietic growth factors, interleukin-3 (IL-3) supports the proliferation and differentiation of early progenitors as well as cells that are committed to several of the myeloid lineages (Ihle, J. N., in *Interleukins: Molecular Biology and Immunology*, Kishimoto, T., ed., Karger, Basel, pp. 65–106 (1992)). The receptor for IL-3 has been shown to be composed of two subunits, an α subunit of 60–70 kDa and a β subunit of 130–140 kDa which are required for high affinity binding of IL-3 (Miyajima, A., et al., *Annu. Rev. Immunol.* 10:295–331 (1992)). Both the α and β subunits contain the extracellular conserved motifs found in the cytokine receptor superfamily. Similar to other members of this superfamily, the cytoplasmic domains of the receptor subunits share only a limited similarity with other cytokine receptors and lack any detectable catalytic domains that might suggest a signal transducing mechanism. In spite of the lack of catalytic domains, considerable evidence suggests that signal transduction involves tyrosine phosphorylation (Metcalf, D., *Nature* 339:27–30 (1989); Miyajima, A., et al., *Annu. Rev. Immunol.* 10:295–331 (1992)). Specifically, activated tyrosine kinases can abrogate the requirement for IL-3 and IL-3 rapidly induces the tyrosine phosphorylation of several cellular substrates as well as the β subunit of the IL-3 receptor complex. For these reasons there has been considerable interest in identifying a protein tyrosine kinase that may associate with the receptor and be activated by ligand binding.

To identify the spectrum of protein tyrosine kinases that are expressed in IL-3 dependent cells which might be involved in signal transduction, polymerase chain reactions (PCR) have been done with degenerative oligonucleotides to conserved protein tyrosine kinase domains (Wilks, A. F.,

*Methods Enzymol.* 200:533–546 (1991)). Using this approach and Northern blot analysis, IL-3 dependent cells have been shown (Mano, H., et al., *Oncogene* 8:417–424 (1993)) to express the genes for a number of protein tyrosine kinases including lyn, Tec, c-fes, Jak1 and Jak2. The potential involvement of lyn kinase in signal transduction was indicated by a recent study that indicated that IL-3 stimulation increased lyn kinase activity in immune precipitates (Torigoe, T., et al., *Blood* 80:617–624 (1992)). However, we have not detected an effect of IL-3 on lyn kinase activity or on the status of lyn tyrosine phosphorylation in the murine IL-3 dependent cells we have examined. We have also not detected any tyrosine phosphorylation or activation of kinase activity of Tec or c-fes. Therefore our efforts focused on developing reagents to assess the role of murine Jak1 and Jak2 genes in IL-3 signal transduction.

The Jak (Janus kinase; alternatively referred to as just another kinase) family of kinases was initially detected in PCR amplification of tyrosine kinase domains in hematopoietic cells (Wilks, A. F., *Proc. Natl. Acad. Sci. USA* 86:1603–1607 (1989)). These studies identified two closely related genes (FD17 and FD22; later termed Jak2 and Jak1) from which the major PCR amplification products were derived. The complete structure of the human Jak1 gene has been reported (Wilks, A. F., et al., *Mol. Cell. Biol.* 11:2057–2065 (1991)) and, recently, a partial sequence of the murine Jak2 gene was published (Harpur, A. G., et al., *Oncogene* 7:1347–1353 (1992)). Independently a third member of the family (Tyk2) was isolated by screening a cDNA library with a tyrosine kinase domain probe from the c-fms gene (Firmbach-Kraft, I., et al., *Oncogene* 5:1329–1336 (1990)). The family is characterized by the presence of two kinase domains, one of which is a carboxyl domain that has all the hallmarks of protein kinases: The second domain is immediately amino terminal and bears all the hallmarks of a protein kinase but differs significantly from both the protein tyrosine and serine/threonine kinases. Amino terminal to the kinase domains, there are no SH2 and SH3 domains that characterize most of the non-receptor tyrosine kinases. However, there is extensive similarity in this region among the Jak family members and a number of homology domains have been defined (Harpur, A. G., et al., *Oncogene* 7:1347–1353 (1992)).

A link between one member of the Jak family of kinases in signal transduction has been established in recent studies examining the cellular response to interferon alpha (IFNα) (Velazquez, L., et al., *Cell* 70:313–322 (1992)). Using a genetic approach, the Tyk2 gene was cloned by its ability to functionally reconstitute the cellular response to IFNα in a mutant human cell line that was unresponsive to IFNα. It has been speculated that the kinase activity of Tyk2 is activated following IFNα binding and is responsible for the phosphorylation of the 113 and 91/84 kDa proteins of the interferon-stimulated gene factor 3 α (ISGFα) complex (Fu, X. Y., *Cell* 70:323–335 (1992); Schindler, C., et al., *Science* 257:809–813 (1992)). Following phosphorylation this complex associates with the ISGF3γ protein and the complex migrates to the nucleus and activates gene expression by binding to the interferon-stimulated response element.

A role for Jak2 in the response to erythropoietin (EPO) is described in Example 2. The studies described demonstrated that EPO stimulation induces tyrosine phosphorylation of Jak2 and activates its in vitro autophosphorylation activity. Using a series of mutants of EPOR, the induction of Jak2 tyrosine phosphorylation was found to correlate with the induction of biological responses. Jak2 was also shown to physically associate with the membrane proximal, cytoplasmic region of the EPO receptor that is required for biological activity.

In the studies presented here we disclose the complete structure of the murine Jak2 gene. We demonstrate that Jak2 is rapidly tyrosine phosphorylated in response to IL-3 and there is an associated activation of its in vitro autophosphorylation activity. The results provide evidence that Jak2 is the protein tyrosine kinase that couples IL-3 stimulation to tyrosine phosphorylation and ultimately to the biological responses. Moreover, the involvement of Jak2 in the responses to both IL-3 and EPO shows that Jak2, or family members, are involved in the mitogenic signalling pathway of a variety of hematopoietic growth factor receptors.

Materials and Methods

Isolation of Murine Jak2 Clones. Polymerase chain reactions (PCR) with degenerative oligonucleotides corresponding to the conserved domain were used to amplify cDNAs from murine bone marrow derived monocytes as previously described (Wilks, A. F., *Proc. Natl. Acad. Sci. USA* 86:1603–1607 (1989)). The Jak2 cDNA clone was $^{32}$P labeled by random priming and used to screen murine monocyte and IL-3 dependent myeloid NFS58 and DA3 cell phage cDNA libraries (Yi and Willman, *Oncogene* 4:1081–1087 (1989); Morishita, K., et al., *Cell* 54:831–840 (1988); Bartholomew and Ihle, *Mol. Cell. Biol.* 11:1820–1828 (1991)). The isolated cDNA fragments were cloned into pBluescript vector and analyzed by restriction mapping and sequencing. Subsequent phage library screenings were done with the most 5' Jak2 cDNA fragments. The longest cDNAs were subcloned into pBluescript vector and the nucleotide sequence was determined by dideoxy chain termination method (Sanger, F., et al., *Proc. Natl. Acad. Sci. USA* 74:5463–5467 (1977)).

Northern Analysis. Total cellular RNA and poly(A)$^+$ RNA were isolated from mouse tissues and cell lines as previously described (Cleveland, J. L., et al., *Mol. Cell. Biol.* 9:5685–5695 (1989)). Approximately 20 µg of total RNA and 4 µg of poly(A)$^+$ RNA were separated on 1.0% agarose/formaldehyde gels and transferred to nitrocellulose filters. The filters were hybridized with $^{32}$P labeled randomly primed 800 bp cDNA fragment derived from the 5' of Jak2. After autoradiography the filters were stripped and probed with β-actin.

Cells and Cell Culture. The properties of the cell lines used in these studies have been described (Ihle and Askew, *Int. J. Cell. Cloning* 1:1–30 (1989)). The cells were maintained in RPMI supplemented with 10% fetal calf serum (FCS) and murine IL-3 (25 U/ml) for IL3 dependent cells. Mouse bone marrow derived monocytes were grown as previously described (Yi and Willman, *Oncogene* 4:1081–1087 (1989)).

Computer Analysis. The DNA and protein databases were searched with the Genetics Computer Group sequence analysis software. The SWISSPROT and GENBANK databases were searched with FASTA and TFASTA programs.

Generation of Antibodies. Synthetic peptides corresponding to the N-terminal portion of Jak2 protein (amino acids 19–31) and to the hinge region between domains 1 and 2 (amino acids 758–776 (SEQ ID NO:5)) were coupled to keyhole limpet hemocyaimn by MES coupling and used for immunization of rabbits. A synthetic peptide to the analogous hinge region of Jak1 (amino acids 786–804 (SEQ ID NO:6)) was similarly prepared and used for competition studies. Unless otherwise indicated reference to Jak2 antibody or anti-peptide antibody, and manipulations involving Jak2 antibody, refer to antibody generated against the hinge region (amino acids 758–776 (SEQ ID NO:5)).

In vitro Translation and Transcription. Full length Jak1 or Jak2 cDNAs were inserted into pBSK (STRATAGENE) and used to make transcripts with T3 RNA polymerase according to the protocol provided. Approximately 3 µg of RNA was used in translation reactions (Stratagene) in the presence of $^{35}$S translabel (NEN). The products were divided equally and either run on SDS-PAGE without manipulation or immunoprecipitated with Jak1 or Jak2 antisera. Peptide competitions were preformed by incubating peptides (100 µg/ml) with antisera for 1 h at 4° C. prior to use in immunoprecipitations.

In Vitro Kinase Assays. Irnmunoprecipitated proteins on Protein A-SEPHAROSE (PHARMACIA) were washed with kinase buffer (50 mM NaCl, 5 mM $MgCl_2$, 5 mM $MnCl_2$, 0.1 mM $Na_3VO_4$, 10 mM HEPES pH 7.4) and subsequently were incubated for 30 min at room temperature with an equal volume of kinase buffer containing 0.25 mCi/ml $^{32}$P-γ-ATP. After extensive washing, proteins were eluted with sample buffer for SDS-PAGE and separated on 7% gels. $^{32}$P-containing proteins were visualized by autoradiography. In vitro phosphorylated Jak2 was isolated from gel slices and the phosphoamino acid content determined by published procedures (Cooper, J. A., et al., Methods Enzymol. 99:387–402 (1983)).

Results

The spectrum of protein tyrosine kinases expressed in hematopoietic growth factor dependent cells was identified by reverse transcriptase/polymerase chain reactions (RT/PCR) using degenerative oligonucleotides corresponding to the conserved regions of the tyrosine kinase domain (Wilks, A. F., Methods Enzymol. 200:533–546 (1991)). One of the most frequently isolated cDNA clones was found to be identical to the clone FD17 (renamed Jak2) (Wilks, A. F., Proc. Natl Acad. Sci. USA 86:1603–1607 (1989)).

Initial expression analysis indicated that Jak2 was abundantly and widely expressed in hematopoietic cells and prompted us to obtain full length cDNA clones for functional studies. Screening of murine myeloid cDNA libraries resulted in the isolation of several overlapping clones, the longest of which (4 kb) contained the entire coding region of Jak2.

The nucleotide sequence of Jak2 contains an open reading frame (ORF) of 3387 bp and the 5' end has three stop codons before the first ATG (FIGS. 1A–1H). Although the first ATG does not fulfill the Kozak consensus flanking sequences, it is immediately followed by an ATG codon in the typical translation initiation environment (Kozak, M., Nucl. Acids Res. 15:8125–8148 (1987)). The 5' end does not contain an obvious signal peptide. The compiled size of the 3' untranslated region of the Jak2 clones is 0.9 kb which would correspond to a 4.4 kb transcript. One cDNA clone diverged at nucleotide 3271 and had a 1.4 kb 3' untranslated region. Transcripts for this cDNA would be 4.8 kb and may correspond to the larger transcript that is typically seen (see below).

The Jak2 ORF encodes a protein of 1129 amino acids with a calculated molecular weight of 130 kDa. Hydrophilicity analysis, using the Kyte and Doolittle algorithm, failed to identify transmembrane regions. During the course of these studies, a partial sequence of Jak2 was published (Harpur, A. G., et al., Oncogene 7:1347–1353 (1992)) which lacked the first 143 amino acids. A comparison of the sequences indicates 71 nucleotide differences in the coding region, resulting in 9 changes in amino acids (FIG. 1A–1H). The cDNA clones we have obtained did not contain the insert of 7 amino acids in position 711 that was found in one of four cDNA clones of the studies of Harpur et al. (Oncogene 7: 1347–1353 (1992)).

The murine Jak2 gene is very closely related to other Jak family members including the human Jak2 and Jak1 genes (42% and 43 % identities respectively). We have also obtained full length cDNA clones for the murine Jak1 gene which has 45.5% identity to Jak2 at the nucleotide level in the coding region.

Like other members of the family, the murine Jak2 protein has a 600 amino acid long N-terminus that lacks obvious SH2 or SH3 domains. Following this is a kinase related domain (domain 2) and a carboxyl kinase domain (domain 1). The carboxyl kinase domain contains all the structural and functional motifs associated with protein tyrosine kinases including the conserved residues in subdomains VI–VIII that are characteristically associated with protein tyrosine kinases (Hanks, S. K., et al, Science 241:42–52 (1988)). The subdomain VIII, which is hypothesized to contribute to substrate recognition, shows a unique F-W-Y motif that is found in all Jak family members. Domain 2 begins at amino acid 543 and all of the 11 conserved structural subdomains of protein kinases can be identified. However, clear differences in the amino acid composition and spacing in critical kinase subdomains I, II, VI and VIII (Hanks, S. K., et al., Science 241:42–52 (1988)) raise the possibility that this domain may have a regulatory function or alternatively displays a presently unknown substrate specificity.

Although the N-terminus of the Jak family proteins is less homologous than the kinase domains (36–39% verses 49–56%), comparison of the N-terminal sequences of the Jak protein reveals several stretches of homology. Database searches with the N-terminal sequence of Jak2 did not show significant homology with other proteins but the presence of several highly conserved amino acid domains show that Jak proteins are functionally related. Close comparisons of the Jak homology domain 3 reveals some similarity to SH2 domains, but the functional significance of this sequence similarity remains to be determined.

The expression pattern of Jak2 was studied by Northern blot analysis in the following murine tissues: bone marrow, oviduct, ovary, testes, stomach, intestine, skeletal muscle, kidney, liver, thymus, spleen, brain, fetal brain, fetal liver, fetal intestine, and fetal lung. The expression pattern of Jak2 was also studied by Northern blot analysis in the following cell lines: fibroblasts (NIH 3T3); myeloid cells (32D.3, NFS-70, NFS-107, NFS-124, DA-3, DA-22, DA-29, DA31, DA-24, M 1), a mast cell line (AFSTh2), B-cells (DA-8, NFS- 112, plasmacytoma), T-cells (DA-2, EL-4, R-12) and a macrophage cell line (BAC1.2F5). Two transcripts of 4.4 and 4.8 kb were detected in all tissues and cell lines tested, but the level of expression and the relative abundance of the two transcripts varied. The smaller transcript was most abundant in skeletal muscle, spleen and oviduct and barely detectable in liver, kidney and intestine. The Jak2 expression level in adult liver was very low, whereas a more abundant message was detected in fetal liver. The Jak2 expression was detected in all 20 cell lines including 3T3 fibroblasts, B lymphoid, T lymphoid and a variety of myeloid cells representing different stages of differentiation and growth requirements.

In order to biochemically characterize Jak2 protein, anti-peptide antisera were prepared against a region (amino acids 758–776 (SEQ ID NO:5)) that was unique for Jak2 relative to the murine Jak1. To initially assess the reactivity of this antiserum, immunoprecipitations were done with in vitro synthesized Jak2. In vitro translation of Jak2 RNA gave an expected 130 kDa protein. This 130 kDa protein was immunoprecipitated by the Jak2 anti-peptide antiserum, but not by an irrelevant antiserum prepared against a peptide, the sequence of which is not found in Jak2. Immunoprecipitation was competed by the homologous peptide to which the Jak2 antiserum was raised, but not by an irrelevant peptide or by a peptide that is the homologous region of Jak1. The Jak2 anti-peptide antiserum did not immunoprecipitate in vitro synthesized Jak1. Lastly the Jak2 anti-peptide antiserum also immunoprecipitated a comparable 130 kDa protein from in vivo methionine labeled cells which was specifically competed by the homologous peptide. These results demonstrate that the Jak2 cDNA encodes a protein of 130 kDa and that the antipeptide antiserum specifically recognizes the Jak2 protein.

IL-3 stimulation of growth factor dependent cells rapidly induces tyrosine phosphorylation of several cellular substrates including the β subunit of the IL-3 receptor (Ihle, J. N., in Interleukins: Molecular Biology and Immunology, Kishimoto, T., ed., Karger, Basel, pp. 65–106 (1992); Sorensen, P., et al., J. Biol. Chem. 264:19253–19258 (1989)). We therefore examined the possibility that Jak2 might be a substrate of tyrosine phosphorylation.

Western blotting of total cell lysates with a monoclonal antibody against phosphotyrosine (4G10) detected the appearance of several proteins following IL-3 stimulation, including a broad band at 130–140 kDa, a minor band at 70 kDa and major bands at 55 kDa, 50 kDa and 38 kDa. When cell extracts were immunoprecipitated with the Jak2 anti-peptide antiserum, a 130 kDa protein was readily detected in stimulated cells but not in unstimulated cells. Also of note is the presence of induced proteins of 110 kDa, 70 kDa and 60 kDa that coimmunoprecipitated with Jak2. These substrates have been consistently seen in immunoprecipitations of Jak2. Immunoprecipitation with an antiserum against the murine Jak1 consistently detected a weak band at 130 kDa indicating that Jak1 may also be a substrate. Inducible tyrosine phosphorylation of the IL-3 β chain was observed in extracts immunoprecipitated with αIL3Rβ antiserum as a diffuse band with a slightly reduced mobility relative to Jak2 in IL-3 stimulated cells. Thus the broad band seen in total cell lysates consists of both Jak2 and the IL-3 β chain.

To further establish that IL-3 induces Jak2 tyrosine phosphorylation, the kinetics of the response and the ability to detect induction with a second monoclonal antibody against phosphotyrosine were examined. When cells were stimulated with IL-3 and the phosphotyrosine containing fraction was isolated by binding to and elution from sepharose beads containing the 1G2 antiphosphotyrosine monoclonal antibody, Jak2 was readily detected in Western blots using the Jak2 anti-peptide antiserum. A comparable 130 kDa band was not detected in unstimulated cells.

Jak2 tyrosine phosphorylation was readily apparent following 5 min of IL-3 stimulation and subsequently decreased in a manner comparable to the general pattern of tyrosine phosphorylation seen following IL-3 stimulation (Isfort, R., et al., J. Biol. Chem. 263:19203–19209 (1988)). During this period (from 0–120 minutes after IL3 stimulation) there was no change in the levels of Jak2 as assessed by Western blotting with the Jak2 anti-peptide antiserum.

To determine whether IL-3 binding affected Jak2 kinase activity, cells were stimulated with IL-3 for 10 min, Jak2 was immunoprecipitated and in vitro kinase assays were performed. The results are shown in FIG. 4. When extracts were immunoprecipitated with normal rabbit serum, no in vitro kinase activity was detected with extracts from unstimulated or stimulated cells. However, when extracts were immunoprecipitated with Jak2 anti-peptide antiserum, a 130 kDa was readily detected with extracts from IL-3 stimulated cells that co-migrated with the immunoprecipitated Jak2. By contrast, the 130 kDa band was not detected when extracts of unstimulated cells were used. Phosphoamino acid analysis of the 130 kDa band demonstrated the presence of predominantly phosphotyrosine.

Interestingly, there were no other major protein bands phosphorylated in these in vitro reactions, including the heavy chain of IgG (FIG. 3). As discussed below this may reflect the substrate specificity of Jak2 kinase. The specificity for Jak2 is indicated by the ability of the corresponding peptide to block precipitation of kinase activity while a peptide to the corresponding region of Jak1 had no effect. Together the data demonstrate that IL3 stimulation results in the tyrosine phosphorylation of Jak2 and activation of its autophosphorylation activity.

Discussion

Our studies provide the first complete sequence of the murine Jak2 gene. Three lines of evidence indicate that the cDNA clones we have obtained contain the entire coding region. First, comparison of the murine Jak2 5' sequence with the published sequences of human Tyk2 and Jak1 show that all proteins start at the same site. Second, the first ATG is preceded by stop codons in all reading frames. Lastly, the sizes of the compiled cDNA sizes are consistent with the 4.4 and 4.8 kb sized transcripts.

The sequence of our murine Jak2 cDNAs varies from the published partial sequence of the gene (Harpur, A. G., et al., Oncogene 7:1347–1353 (1992)) and includes nine amino acid changes, seven of which are conservative substitutions. Our cDNA clones lacked an insert of 7 amino acids found in one of four Jak2 cDNA clones in the published sequence. A similar putative additional exon was also observed in the human Tyk2 cDNA (Velazquez, L., et al., Cell 70:313–322 (1992)).

IL-3 stimulation of hematopoietic growth factor dependent cells has been shown to rapidly induce tyrosine phosphorylation of a number of cellular substrates (Ihle, J. N., in Interleukins: Molecular Biology and Immunology, Kishimoto, T., ed., Karger, Basel, pp. 65–106 (1992); Ihle, J. N., in Peptide Growth Factors and Their Receptors, Sporn and Roberts, eds., Springer Verlag, New York (1990)). Our results demonstrate that one of these substrates is Jak2 (Ihle, J. N., in Interleukins: Molecular Biology and Immunology, Kishimoto, T., ed., Karger, Basel, pp. 65–106 (1992)). Among the protein tyrosine kinases that are expressed in IL-3 dependent cells and which we could examine, there was a remarkable specificity for Jak2.

In particular, we have not detected any changes in the tyrosine phosphorylation of lyn, tec or c-fes. However we have consistently seen a low level of tyrosine phosphorylation of Jak1 following IL-3 stimulation. This is not due to cross-reactivity of the antisera used and, since both Jak1 and Jak2 are expressed at comparable levels in the cells, is not due to differences in protein levels. Therefore, it is likely that Jak1 shares sufficient similarity to Jak2 to weakly associate with the IL-3 receptor complex. Alternatively, since there is considerable sequence homology between Jak1 and Jak2 at the potential autophosphorylation site, Jak1 may be a substrate for Jak2. To date, we have not detected an effect of IL-3 stimulation on Jak1 in vitro kinase activity.

IL-3 stimulation results in both the induction of tyrosine phosphorylation of Jak2 and activation of Jak2 in vitro kinase activity. The carboxyl protein tyrosine kinase domain of Jak2 contains the characteristic autophosphorylation site that is associated with the activation kinase activity of a number of kinases (Hanks, S. K., et al., Science 241:42–52 (1988)). The in vivo tyrosine phosphorylation is expected to occur at this site based on the concomitant appearance of tyrosine phosphorylation and detectable in vitro kinase activity.

The requirement for IL-3 binding for detection of kinase activity indicates that Jak2 kinase activity is highly regulated in cells, consistent with a major role in growth regulation. The primary substrate of the in vitro kinase reactions was Jak2. In particular, there was no detectable phosphorylation of immunoglobulins nor is enolase a substrate for Jak2, indicating that Jak2 may have a strict substrate specificity. The requirement for receptor activation and the substrate specificity may account for the inability to demonstrate Jak1 protein tyrosine kinase activity under a variety of conditions in previous studies (Wilks, A. F., et al., *Mol. Cell. Biol.* 11:2057–2065 (1991)).

Jak2 is also tyrosine phosphorylated and activated following EPO stimulation (see Example 2). Moreover, these studies demonstrated that Jak2 physically associates with a membrane proximal region of the cytoplasmic domain of the EPO receptor (EPOR) that is essential for function. Whether Jak2 physically associates with one or both subunits of the IL-3 receptor is currently-being examined. However, like EPOR, the β subunit of the IL-3 receptor is rapidly tyrosine phosphorylated and it can be hypothesized that this phosphorylation is mediated by Jak2.

In the case of EPOR, tyrosine phosphorylation occurs at sites in the cytoplasmic, carboxyl end and this region is not required for mitogenesis. Whether the tyrosine phosphorylation of the IL-3 β subunit contributes to the biological response is not known.

The ability of both IL-3 and EPO to induce the tyrosine phosphorylation and activation of Jak2 shows the possibility that Jak2 may be a component in the signal transducing pathways of several cytokine receptors. We have also found that GM-CSF and G-CSF induce the tyrosine phosphorylation of Jak2. This is consistent with several studies that have shown that these hematopoietic growth factors induce comparable patterns of tyrosine phosphorylation (Ihle, J. N., in *Interleukins: Molecular Biology and Immunology*, Kishimoto, T., ed., Karger, Basel, pp. 65–106 (1992)). We have also observed tyrosine phosphorylation of Jak2 in response to IFNγ in a macrophage cell line.

The hematopoietic growth factor receptors are members of a receptor superfamily that also includes the receptors for growth hormone, the prolactin receptor, ciliary neurotropic factor and others (Bazan, J. F., *Science* 257:410–413 (1992)). Moreover, the receptors for interferon, although more distantly related, have been speculated to have evolved from a common progenitor. Recent studies (Velazquez, L., et al., *Cell* 70:313–322 (1992)) have shown that Tyk2 is involved in IFNα signalling. Our studies have shown that Tyk2 are involved in the signalling pathways of IL-3 and EPO (see Example 2) as well as G-CSF, GM-CSF and IFNγ. In addition, recent studies have implicated Jak2 in the response to growth hormone. Therefore Jak family kinases are involved in the signal transducing pathways utilized by several members of the cytokine/interferon superfamily of receptors. Moreover, the Jak family of kinases may also regulate gene expression through comparable pathways involving family members related to the ISGF3α proteins (Schindler, C., et al., *Proc. Natl. Acad. Sci. USA* 89:7836–7839 (1992); Fu, X-Y., et al., *Proc. Natl. Acad. Sci. USA* 89:7840–7843 (1992)) and the ISGF3γ related DNA binding proteins including ICSBP, IRF1, IRF2 and possibly myb (Veals, S. A., et al., *Mol. Cell. Biol.* 12:3315–3324 (1992)).

Example 2
Jak2 Associates with the Erythropoietin Receptor and Is Tyrosine Phosphorylated and Activated Following Stimulation With Erythropoietin Summary Erythropoietin (EPO) regulates the proliferation and terminal differentiation of erythroid lineage cells through its interaction with its receptor (EPOR). EPOR is a member of the cytokine receptor family and contains a cytoplasmic domain that lacks an identifiable kinase catalytic domain. Binding of EPO, however, rapidly induces tyrosine phosphorylation of EPOR as well as a number of cellular proteins. The ability to induce tyrosine phosphorylation is tightly correlated with the ability of the receptor to induce transcription of immediate early genes and to be mitogenic. These biological responses have been shown to require a membrane proximal region of the receptor cytoplasmic domain. Here we demonstrate that one of the substrates of protein tyrosine phosphorylation is the 130 kDa Jak2, a protein tyrosine kinase. Moreover, EPO stimulation activates Jak2 in vitro autophosphorylation activity. Using a series of mutants of EPOR, the induction of Jak2 tyrosine phosphorylation and autophosphorylation activity were found to correlate with the induction of biological responses. Furthermore, we show that Jak2 physically associates with the membrane proximal region of the EPOR cytoplasmic domain that is required for biological activity. Together the results indicate that Jak2 is the kinase that couples EPO binding to tyrosine phosphorylation and ultimately the biological responses that are required for erythropoiesis.

Introduction

Hematopoiesis is regulated through the interaction of a variety of hematopoietic growth factors with their cognate receptors (Clark and Kamen, *Science* 236:1229–1237 (1987); Metcalf, D., *Nature* 339:27–30 (1989)). The majority of hematopoietic growth factor receptors belong to a common cytokine receptor family that is characterized by the presence of four positionally conserved cysteines and a WSXWS (SEQ ID NO:1) motif in the extracellular domain. The family is also characterized by variably sized cytoplasmic domains that show very limited sequence similarity and which do not contain identifiable motifs that might indicate the signal transducing mechanisms. Erythropoietin (EPO) is the hematopoietic growth factor which uniquely supports the proliferation and terminal differentiation of cells committed to the erythroid lineage (Krantz, S. B., *Blood* 77:419–434 (1991)). The EPO receptor (EPOR) was cloned by expression cloning (D'Andrea et al., *Cell* 57:277–285 (1989)) and the sequence of the cDNA predicts a protein of 507 amino acids with a single membrane-spanning domain and the motifs associated with the cytokine receptor superfamily. Unlike several of the hematopoietic growth factor receptors, a single gene product has been shown to be sufficient for EPO binding and function (D'Andrea et al., *Cell* 57:277–285 (1989)).

Introduction of the EPOR into IL-3 dependent cell lines confers on the cells the ability to proliferate in response to EPO and this has provided an important model to study receptor signal transduction (D'Andrea et al., *Cell* 57:277–285 (1989); Miura et al., *Mol. Cell Biol.* 11:4895–4902 (1991)). In transfected cells, EPO induces the expression of a series of immediate early genes including c-myc, c-fos, c-pim-1 and egr-1 (Miura et al., *Mol. Cell. Biol.* 13:1788–1795 (1993)). In addition, EPO induces the rapid tyrosine phosphorylation of a series of cellular substrates (Linnekin et al., *Proc. Natl. Acad. Sci. USA* 89:6237–6241 (1992); Dusanter-Fourt et al., *J. Biol. Chem.* 267:10670–10675 (1992); Quelle and Wojchowski, *J. Biol. Chem.* 266:609–614 (1991); Miura et al., *Mol. Cell Biol.* 11:4895–4902 (1991); Yoshimura and Lodish, *Mol. Cell. Biol.* 12:706–715 (1992); Damen et al., *Blood*

80:1923–1932 (1992)), suggesting that EPOR may function by coupling ligand binding to the activation of a protein tyrosine kinase. One of the substrates of EPO induced tyrosine phosphorylation is the receptor (Dusanter-Fourt et al., *J. Biol. Chem.* 267:10670–10675 (1992); Yoshimura and Lodish, *Mol. Cell. Biol.* 12:706–715 (1992); Miura et al., *Mol. Cell Biol.* 11:4895–4902 (1991)).

The cytoplasmic domain of EPOR consists of 236 amino acids and contains some amino acid sequence similarity to the cytoplasmic domain of the IL-2 receptor β chain (D'Andrea et al., *Cell* 58:1023–1024 (1989)). EPOR also contains a region that has similarity to the cytokine receptor conserved domains, termed box 1 and 2, which were initially defined in the IL-6 signal transducing gp130 protein (Murakami et al., *Proc. Natl. Acad. Sci. USA* 88:11349–11353 (1991)). The membrane proximal region of the cytoplasmic domain has been shown to be essential for the biological activities of the receptor. Carboxyl truncation of 108 amino acids has no effect on the ability of the receptor to induce immediate early genes, induce tyrosine phosphorylation or cause mitogenesis (Miura et al., *Mol. Cell. Biol.* 13:1788–1795 (1993); Miura et al., *Mol. Cell Biol.* 11:4895–4902 (1991)). In some cells lines, carboxyl truncations have increased the mitogenic response (D'Andrea et al., *Mol. Cell Biol.* 11: 1980–1987 (1991a)), suggesting that the membrane distal region negatively affects the response to EPO.

Within the membrane proximal region, carboxyl truncations or deletions of the box 1 and box 2 domains can inactivate the receptor for all biological activities (Miura et al., *Mol. Cell. Biol.* 13:1788–1795 (1993); Miura et al., *Mol. Cell Biol.* 11:4895–4902 (1991)). The importance of this region was further demonstrated by the inactivation of receptor functions by mutation of a conserved Trp residue between box 1 and box 2. Together the results demonstrate that the membrane proximal region of EPOR is essential for all the biological responses that have been examined, including the induction of tyrosine phosphorylation.

Although the importance of EPOR to couple to protein tyrosine phosphorylation for biological activities has been clearly demonstrated, very little has been known concerning the kinases that might be involved. The rapid induction of tyrosine phosphorylation of the carboxyl region of EPOR (Miura et al., *Mol. Cell Biol.* 11:4895–4902 (1991); Yoshimura and Lodish, *Mol. Cell. Biol.* 12:706–715 (1992); Dusanter-Fourt et al., *J. Biol. Chem.* 267:10670–10675 (1992)) suggests that the receptor is closely associated with a kinase either constitutively or following ligand binding. One study (Yoshimura and Lodish, *Mol. Cell. Biol.* 12:706–715 (1992)) identified a non-glycosylated protein of 130 kDa that could be cross-linked with the receptor and which was tyrosine phosphorylated either in vivo or in in vitro kinase assays as assessed by its ability to be detected by an antiphosphotyrosine antibody. Whether the 130 kDa was a kinase could not be determined. Recent studies (Linnekin et al., *Proc. Natl. Acad. Sci. USA* 89:6237–6241 (1992)) also identified a 97 kDa substrate of tyrosine phosphorylation which could be radiolabeled with an azido derivative of ATP, suggesting that it was a kinase. Whether the 130 kDa or 97 kDa potential kinases are previously characterized kinases was not determined.

To detect potentially novel protein tyrosine kinases that might be involved in EPO signal transduction, we have utilized PCR amplification approaches comparable to those described by Wilks, A. F., *Proc. Natl. Acad. Sci. USA* 86:1603–1607 (1989). Similar to the studies of Wilks et al. (Wilks, A. F., *Proc. Natl. Acad. Sci. USA* 86:1603–1607 (1989); Wilks et al., *Mol. Cell. Biol.* 11:2057–2065 (1991)) as well as others (Partanen et al., *Proc. Natl. Acad. Sci. USA* 87:8913–8917 (1990)), two of the products encode two closely related genes (Jak1 and Jak2) which constitute a relatively new kinase subfamily termed the Janus kinases (alternatively referred to as just another kinase family) that also includes the Tyk2 gene (Firmbach-Kraft et al., *Oncogene* 5:1329–1336 (1990)). The Tyk2 gene product has recently been implicated in signal transduction through the interferon a (INFα) receptor (Velazquez et al., *Cell* 70:313–322 (1992)). To explore the potential role of Jak1 and Jak2 genes in hematopoietic signal transduction we have isolated full-length cDNA clones for the murine genes and prepared antisera against the proteins (see Example 1). We report here that EPO stimulation rapidly induces the specific tyrosine phosphorylation of Jak2 and activates its in vitro kinase activity. The induction of tyrosine phosphorylation and activation of kinase activity is dependent upon a membrane proximal region of the EPOR cytoplasmic domain that is essential for mitogenesis. Finally, we demonstrate that Jak2 physically associates with the EPOR and this association requires the membrane proximal region. Together the data demonstrate that Jak2 is involved in EPOR signal transduction.

Results

Jak2 is Specifically and Rapidly Tyrosine Phosphorylated Following EPO Stimulation EPO rapidly induces the tyrosine phosphorylation of a number of cellular substrates, including the receptor for EPO, suggesting that the receptor associates with a cytoplasmic tyrosine kinase(s) (Yoshimura et al., *Nature* 348:647–649 (1990); Damen et al., *Blood* 80:1923–1932 (1992); Quelle and Wojchowski, *J. Biol. Chem.* 266:609–614 (1991); Quelle et al., *J. Biol. Chem.* 267:17055–17060 (1992); Miura et al., *Mol. Cell Biol.* 11:4895–4902 (1991); Linnekin et al., *Proc. Natl. Acad. Sci. USA* 89:6237–6241 (1992); Dusanter-Fourt et al., *J. Biol. Chem.* 267:10670–10675 (1992)). To identify the kinases that might be involved, we and others (Wilks, A. F., *Proc. Natl. Acad. Sci. USA* 86:1603–1607 (1989); Wilks et al., *Mol. Cell. Biol.* 11:2057–2065 (1991); Partanen et al., *Proc. Natl. Acad. Sci. USA* 87:8913–8917 (1990); see Example 1) have used PCR approaches to detect known and potentially novel kinases that are present in hematopoietic growth factor dependent cell lines. These studies, coupled with Northern blot analysis, identified transcripts for lyn, c-fes, tec, Jak1 and Jak2 in DA3 myeloid cells (Mano et al., *Oncogene* 8:417–424 (1993)).

To initially determine whether any of these kinases might be involved in EPO signal transduction we examined their ability to be induce tyrosine phosphorylated as follows. DA3(EPOR) cells were removed from growth factors for approximately 14 hr. The cells were either not stimulated (−) or stimulated (+) with 30 U/ml of human EPO for 10 minutes. The cells were subsequently collected by centrifugation and cell extracts prepared as described in Experimental Procedures below. Aliquots of extracts ($2 \times 10^7$ cells) from unstimulated and stimulated cells were immunoprecipitated with antisera against Jak2, Jak1, c-fes, lyn or tec. The immunoprecipitates were resolved by SDS-PAGE, transformed to nitrocellulose filters and the filters were probed with the 4G10 anti-phosphotyrosine monoclonal antibody as described in Experimental Procedures. To assess the levels of each of the immunoprecipitated tyrosine kinases, comparable blots were probed with antisera against the individual kinases as described in Experimental Procedures below.

In experiment described above, EPO stimulation resulted in the appearance of a p130 kDa band that was immunoprecipitated by an antiserum against Jak2. This band was not observed when the inmunoprecipitation was done in the presence of the peptide to which the antiserum was raised. Comparable results were also obtained when the blots were probed with a different monoclonal antibody against phosphotyrosine (PY20). In contrast, there was no apparent induction of tyrosine phosphorylation of lyn, fes or tec under comparable conditions.

A weak 130 kDa band was seen with antiserum against Jak1 in several experiments conducted as described above. This was not due to the cross-reactivity of the antisera. Both antisera were prepared against peptides with minimal sequence identity between Jak1 and Jak2 and only immunoprecipitate the appropriate kinase from in vitro translation reactions (see Example 1). Together the results show that the Jak kinases are inducibly tyrosine phosphorylated in response to EPO but that Jak2 is preferentially phosphorylated.

To further establish that EPO stimulation induces tyrosine phosphorylation of Jak2, we examined the ability of the monoclonal antibody 1G2 to detect changes in phosphorylation. Cells were treated as above, lysed and the phosphotyrosine containing fraction of proteins was isolated by binding to and elution from 1G2 monoclonal antibody sepharose beads as previously described (Frackelton et al., Mol. Cell Biol. 3:1343–1352 (1983); Isfort et al., J. Biol. Chem. 263:19203–19209 (1988)). The eluted proteins were resolved by SDS-PAGE, blotted to filters and the filters were probed with an antiserum against Jak2. The results were as follows. EPO induced the appearance of a p130 kDa band that was readily detectable with the antiserum against Jak2 in the 1G2 eluates. Western blotting of total cell lysates indicated comparable levels of the p130 kDa Jak2 in both stimulated and unstimulated cells. Probing of blots with antisera against lyn, tec or c-fes failed to detect these kinases.

To determine the kinetics of appearance of tyrosine phosphorylated Jak2, extracts from DA3(EPOR) cells were prepared at 0, 5, 10, 30 and 60 minutes following EPO treatment, immunoprecipitated with antisera against Jak2 and the immunoprecipitates were resolved by SDS-PAGE. The proteins were transferred to nitrocellulose and Western blotted with the 4G10 monoclonal antibody. Under these conditions the induction of a 130 kDa band was readily evident. Stimulation was maximal at 5 min and subsequently declined and was not evident at 1 hour.

Together the above results indicated that EPO stimulation results in the rapid and specific tyrosine phosphorylation of Jak2, relative to other protein tyrosine kinases, in growth factor dependent cells.

EPO Stimulation Activates Jak2 In Vitro Kinase Activity

Tyrosine phosphorylation of protein tyrosine kinases is commonly associated with the activation of kinase activity (Hanks et al., Science 241:42–52 (1988)). We therefore examined the in vitro Jak2 kinase activity in immunoprecipitates. In these experiments cells were stimulated with EPO for 10 minutes, then cell extracts were prepared and immunoprecipitated with either normal rabbit serum (NRS) or antiserum-specific for Jak2, in vitro kinase assays were performed and the phosphorylated proteins resolved by SDS-PAGE. Immunoprecipitates of extracts with normal rabbit serum, from unstimulated or EPO stimulated cells, had no detectable in vitro kinase activity. In contrast, immunoprecipitates of extracts with Jak2 antiserum from EPO stimulated cells had readily detectable kinase activity. The major product of phosphorylation was a 130 kDa protein that co-migrated with Jak2. A comparable activity was not detected in extracts from unstimulated cells. The specificity for Jak2 was indicated by the ability of the peptide to which the Jak2 antiserum was raised to block immunoprecipitation of kinase activity while a peptide to the comparable region of Jak1 had no effect. The primary phosphoamino acid in the in vitro kinase assays detected by 2 dimensional thin layer electrophoresis was determined to be tyrosine.

Tyrosine Phosphorylation of Jak2 and Activation of In Vitro Kinase Activity Correlates with Mitogenesis Our previous studies (Miura et al., Mol. Cell Biol. 11:4895–4902 (1991); Miura et al., Mol. Cell. Biol. 13:1788–1795 (1993)) defined a membrane proximal region of the cytoplasmic domain of EPOR that is essential for induction of tyrosine phosphorylation, induction of the expression of several immediate early genes and for mitogenesis. It was therefore important to determine whether the induction of Jak2 phosphorylation required a comparable domain and whether Jak2 phosphorylation could be correlated with these biological responses. We therefore examined EPO-induced tyrosine phosphorylation mediated by a series of mutated receptors. The H mutant of EPOR lacks the carboxyl terminal 108 amino acids but retain complete biological activity (Miura et al., Mol. Cell. Biol. 13:1788–1795 (1993)).

EPO stimulation of cells expressing the H mutant resulted in the tyrosine phosphorylation of a 130 kDa band. It should also be noted that the observed Jak2 tyrosine phosphorylation with cells expressing the H mutant was stronger than with cells expressing the wild-type receptor. This could be due to somewhat higher levels of Jak2, indicated in the lower panel, or could be due to the removal of a negatively acting domain in the carboxyl region of the receptor (D'Andrea et al., Mol. Cell Biol. 11: 1980–1987 (1991)). Also of note in these experiments is the presence of an inducible 72 kDa phosphoprotein that is detected in the Jak2 immunoprecipitates from extracts of cells expressing the wild-type receptor. This is the size expected for EPOR and the possibility that it is EPOR is further supported by the absence of a comparable band in the experiments with the H mutant in which the carboxyl truncation removes the sites of tyrosine phosphorylation (Miura et al., Mol. Cell Biol. 11:4895–4902 (1991)). This observation showed that EPOR may physically associate with Jak2.

Carboxyl deletions that extend further than the H mutant, such as is present in the S mutant which lacks the carboxyl 146 amino acids of the receptor, inactivate the receptor for induction of tyrosine phosphorylation, induction of the immediate early genes and mitogenesis in DA-3 cells (Miura et al., Mol. Cell Biol. 11:4895–4902 (1991)). No induction of tyrosine phosphorylation was evident following EPO stimulation of cells expressing this mutant.

We also previously demonstrated that the deletion of 20 amino acids (PB mutant) in the membrane proximal region of the cytoplasmic domain inactivates the receptor for all biological activities. No tyrosine phosphorylation of Jak2 was detected in EPO treated cells expressing this mutant.

Lastly we examined a point mutant, PM4, which contains the inactivating mutation $W^{282}$ to R of the conserved W residue between the box 1 and box 2 regions (Miura et al., Mol. Cell. Biol. 13:1788–1795 (1993)). No tyrosine phosphorylation of Jak2 was seen in cells expressing this mutant.

We next examined the correlation between induction of Jak2 tyrosine phosphorylation and mitogenesis with the ability to activate in vitro Jak2 kinase activity. Clones of cells expressing the various mutant receptors were either not stimulated or stimulated with EPO for 10 min. The cells were lysed and Jak2 was immunoprecipitated and the precipitates used in in vitro kinase assays as above. Phosphorylations were assessed by resolving the immunoprecipitates by SDS-PAGE and autoradiography.

As in the previously described results, the major product of phosphorylation detected in the reactions was a 130 kDa phosphoprotein that migrates at the position of Jak2. Phosphorylation of Jak2 was evident in cells stimulated with EPO that expressed the mitogenically active H mutant. No kinase activity was detected in immunoprecipitates of EPO stimulated cells-expressing the mitogenically inactive S truncation mutation, the PB deletion mutant or the PM4 point mutant. These results demonstrate that the membrane proximal region, which is essential for biological activity, is also required for induction of Jak2 tyrosine phosphorylation and for activation of its kinase activity.

Induction of Jak Tyrosine Phosphorylation in 3T3 Cells Expressing EPOR

Jak2 is expressed in a wide variety of cell lineages (see Example 1); Harpur et al., *Oncogene* 7:1347–1353 (1992)). We therefore determined whether Jak2 might couple with EPOR and be inducibly tyrosine phosphorylated in a non-hematopoietic lineage. For this, we examined the response of 3T3 fibroblasts that had been transfected with EPOR expression constructs and express high affinity receptors for EPO.

To initially determine whether EPO stimulation is coupled to tyrosine phosphorylation in fibroblasts expressing the receptor, the ability of EPO to induce tyrosine phosphorylation of cellular proteins as well as the receptor was examined. When blots of extracts from 3T3(EPOR) cells were probed with a antiphosphotyrosine monoclonal antibody, a variety of bands were detected and no detectable differences were seen in cells treated with EPO. However, when the extracts were first immunoprecipitated with an antiserum against EPOR and the blots were probed for phosphotyrosine containing proteins, a 72 kDa protein was detected in EPO stimulated cells, consistent with the induction of tyrosine phosphorylation of EPOR.

When cell extracts were first immunoprecipitated with antiserum against Jak2 and then Western blotted for phosphotyrosine containing proteins or Jak2, the results obtained were as follows. Immunoprecipitates from unstimulated and EPO stimulated fibroblasts contained comparable levels of Jak2 as assessed by probing the blots with an antiserum against Jak2. Following stimulation of the cells with EPO, a 130 kDa band, co-migrating with Jak2, was readily detected by a monoclonal antibody against phosphotyrosine (4G10). A comparable band was not detected in control fibroblasts that did not contain EPOR. These data demonstrate that EPOR can functionally couple with Jak2 in fibroblasts and mediate EPO induced tyrosine phosphorylation of Jak.

Jak2 Associates with Mitogenically Active Receptors for Erythropoietin

The rapid induction of tyrosine phosphorylation of EPOR and Jak2 showed the possibility that Jak2 physically associates with EPOR. This possibility was particularly intriguing since previous studies (Yoshimura and Lodish, *Mol. Cell. Biol.* 12:706–715 (1992)) identified a 130 kDa protein which could be cross-linked to EPOR and which could be phosphorylated in vitro. The possibility of an association of Jak2 and EPOR was also indicated in several experiments in which a phosphotyrosine containing 72 kDa protein co-immunoprecipitated with Jak2.

To directly examine the ability of Jak2 to physically associate with EPO, a series of GST (glutathione-S-transferase)-fusion proteins containing the cytoplasmic domains of wild type and mutant EPORs were constructed and expressed in bacteria. The fusion proteins were purified by affinity binding to glutathione-sepharose beads and the proteins, on affinity beads, were incubated with extracts of unstimulated or EPO stimulated DA3(EPOR) cells. The bound proteins were recovered from the beads, resolved on SDS-PAGE and the gels blotted to nitrocellulose. The blots were subsequently probed with antisera against various tyrosine kinases.

A 130 kDa protein was readily detectable when extracts from either unstimulated or stimulated cells were used and the blots were probed with an antiserum against Jak2. The 130 kDa protein was not detected when the antiserum was incubated with an excess of the peptide to which it was raised. A 130 kDa protein was also detected with an antiserum against Jak1, although at much lower levels than that seen with antiserum against Jak2. Bands were not detected that would be consistent with the presence of lyn, c-fes or tec when the blots were probed with the respective antisera. These results demonstrated that among the tyrosine kinases examined, Jak2 associated with the GST fusion protein containing the cytoplasmic domain of EPOR.

If the physical association of Jak2 and EPOR detected above was biologically relevant it might be predicted that mutations which affect the receptor's mitogenic activity would alter binding and, conversely, truncations of the receptor that do not affect biological activity would not affect binding. To explore this possibility, fusion proteins were constructed that contained the cytoplasmic portion of the truncated, but mitogenically active, H mutant as well as the mitogenically inactive PB and PM4 mutants. When cell extracts were incubated with GST alone bound to glutathione-sepharose and the blots were probed with an antiserum against Jak2, a 130 kDa protein was not detected. In contrast, when fusion proteins containing either the complete cytoplasmic domain or the carboxyl-truncated cytoplasmic domain of the H mutant were used, a 130 kDa protein was readily detectable. The 130 kDa protein was not detected when extracts were incubated with a fusion protein containing the PB mutant deletion. However, the 130 kDa protein was detected when a fusion protein containing the mitogenically inactive PM4 mutation was used. This may be due to the differences in the assays to detect functional verses physical interactions as discussed below. These results show that the membrane proximal domain that is required for mitogenesis also mediates the association of EPOR and Jak2.

Discussion

These studies are the first to identify a protein tyrosine kinase that associates with EPOR and which is tyrosine phosphorylated and activated in response to ligand binding. Previous studies have demonstrated that EPO binding rapidly induces tyrosine phosphorylation of cellular substrates, as well as EPOR, and that this ability is tightly coupled to the induction of mitogenesis (Miura et al., *Mol. Cell Biol.* 11:4895–4902 (1991); Miura et al., *Mol. Cell. Biol.* 13:1788–1795 (1993)). Therefore there has been considerable interest in identifying the kinase (or kinases) that couples EPO binding to the biological responses. Using PCR approaches (Wilks, A. F., Proc. Natl. Acad. Sci. USA 86:1603–1607 (1989); Wilks, A. F., Meth. Enzymol. 200:533–546 (1991); Partanen et al., Proc. Natl. Acad. Sci. USA 87:8913–8917 (1990); Mano et al., Oncogene 8:417–424 (1993)), attempts have been made to define the spectrum of protein tyrosine kinases that are present in myeloid cells and which might contribute to signal transduction.

Among the kinases expressed in IL-3/EPO dependent cells, there has been an interest in lyn, a member of the src gene family kinase, in signal transduction. This was based on the demonstration that IL-2 stimulation of T cells causes an increase in the kinase activity of the highly related 1ck kinase (Horak et al., Proc. Natl. Acad. Sci. USA 88:1996–2000 (1991)) and the demonstration of a physical association of 1ck with the cytoplasmic domain of the IL-2 receptor β chain (Hatakeyama et al., Science 252:1523–1528 (1991)). It should be noted however, that 1ck associates with a region of the IL-2 receptor β chain which is not required for mitogenesis (Hatakeyama et al., Cell 59:837–845 (1989); Hatakeyama et al., Science 252:1523–1528 (1991)). A role for lyn in IL-3 signal transduction was indicated by a report showing that IL-3 stimulation induces an increase in lyn kinase activity (Torigoe et al., Blood 80:617–624 (1992)). However, we have been unable to see a consistent effect of either IL-3 or EPO on lyn kinase activity in the hematopoietic growth factor dependent cells we have examined. As illustrated here, we have also been unable to detect any effect of EPO binding on the state of tyrosine phosphorylation of lyn nor have we been able to demonstrate association of lyn with EPOR.

We have also been unable to detect any changes in tec tyrosine phosphorylation, activation of kinase activity or association with EPOR. Tec is expressed in myeloid cells (Mano et al., Oncogene 8:417–424 (1993)) and its potential importance has been suggested by the identification of highly related kinases in T-cells, itk (IL-2 inducible T cell kinase) and in B-cells BPK/atk (B-cell progenitor kinase, agammaglobulinemia tyrosine kinase) (Silicano et al., Proc. Natl. Acad. Sci. USA 89:11194–11198 (1992); Tsukada et al., Cell (in press, 1993); Vetrie et al., Nature 361:226–233 (1993)). The BPK/atk gene is tightly linked to X-linked agammaglobulinemia (XLA) and kinase activity is reduced or absent in XLA pre-B and B-cell lines (Tsukada et al., Cell (in press, 1993)). Moreover, genetically acquired mutations that would be predicted to inactivate the kinase have been detected in BPK/atk in patients with XLA (Vetrie et al., Nature 361:226–233 (1993)). Therefore BPK/atk is likely to play a critical role in B-cell signalling. The possibility that tec is involved in a more specialized responses of myeloid cells is currently being examined.

We have also not observed evidence for a role for the c-fes gene in EPO signal transducing pathways that regulate cell proliferation. Recent studies have suggested that c-fes may be involved in the terminal differentiation of myeloid cells (Borellini et al., J. Biol. Chem. 266:15850–15854 (1991)) since the levels of c-fes expression increase with differentiation, introduction of an activated form of c-fes into myeloid cells promotes their differentiation (Borellini et al., J. Biol. Chem. 266:15850–15854 (1991)) and c-fes antisense constructs interfere with differentiation (Ferrari et al., Cell Growth Differ. 1:543–548 (1990)).

In contrast to the results obtained with lyn, tec or fes, the experiments with Jak2 readily demonstrated an effect on tyrosine phosphorylation, activation of kinase activity and the ability to associate with EPOR. Moreover, the results were quite striking in the specificity for Jak2 relative to Jak1. Jak1 and Jak2 are highly related and have considerable amino acid sequence identity in both the catalytic domains as well as the amino terminal region (Harpur et al., Oncogene 7:1347–1353 (1992); see also Example 1 herein). The amino acid sequence of Jak2 encodes a protein of 1129 amino acids with a calculated size of 130 kDa which has 45.5% identity with the murine Jak1 kinase.

Although there was a clear specificity for Jak2 in our studies, Jak1 was consistently detected in all assays at low levels. This was not due to cross-reactivity of the antisera since all the antisera used were against peptides from regions that do not contain extensive amino acid identity. In addition the lack of cross-reactivity of the antisera has been established by examining the reactivity with in vitro translated proteins (see Example 1). The difference in reactivity is also not due to differences in the levels of the expression of the two kinases, since both are expressed at comparable levels. Therefore, there appears to be sufficient similarity between Jak1 and Jak2 to allow Jak1 to associate with EPOR but with a much lower affinity.

EPO induction of Jak2 tyrosine phosphorylation was assessed by changes in reactivity with monoclonal antibodies against phosphotyrosine. Importantly, tyrosine phosphorylation was readily demonstrable with both the 4G10 and PY20 monoclonal antibodies by Western blotting techniques. In addition, Jak2 could be isolated from EPO stimulated cells, but not from unstimulated cells, by affinity purification with the 1G2 anti-phosphotyrosine monoclonal antibody coupled to sepharose. These approaches are commonly used to detect changes in protein tyrosine phosphorylation.

Our results demonstrate that EPO stimulation activates the in vitro kinase activity of Jak2 and that the primary substrate is Jak2. Previous studies have found it difficult to demonstrate the kinase activity of Jak1. In particular Wilks et al., Mol. Cell. Biol. 11:2057–2065 (1991) were unable to demonstrate protein tyrosine kinase activity in immunoprecipitates of Jak1 under a variety of conditions. However, they were able to demonstrate protein tyrosine phosphorylation in bacteria with an expression construct containing a fusion protein with the carboxyl kinase domain of Jak1. A comparable fusion protein containing the amino terminal kinase-like domain had no activity. Interestingly, relatively few bacterial proteins were phosphorylated, suggesting that Jak1 may have a restricted substrate specificity. Our results would show that the inability to detect in vitro Jak1 kinase activity is due to lack of appropriate activation in vivo since the ability to detect Jak2 kinase activity was absolutely dependent upon stimulation of the cells with EPO. In this regard, we have been unable to demonstrate Jak1 in vitro kinase activity although Jak1 appears to weakly associate with EPOR and is weakly tyrosine phosphorylated following EPO stimulation.

The primary substrate of tyrosine phosphorylation in the in vitro reactions was Jak2 and specifically no phosphorylation of the immunoglobulin heavy chain was detected. This shows that Jak2 may have very specific substrate specificities. Regarding the mechanism of Jak2 activation, it is possible that ligand binding promotes Jak2 association such that intermolecular phosphorylations occur and result in the activation of kinase activity. Activated Jak2 then has the ability to continue such intermolecular phosphorylations in vitro in immunoprecipitates in a manner that is completely analogous to the receptor protein tyrosine kinases (Ohtsuka et al., Mol. Cell. Biol. 10:1664–1671 (1990); Yarden and Schlessinger, Biochemistry 26:1434–1442 (1987)).

EPO stimulation results in the rapid tyrosine phosphorylation of the EPOR receptor with kinetics that are comparable to that of the tyrosine phosphorylation of Jak2. This indicates that Jak2 is the kinase that is responsible for the EPOR phosphorylation. Phosphorylation of EPOR occurs in the membrane distal carboxyl domain, a region that is not required for mitogenesis. This phosphorylation does not occur in mutants containing a 20 amino acid deletion in the membrane proximal region or with the $W^{282}$ to R mutation in this region. Since both of these mutations also affect Jak2 phosphorylation and kinase activation and the amino acid deletion eliminates the ability of Jak2 to associate with EPOR in vitro, it is likely that Jak2 is the kinase responsible for EPOR phosphorylation. Alternatively, another kinase may associate with Jak2 and thereby be brought into the region of the receptor. If so this additional kinase may also be required for the phosphorylation of Jak2.

With the exception of Jak2 and EPOR, relatively little is known concerning the substrates of EPO induced tyrosine phosphorylation. Substrates of 92 kDa, 70 kDa and 55 kDa have been consistently detected in our studies (Miura et al., *Mol. Cell Biol.* 11:4895–4902 (1991)) and others have identified similar as well as additional substrates (Damen et al., *Blood* 80:1923–1932 (1992); Quelle and Wojchowski, *J. Biol. Chem.* 266:609–614 (1991); Quelle et al., *J. Biol. Chem.* 267:17055–17060 (1992); Linnekin et al., *Proc. Natl. Acad. Sci. USA* 89:6237–6241 (1992); Dusanter-Fourt et al., *J. Biol. Chem.* 267:10670–10675 (1992)). It is also important to note that there are readily detectable substrates of inducible tyrosine phosphorylation of 55 and 70 kDa that co-immunoprecipitate with Jak2. We have excluded a number of potentially interesting substrates including vav, rat, GAP and SHC. However, we have not examined the ISGF3α proteins of 113 and 91/84 kDa which may be substrates of the Jak family kinase Tyk2 and which are involved in the INFα response (Schindler et al., *Science* 257:809–813 (1992); Fu, X. Y., *Cell* 70:323–335 (1992)). Alternatively, related proteins may exist that interact with Jak2 which specifically mediate the transcriptional activation of the genes associated with the response to EPO.

Previous studies identified a 130 kDa phosphoprotein that associates with the EPOR (Yoshimura and Lodish, *Mol Cell. Biol.* 12:706–715 (1992)). By cross-linking, it was shown to be associated with EPOR suggesting the possibility that it was a subunit of a receptor complex comparable to the β chain of the IL-3 or GM-CSF receptor or the pp130 chain of the IL-6 receptor. However, unlike these proteins, the p130 was not N-glycosylated suggesting the it might be a cytosolic protein. The tyrosine phosphorylation of p130 was demonstrated by immunoprecipitation with an anti-phosphotyrosine antibody. However it was not possible to determine whether tyrosine phosphorylation was induced by EPO because of the procedures used to isolate the EPOR/p130 complex. Irrespective, the properties of the p130 are consistent with the hypothesis that it is Jak2.

Our results demonstrate that Jak2 tyrosine phosphorylation and receptor association requires a membrane proximal region that is essential for mitogenesis. This was most strikingly illustrated by the deletion mutant (PB) and by the $W^{282}$ to R point mutant, both of which are mitogenically inactive and concomitantly fail to couple to Jak2 tyrosine phosphorylation or activation of kinase activity. However, only the mutant with the 20 amino acid deletion (PB) lost the ability to physically associate with Jak2. It is likely that the point mutation is sufficient to disrupt a functional interaction of EPOR and Jak2 in vivo, but does not sufficiently lower the affinity of the interaction to eliminate physical interaction in vitro at high protein concentrations.

Our results show that Jak2 association with EPOR is independent of ligand binding. Therefore it can be hypothesized that Jak2 phosphorylation occurs as a consequence of changes affecting the receptor/Jak2 complex. Considerable evidence supports the hypothesis that EPO binding induces dimer- and oligomerization of the receptor and that this is critical for receptor function (Watowich et al., *Proc. Natl. Acad. Sci. USA* 89:2140–2144 (1992)). This is supported by the existence of a mutant EPOR ($R^{199}$ to C) which results in constitutive activation of the receptor (Yoshimura et al., *Nature* 348:647–649 (1990)). This mutation requires the cysteine conversion and results in the ability to form disulfide-linked oligomers in the absence of ligand (Watowich et al., *Proc. Natl. Acad. Sci. USA* 89:2140–2144 (1992)). In cells expressing this mutation, in the absence of EPO, Jak2 kinase is constitutively tyrosine phosphorylated and has in vitro kinase activity. Based on these data, we would further hypothesize that EPO binding causes oligomerization of the EPOR/Jak2 complexes, bringing the kinase molecules in sufficient proximity to result in intermolecular tyrosine phosphorylations. This model is identical to that proposed for several receptor protein tyrosine kinases (Ulhrich and Schlessinger, Cell 61:203–212 (1990)).

Studies with the IFNα receptor have suggested that high affinity binding may require the association of Tyk2 (Firmbach-Kraft et al., *Oncogene* 5:1329–1336 (1990)). This possibility also exists for EPOR. In particular, since Jak2 is ubiquitously expressed, the binding affinities of the receptor have not been measured in the absence of Jak2. Moreover, as demonstrated here, EPOR can functionally associate with Jak2 in fibroblasts. Therefore it will be necessary to express the receptor in phylogenetically distant cells which do not contain a Jak kinase with sufficient homology to associate with the receptor. Under such conditions, it should be possible to address the role of Jak2 binding on the affinity of the receptor.

Jak family kinases are ubiquitously expressed (Wilks et al., *Mol. Cell. Biol.* 11:2057–2065 (1991); see also Example 1). Therefore it was important to determine whether, in fibroblasts, expression of the EPOR was sufficient to couple to activation of tyrosine phosphorylation. As demonstrated, tyrosine phosphorylation of both EPOR and Jak2 was detected following EPO stimulation. Due to the high background of protein tyrosine phosphorylation in the cells used, we were not able to determine whether EPO stimulation resulted in the tyrosine phosphorylation of other cellular substrates. However, EPO stimulation of serum starved cells, does not induce a mitogenic response suggesting that some components required for coupling ligand binding to cell proliferation are missing. Alternatively, insufficient receptors may be expressed. In contrast, a recent report (Watanabe et al., *Mol. Cell. Biol.* 13:1440–1448 (1993)) demonstrated that a reconstituted GM-CSF receptor complex in fibroblasts can transduce a growth-promoting signal.

The membrane proximal region of the EPO receptor with which Jak2 associates contains limited sequence similarity with other hematopoietic growth factor receptors (Murakami et al., *Proc. Natl. Acad. Sci. USA* 88:11349–11353 (1991)). In all cases examined, this region has been shown to be essential for mitogenesis. Thus it will be important to determine whether other members of the hematopoietic cytokine receptor superfamily associate with Jak2, or possibly another member of the Jak family of kinases. In this regard, we have found that IL-3, GM-CSF and G-CSF also induce the specific tyrosine phosphorylation of Jak2. It will be important to further explore the role of Jak family kinases in the responses to other cytokines including IL-2, IL-4 and IL-6.

The ubiquitous expression of the Jak kinases further indicates that they may couple ligand binding to mitogenesis with other non-hematopoietic members of the cytokine receptor superfamily. It has been recognized that there exists structural relationships in the extracellular domains of endocrine growth hormones, the hematopoietic cytokine receptors and a more distant possible relationship with the receptors for tissue factor and interferons (Bazan, J. F., *Immunol. Today* 10:350–354 (1991); Bazan, J. F., *Proc. Natl. Acad. Sci. USA* 87:6934–6938 (1990); De Vos et al., *Science* 255:306–312 (1992)). If these relationships reflect a divergent evolution of a class of signaling receptors, it is possible that they couple signal transduction in a similar manner through interactions with members of the Jak kinase family. Thus the INFα receptor couples through Tyk2 while the receptors for IL-3, GM-CSF, G-CSF and EPO couple through Jak2. Consistent with this we have found that IFNγ induces the tyrosine phosphorylation of Jak2 in a macrophage cell line. In addition recent studies have found that the growth hormone receptor binds to and activates Jak2. It will be of considerable interest to identify which of the Jak kinases other members of the cytokine receptor superfamily associate with and activate.

It will also be of interest to determine whether the Jak family of kinases utilize similar mechanisms to affect gene regulation. Considerable evidence suggests that Tyk2 couples INFα/β binding to tyrosine phosphorylation of the 113 kDa and 91/84 kDa proteins of the ISGF3α (interferon-stimulated gene factor 3) complex (Fu, X. Y., *Cell* 70: 323–335 (1992)). Following phosphorylation this complex associates with the 48 kDa ISGF3γ protein and the complex migrates to the nucleus where it binds the interferon-stimulated response element and activates gene expression. Recent studies (Shuai et al., *Science* 259:1808–1812 (1992)) have demonstrated that IFNγ also induces tyrosine phosphorylation of the 91 kDa protein, but not of the 113 kDa protein, and that it migrates to the nucleus and binds a γ-activated site. As noted above, Jak2 is inducibly tyrosine phosphorylated following IFNγ binding and thus may be the kinase involved. If correct, stimulation of cells with EPO, IL-3, GM-CSF or G-CSF may result in the tyrosine phosphorylation of the 91 kDa ISGF3γ protein or a member of this gene family. In this regard it is important to note that one of the major substrates of tyrosine phosphorylation seen in response to EPO or IL-3 is a protein of approximately 92 kDa (Miura et al., *Mol. Cell Biol.* 11:4895–4902 (1991); Miura et al., *Mol. Cell. Biol.* 13:1788–1795 (1993)). From the above, it can by hypothesized that members of the cytokine receptor superfamily couple ligand binding to inducing gene expression, in part, by the activation of Jak family kinases by autophosphorylation following ligand binding which results in the phosphorylation of members of the ISGF3γ family which, in turn, associate with members of the ISGF3α family of DNA binding proteins, including ICSBP, IRF-1, IFR-2 and c-myb (Veals et al., *Mol. Cell. Biol.* 12:3315–3234 (1992)).

Experimental Procedures
Cell Lines and Culture Conditions
DA3(EPOR) cells expressing the wild type receptor and DA3 cells expressing various mutations were maintained on RPMI-1640 supplemented with 5 mM glutamine, 10% FCS 1 U/mi EPO and G418 as previously described (Miura et al., *Mol. Cell Biol.* 11:4895–4902 (1991)). Starvation of cells was done by washing cells with PBS three times and incubating in RPMI-1640 supplemented with 5 mM glutamine and 10% FCS in the absence of growth factor for 12 to 16 hr. Cells were stimulated with 10–30 U/ml EPO.

Reagents
The preparation and properties of rabbit polyclonal antisera against peptides from Jak1 and Jak2 is described in Example 1. The antiserum against c-fes was kindly provided by J. Downing (St. Jude Children's Research Hospital, Memphis) and its properties have been described (Haynes and Downing, *Mol. Cell. Biol.* 8:2419–2427 (1988)). The antiserum against lyn has also been described (Yi et al., *Mol. Cell. Biol.* 11:2391–2398 (1991)). The antiserum against murine Tec was prepared against GST-fusion proteins and specifically immunoprecipitates a 70 kDa protein from cells expressing Tec but not from control cells. Antiphosphotyrosine monoclonal antibodies included 4G10 (UBI), 1G2 (Oncogene Sciences) and PY20 (ICN) which were purchased from commercial sources. Human EPO was provided by Amgen.

Transfection of 3T3 cells with the pXM EPOR
The plasmid pXM-EPOR (D'Andrea et al., *Cell* 57:277–285 (1989b)) was transfected into 3T3 fibroblast by electroporation as previously described (Miura et al., *Mol. Cell Biol.* 11:4895–4902 (1991)). The cells were maintained in Dulbecco's modified Eagles Media (DMEM) with 10% FCS. In the experiments the cells were starved of growth factors by culturing overnight in media containing 0.5% FCS. The cells were subsequently stimulated with EPO (3 U/ml) in the same medium.

Construction of Fusion Proteins
Bacterially expressed fusion proteins were prepared which contain an amino-terminal glutathione-S-transferase (GST) domain and a carboxyl portion of the murine EPOR cytoplasmic domain. Constructs containing the full length EPOR cytoplasmic domain (amino acids 257–483) were prepared by inserting a blunt-ended BgIII-Kpnl fragment of the EPOR cDNA into the SmaI site of pGEX-2T. Constructs containing the membrane proximal cytoplasmic domain of EPOR (amino acids 257–375) were obtained by inserting a blunt-ended BgIII-HindIII fragment of the EPOR cDNA into the SmaI site of pGEX-2T. Identical constructs were prepared using EPOR cDNAs containing the PB and PM-4 mutations previously described (Miura et al., *Mol. Cell Biol.* 11:4895–4902 (1991)). Fusion proteins then were obtained from *E. coli* strain DH5-alpha transformed with the plasmid constructs and were affinity-purified on glutathione-sepharose (PHARMACIA) as previously described (Smith and Johnson, *Gene* 67:3140 (1988)).

Fusion Protein Binding Assays
Following growth factor stimulation, cells were lysed at $5 \times 10^7$ cells/ml in lysis buffer [1 % Triton X-100, 50 mM NaCl, 30 mM $Na_4P_2O_7$, 50 mM NaF, 0.1 mM $Na_3VO_4$, 5 mM EDTA, 0.1% bovine serum albumin (BSA), 0.05 mg/ml phenylmethylsulphonyl fluoride (PMSF), 10 mM Tris pH 7.6]. Lysates were cleared of debris at 12,000 x g for 10 min and were subsequently incubated with GST-EPOR fusion proteins immobilized on glutathione sepharose. Resins were extensively washed in lysis buffer without BSA and associated proteins then were eluted with sample buffer for SDS-PAGE. Eluted proteins were separated on 8% SDS-PAGE gels and immunoblotted with various antisera.

In Vitro Knase Assays
Immunoprecipitated proteins on Protein A-SEPHAROSE (PHARMACIA) were washed with kinase buffer (50 mM NaCl, 5 mM $MgCl_2$, 5 mM $MnCl_2$, 0.1 mM $Na_3VO_4$, 10 mM HEPES pH 7.4) and subsequently were incubated for 30 min at room temperature with an equal volume of kinase buffer containing 0.25 mCi/ml $^{32}$P-γ-ATP. After extensive washing, proteins were eluted with sample buffer for SDS-PAGE and separated on 7% gels. $^{32}$P-containing proteins were visualized by autoradiography. In vitro phosphorylated Jak2 was isolated from gel slices and the phosphoamino acid content determined by published procedures (Cooper et al., *Methods Enzymol.* 99:387–402 (1983)).

Immunoprecipitation, SDS-PAGE and Western Blotting

Cells were harvested and lysed for 20 min in 1 ml of ice cold lysis buffer (50 mM) Tris-HCl (pH 7.5), 150 mM NaCl, 1% (vol/vol) Triton-X 100, 100 μM sodium vanadate, 1 mM phenylmethylsulfonylfluoride, and 1 mM EDTA. Lysates were pre-cleared by centrifugation for 30 min at 4° C. Supernatant was removed and incubated with preimmune serum and protein A-SEPHAROSE (40 μl of 50% slurry) for 1 hr. The designated serum or monoclonal antibody were then added and incubated at 40° C. for 1–2 hr. Protein A-SEPHAROSE (40 μl of 50% slurry) was added when required, the immunoprecipitates were washed three times in 1 ml of cold lysis buffer, resuspended in Lamelli's samples buffer 10% (vol/vol) glycerol, 1 mM DTT, 1% (wt/vol) SDS, 50 mM M Tris-HCl (pH 6.8) and 0.002% (wt/vol) bromophenol blue and subjected to 7.5% SDS-PAGE. Gels were then transferred electrophoretically to nitrocellulose. The filters were incubated for 2 hr in blotto (5% dehydrated milk in TBSS, 10 mM Tris-HCl pH 7.6 and 137 mM NaCl), then incubated in relevant primary antibody for 1 hr, rinsed in TBSS and incubated for 1 hr in horseradish peroxidase (Amersham) or alkaline phosphatase (Promega) conjugated anti-mouse or anti-rabbit. The filters were then washed and exposed to ECL™ (Amersham Life Science) or 5-bromo-4-chloro-3-indoyl phosphate/nitroblue tetrasodium detection. The ECL detection was subsequently recorded on Kodak XAR-5 film. Competition studies using synthetic peptides were done by incubating the antiserum with 100 μg/ml of peptide for 1 hr at 4° C. prior to adding the mixture to cell lysates or dilution in solutions for Western blotting.

Example 3

Identification of Jak2 as a growth hormone receptor-associated tyrosine kinase

Summary

Growth hormone receptor (GHR) forms a complex with a tyrosine kinase, suggesting involvement of a ligand-activated tyrosine kinase in intracellular signaling by growth hormone (GH). Here we identify Jak2, a nonreceptor tyrosine kinase, as a GHR-associated tyrosine kinase. Immunological approaches were used to establish GH-dependent complex formation between Jak2 and GHR, activation of Jak2 tyrosine kinase activity, and tyrosyl phosphorylation of both Jak2 and GHR. The Jak2-GHR and Jak2-erythropoietin receptor interactions described here and in the accompanying Example 2 provide a molecular basis for the role of tyrosyl phosphorylation in physiological responses to these ligands, thus evidencing shared signaling mechanism among members of the cytokine/hematopoietin receptor family.

Introduction

Although the ability of growth hormone (GM) to promote growth and regulate metabolism has been known for many years (Cheek, D. B. and Hill, D. E., "Effect of growth hormone on cell and somatic growth," in E. Knobli and W. H. Sawyer, eds., *Handbook of Physiology, Vol.* 4:159–185, Washington, D.C. (1974); Davidson, M. B., *Rev.* 8:115–131 (1987)), the molecular mechanism by which GH binding to its receptor elicits its diverse responses has remained an enigma. New insight into GH signaling mechanisms was recently provided by the demonstration that a tyrosine kinase activity is present in a complex with GH receptor (GHR) prepared from GH-treated fibroblasts (Carter-Su., C. et al., *J. Biol. Chem.* 264:18654–18661 (1989); Stred, S. E. et al., *Endocrinol.* 130:1626–1636 (1992); Wang, X. et al., *J. Biol. Chem.* 267: 17390–17396 (1992)). Additional studies in 3T3-F442A cells showing rapid GH-dependent tyrosyl phosphorylation of multiple proteins, tyrosyl phosphorylation of microtubule-associated protein kinases, and stimulation of microtubule-associated protein kinase activity, as well as the inhibition of these actions by inhibitors of the GHR-associated tyrosine kinase (Campbell, G. S. et al., *J. Biol. Chem.* 268:7427–7434 (1993)), suggest a central role for a GHR-associated tyrosine kinase in signaling by GH. Recently, a nonreceptor tyrosyl phosphorylated 122 kd protein was identified in a kinase-active GH-GHR preparation (Wang, X. et al., *J. Biol. Chem.* 268:3573–3579 (1993)). Since autophosphorylation is often a manifestation of an activated kinase, it was hypothesized that this 121 kd phosphoprotein is the GHR-associated kinase.

In this study, we identify Jak2, a 130 kd tyrosine kinase (Harpur, A. G. et al., *Oncogene* 7:1347–1553 (1992)) as a GHR-associated kinase. Jak2 is a member of the recently described Janus family of tyrosine kinases including Jak1, Jak2, and Tyk2. In addition to having a kinase domain, these proteins are characterized by the presence of a second kinase-like domain and the absence of Src homology 2 (SH2), SH3, and membrane-spanning domains (Wilks, A. F. et al., *Mol. Cell. Biol.* 11:2057–2065 (1991); Firmbach-Kraft, I. et al., *Oncogene* 5:1329–1336 (1990); Harpur, A. G. et al., *Oncogene* 7:1347–1553 (1992)).

Here we show that GH binding promotes association of Jak2 with GHR, activation of Jak2, and tyrosyl phosphorylation of both Jak2 and GHR. The identification of Jak2 as a signaling molecule early in the GHR signal transduction pathway provides important insight into signaling by GHR and into the function of Jak2. Work presented in the accompanying Example 2 indicates that Jak2 also associates with the receptor for erythropoietin (EPO), and other data indicate that at least four other members of the cytokine/hematopoietin receptor family (receptors for interleukin [IL]-3), granulocyte-macrophage colony-stimulating factor [GM-CSF], granulocyte colony-stimulating factor [G-CSF], and prolactin) and the more distantly related IFN-γ receptor activate Jak2 (see accompanying Examples). It therefore seems likely that the Jak2-GHR and Jak2-EPO receptor interactions shown herein serve as prototypes for signaling through many members of this large receptor superfamily.

Results

GH Stimulates Pyrosyl Phosphorylation of Jak2

On the basis of previous studies establishing the existence of a GHR-associated tyrosine kinase (Carter-Su., C. et al., *J. Biol. Chem.* 264:18654–18661 (1989); Stred, S. E. et al., *Endocrinol.* 130:1626–1636 (1992); Wang, X. et al., *J. Biol. Chem.* 268:3573–3579 (1993); Campbell, G. S. et al., *J. Biol. Chem.* 268:7427–7434 (1993)), the GHR-associated tyrosine kinase would be expected; first, to be a protein of ~120 kd; second, to be tyrosyl phosphorylated in response to GH; third, to be present in a complex with GHR; and fourth, to exhibit increased activity in response to GH.

Jak2 is a tyrosine kinase of the correct size ($M_r$ of ~130,000; see example 1) to be the GHR-associated kinase and was therefore tested for its ability to be phosphorylated in response to GH. Solubilized proteins from GH-treated 3T3-F442A fibroblasts were immunoprecipitated using antiserum to Jak2 (αJak2) and analyzed by anti-phosphotyrosine antibody (αPY) immunoblot. Cells were incubated with varying physiological concentrations of GH in ranging in 10-fold increments from 0.5 ng/ml to 500 ng/ml (the standard concentration used) for 0, 0.5, 5, 50, and 60 minutes.

GH-dependent tyrosyl phosphorylation of a protein with an $M_r$ (~130,000) appropriate for Jak2 was clearly evident at times as early as 30 seconds and at physiological concentrations of GH as low as 5.0 ng/ml (230 pM). Phosphorylation was transient, being greatly diminished by 60 min after addition of GH. The 130 kd phosphoprotein was detected in αPY immunoblasts of αJak2 immunoprecipitates. The appearance of this 130 kd protein corresponded in time course and GH dose response with the appearance in whole cell lysates of a tyrosyl-phosphorylated protein designated pp121 in previous work (Campbell, G. S. et al., *J. Biol. Chem.* 268:7427–7434 (1993); Wang, X. et al., *J. Biol. Chem.* 268:3573–3579 (1993)). The identity of these two proteins is suggested by their co-migration in cell lysates of tyrosyl phosphorylated pp121 and Jak2 and depletion of tyrosyl-phosphorylated pp121 from cell lysates following immunoprecipitation with αJak2.

The 130 kd phosphoprotein was precipitated specifically by αJak2. Non-immune serum, an unrelated immune serum (αG-LUT-1), and αJak2 preadsorbed with the peptide used to make the antibody failed to immunoprecipitate pp130. Preadsorption of αJak2 with the analogous peptide from murine Jak1 (see Example 1) did not interfere with precipitation of the 130 kd phosphoprotein by αJak2. In contrast with these results using αJak2, immunoprecipitation of 3T3-F442A and IM-9 cell lysates, respectively, with antibodies specific for Jak1 (αJak1) and Tyk2 (αTyk2) revealed little (αJak1) or no (αTyk2) GH-dependent tyrosyl phosphorylation of a ~130 kd protein, despite the presence of these kinases in the respective cell types.

Tyrosyl phosphorylation of the 130 kd protein precipitated from 3T3-F442A cells by αJak2 was increased specifically by GH. Phosphorylation was not increased by platelet-derived growth factor, epidermal growth factor, or insulin-like growth factor 1. These growth factors stimulate tyrosine kinase activity intrinsic to their receptors (Ulrich, A. and Schlessinger, J., *Cell* 61:203–212 (1990)) and promote tyrosyl phosphorylation of multiple proteins in 3T3-F442A fibroblasts (Campbell, G. S. et al., *J. Biol. Chem.* 268:7427–7434 (1993)). The inability to stimulate Jak2 tyrosyl phosphorylation is consistent with the previously reported inability of these growth factors to stimulate tyrosyl phosphorylation of pp121 in whole-cell lysates (Campbell, G. S. et al., *J. Biol. Chem.* 268:7427–7434 (1993)).

Jak2 Associates with the GH Receptor

To determine whether Jak2 forms a complex with GHR, GH-GHR complexes and associated proteins were immunoprecipitated from solubilized, GH-treated 3T3-F442A fibroblasts using antibody to GH (αGH). The presence of Jak2 in αGH immunoprecipitates was assessed either by immunoblotting with αJak2 or by immunoprecipitating with αJak2 and immunoblotting with αPY. When material precipitated using αGH was analyzed, αJak2 was found to immunoblot a 130 kd protein and to immunoprecipitate a tyrosyl-phosphorylated 130 kd protein that co-migrates with a protein recognized by αJak2, indicating that Jak2 associates with GH-GHR complexes. When instead of αGH, the initial immunoprecipitation was performed with antibody to either the cytoplasmic or extracellular domains of GHR (αGHR), αJak2 recognized a 130 kd protein only when cells had been incubated with GH. Consistent with the presence of Jak2 in the αGHR precipitate because of its association with GH-bound GHR, no signal was detected in αJak2 immunoblots of αGH immunoprecipitates when cells had not been incubated with GH nor when immunoprecipitation was performed using an unrelated immune serum (αGLUT-1). These results provide evidence that GH binding to its receptor is necessary to the formation of a complex between GHR and Jak2.

In addition to the 130 kd phosphoprotein believed to be Jak2, a diffusely migrating phosphoprotein of ~120 kd identified by αPY immunoblot was precipitated by αGH, αGHR, and to a lesser extent by αJak2. Consistent with this diffuse band being GHR, its size corresponds to that previously reported for GHR in these cells (Schwartz, J. and Carter-Su, C., *Endocrinology* 122:2247–2256 (1988); Stred, S. E. et al., *Endocrinol.* 130:1626–1636 (1992)), and it co-migrates with a similarly diffuse ~120 kd band identified by αGHR in Western blots of αGH immunoprecipitates. The finding that tyrosyl residues are phosphorylated in the diffuse 120 kd protein present in αGHR immunoprecipitates only when the cells have been incubated with GH offers evidence that tyrosyl phosphorylation of GHR, like tyrosyl phosphorylation of Jak2, is GH dependent. Additional evidence that both Jak2 and GHR are tyrosyl phosphorylated in response to GH is provided by the finding that in a transfected Chinese hamster ovary cell line (CHO4) that expresses a smaller (84 kd) GHR (Eminer, M. et al., *Mol. Endocrinol.* 4:2014–2020 (1990); Wang, X. et al., *J. Biol. Chem.* 268:3573–3579 (1993)), tyrosyl phosphorylation of a 130 kd protein in αGH, αGHR, and αJak2 immunoprecipitates and a diffusely migrating 84 kd protein in αGH and αGHR immunoprecipitates is GH dependent.

Stimulation by GH of Jak Kinase Activity

Previous studies have established that when αGH precipitates are prepared from GH-treated CHO4 cells, the addition of ATP results in the tyrosyl phosphorylation of both a 130 kd and a 84 kd protein (Wang, X. et al., *J. Biol. Chem.* 268:3573–3579 (1993)). To determine whether the 130 kd and 84 kd proteins phosphorylated in this in vitro kinase assay are Jak2 and GHR, respectively, GH-GHR complexes and associated proteins were precipitated from GH-treated and control CHO4 cells using αGH, incubated with [γ-$^{32}$P]ATP, dissociated by boiling in buffer containing SDS, β-mercaptoethanol, and dithiothreitol (DTT), and re-precipitated using either αJak2 or αGHR. In this experiment αJak2 was able to precipitate a 130 kd $^{32}$P-labeled protein appropriate for Jak2, and αGHR was able to precipitate an 84 kd $^{32}$P-labeled protein appropriate for GHR, indicating that both Jak2 and GHR incorporate $^{32}$P in the in vitro kinase assay.

To verify that Jak2 functions as a GH-dependent tyrosine kinase, Jak2 was purified from GH-treated and control 3T3-F442A cells either by direct immunoprecipitation with αJak2 or, to permit a higher degree of purification, by sequential immunoprecipitation using αPY followed by αJak2. When the αJak2 immune complexes were incubated with [γ-$^{32}$P]ATP. $^{32}$P-labeled proteins migrating with a $M_r$ (130,000) appropriate for Jak2 were detected only when the cells had been incubated with GH, indicating an exquisite sensitivity of Jak2 to activation by GH. To verify that Jak2 incorporates phosphate into tyrosyl residues, phosphoamino acid analysis was performed on the $^{32}$P-labeled 130 kd protein isolated from GH-treated 3T3-F442A cells. $^{32}$P was found incorporated almost exclusively into tyrosyl residues, consistent with Jak2 being a GH-sensitive tyrosine kinase. However, the incorporation of a small amount of $^{32}$P (under 1%) into threonine residues in the αJak2 immunoprecipitate leaves open the possibility that Jak2 is a mixed function threonine/serine/tyrosine kinase.

Discussion

Identification of Jak2 As a Signaling Molecule for GHR

The identification of Jak2 as a GH-dependent, GHR-associated tyrosine kinase has important. implications for signal transduction by both GHR and Jak2. With regard to GHR, Jak2 is identified as a signaling molecule that interacts with GHR and is activated in response to GH binding. Its sensitivity to GH and rapid onset following GH addition make tyrosyl phosphorylation of Jak2 among the most sensitive and rapid responses known for GH; activation of Jak2 is an initiating step for GH signal transduction.

Tyrosine kinases have been shown to elicit responses similar to those attributable to GH, including metabolic responses (e.g., insulin receptor), and differentiation (e.g., nerve growth factor receptor) (reviewed by Davidson, M. B., *Rev.* 8:115–131 (1987); Isaksson, O. G. P. et al., *Endocrinol. Rev.* 8:426–438 (1987); levi-Montaicini, R., *Science* 237:1154–1162 (1987); Kaplan, D. R. et al., *Science* 252:554–558 (1991)). Therefore, Jak2 plays a vital role in eliciting the known responses to GH. Consistent with this, no biological functions, other than binding of GH, have been reported for GHR expressed in cells that have low levels of GHR-associated tyrosine kinase activity (e.g., COS-7 and mouse L cells; Leung, D. W. et al., *Nature* 330:537–543 (1987); Wang, X. et al., *J. Biol. Chem.* 267:17390–17396 (1992)). In contrast, a variety of biological functions (e.g., insulin synthesis in RIN5-AH cells and protein synthesis, microtubule-associated protein kinase activity, C-fos gene expression, and lipid synthesis in Chinese hamster ovary cells) can be activated by GH binding when the cloned liver GHR is expressed in cells that have reasonably high levels of GHR-associated kinase activity (Bitlestrup, N. et al., *Proc. Natl. Acad. Sci. USA* 87:7210–7214 (1990); Eminer, M. et al., *Mol. Endocrinol.* 4:2014–2020 (1990); Moller, C.; in *Aspects of the Mechanism of Growth Hormone Action,* Ph.D. Thesis, Karolinska Institute, NO-VUM, Huddinge, Sweden (1992), pp. 1–9; Wang, X. et al., *J. Biol. Chem.* 267:17390–17396 (1992); Moller, C. et al., *J. Biol. Chem.* 267:23403–23408 (1992)).

Furthermore, in 3T3-F442A cells, multiple proteins exhibit GH-dependent increases in tyrosyl phosphorylation. Consistent with activation of Jak2 being required for these phosphorylations, tyrosyl phosphorylation of Jak2/pp121 is simultaneous with or precedes tyrosyl phosphorylation of all the proteins exhibiting GH-dependent tyrosyl phosphorylation, at all GH concentrations tested (this work and Campbell, G. S. et al., *J. Biol. Chem.* 268:7427–7434 (1993)).

Jak2 serves as a signaling molecule for GHR by phosphorylating other proteins. Two proteins have been identified as substrates of Jak2: Jak2 itself and GHR.

Studies using truncated GHR indicate that in the cytoplasmic domain of the GHR, at least 1 of the 4 tyrosyl residues most proximal to the membrane is phosphorylated in response to GH. Studies are underway to identify which of the 4 tyrosines are phosphorylated by Jak2, as well as to identify tyrosines in the C-terminal portion of GHR that might also be phosphorylated. It is important to determine the identity and number of tyrosines phosphorylated in Jak2 and GHR, because these sites are likely to be binding sites for SH2-containing proteins (e.g., phospholipase C-γ, p85 phosphatidylinositol-3 kinase, and GTPase-activating protein; Koch, A. A. et al., *Science* 252:668–674 (1991)) in intercellular signaling pathways. Signaling pathways involving SH2-containing proteins that bind to phosphorylated Jak2 would be expected to be shared by all ligands that activate Jak2, whereas SH2-containing proteins that bind to phosphorylated tyrosyl residues in GHR could provide specificity to a signaling mechanism that utilizes a kinase (i.e., Jak2) with the apparent capacity to service more than one receptor (see below).

Jak2 has also been shown to be activated following the binding of EPO to its receptor (Example 2). Other data indicate that IL-3, GM-CSF, G-CSF, IFN-γ, and prolactin also activate Jak2 ( see Example 1). Thus, Jak2 serves as a kinase for multiple members of the cytokine/hematopoietin receptor family. Since each ligand elicits a separate constellation of responses, kinase activation alone cannot account for specificity. As mentioned above, a set of responses dependent upon phosphorylation of the receptor could provide the specificity. Additionally, specificity could be obtained by interaction between multiple signaling pathways or by the expression of only one receptor type in a particular cell type. This latter mechanism is suggested by the ability of GH, G-CSF, and EPO to stimulate proliferation of IL-3-dependent cells transfected with the cDNA from the appropriate receptor (Fuknaga, R. et al., *EMBO J.* 10:2855–2865 (1991); Ishizaka-Ikeda, E. et al., *Proc. Natl. Acad. Sci. USA* 90:123–127 (1993); Yoshimura, A. et al., *Proc. Natl. Acad. Sci. USA* 87:4139–4143 (1990)).

The commonality of Jak2 activation suggests that there will be shared pathways activated by the ligands that bind Jak2-coupled receptors. Of particular interest for gaining insight into regulation of gene transcription by GH is a pathway initiated by IFN-γ. In response to IFN-γ, the 91 kd protein of the ISGF-3 (IFN-stimulated gene factor 3) complex undergoes tyrosyl phosphorylation and then translocates to the nucleus, where it binds to DNA at the γ-activated site (Shuai, K. et al., *Science* 258:1808–1812 (1992)). Identification of the 90 kd protein phosphorylated in response to GH (Campbell, G. S. et al., *J. Biol. Chem.* 268:7427–7434 (1993)) as the 91 kd protein of the ISGF-3 complex or a family member would implicate one pathway by which GH might elicit some of the effects on gene transcription.

Activation of Jak2 by GH

The exact mechanism by which GH activates Jak2 is not yet known. Earlier studies using an exogenous substrate (poly Glu, Tyr) established that more tyrosine kinase activity is present in a complex with GHR when GHR is prepared from GH-treated cells than from control cells (Stred, S. E. et al., *Endocrinol.* 130:1626–1636 (1992)). The present study shows that this GH-induced increase in kinase activity results from both an increase in affinity of GHR for Jak2 and an increase in Jak2 activity. Jak2 appears to bind directly to GHR, since only two proteins, migrating with sizes appropriate for Jak2 and GHR, are visualized when highly purified kinase-active GH-GHR complexes are isolated from GH-treated $^{35}$S-labeled 3T3-F442A fibroblasts by sequential immunoprecipitation using αPY and then either αGHR or αGH (Stred, S. E. et al., *Endocrinol.* 130:1626–1636 (1992)). The mechanism by which GH promotes association of Jak2 with GHR and Jak2 activation is likely to require dimerization of GHR, since GH-induced tyrosyl phosphorylation of cellular proteins appears to require dimerization of GHR (Silva, C. M. et al., *Endocrinol.* 32:101–108 (1993)). An important role for receptor dimerization in signaling via Jak2 is further suggested by work relating Jak2 activation to EPO receptor dimerization discussed in Example 2.

The results reported herein provide evidence that binding of GH by GHR results in the formation of a ligand-bound GHR dimer capable of binding Jak2. Recruitment of Jak2 leads to the formation of a GH-GHR-Jak2 complex, stimulation of Jak2 tyrosine kinase activity, and tyrosyl phosphorylation of Jak2, GHR, and presumably other proteins. Whether activated Jak2 is present only in a complex with GHR or can dissociate from GHR and phosphorylate proteins that are physically distant from GHR is currently being investigated. Also under investigation is the possibility that GHR can form complexes with kinases other than, or in addition to, Jak2. Obvious candidate kinases include other members of the Jak family. In 3T3-F442A and IM-9 cells, respectively, Jak1 and Tyk2 do not appear to associate with GHR to the same extent as Jak2. However, they or other as yet unidentified Jak kinases may do so in other cell types or under different physiological conditions.

In summary, the experiments presented here, in combination with the similar findings for the EPO receptor presented in Example 2 and other receptors for IL-3, GM-CSF, G-CSF, prolactin, and IFN-γ (see Example 1), indicate that the activation of Jak2 kinase activity by GH and EPO by a mechanism involving a Jak2-receptor complex is a prototype for signaling by many members of the cytokine/hematopoietin family receptors. The finding that GHR shares an important and early signaling molecule with other members of the cytokine/hematopoietin receptor family shows that GH, IL-3, EPO, prolactin, GM-CSF, G-CSF and IFN-γ are likely to share some signaling pathways. However, specificity could still be achieved, since phosphorylation of each receptor offers signaling capabilities unique to each ligand. The variable expression of individual receptors, the potential presence of only a subset of all possible signaling pathways in different cell types, and regulation of the signaling molecules in these pathways by other stimuli permits an additional level of specificity. This finding is likely to lead to the identification of new actions for GH as well as for these other cytokines.

Experimental Procedures

Materials

Stocks of 3т3-F442A and CHO4 cells were kind gifts of H. Green (Harvard University, Cambridge, Mass.) and G. Norstedt (Karolinska Institute, Novum, Sweden), respectively. Recombinant human GH (hGH) was provided by Eli Lilly. Platelet-derived growth factor (recombinant human BB) and recombinant epidermal growth factor came from Collaborative Research. Recombinant insulin-like growth factor 1 was a gift of Kabl/PHARMACIA. Triton X-100 (SURFACT-AMPS X-100) came from Pierce Chemical Company, aprotinin and leupeptin from BOEHRINGER MANNHEIM, recombinant protein A-agarose from REPLIGAN, [γ-$^{17}$P]ATP (6000 Cl/mmol) from New England Nuclear Corporation, and the enhanced chemiluminescence detection system from Amersham Corporation.

Antibodies

αGH (NIDDK-anti-hGH-1C3, lot C11981) came from the National Institute of Diabetes and Digestive and Kidney Diseases/National Hormone and Pituitary Program, University of Maryland and School of Medicine (Baltimore). αPY-Shafer was a gift of Dr. J. A. Shafer (Merck, Sharp, and Dohme Research Laboratory, West Point, Pa.; Pang, D. T. et al., *Arch. Biochem. Biophys.* 242:176–186(1985)), and αPY-41G10 was purchased from UBI. αJak2 was prepared in rabbits against a synthetic peptide corresponding to the hinge region between domains 1 and 2 of murine Jak2 (amino acids 758–776 (SEQ ID NO:5); see Example 1). αJak1 was prepared against a synthetic peptide to a corresponding region in murine Jak1 (amino acids 786–804; see Example 1). One αGHR (αGHR-C1) was prepared in rabbits against a fusion protein composed of glutathione S-transferase fused to the cytoplasmic domain of the cloned mouse liver GHR and affinity purified using immobilized GHR cytoplasmic domain. A second αGHR (αGHBP-poly), kindly provided by Dr. W. R. Baumbach (American Cyanamid, Princeton, N.J.), was produced in rabbits using Recombinant rat GH-binding protein produced in *Escherichia coli* (Sadeghi, H. et al., *Mol. Endocrinol.* 4:1799–1805 (1990)). αTyk2 was a gift of Dr. J. J. Krolewski (Columbia University, New York). αGLUT-1 was prepared in rabbits using band 4.5 purified from human erythrocytes. It recognizes both human and rodent GLUT-1 (Tal, P. -K. et al., *J. Biol. Chem.* 265:21828–21834 (1990)).

Immunoprecipitation and Western Blotting

Cells were grown to confluence and deprived of serum overnight as described previously (Wang, X. et al., *J. Biol. Chem.* 268:3573–3579 (1993)). Cells were incubated for the indicated times with hormone or growth factor as indicated at 37° C. in 95% air, 5% $CO_2$, rinsed with three changes of ice-cold 10 mM sodium phosphate (pH 7.4), 137 mM NaCl, 1 mM $Na_3VO_4$, and scraped in lysis buffer (50 mM Tris (pH 7.5), 0.1% Triton X-100, 137 mM NaCl, 2 mM EGTA, 1 mM $Na_3VO_4$, 1 mM phenylmethylsulfonyl fluoride, 10 μg/ml aprotinin, and 10 μg/ml leupeptin) on ice. Cell lysates were centrifuged at 12,000×g for 10 min, and the resulting supernatants were incubated on ice 90 min with the indicated antibody. Immune complexes were collected on protein A-agarose during a 30–60 min. incubation at 8° C., washed three times with wash buffer (50 mM Tris (pH 7.5), 0.1% Triton X-100, 137 mM NaCl, 2 mM EGTA) and boiled for 5 min in a mixture (80:20) of lysis buffer and (250 mM Tris [pH 6.8], 10% SDS, 10% β-mercaptoethanol, 40% glycerol). Unfractionated lysates were brought to the same final concentrations of Tris, SDS, β-mercaptoethanol, and glycerol and boiled for 5 min. The immunoprecipitates and lysates were subjected to SDS-PAGE followed by Western blot analysis with the indicated antibody (1:1000 to 1:5000 dilution used) using the enhanced chemiluminescence detection system (Campbell, G. S. et al., *J. Biol. Chem.* 268:7427–7434 (1993)). In some experiments, the proteins were dissociated from the immune complexes and then re-immunoprecipitated before analysis by Western blot.

Dissociation and Re-Immunoprecipitation of Immune Complexes

The immune complexes from the initial immunoprecipitation were washed once with 50 mM Tris, 137 mM NaCl (pH 7.5), brought to a final concentration of 0.75% SDS, 2% β-mercaptoethanol, 100 mM DTT, 100 μg/ml aprotinin, and 100 μg/ml leupeptin by addition of an equal volume of a 2× concentrated stock, and then boiled for 5 min.

The eluted proteins were diluted 10-fold with lysis buffer. A portion was removed, mixed (80:20) with SDS-PAGE sample buffer, and boiled for 5 min. The remaining sample was incubated with the second antiserum on ice for 60–90 min and with protein A-agarose at 8° C. for 1 hr. The immune complexes were washed three times with lysis buffer and boiled for 5 min in a mixture (80:20) of wash buffer and SDS-PAGE sample buffer.

Immunoprecipitation for Kinase Assays

Serum-deprived cells were incubated at 25° C. in the absence of presence of 30 ng/ml hGH for 60 min. The relatively long incubation period, low GH concentration, and low temperature were used to maximize the in vitro incorporation of $^{32}P$ into pp130 and GHR during the kinase assay. Cells were washed with phosphate-buffered saline, solubilized in 25 mM HEPES, 2 mM $Na_2CO_4$, 0.1% Triton X-100, 0.5 mM DTT, 1 mM phenylmethylsulfanyl fluoride, 10 μg/ml aprotinin, 10 μg/ml leupeptin (pH 7.4) (HVT), and centrifuged at 200,000×g for 1 hr at 4° C. Soluble proteins were incubated on ice for 1 hr with either αGH (1:10,000 dilution), αPY-Shafer (15 μg per plate of cells), or αJak2 (1:1,500 dilution) (Carter-Su., C. et al., *J. Biol. Chem.* 264:18654–18661 (1989)). Protein A-agarose was added for an additional 1 hr at 8° C. Immune complexes were washed three times with 50 mM HEPES, 150 mM NaCl, 0.1% Triton X-100, 0.5 mM DTT (pH 7.6) (NHT) and then once with 50 mM HEPES, 100 mM NaCl, 6.25 mM MnCl$_3$, 0.1% Triton X-100, 0.5 mM DTT (pH 7.6) (HNMT).

Sequential Immunoprecipitation With αPY and αJak2

Proteins immobilized on αPY-protein A-agarose complexes were transferred to a small plastic column and equilibrated for 5 min with 10 mM p-nitrophenyl phosphate, 20 μg/ml aprotinin, 20 μg/ml leupeptin in HNMT (eluting buffer). Phosphoproteins were then eluted with 180 μl of eluting buffer, αJak2 (1:200 dilution) was added, and the mixture was incubated on ice for 1 hr. Protein A-agarose and 0.7 ml of HNMT containing 20 μg/ml aprotinin, 20 μg/ml leupeptin (phosphorylation buffer) was added, and incubation continued at 6° C. for 1 hr. Immune complexes were washed three times with NHT and once with phosphorylation buffer.

In Vitro Kinase Assay and Phosphoamino Acid Analysis

Proteins immobilized on αJak2 or αGH were mixed with 95 μl of phosphorylation buffer. [γ$^{32}$P]ATP was then added to yield a final concentration of 10 μM ATP and 5 mM MnCl$_2$. After 10 min at 30° C., the reaction was stopped with the addition of 10 mM EDTA in NHT. The immune complexes were washed three times with NHT and once with phosphorylation buffer. $^{32}$P-labeled proteins were either subjected to a second immunoprecipitation or boiled for 5 min in SDS-PAGE sample buffer, resolved by SDS-PAGE, and visualized by autoradiography. The phosphoamino acid content of phosphorylated proteins was determined by limited acid hydrolysis using a modification of the procedure of Hunter and Selton (Hunter, T. and Selton, B. M., *Proc. Natl. Acad. Sci. USA* 77:1311–1315 (1980)) as described previously (Carter-Su., C. et al.,*J. Biol. Chem.* 264:18654–18661 (1989); Stred, S. E., et al., *Endocrinol.* 127:2506–2516 (1990); Wang, X. et al., *J. Biol. Chem.* 267:17390–17396 (1992)).

SDS-PAGE and Densitometry

Proteins were separated by SDS-PAGE on 3%–10% gradient gels (30:0.05 acrylamide:bisacrylamide) as described previously (Carter-Su., C. et al., *J. Biol. Chem.* 264:18654–18661 (1989)). Densitometry was performed using a Bio-Med Instruments laser scanning densitometer attached to an Apple IIE computer (Bio-Med Instruments VIDEOPHORESIS II data analysis computer program).

Example 4
Complementation of a Mutant Cell Line Defective in the Interferon-γ Signal Transduction Pathway by the Protein Tyrosine Kinase Jak2
Summary The cell surface marker CD2 was placed under the control of the interferon-inducible 9–27 gene promoter and introduced into human HT1080 cells. A clone of cells showing a good response of CD2 to interferons-α, -β and -γ was selected and pools of mutagenized cells were screened for defective cell surface expression of CD2 and Class I HLAs in response to interferon-γ. Mutants in different complementation groups were isolated. Mutant γ-1 is deficient in the induction of all interferon-γ-inducible genes tested but retains a normal response to interferons-α and -β. Transfection of mutant γ-1 with protein tyrosine kinase Jak2 restored the wild-type phenotype. A role for Jak2 in the primary response to interferon-γ is indicated.

Introduction

The interferons (IFNs) confer an antiviral state on cells and can affect both cell growth and function (Pestka, S., et al., *Annu. Rev. Biochem.* 56:727–777 (1987)). There are three major antigenic types of human IFN: alpha (α), beta (β) and gamma (γ). Gene induction by IFNs-αβ and IFN-γ is through separate receptors. The existence of a minor IFN-β specific receptor cannot be excluded (Pellegrini, S., et al., *Mol. Cell. Biol.* 9:4605–4612 (1989)) and the multiplicity of IFN-α subtypes shows that the interaction of these with the IFN-αβ receptor(s) is likely to be complex.

The isolation of mutants affecting both the IFN-αβ and the IFN-γ signal transduction pathways has indicated that common factors are involved (John, J., et al., *Mol. Cell. Biol.* 11:4189–4195 (1991); McKendry, R., et al., *Proc. Natl. Acad. Sci. USA* 88:11455–11459 (1991)). One such factor (p91, below and Example 4) has recently been identified (Schindler, C., et al., *Science* 258:1808–1812 (1992); Shuai, K., et al., *Science* 258:1808–1812 (1992)). IFN-binding components have been cloned for both major receptors (Aguet, M., et al., *Cell* 55:273–280 (1988); Uze, G., et al., *Cell* 60:225–234 (1990)). Signal transduction subunits have yet to be isolated, but the p48, p84, p91 and p113 polypeptide components of the primary transcription factor ISGF3, activated in response to IFNs-α and -β, have been cloned and characterized (Veals, S. A., et al., *Mol. Cell. Biol.* 12:3315–3324 (1992); Schindler, C., et al., *Proc. Natl. Acad. Sci. USA* 89:7836–7839 (1992); Schindler, C., et al, *Proc. Natl. Acad. Sci. USA* 89:7840–7843 (1992)). There is rapid phosphorylation on tyrosine of p91, p84 and p113 in response to IFN-α and of p91 and p84 in response to IFN-γ (Shuai, K., et al., *Science* 258:1808–1812 (1992)). In addition, complementation of mutant U1A (11.1) which was isolated from cells expressing a drug-selectable marker under the control of the predominantly IFN-αβ-responsive 6–16 gene promoter, has revealed a role for the protein tyrosine kinase Tyk2 in the IFN-αβ response pathway (Velazquez, L., et al., *Cell* 70:313–322 (1992)). Here, using an alternative selection technique, complementation of a mutant in the IFN-γ response by Jak2, another member of the same family of protein tyrosine kinases (Wilks, A. F. et al., *Mol. Cell. Biol.* 11:2057–2065 (1991); Harpur, A. G., et al., *Oncogene* 7:1347–1353 (1992); Firmbach-Kraft, I., et al., *Oncogene* 5:1329–1336 (1990); Example 1), is reported.

Results

The 9–27 gene promoter is inducible by IFN-γ as well as IFNs-α and -β (Reid, L. E., et al., *Proc. Natl. Acad. Sci. USA* 86:840–844 (1989)). Significant constitutive expression from this promoter precluded a drug selection protocol. Accordingly a clone of cells (2C4) expressing the simple cell-surface marker CD2 (normally expressed only on T-cells) under the control of the 9–27 promoter was derived and the fluorescence activated cell sorter (FACS) used to screen for loss or gain of IFN-γ inducibility. IFN-inducible expression of endogenous Class I and II HLAs was also monitored. In 2C4 cells good induction of all three antigens by IFN-γ and of CD2 and Class I by IFN-α was observed.

Mutant γ-1 was isolated by mutagenesis of 2C4 and several rounds of sorting. To enhance the isolation of trans rather than cis mutants and of mutants in the primary rather than secondary IFN-γ response pathways, the final two sorts were on both CD2 and Class I. Mutant γ-1 is defective in the response to IFN-γ but not to IFN-α or IFN-β. Transfection of this mutant with a murine Jak2 expression construction (Example 1), however, restored the IFN-γ response of all three cell surface markers in an enriched population and clones of transfectants. Transfection with murine Jak1, in the same construct, was without effect.

The expression of a spectrum of IFN-γ-inducible mRNAs was also monitored by RNase protection. For all eight IFN-inducible mRNAs tested the positive IFN-γ response (minimal for IRF1 and GBP) was the same for 2C4, mutant γ-1 and the γ-1/Jak2 transfectants, whereas for IFN-γ the response observed in 2C4 was lost in γ-1 but restored in the γ-1/Jak2 transfectants. A gamma activation sequence (GAS) motif has recently been identified as mediating the primary IFN-γ response of the GBP and ITF1 genes through p91 (see Example 1; Decker, T., et al., *EMBO J.* 10:927–932 (1991); Kanno, Y., et al., *Mol. Cell. Biol.* 13:3951–3963 (1993)). The DNA elements and/or factors governing the primary IFN-γ response of the remainder of the genes tested have yet to be rigorously established. The fact, however, that all of the genes tested are affected is consistent with the defect in mutant γ-1 being in the primary IFN-γ response pathway.

In all cases the IFN-γ response was restored by Jak2 and the IFN-γ dose response curves for the wild-type 2C4 and γ-1/Jak2 transfectants were essentially identical: a clear response was seen at 10 IU/ml and an approaching maximal response at 100 IU/ml. No restoration of IFN-γ response was observed on transfection of γ-1 cells with a functional Tyk2 expression clone and, in an inverse experiment, Jak2 did not complement the defect in Tyk2 in a U1 mutant.

The defect in mutant γ-1 cells does not reflect the absence of Jak2 protein since levels comparable to wild-type were observed on western transfer as was the case for Jak1 and Tyk2. The anti-peptide antibody used to immunoprecipitate Jak2 and to probe the western transfer was designed to distinguish between Jak1 and Jak2 and has high specificity for Jak2 (see Examples 1–2). The mutation in γ-1 may, therefore, reflect point or other minor mutations affecting the function but not the production of Jak2. Alternatively, the mutation could be in an upstream component which, once mutated, fails to interact productively with normal levels of endogenous human Jak2, but is rescued by high levels (see Example 5) of the transfected murine Jak2.

It will require substantial additional work before one can be certain of the precise nature of the mutation involved. The defect in mutant γ-1 is, however, without any apparent major effect on the biding of IFN-γ to its receptor. Essentially identical binding was reproducibly observed with wild-type 2C4 and mutant γ-1 cells. This is in contrast to the situation with mutant U1A (originally coded 11.1) in which the defect in Tyk2 results in loss of high affinity receptor binding for IFN-α (Pellegrini, S., et al., *Mol. Cell. Biol.* 9:4605–4612 (1989)). It will be of interest to determine whether this difference reflects the absence of Tyk2 but not Jak2 protein in U1A and γ-1 respectively, or a more fundamental difference in the presumptive interaction of the two kinases with their respective receptor complexes. The Jak2 protein, like Tyk2, does not appear to be significantly induced in response to IFNs γ or -α in the wild-type cells.

Discussion

Here it is shown that a mutant human cell line, defective in the IFN-γ response of all genes tested, is complemented by murine Jak2. Example 5 shows: (1) direct evidence that the defect in mutant γ-1 is early in the primary response pathway; (2) that Jak2 is rapidly phosphorylated on tyrosine in response to IFN-γ; and (3) results consistent with the rapid activation and (auto)phosphorylation of Jak2 in response to IFN-γ in wild-type but not mutant cells.

Irrespective of the precise nature of the mutation in γ-1, these data indicate an essential role for Jak2 in the primary IFN-γ response. The availability of antibody to Jak2 and of mutants in additional complementation groups in the IFN-γ response pathway should prove invaluable in determining the number and nature of the components involved in this response.

Methods and Materials

Cell surface expression of transfected CD2 and endogenous Class I and II HLAs in response to IFNs-α or -γ on wild-type 2C4, mutant γ-1 cells and mutant γ-1 cells stably transfected with a murine Jak2 cDNA expression construct. Data was generated for an enriched population and a clone of γ-1/Jak2 transfectants using FACSCAN (BECTON DICKINSON) analyses (3000 data points, Consort 30). Cells were plated at $5 \times 10^5/10$ cm dish and treated the following day with $10^3$ IU/ml of a highly purified mixture of α-IFNs (WELLFERON $1.5 \times 10^8$ IU/mg protein, kindly supplied by WELLCOME RESEARCH. LABORATORIES, Beckenham, UK) or recombinant human IFN-γ ($4 \times 10^7$ IU/mg protein, obtained from Dr. Gunter Adolf, Ernst Boehringer Institut fur Arzneimittelforschung, Vienna, Austria, and commercially or readily available).

Cells ($10^6$) were stained for 30 min at 0° C. with R-phycoerythrin-conjugated murine monoclonal antibody to human CD2 (DAKO-CD2 MT910, DAKO A/S Denmark) or HLA DRA (clone L243, Becton Dickinson), or FITC-conjugated murine monoclonal antibody to human HLA ABC (shared determinant, clone W6/32, SERALAB, UK) and fixed in 1% paraformaldehyde. Clone 2C4 was derived by stable co-transfection of human HT1080 cells with pDW9-27CD2 and pTKNco and FACSCAN analysis of G418-resistant clones. pDW9-27D2 is a modification of PJ3omega (Morgaenstern, J. P. et al., *Nucl. Acids Res.* 18: 1068 (1990)) in which the SV40 promoter was replaced by the 1.8 kb HindIII to BspMII promoter fragment of the 9–27 gene (Reid, L. E., et al., *Proc. Natl. Acad. Sci. USA* 86:840–844 (1989)) and which carries a full length CD2 cDNA (Sewel, W. A., et al., *Proc. Natl. Acad. Sci. USA* 83:8718–8722 (1986)) in the EcoRI site of the polylinker.

Mutagenesis (five rounds) with ICR191 was as previously described (McKendry, R., et al., *Proc. Natl. Acad. Sci. USA* 88:11455–11459 (1991)). Cells not responsive to IFN-γ were "selected" using a FACSTAR Plus cell sorter (Becton Dickinson). $5 \times 10^7$ mutagenized cells were treated with 500 IU/ml of recombinant human IFN-γ for 48 h, resuspended and stained with phycoerythrin-conjugated antibody to CD2 and (in the last two sorts) FITC-conjugated antibody to HLA Class I (above) and sorted immediately. The bottom 5% of fluorescing cells were collected.

After six rounds of sorting clone γ-1 was isolated by limiting dilution of the enriched population. It showed a novel IFN-γ⁻ -α⁺-β⁺ phenotype distinct from other IFN-γ mutants previously described (Loh, J. E., et al., *EMBO J.* 11:1351–1363 (1992); Mao, C., et al., *Proc. Natl. Acad. Sci. USA* 90:2880–2884 (1993)). The phenotype was stable on continuous culture for at least three months.

Mutant γ-1 was complemented by transfection with a full length cDNA of murine Jak2 downstream of the CMV promoter in pRK5 in the presence of a puromycin-selectable marker plasmid. The puromycin-resistant population of stable transfectants were treated with recombinant IFN-γ, FACS sorted and the top 7% of responder cells were collected and analyzed. Clones of γ-1/Jak2 transfected cells, obtained by limiting dilution of the enriched population, were also analyzed, for which full restoration of the IFN-γ response was observed.

IFN-inducible gene expression in wild type 2C4, mutant γ-1 and mutant γ-1/Jak2 transfected cells: mRNA expression in response to IFNs-α or -γ was monitored by RNase protection using probes to detect the IFN-inducible mRNAs of: the 9–27, 6–16, 2–5A synthetase and ISGF3γ genes and the p91 and p84 alternatively spliced products of the p91/84 ISGF3α gene and the IRF1 and GBP genes. The protection of γ-actin mRNA served as an internal loading control. Cytoplasmic RNA was prepared from monolayer cells by NP40 lysis and phenol/chloroform extraction (Porter, A. C. G., et al., *EMBO J.* 7:85–92 (1988)). RNase protection was with RNA probes labeled with $^{32}$P UTP to 2–5×10$^8$ cpm/µg of input DNA (Melton, D. A., et al., *Nucl. Acids Res.* 12:7035–7056 (1984)). One to 3×10$^5$ cpm of each probe and 10 µg of RNA were used in each assay.

Expression of Jak2 in wild-type 2C4, mutant γ-1 cells and mutant γ-1 cells transfected with murine Jak2 (γ-1Jak2tr): Jak2 protein was immunoprecipitated from precleared whole cell extracts (10$^7$ cells) with antiserum to Jak2 (Example 1) and protein A SEPHAROSE (PHARMACIA; John, J., et al., *Mol. Cell. Biol.* 11:4189–4195 (1991)) and analyzed by SDS-PAGE and western transfer using the antibody to Jak2 and the ECL detection system (Amersham International, UK). For the mutant γ-1 cell extracts immunoprecipitation was carried out in the absence (no peptide) or presence (30 µg/ml) of the Jak2 peptide to which the antiserum was raised (Jak2 pept) or, as a non-specific control, an unrelated Jak1 peptide (Jak1).

Binding of $^{125}$I-labeled IFN-γ to 2C4 and mutant γ-1 cells: $^{125}$I-IFN-γ (667 Ci/mMole, Amersham International, UK) treatment was of triplicate samples of 10$^6$ cells for 90 min at 0° C. Non-specific binding was subtracted. It was determined in parallel in the presence of a 200 fold excess of unlabeled IFN-γ and represented approximately 40% of the total radioactivity bound. In a parallel antiviral assay versus EMC virus 1 fmole of $^{125}$I-IFN-γ was equivalent to 0.15 IU. Specific binding at the highest IFN-γ concentration here corresponded to about 6000 receptors per cell. On dilution of the IFN to a lower specific activity saturation binding was observed at approximately 10,000 receptors per cell.

Example 5
Activation of the Protein Tyrosine Kinase Jak2 in Response to Interferon-γ
Summary Mutant γ-1 cells respond normally to interferons-α and -β but are defective in the response of all genes tested to interferon-γ. The mutants can be complemented by the protein tyrosine kinase Jak2 (Example 4). In wild-type cells the transcription factor p91, which plays a central role in the primary interferon-γ signal transduction pathway, is rapidly phosphorylated on tyrosine in response to interferon-γ. No such phosphorylation occurs in mutant γ-1 cells, but it is restored on complementation of γ-1 cells with Jak2. Moreover, Jak2 is itself rapidly phosphorylated on tyrosine in response to interferon-γ in wild-type cells. Interferon-γ dependent phosphorylation of Jak2. is also observed in in vitro kinase assays of immunoprecipitates from human and mouse cells. No such phosphorylation is seen in mutant γ-1 cells or in response to interferon-α. These results indicate a role for Jak2 early in the primary interferon-γ signal transduction pathway.

Results

Interferons (IFNs) -α, -β and -γ induce overlapping sets of genes through distinct receptors (Pestka et al., *Ann. Rev. Biochem.* 56:727–777 (1987)). There has been rapid recent progress in the understanding of the signal transduction pathways involved. Central to this has been the realization that p91, a component of the complex IFN-αβ-inducible transcription factor ISGF3, plays a dual role in the IFN-αβ and -γ response pathways.

p91 is rapidly phosphorylated on tyrosine in response to either type of IFN (Schindler et al., *Science* 257:809–813 (1992); Shuai et al., *Science* 258:1808–1812 (1992)). Consistent with this, p91 is required for the IFN-γ response of a wide spectrum of genes. It appears to correspond to the gamma activation factor (GAF) which was first identified as being necessary for the activation of transcription of the GBP gene (Decker et al., *EMBO J.* 10:927–932 (1991)) and has since been implicated in the activation of a number of additional genes in response to IFN-γ through a common DNA motif (Shuai et al., *Science* 258:1808–1812 (1992); Pearse et al., *Proc. Natl. Acad. Sci. USA* 90:4314–4318 (1993); Kanno et al., *Mol. Cell. Biol.* 13:3951 (1993)). Mutant γ-1 was, therefore, assayed for phosphorylation of p91. Phosphorylation of p91, monitored by incorporation of $^{32}$P$_i$, occurs rapidly in wild-type 2C4 cells. No such phosphorylation was observed in mutant γ-1.

Phosphorylation of p91 did occur in γ-1 cells complemented by Jak2 as monitored by incorporation of $^{32}$P$_i$ or with antibodies to phosphotyrosine. Normal levels of p91 were present and, interestingly, phosphorylation of the p91 and p113 components of ISGF3α by IFN-α was normal in the mutant cells (Phosphorylation of the p84 component of ISGF3α in response to IFNs -α or γ is always lower and frequently difficult to detect (Schindler et al., *Science* 257:809–813 (1992); Shuai et al., *Science* 258:1808–1812 (1992)).

In addition, γ-1 cells are not complementable by a functional p91 expression construct. The defect in γ-1 cells is, therefore, upstream of p91.

Tyrosine phosphorylation of Jak2 was monitored by immunoprecipitation with specific antibody followed by western transfer analysis of the immune precipitates with antibody to phosphotyrosine. On this basis, Jak2 is rapidly phosphorylated on tyrosine in response to IFN-γ in wild-type but not in mutant γ-1 cells. No such phosphorylation of Jak2 was observed in response to IFN-α under conditions identical to those under which phosphorylation of Tyk2 by IFN-α is readily detected.

Tyrosine phosphorylation of p91 in response to IFN-γ and of p91 and p113 in response to IFN-α were monitored in parallel as internal controls both for IFN activity and detection of phosphotyrosine using a mixture of Py-20 and 4G10 antiphosphotyrosine antibodies. On reprobing the same transfer with antibody to Jak2, comparable levels of Jak2 protein were detected in wild-type and γ-1 mutant cells. The defect in γ-1 is, therefore, in the phosphorylation/function rather than the production of Jak2 (see Example 4).

A priori the apparent phosphorylation of Jak2 could be of an immunologically cross-reacting protein. The antiserum used, however, was raised against a Jak2 peptide which is not conserved in Jak1 and has high specificity for Jak2 (see Examples 1 and 2). Consistent with this, phosphorylated protein was not recovered when the immune precipitation was carried out in the presence of the appropriate competing peptide.

In γ-1/Jak2 transfectants there is a high "background" level of tyrosine phosphorylation of the overexpressed exogenous murine Jak2 even in the absence of IFN-γ treatment. The basis for this is not known. Against this background a variable increase in total tyrosine phosphorylation of Jak2 is seen in response to IFN-γ in the complemented cells. Interestingly, however, even in experiments in which no obvious increase in Jak2 phosphorylation was observed in the γ-1/Jak2 transfectants when assayed, a substantial response to IFN-γ was consistently observed in parallel in vitro kinase assays (see below). Transfected Jak2 can, therefore, be phosphorylated in response to IFN-γ. It is reasonable to conclude that the phosphorylation observed in wild-type cells in response to IFN-γ is due to Jak2.

Activation of protein tyrosine kinases in response to growth factors classically results in kinase activity which can be detected in an immune precipitate of the activated enzyme. Jak2, activated in response to IL3 (Example 1) and erythropoietin (Example 2), shows similar apparent in vitro kinase activity. This is also the case for Jak2 in response to IFN-γ. IFN-γ-dependent kinase activity was observed upon assay of Jak2 immunoprecipitates from wild-type 2C4 or mutant γ-1/Jak2 transfected cells. No such activity was observed in response to IFN-α or when the immunoprecipitates were prepared from mutant γ-1 cells or from wild-type cells in the presence of competing Jak2 peptide. Phosphorylation of Jak2 is not restricted to human HT1080 derived cells, and is also seen in response to IFN-γ but not -α in other human and a variety of mouse cell lines, including mouse L-cells.

Discussion

The results presented here together with those in Example 4 indicate that Jak2 is activated in response to IFN-γ and such activation plays a role early in the primary IFN-γ response pathway. Granted that p91 is phosphorylated at the same site (Tyr 701) in response to IFN-α and γ (Schindler et al., Science 257:809–813 (1992); Shuai et al., Science 258:1808–1812 (1992)), the normal phosphorylation of p91 in the γ-1 mutant in response to IFN-α is of interest in this regard. One can conclude either that Tyk2 or Jak2 can each carry out phosphorylation of the same tyrosine or, more intriguingly, that there is an additional kinase(s) involved.

Turning to the activation of Jak2, in the case of erythropoietin this appears to occur through direct interaction of Jak2 with the erythropoietin receptor (Example 2). It will obviously be of considerable interest if there is a similar interaction in the case of the IFN-γ pathway. The common activation of Jak2 by erythropoietin, IL3 and a number of other cytokines (see Examples 1–3) raises obvious questions. A major thrust of future work will be to identify the nature of the proteins interacting with Jak2 and the factors determining the specificity of the response.

Methods and Materials

Tyrosine phosphorylation of p91 in response to IFN-γ in normal and mutant γ-1 cells: Phosphorylation of p91 in response to IFN-γ in wild-type (2C4), mutant γ-1 and mutant γ-1 cells transfected with Jak2 (γ-Jak2tr) was monitored by incorporation of $^{32}P113_i$ or by western transfer with antibody to phosphotyrosine. p91 protein levels were monitored by western transfer as was tyrosine phosphorylation of the p91 and p113 components of ISGF3 in response to INF-α at $10^3$ IU/ml for 15–30 minutes. p91 was immunoprecipitated from precleaned whole cell extracts ($10^7$ cells) with antiserum to p91 and protein A SEPHAROSE (PHARMACIA) as described previously (Schindler et al., Science 257:809–813 (1992); Shuai et al., Science 258:1808–1812 (1992)) and analyzed by SDS-PAGE and western transfer using a mixture of PY20 (ICN) and 4G10 (UBI) antiphosphotyrosine antibodies and, after stripping in 0.1M Tris H1 pH 8.0, antibody to p91. p91 and p113 (complexed in IFN-α-activated ISGF3α) were co-immunoprecipitated with antibody to p113 (Schindler et al., Science 257:809–813 (1992)) and analyzed by SDS-PAGE and western transfer with antiphosphotyrosine antibodies as above. In the western transfers detection was by ECL (Amersham, UK) except for the p91 antibody screened transfer which was stained with diaminobenzidine (Amersham UK).

Tyrosine phosphorylation of Jak2 in response to IFN-γ but not -α in wild-type 2C4, mutant γ-1 and mutant γ-1/Jak2 transfected cells: Phosphorylation of Jak2, and of p91 and p113 as controls, were monitored by immunoprecipitation, SDS-PAGE and western transfer for phosphotyrosine using a mixture of Py-20 and 4G10 antiphosphotyrosine antibodies and detection by ECL (Amersham International). Extracts from INF-γ treated cells were immunoprecipitated with a mixture of antibodies to Jak2 and p113 (the latter co-precipitates 091 in IFN-α-activated ISGF3). The same blot was stripped (as described above), and reprobed with antibody to Jak2. Extracts from cells treated with INF-γ for 15 min were immunoprecipitated with antibody to Jak2 in the presence or absence, as indicated, of 0.1 mg/ml of the Jak2 peptide against which the antibody to Jak2 was raised (Example 1) or an unrelated Jak1 peptide. The immunoprecipitates were analyzed by SDS-PAGE and western transfer using antibodies to phosphotyrosine as above. Growth of the cells and treatment with $10^3$ IU/ml of highly purified IFN-γ or -α was as described above.

In vitro kinase assays: IFN-dependent phosphorylation of Jak2 was assayed in immunoprecipitates from (A) wild type (2C4) and mutant γ-1/Jak2 transfected cells, (B) wild type (2C4) and mutant γ-1 cells and (C) mouse L-cells. Treatment with IFN-γ or -α (500 IU/ml) as indicated was for 15 min. Immune precipitates on protein A SEPHAROSE (PHARMACIA) were washed in 50 mM NaCl, 5 mM $MgCl_2$, 5 mM $MnCl_2$, 0.1 mM $Na_3VO_4$, 10 mM HEPES pH 7.4 and incubated in the same buffer containing 0.25 mCi/ml of $^{32}P$-γ-ATP for 30 min at room temperature (see Examples 1–2). After extensive washing proteins were eluted in sample buffer and analyzed by SDS-PAGE. Detection was by autoradiography or by western transfer for phosphotyrosine as described above. Growth and IFN treatment of human cells was as described above. Growth and IFN treatment of mouse L-cells was similar, but with recombinant murine IFN-γ (1–2×$10^7$ IU/mg protein, a generous gift from Dr. Gunter Adolf, Ernest Boehringer Institut fur Arzneimittelforschung, Vienna, Austria) or recombinant human IFN-α A/D (Bgl), a hybrid highly active on mouse cells (2×$10^8$ IU/mg protein kindly supplied by Dr. Sidney Pestka, Robert Wood Johnson Medical School, NJ, USA).

Example 6

An Inhibitor of EPO Activity (Genestein) Inhibits Jak2 Kinase Activity

The biochemical activity of Jak2 may be demonstrated by use of an in vitro kinase assay. In this assay, purified Jak2 is precipitated from cell lysates using Jak2-specific antisera bound to protein A-sepharose. The immunoprecipitated Jak2 is then washed with kinase buffer (50 mM NaCl, 5 mM $MgCl_2$, 5 mM $MnCl_2$, 0.1 mM $Na_3VO_4$, 10 mM HEPES pH 7.4) and subsequently incubated for 30 minutes at room temperature with an equal volume of kinase buffer containing 0.25 mCi/ml $^{32}P$-gamma-ATP. After extensive washing, proteins are eluted with sample buffer for SDS-PAGE and separated on 7% gels. $^{32}P$-containing proteins are then visualized by autoradiography.

Using this assay system, active Jak2 kinase has been demonstrated to be present only in mammalian cells which have been treated with an appropriate cytokine, such as erythropoietin (EPO) or interleukin-3 (IL-3). Thus, activation of the Jak2 catalytic activity is correlated with the biological activities of these cytokines.

This correlation is further supported by studies using the tyrosine kinase-specific inhibitor known as genestein. Genestein is known to inhibit the ability of EPO to stimulate cell growth.

Inclusion of genestein at 0.1 mM in the in vitro kinase assay described above results in a 2-fold reduction in the tyrosine kinase activity of Jak2. Thus, the inhibitory effect of genestein on EPO-induced cell proliferation can be explained by its inhibition of Jak2.

Example 7
Production of a Constitutively Active Jak2 Kinase From Insect Cells Since the active form of Jak2 may be isolated from mammalian cells only after stimulation with in appropriate cytokine, we have developed a system for the expression of catalytically active Jak2 which does not require cytokine stimulation. Specifically, when expressed at high levels in insect cells Jak2 is constitutively in an active state. This expression was accomplished by insertion of the Jak2 cDNA between the NotI and SmaI sites of the baculovirus transfer vector pVL1392 (PHARMINGEN, San Diego, Calif.). This Jak2/vector construct then was co-transfected into insect cells with a defective baculovirus DNA (BACULOGOLD DNA, PHARMINGEN, San Diego, Calif.).

Example 8
Cloning, Expression and Activity of Jak3

Many cytokines regulate growth and differentiation through interaction with receptors of the cytoline receptor superfamily. Although lacking catalytic domains, cytokine receptors couple ligand binding to induction of protein tyrosine phosphorylation. Recent studies have shown that one or more of the Janus kinase (Jak) family members associate with cytokine receptors and are tyrosine phosphorylated and activated following ligand binding. None of the reported Jak family members have yet been implicated in IL-2 or IL-4 signalling. Here we describe a new Jak family kinase, Jak3, and demonstrate that Jak3, and to a lesser extent Jak1, are tyrosine phosphorylated and Jak3 is activated in the responses to IL-2 and IL4 in T cells as well as in myeloid cells.

Janus kinase (Jaks) DNAs have identified by low stringency screening (Firmbach-Kraft, et al. *Oncogene* 5:1329–1336 (1990)) and by polymerase chain amplification (PCR) approaches (Wilks, A. F., *Proc. Natl. Acad. Sci. U.S.A.* 86:1603–1607 (1989); Partanen et al., *Proc. Natl. Acad. Sci USA* 87:8913–8917 (1990)). A variety of cytokines induce the tyrosine phosphorylation and activation of Jaks. Jak2 is activated by erythropoietin (EPO) (Witthuhn et al., *Cell:*227–236 (1993)), growth hormone (Artgetsinger et al., *Cell* 74:237–244 (1993)), prolactin hormone (Campbell et al., *Proc. Natl. Acad. Sci. USA* in press, (1993)), granulocyte-specific colony stimulating factor (G-CSF), interleukin-3 (IL-3) (Silvennoinen, *Proc. Natl. Acad. Sci. USA* 90:8429–8433 (1993)) and granulocyte-macrophage colony stimulating factor (GM-CSF) (Quelle et al., *Mol. Cell. Biol.* submitted, (1994)). Interferon (IFN)-$\alpha/\beta$ responses activate and require Jak1 and another family member, Tyk2 (Velazques et al., *Cell* 70:313–322 (1992); Muller et al., *Nature* 366, 129–135 (1993)); while Jak1 and Jak2 are activated and required for the response to IFN-$\gamma$ (Muller et al., *Nature* 366, 129–135 (1993); Watling et al., *Nature* 366, 166–170 (1993)). Lastly, cytokines that utilize a common gp130, or gp130 related subunit, including IL-6, oncostatin M, leukemia inhibitor factor (LIF) and ciliary neurotrophic factor (CNTF) activate Jak1 and Jak2 and to some extent Tyk2 (Stahl et al., *Science* 263:92–95 (1994); Narazaki et al., *Proc. Natl. Acad. Sci. USA,* in press, (1994)). Notably, no activation of Jak1, Jak2 or Tyk2 has been reported in the responses of IL-2 or IL-4, which also utilize receptors of the cytokine receptor superfamily. We therefore looked for additional Jak family members that might be activated by IL-2 and IL-4.

Previously PCR approaches were used to identify protein tyrosine kinases in breast cancer cell lines (Cance et al., *Int. J. Cancer* 54:571–577 (1993)) from which a cDNA fragment was obtained that encoded a novel Jak family member. The same kinase was recently detected by PCR in rat hippocampal neurons (Sanchez et al., *Proc. Natl. Acad. Sci. USA* 91: 1819–1823 (1994)). Using the fragment from breast cancer cell lines, we obtained four overlapping cDNA clones from a murine B-cell cDNA library. The longest cDNA was 3.8 kb (JAK3 Kinase Plasmid DNA in pBluescript SK +/− (pBSK)) deposited at the American Type Culture Collection, Manassas VA on Feb. 7, 2000 and assigned number PTA-1338 and contained a long open reading frame which would encode a protein with 1099 amino acids and a predicted size of 122.6 kDa. The predicted sequence (FIGS. 6A–6D) is highly related to the Jaks and was termed Jak3. Murine Jak3 is 47%, 36% and 36% identical to amino acids in murine Jak2, murine Jak1 and human Tyk2 respectively. Jak3 contained atypical protein tyrosine kinase catalytic domain as well as an amino terminal kinase-like domain. In addition, there are blocks of similarity between Jak3 and the other Jak family members in the amino terminal region.

Figure 7A:
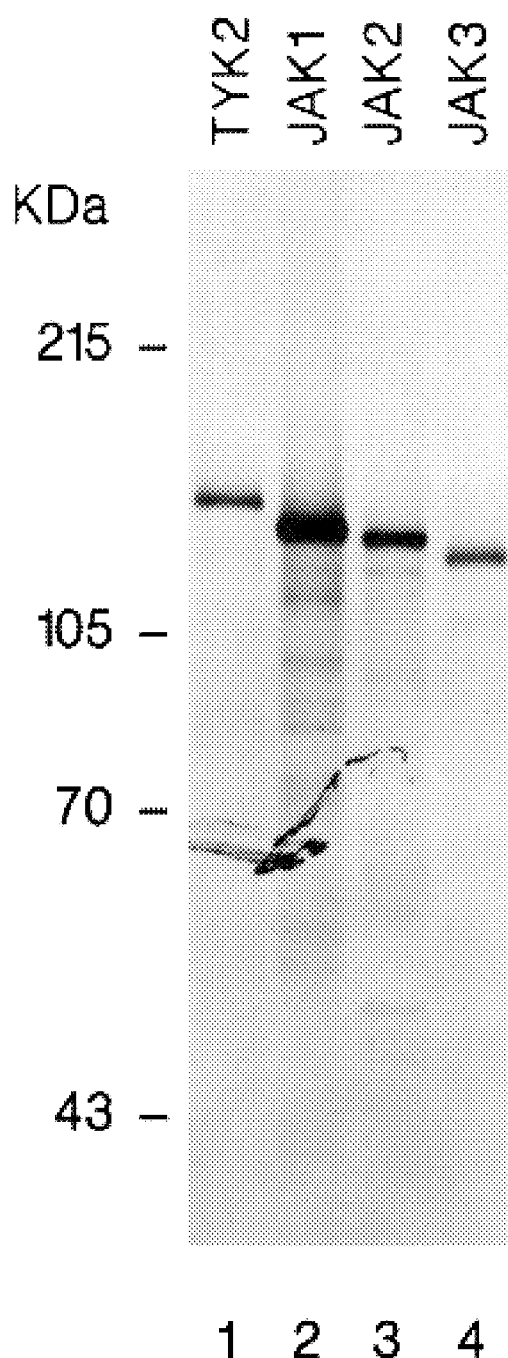
FIGS. 7A–B. In vitro translation of cDNAs for Jak family members and characterization of antisera.
Figure 7B:
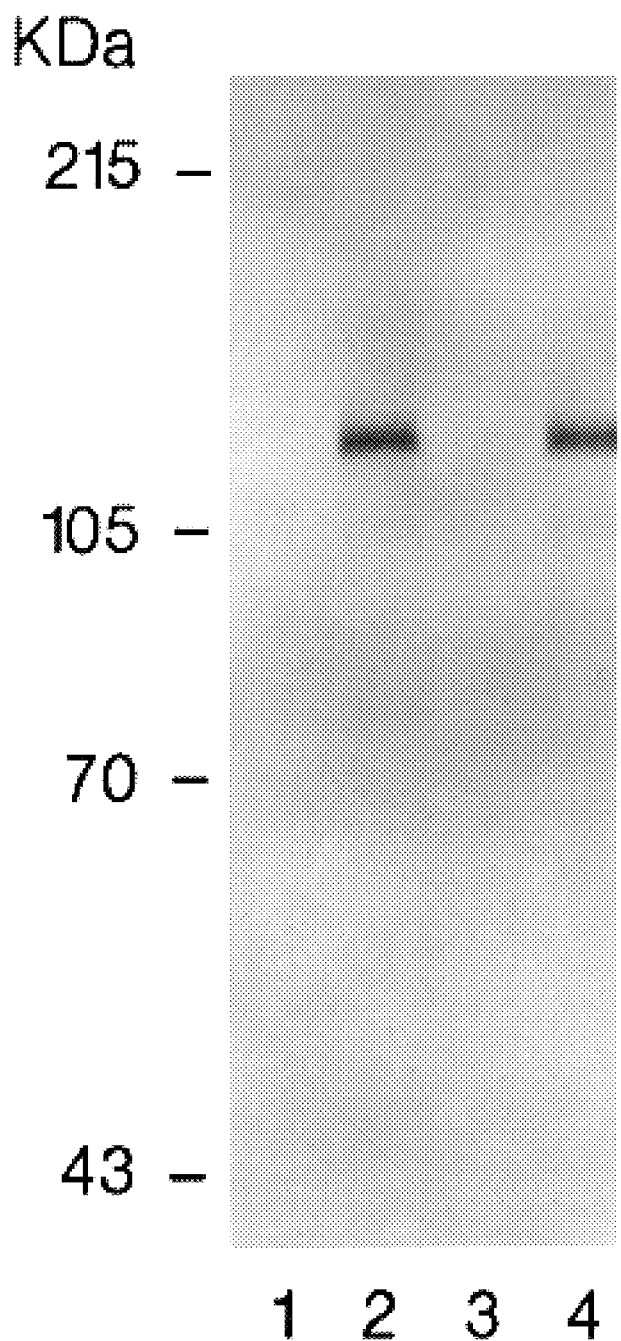

Translation of the Jak3 cDNA in vitro (FIGS. 7A–B) gave a 120 kDa product. Comparison of the in vitro translation products of cDNAs for murine Jak1, murine Jak2 and human Tyk2 demonstrated that each could be distinguished by size; Tyk2 migrates the slowest followed by Jak1, Jak2 and Jak3 consistent with their predicted sizes. The in vitro translated proteins were used to determine the specificity of anti-peptide antisera (FIG. 7B). Antiserum against a kinase domain peptide of Jak3 immunoprecipitated Jak3 (lane 2) but not Jak1, Jak2 or Tyk2. This precipitation was not seen with pre-immune serum (lane 1) and was competed by the immunizing peptide (lane 3) but not an irrelevant peptide (lane 4). Similarly, anti-peptide antisera against Jak1 or Jak2 (Silvennoinen, *Proc. Natl. Acad. Sci. USA* 90:8429–8433 (1993)) were specific and did not immunoprecipitate Jak3. Lastly, an anti-peptide antiserum against a region of Tyk2 from between the kinase domains was made. Unlike the others, this antiserum was cross-reactive and recognized Jak3 and Jak1 as well as Tyk2 but only weakly immunoprecipitated Jak2. However, a commercially available anti-peptide antiserum against Tyk2 (Santa CRUZ BIOTECHNOLOGY Inc.) was specific and did not cross-react with Jak1, Jak2 or Jak3.

Figure 8:
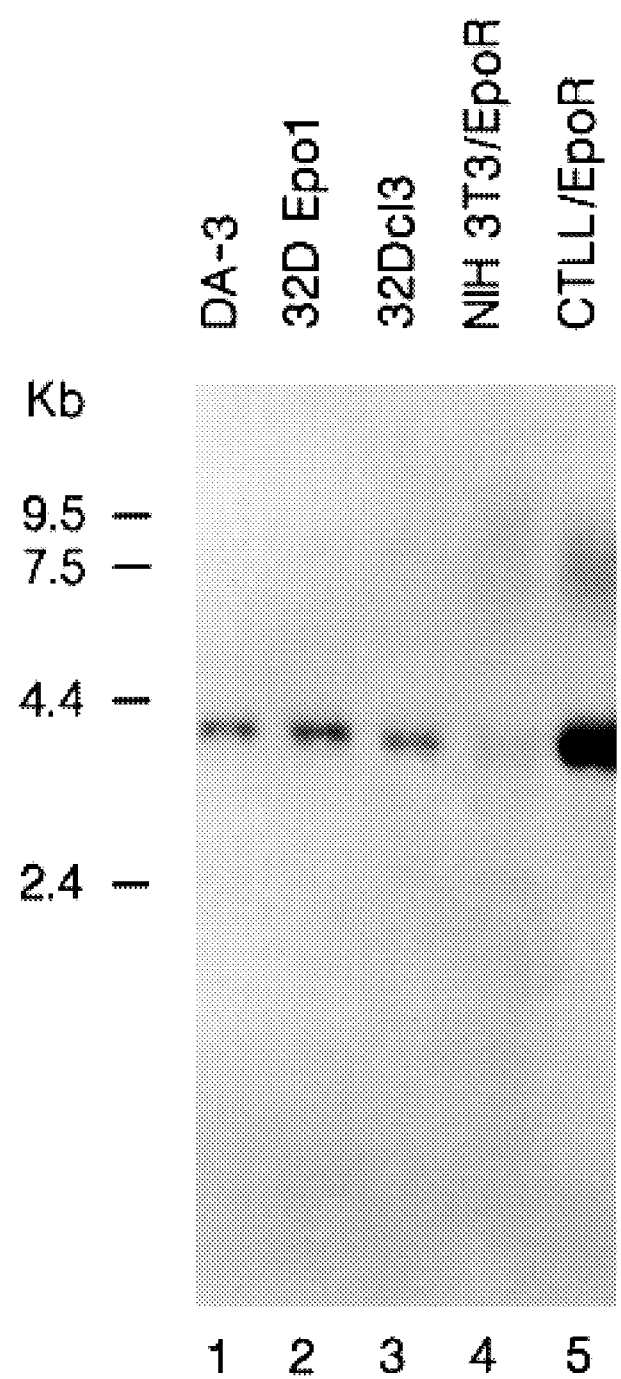
FIG. 8. Jak3 expression in murine cell lines. RNA was prepared from the indicated cells by previously described techniques 1. Approximately 15 µg of total RNA was resolved by electrophoresis and blotted to filters for hybridization. The RNAs included (lane 1) an IL-3 dependent myeloid cell line (DA3); (lane 2) an IL-3 dependent myeloid cell line, 32D(Epo1), that expresses the endogenous EPO receptor and expresses differentiated functions in response to EPO (Migliaccio et al., *J. Cell Biol.* 109:833–841 (1989)); (lane 3) an IL-3 dependent myeloid cell line, 32Dc13, that can differentiate along the granulocytic pathway in response to G-CSF (Migliaccio et al., *J. Cell Biol.* 109:833–841 (1989)); (lane 4) NIH 3T3 fibroblasts transfected with the wild-MV EPO receptor; and (lane 5) a clone of an IL-2 dependent cytotoxic T cell line that was stably transfected with the EPO receptor, CTLLpoR. The position of migration of RNA standards are shown. The single Jak3 transcripts migrates with an apparent size of 4.0 kb. RNA samples were obtained from cells by standard procedures. The RNA samples were electrophoresized on 2.2 M formaldehyde-1% agarose gels and transferred to Zeta bind (NEN) membranes. The probe consisted of a 1 kb SstI fragment of the CDNA, labeled by random priming. The filters were hybridized at 65° in 750 mM NaCl, 1 mM EDTA, 10 mM Tris-HCL pH 7.5, 10% ficoll, 1% polyvinylpyrrolidone, 0.1% SDS and 100 μg/ml salmon sperm DNA. The filters were washed to a final stringency of 15 mM NaCl at 65° and exposed for 14 hours.

Jak1, Jak2 and Tyk2 are ubiquitously expressed (Firmbach-Kraft, et al. *Oncogene* 5:1329–1336 (1990); Silvennoinen, *Proc. Natl. Acad. Sci. USA* 90:8429–8433 (1993); Harpur et al., *Oncogene* 7:1347–1353 (1992); Wilks et al., *Mol. Cell Biol.* 11:2057–2065 (1991)). To determine if Jak3 was similarly expressed, a series of cell lines and mouse tissues were examined for expression by Northern blot analysis. As illustrated in FIG. 8, the highest levels of transcripts were detected in an IL-2 dependent cytotoxic T-cell line (CTLL) which contained a single 4 kb transcript. A comparably sized transcript was detected at somewhat lower levels in IL-3 dependent myeloid cell lines. However, Jak3 transcripts were not detected in fibroblasts or a glioblastoma cell line. Among tissues, transcripts were detected at the highest levels in spleen and to lesser extent in liver, kidney, lungs and heart but were not detected in brain or testes. Consistent with the initial PCR amplification results (Cance et al., *Int. J. Cancer* 54:571–577 (1993)), Jak3 is also expressed breast tissue derived cell lines. Therefore, unlike other Jak family members, Jak3 expression is much more restricted and one of the sites of expression is the hematopoietic lineages.

Figure 9A:
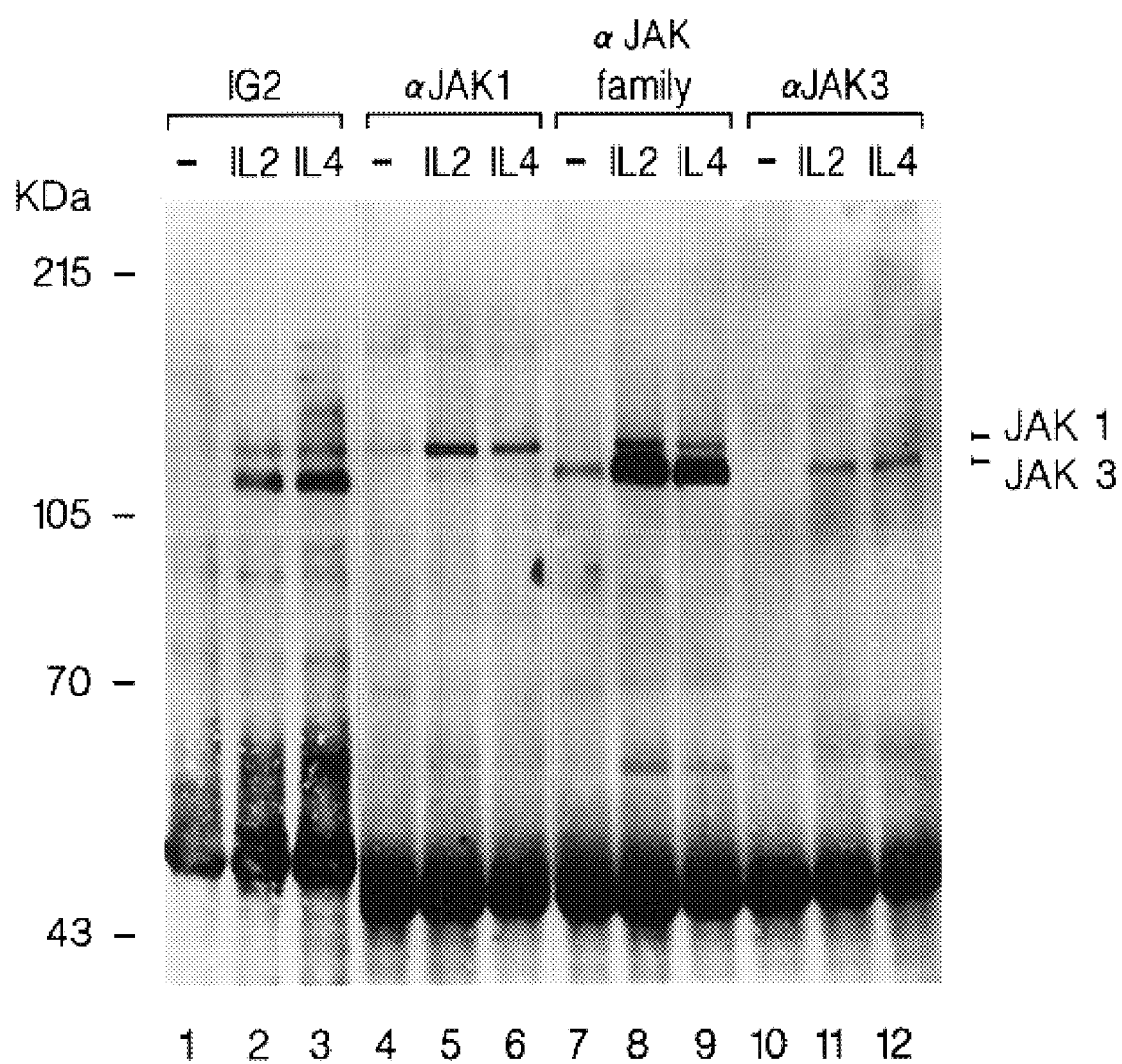
FIGS. 9A–D. IL-2 and IL-4 stimulation of Jak1 and Jak3 tyrosine phosphorylation and activation of Jak3 in vitro kinase activity.

To assess the role of Jak3 in signalling, the ability of several cytokines to induce Jak3 tyrosine phosphorylation was examined by immunoprecipitation and western blotting with a monoclonal antibody against phosphotyrosine. In a series of IL-3 dependent myeloid cell lines, no constitutive or inducible tyrosine phosphorylation of Jak3 was seen with EPO, IL-3, GM-CSF, G-CSF, IFN-α, IFN-γ or IL-6. However, Jak3 was tyrosine phosphorylated in IL-2 or IL-4 stimulated CTLL cells (FIGS. 9A–D). In CTLL cells, IL-2 and IL-4 induced the tyrosine phosphorylation of several cellular proteins including a protein doublet of 120 and 130 kDa, consistent with recently published results (Kirken et al., *J. Biol. Chem.* 268:22765–22770 (1993)). As illustrated in FIG. 9A, IL-2 and EL-4 induced tyrosine phosphorylation of Jak3 (αJak3) which migrated at the position of the major 120 kDa substrate. IL-2 and IL-4 also induced tyrosine phosphorylation of Jak1 (αJak1) which co-migrated with the 130 kDa substrate. No tyrosine phosphorylation of Jak2 or Tyk2 was detected with Jak2 or Tyk2 specific antiserum. Lastly, the Jak3/Jak1 cross-reactive antiserum against Tyk2 did not precipitate a tyrosine phosphorylated protein of the size of Tyk2 but did immunoprecipitate tyrosine phosphorylated proteins that migrated at positions comparable to Jak1 and Jak3, consistent with the results with the specific antiserum. Phosphorylation of the Jaks in response to IL-2 or IL-4 was detectable within one minute following stimulation, peaked at 20–30 minutes and subsequently declined similar to the pattern seen in phosphorylation of Jak2 by growth hormone, IL-3 or EPO (Witthuhn et al., *Cell*:227–236 (1993); Artgetsinger et al., *Cell* 74:237–244 (1993); Silvennoinen, *Proc. Natl. Acad. Sci. USA* 90:8429–8433 (1993)).

Figure 9B:
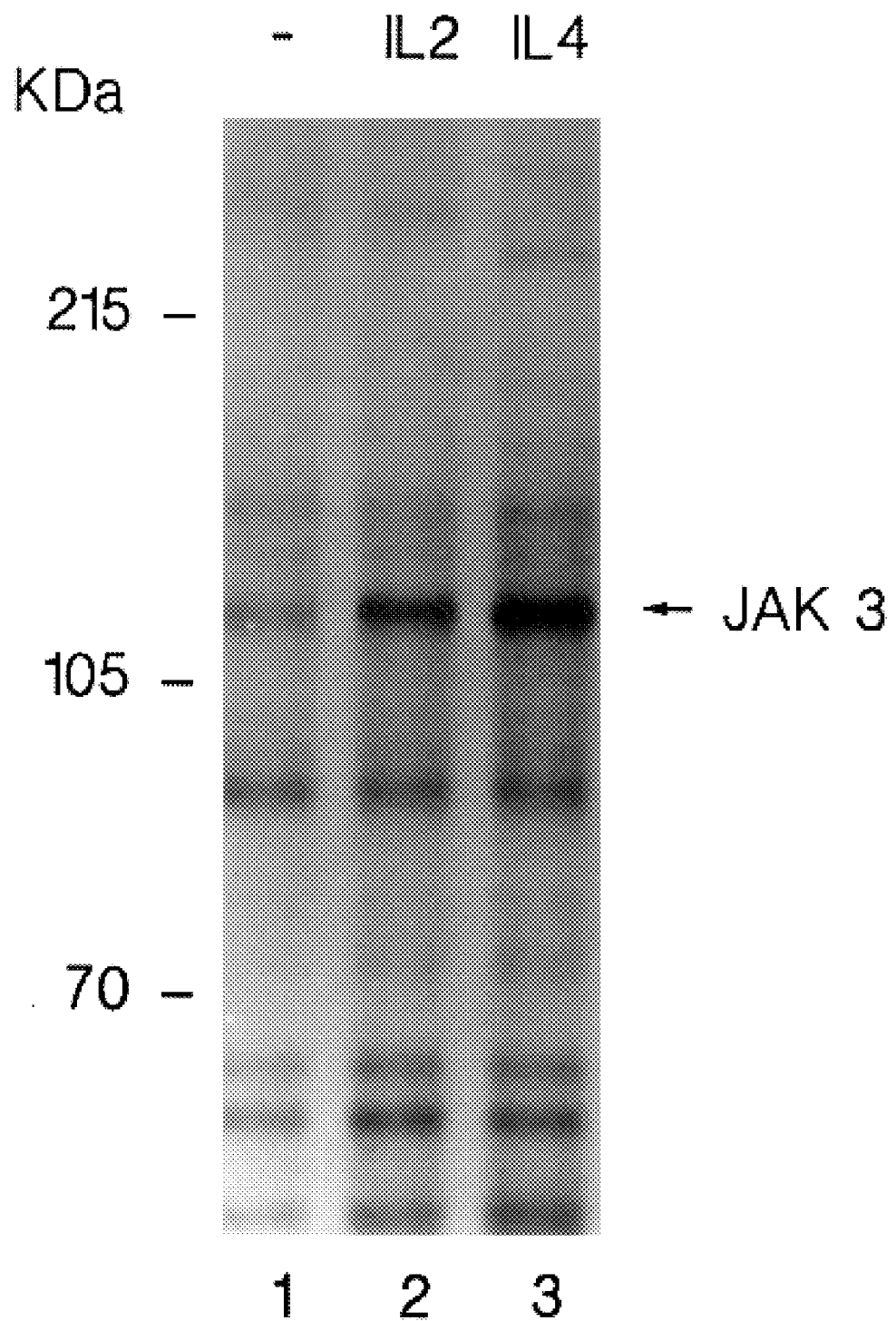

Cytokine induced tyrosine phosphorylation of other Jaks activates their in vitro kinase activity (Witthuhn et al., *Cell*:227–236 (1993); Artgetsinger et al., *Cell* 74:237–244 (1993); Silvennoinen, *Proc. Natl. Acad. Sci. USA* 90:8429–8433 (1993); Muller et al., *Nature* 366, 129–135 (1993); Stahl et al., *Science* 263:92–95 (1994)). We therefore examined the effects of IL-2 or IL-4 Jak1 or Jak3 kinase activity. The tyrosine phosphorylation of Jak1 was not associated with the activation of demonstrable kinase activity in immunoprecipitates comparable to the response seen to EPO (Witthuhn et al., *Cell*:227–236 (1993)). However, tyrosine phosphorylation of Jak1 in the response to IL-6 or CNTF is associated with activation of kinase activity (Stahl et al., *Science* 263:92–95 (1994); Narazaki et al., *Proc. Natl. Acad. Sci. USA*, in press, (1994)). Jak3 kinase activity was not detected in immunoprecipitates with the Jak3 specific anti-peptide antiserum. However, this antiserum is against a peptide (SEQ ID NO:15) containing the putative autophosphorylation site (KDYY) which may interfere with kinase activity as well as immunoprecipitation. We therefore assayed immunoprecipitates obtained with the Jak1/Jak3 cross-reactive antiserum against Tyk2. Activation of in vitro kinase activity was readily detectable in immunoprecipitates from cells stimulated with either IL-2 or IL-4 (FIG. 9B). Moreover, there was a single phosphorylated protein in the Jaks size range which co-migrated with Jak3. No detectable phosphorylation of a protein migrating at the position of Jak1 was seen, consistent with the results obtained with the Jak1 specific antiserum. Amino acid analysis of the in vitro phosphorylated protein indicated that phosphorylation occurred exclusively on tyrosine.

Figure 9C:
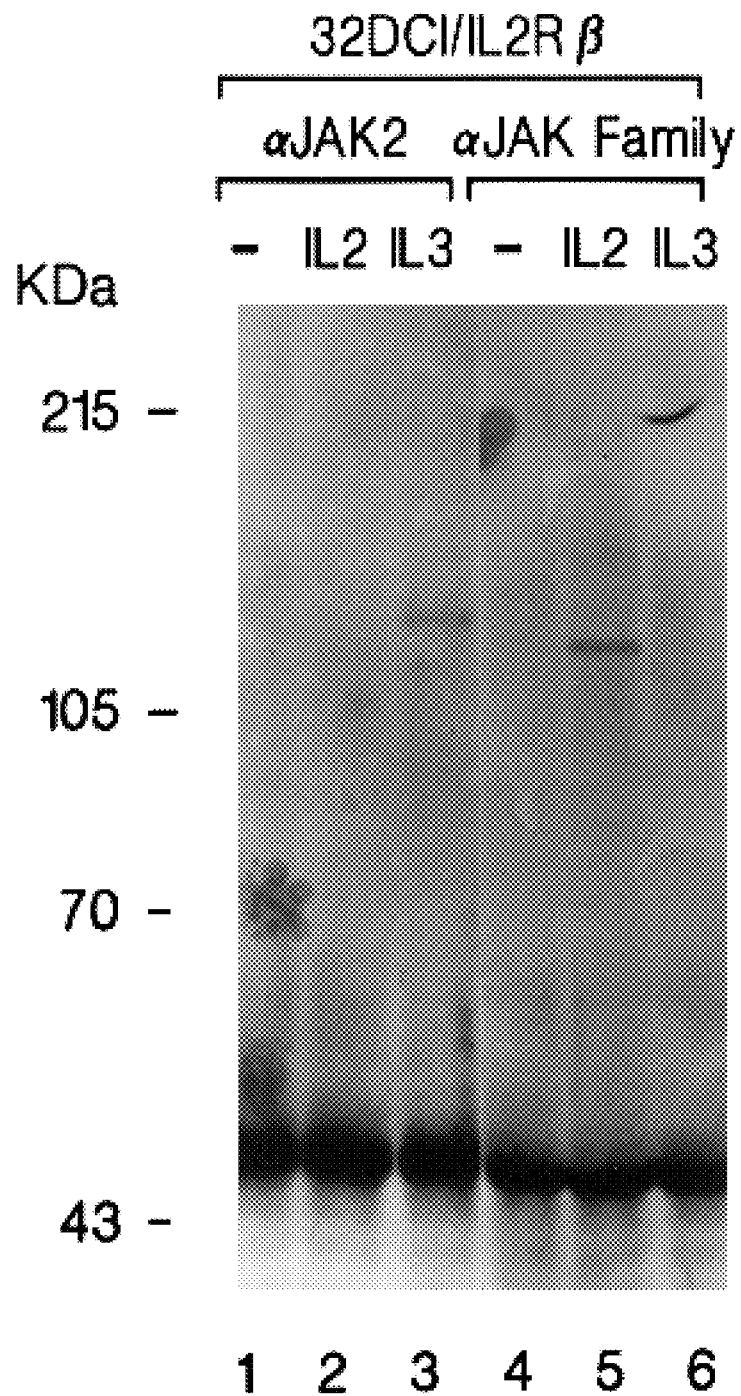

The cytoplasmic domains of the EPO receptor and the IL-β chain have considerable homology (D'Andrea, *Cell* 58:1023–1024 (1989)). We therefore assessed the specificity of the tyrosine phosphorylation of Jak3 in cells that expressed the EPO receptor. CTLL cells, transfected with the full-length, wild-type EPO receptor, express levels of high affinity EPO receptors comparable to transfected myeloid cells. Although the cells do not proliferate in response to EPO, EPO induces tyrosine phosphorylation of Jak2 (FIG. 9C). However, neither IL,2 nor IL-4 induced tyrosine phosphorylation of Jak2. Conversely, while IL-2 induced tyrosine phosphorylation of Jak3, EPO had no effect on Jak3 phosphorylation.

Figure 9D:
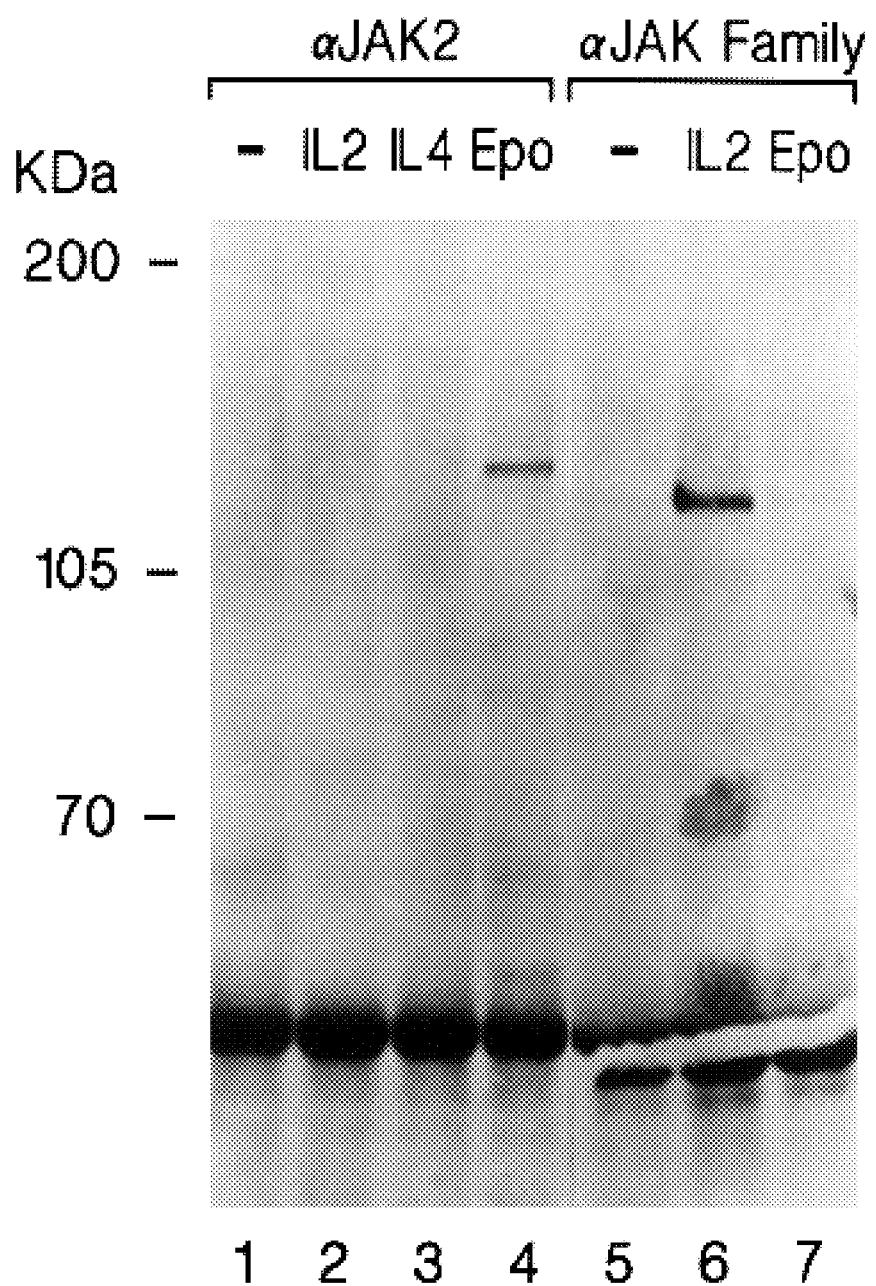

An IL-3 dependent cell line, 32Dc13(IL2Rβ), expressing the human IL-2 receptor 16 chain were also examined (FIG. 9D). These cells proliferate in response to human IL-2 comparable to IL-3. IL-3 induced the tyrosine phosphorylation of Jak2 but not Jak3. Nor was there detectable tyrosine phosphorylation of Jak1 or Tyk2 in IL-3 stimulated cells. Stimulation with IL-2 resulted in the tyrosine phosphorylation of Jak3 but no detectable tyrosine phosphorylation of Jak2 or Tyk2. Importantly, there was also no detectable tyrosine phosphorylation of Jak1. Thus, IL-2 and IL-4 cause the specific and consistent tyrosine phosphorylation of Jak3 but not of the other Jak family members. Previous studies have shown that the acidic region of the IL-2 receptor chain is required for association and activation of the p5611$^{lck}$ (Hatakeyama et al., *Cell* 59:837–845 (1989)). We therefore examined 32Dc13 cells transfected with an IL-2 receptor β chain containing an internal, 70 amino acid deletion of the serine rich region. This mutant is the previously characterized A mutant which supports mitogenesis but not p56$^{lck}$ activation (Hatakeyama et al., *Science* 252:1523–1528 (1991); Hatakeyama et al., *Cell* 59:837–845 (1989)). Stimulation of cells expressing this mutant resulted in induction of Jak3 tyrosine phosphorylation comparable to that seen in cells expressing the wild-type receptor.

The result demonstrate that, among the cytokines examined, Jak3 is specifically tyrosine phosphorylated and activated in the cellular responses to IL-2 and IL-4. IL-2 also increases the kinase activity of p56$^{lck}$, p59$^{fyn}$, or p53/56$^{lyn}$ (Taniguchi, T. & Minami, Y., *Cell* 73:5–8 (1993)). However, activation of the Src kinases requires the acidic domain of the IL-2 receptor β chain, which is dispensable for mitogenesis and for the activation of Jak3. Thus the role for activation of Src kinases has been unclear. In contrast, the membrane proximal, serine rich domain of the IL-2 P chain, which contains the box 1/box 2 motifs is required for mitogenesis. A similar region of the EPO receptor is required for association with Jak2 and for mitogenesis (Witthuhn et al., *Cell*:227–236 (1993)). Experiments are currently in progress to assess the requirement for this region for Jak3 activation.

IL-2 induces the tyrosine phosphorylation of a 116 kDa protein which could be cross-linked to the β chain (Kirken et al., *J. Biol. Chem.* 268:22765– 22770 (1993)). These studies are similar to those which identified a 130 kDa phosphoprotein cross-linked to the EPO receptor (Yoshimura & Lodish, *Mol. Cell Biol.* 12:706–715 (1992)) which was subsequently shown to be Jak2 (Witthuhn et al., *Cell*:227–236 (1993)). Based on the role of the box 1 and box 2 regions in association of other receptors with Jaks, we would hypothesize that Jak3 associates with the IL-2 receptor β chain. Experiments are currently in progress to assess this hypothesis.

The activation of Jaks is often associated with the tyrosine phosphorylation and activation of the DNA binding activity of members of the signal transducers and activators of transcription (STAT) family. In particular, IFN-α activates STAT1 (p91) and STAT2 (p113), IFN-γ activates STAT1 (Pellegrini & Schindler, *Trends in Biochemical Sciences* 18:338–342 (1993)), IL-6 activates a new family member termed APRF or STAT3 (Akira et al., *Cell* in press, (1994)) and IL-3 activates a protein with properties of a novel STAT protein (Lamer et al., *Science* 261, 1730–1733 (1993)). In this regard, IL-4 induces the tyrosine phosphorylation of a DNA binding activity with properties of another novel STAT protein (Kotanides & Reich, *Science* 262:1265–1267 (1993)). A similar DNA binding activity is induced in CTLL cells by IL-2. It will be important to determine whether the IL-2/IL-4 induced STAT like proteins are members of the STAT family and constitute specific substrates of Jak3. Nevertheless, it can be hypothesized that cytokine induced activation of Jaks and STATs may be a very general mechanism by which cytokine binding is coupled to the regulation of gene expression.

Recombination events between the defective baculovirus DNA and the Jak2/vector DNA results in DNA encoding a viable baculovirus which will constitutively express Jak2. Infection of insect cells with this recombinant baculovirus results in the high level expression of active Jak2 which may be purified by immunoprecipitation with Jak2-specific antisera. This source of active Jak2 will be useful in the study of biochemical properties of this enzyme, and can also be used in assays for inhibitors of Jak2 kinase activity based upon the in vitro Jak kinase assay described herein.

Example 9
Activation of a Jak by IL-3 and IL-5 demonstrated in huIL-5Rα transfected Ba/F3 and FDCP-I cells Similarly as presented in the above examples, Ba/F3-huIL-5Rα and FDCP-I-huIL-5Rα cells deprived of growth factor for 16 hrs were either unstimulated or stimulated with either IL3 or IL5 for 10 min. Cells were harvested and lysed for 20 minutes in 1 ml of ice cold lysis buffer. The lysates were incubated with anti-Jak2 sera and subjected to 7.5% SDS-PAGE. Gels were then transferred electrophoretically to nitrocellulose. When filters were probed with the 4G10 monoclonal antibody against phosphotyrosine, two bands that migrated at 130 kd and 150 kd were observed in cells stimulated with both IL3 and IL5. Comparable blots were probed with Jak2 sera showing that there are equivalent amounts of Jak2 in stimulated and unstimulated cells. IL3 and IL5 stimulation resulted in specific tyrosine phosphorylation of a band that co-migrates with Jak2. The tyrosine phosphorylated band above Jak2 is attributable to the association of Jak2 with the common beta subunit shared between IL3, GM-CSF and IL5.

Example 10
Activation of Jak3 by IL-7 in the preB-cell line by IL-7

Similarly as presented in the above examples, D1F9 cells deprived of growth factor for 16 hrs were either unstimulated or stimulated with IL7 for 10 min. Cells were harvested and lysed for 20 minutes in 1 ml of ice cold lysis buffer. The lysates were incubated with anti-Jak family sera and subjected to 7.5% SDS-PAGE. Gels were then transferred electrophoretically to nitrocellulose. When filters were probed with the 4G10 monoclonal antibody against phosphotyrosine two bands were observed in cells stimulated with IL7. The migration of the bands identified them as Jak1 and Jak3. These results are similar to those seen in cells stimulated with IL2 and IL4, which is expected as the IL2R-γ subunit is a component of the IL7 receptor.

Example 11
Activation of a Jak by IL-9 in human M-07 cells recognized by muJak2 sera Similarly as presented in the above examples, M07 cells deprived of growth factor for 16 hrs were either unstimulated or stimulated with huIL3 and huIL9 for 10 min. Cells were harvested and lysed for 20 minutes in 1 ml of ice cold lysis buffer. The lysates were incubated with anti-Jak2 sera and subjected to 7.5% SDS-PAGE. Gels were then transferred electrophoretically to nitrocellulose. When filters were probed with the 4G10 monoclonal antibody against phosphotyrosine the expected band representing Jak2 in IL3 stimulated cells was observed. In the lane representing IL9 stimulation a single band that migrated faster than Jak2 was observed. The migration of this band shows that it is likely Jak3.

Example 12
Activation of a Jak by IL-11 in the fibroblast cell line, 3T3-LI

Similarly as presented in the above examples, serum starved 3T3-LI cells were either unstimulated or stimulated with IL-11 for 10 min. Cells were harvested and lysed in 1 ml of ice cold lysis buffer. The lysates were incubated with anti-Jak1 or Jak2 sera and subjected to 7.5% SDS-PAGE. Gels were then transferred electrophoretically to nitrocellulose. When filters were probed with the 4G10 monoclonal antibody against phosphotyrosine a band representing Jak1 in IL11 stimulated cells was observed. No comparable tyrosine phosphorylation of Jak2 was observed in response to IL11. Comparable blots were probed with Jak2 sera and Jak1 sera showing that there are equivalent amounts of Jak2 and Jak1 in stimulated and unstimulated cells.

Example 13
Activation of a Jak by G-CSF

Similarly as presented in the above examples, induction of tyrosine phosphorylation of Jak1 and Jak2 in NFS60, Ba/F3/G-CSFR, 32DC13/G-CSF and FDCP-I/G-CSF was performed. NFS60, Ba/F3/G-CSFR, 32DC13/G-CSF and FDCP-I/G-CSF cells deprived of growth factor for 16 hrs were either unstimulated or stimulated with G-CSF for 10 min. Cells were harvested and lysed for 20 minutes in 1 ml of ice cold lysis buffer. The lysates were incubated with anti-Jak2 and anti-Jak1 sera, subjected to 7.5% SDS-PAGE and transferred electrophoretically to nitrocellulose. When filters were probed with the 4G10 monoclonal antibody against phosphotyrosine a readily detectable band is evident in the G-CSF stimulated cells for Jak2 immunoprecipitation and a lesser intense band is seem in the Jak1 immunoprecipitated lysates. Comparable blots were probed with Jak2 sera and Jak1 sera showing that there are equivalent amounts of Jak2 and Jak1 in stimulated and unstimulated cells.

G-CSF receptor mutants characterized by their ability to support G-CSF dependent growth were utilized to examine whether a G-CSF dependent growth correlated with Jak activation as demonstrated in IL3 and Epo receptor mutants. Cells expressing G-CSF receptors and receptor mutants were examined. The ability to tyrosine phosphorylate Jak2 is correlated to a G-CSF dependence in all case with the exception of a Box I point mutation. In this case although the receptor supports G-CSF dependent growth Jak2 is not tyrosine phosphorylated.

Activation of kinase activity was examined by in vitro kinase assays on Jak1 and Jak2 immunoprecipitates of stimulated and unstimulated NFS-60 cells extracts. Jak1 immunoprecipitations showed no evidence of increased autophosphorylation in G-CSF stimulated NFS-60. No examination of Jak1 in vitro kinase activity has been preformed in Ba/F3/G-CSFR, 32DC13/G-CSF and FDCP-I/G-CSF where the Jak1 tyrosine phosphorylation appears to be increased in relationship to the NFS-60 cells. Jak2 immunoprecipitations have a major phosphorylated band that co-migrates with Jak2 in response to G-CSF whereas no comparable band was detected in unstimulated cells.

Example 14
Activation of a Jak by GM-CSF

Similarly as presented in the above examples, induction of tyrosine phosphorylation of Jak1 and Jak2 in cells expressing GM-CSF receptors is performed. GM-CSF receptor cells deprived of growth factor for 16 hrs are either unstimulated or stimulated with GM-CSF for 10 min. Cells are harvested and lysed for 20 minutes in 1 ml of ice cold lysis buffer. The lysates are incubated with anti-Jak2 and anti-Jak1 sera, subjected to 7.5% SDS-PAGE and transferred electrophoretically to nitrocellulose. When filters are probed with a monoclonal antibody against phosphotyrosine a readily detectable band is expected to be evident in the GM-CSF stimulated cells for Jak2 immunoprecipitation and a lesser intense band is seem in the Jak1 immunoprecipitated lysates. Comparable blots are probed with Jak2 sera and Jak1 sera showing that there are equivalent amounts of Jak2 and Jak1 in stimulated and unstimulated cells.

GM-CSF receptor mutants characterized by their ability to support GM-CSF dependent growth are utilized to examine whether a GM-CSF dependent growth correlated with Jak activation as is demonstrated in IL3 and Epo receptor mutants. Cells expressing GM-CSF receptors and receptor mutants are examined. The ability to tyrosine phosphorylate Jak2 is expected to correlated with a GM-CSF dependence in most cases.

Activation of kinase activity is examined by in vitro kinase assays on Jak1 and Jak2 immunoprecipitates of stimulated and unstimulated GM-CSF receptor containing cell extracts. Jak1 immunoprecipitations is expected to showed little evidence of increased autophosphorylation in GM-CSF stimulated cells. Jak1 tyrosine phosphorylation appears to be increased in relationship to the GM-CSFR cells. Jak2 immunoprecipitations are expected to have a major phosphorylated band that co-migrates with Jak2 in response to GM-CSF whereas no comparable band is expected to be detected in unstimulated cells.

Example 15
The JAK Family of Kinases are Involved in Signal Transduction by the CNTF Family of Factors

Materials and Methods

Reagents

Antisera specific for LIFRβ (Stahl et al., *J. Biol Chem.* 268:7628–7631 (1993), gp130 (Davis et al., *Science* 260:1805–1808 (1993), Jak1 and Jak2 (Silvennoinen et al., *Proc. Natl. Acad. Sci. USA*, 1993 (in press) have been described. The rabbit antiserum against Tyk2 was raised and purified against a portion of Tyk2 expressed as a glutathione-S-transferase (GST) fusion protein (Velazquez et al., *Cell* 70:313–322 (1992)). Expression plasmids appropriate for COS expression of epitope-tagged LIFRβ and gp130 were previously described (Davis et al., *Science* 260:1805–1808 (1993), except that the LIFRβ coding sequence was modified to contain 3 successive copies of the myc epitope to improve selectability. Full length cDNA for murine Jak1 and Jak2 were provided in the plasmid pRK5.

Methods

Cell lines were passaged and maintained as previously described (Ip et al., *Cell* 69:1121–1132 (1992). COS cell transfections were carried out by a DEAE protocol (Davis et al., *Science* 260:1805–1808 (1993)). Plates of cells were starved in serum-free RPMI medium for 2–4 hours, then stimulated with 50 ng/ml of the indicated factor for 5 minutes. Cells were harvested and lysed as previously described (Stahl et al., *J. Biol. Chem.* 268:7628–7631 (1993)), except that 1% Brij 96 (Sigma) or 1% NP-40 (Boehringer) was used as indicated. Immunoprecipitation, electrophoresis, and anti-phosphotyrosine immunoblotting with monoclonal antibody 4G10 (Upstate Biotechnology) and detection via enhanced chemiluminescence (Amersham) was carried out as previously described (Id). For in vitro kinase assays, the washed beads were incubated for 15 min at room temperature in 20 mM Hepes (pH 7.2), 10 mM MnCl2, 30 mM sodium orthovanadate and 10 MCi of (g-$^{32}$P)ATP (NEN DUPONT). Electrophoresis sample buffer was added and the samples were boiled, subjected to SDS PAGE, and electroblotted to PVDF. The membrane was then incubated in 1 M NaOH at 65° C. for 60 min to destroy serine and threonine phosphate before autoradiography.

Results

CNTF-Induced Responses are Associated with a 130 kDa Protein

Following addition of CNTF, a receptor complex forms that consists of CNTF, CNTFRα, gp130, and LIFRβ. Immunoprecipitation (IP) of the receptor complex with antibodies against LIFRβ or gp130 (not shown) following cell lysis in the detergent Brij 96 results in the co-purification of a 130 kDa protein that is tyrosine phosphorylated. LIF and OSM, which also bind to and heterodimerize gp130 and LIFRβ (Gearing et al., *Science* 260:1434–1437 (1992); Baumann et al., *J. Biol. Chem.* 268:8414–8417 (1993); Davis et al., *Science* 250:1805–1808 (1993)), also show association and tyrosine phosphorylation of a protein with an identical appearance. The purified receptor complex also shows associated protein tyrosine kinase activity in vitro giving rise to tyrosine phosphorylation of both gp130 and LIFRβ, as well as the associated 130 kDa protein. Tyrosine kinase activity is also associated with LIFRβ in the absence of CNTF, although the 130 kDa protein is either not present or not significantly phosphorylated in the absence of the factor. Other experiments showing that this in vitro kinase activity has the same sensitivity to staurosporine as that observed upon addition of CNTF to intact cells suggested that this associated tyrosine kinase activity is relevant to that which is required in the cell to mediate CNTF-induced responses. Furthermore, the 130 kDa protein appears to be a good candidate for this kinase since lysis of the cells in NP-40 does not give co-purification of either the 130 kDa protein or tyrosine kinase activity (not shown).

CNTF and Related Factors Induce Tyrosine Phosphorylation of Jak1, Jak2 and Tyk2

Experiments using specific antisera raised against portions of Jak1, Jak2, or Tyk2 reveal that all 3 of these kinases can become tyrosine phosphorylated following stimulation by CNTF, LIF, OSM, and IL6. CNTF induces tyrosine phosphorylation of both Jak1 and Jak2 in EW1 cells, and these proteins appear to co-migrate with 130 and 131 kDa proteins that co-purify with the receptor complex immunoprecipitated with α-LIFRβ. Furthermore, the addition of IL6+sIL6Rα, as well as LIF and OSM (not shown) to EW-1 calls also results in phosphorylation of Jak1 and Jak2 but not Tyk2. In contrast, IL6 stimulated U266 cells give tyrosine phosphorylation of Tyk2 and Jak1 without apparent change in the phosphorylation status of Jak2. OSM treated SK-MES cells reveal tyrosine phosphorylation of primarily Jak2, with smaller changes in Tyk2 and Jak1. In each of these cases, tyrosine phosphorylation of the Jaks or Tyk2 is associated with an increase in their in vitro tyrosine kinase activity (not shown). These results stand in contrast to previous results showing that stimulation with GM-CSF, EPO, G-CSF, IFN-γ, or IL-3 only result in tyrosine phosphorylation of Jak2 ((Argetsinger et al., *Cell* 74:237–244 (1993); Silvennoinen et al., *Proc. Natl. Acad. Sci. USA* (in press; 1993); Witthuhn et al., *Cell* 74:227–236 (1993)). We conclude from these experiments that the CNTF family of factors can activate Jak1, Jak2, and Tyk2, although there is some variability in which Jak/Tyk family member is activated in a particular cell.

The Jaks Associate with CNTF β Receptor Components

Transient transfections in COS cells were used to determine whether the Jaks could associate with the β receptor components in the absence of factors. These experiments used carboxyl terminally epitope-tagged versions of LIFRβ containing the 10 amino acid portion of c-myc that is recognized by the monoclonal antibody 9E10 (Davis et al., *Science* 253:59–63 (1991)). COS cells were co-transfected with appropriate expression vectors encoding full length versions of LIFRβ and Jak1 or Jak2, and Brij 96 lysates were immunoprecipitated with 9E10 and then blotted with the antisera against either Jak1 or Jak2. These experiments show that either Jak can associate with LIFRβ in the absence of any added ligand. Furthermore, a truncated version of LIFRβ which retains only the first 76 amino acids of the cytoplasmic domain is fully capable of binding to Jak1 and Jak2 as well. This implicates the membrane proximal region of LIFRβ as the Jak binding domain, which is consistent with the homology between this region of the receptor with those in gp130 and EPOR that have been shown to be required for signal transduction upon factor binding (Murakami et al., *Science* 260:11349–11353 (1991); Witthuhn et al., *Cell* 74:227–236 (1993)).

Co-Transfection with Receptor β-Components and Jaks Results in Ligand Induced Functional Response Further experiments in COS cells were undertaken to establish whether co-transfection of the receptor β-components with the Jaks could reconstruct a ligand-induced functional response. Epitope-tagged gp130FLAG and IL6 were chosen for these experiments, since gp130 homodimerizes and becomes tyrosine phosphorylated in response to IL6+soluble IL6Rα, obviating the need for co-transfection with LIFRβ (Murakami et al., *Proc. Natl. Acad. Sci. USA* 88:11349–11353 (1993); Davis et al., *Science* 260:1805–1808 (1993)). Following stimulation with IL6+sIL6Rα, neither mock transfected nor gp130FLAG transfected COS cells revealed substantial tyrosine phosphorylation of gp130 following immunoprecipitation with anti-FLAG and α-PTyr immunoblotting. In contrast, co-transfection with either Jak1, Jak2, or both Jak1 and Jak2 gives rise to a substantial increase in the induced tyrosine phosphorylation of gp130 upon stimulation with IL6+sIL6Rα.

Discussion

Altogether, these results indicate that the Jaks can associate with the CNTF receptor β components, and become tyrosine phosphorylated in response to CNTF, LIF, IL6, or OSM, with concomitant activation of the tyrosine kinase. This most likely occurs through transphosphorylation as ligand-induced hetero- or homo-dimerization of the β components brings their bound Jaks into close apposition (Stahl and Yancopoulos, *Cell* 74:587–590 (1993)). The functional reconstruction in COS cells of ligand-induced tyrosine phosphorylation of gp130 upon co-transfection with either Jak1 or Jak2 is consistent with the notion that Jak1, Jak2, or Tyk2 can function as the first kinases activated inside the cell upon receptor β subunit dimerization, thus placing the Jak family of kinases as the most proximal intracellular step in mediating signal transduction of the CNTF family of factors.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in fight of the teachings and guidance presented herein, in combination with the knowledge of one of ordinary skill in the art.

What is claimed is:

1. A method for inhibiting or enhancing the biological response of a eukaryotic cell to a cytokine, comprising (A) inhibiting or enhancing the tyrosine kinase activity of a murine or human Jak kinase in said eukaryotic cell, wherein said response is mediated by the activation of said Jak kinase, and wherein, when said Jak kinase is Jak2, said cytokine is other than erythropoietin (EPO) or interleukin-3 (IL-3).

2. A method according to claim 1, wherein the activity of said Jak kinase is inhibited by introducing into said eukaryotic cell effective amounts of a composition capable of inhibiting the expression of said Jak kinase in said eukaryotic cell.

3. A method according to claim 1, wherein the activity of said Jak kinase is inhibited by introducing into said eukaryotic cell effective amounts of a composition capable of inhibiting said activity.

4. A method according to claim 1, wherein said Jak kinase is murine Jak3.

5. A method for treating a disease condition in an animal caused by cytokine-induced activation of at least one member of a Jak kinase family, the method comprising, inhibiting tyrosine kinase activity of said Jak kinase in said cells, wherein when said Jak kinase is Jak2, said cytokine is not erythropoietin (EPO) or interleukin-3 (IL-3).

6. A method for identifying a composition capable of inhibiting or enhancing the biological response of a eukaryotic cell to a cytokine whose induction of tyrosine kinase activity is mediated by the activation of a Jak kinase, comprising detecting the ability of said composition to inhibit or enhance the in vitro or in vivo kinase activity or activation of said Jak kinase, wherein, when said Jak kinase is Jak 2, said cytokine is not erythropoietin (EPO) or interleukin-3 (IL-3).

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 5 amino acids
      (B) TYPE: amino acid
      (D) TOPOLOGY: linear (xi) SEQUENCE DESCRIPTION: SEQ ID NO:1:

Trp Ser Xaa Trp Ser
1         5

(2) INFORMATION FOR SEQ ID NO:2:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:2:

```
Val Leu Pro Gln Asp Lys Glu Tyr Tyr Lys Val Lys Glu Pro Gly
1               5                   10                  15
```

(2) INFORMATION FOR SEQ ID NO:3:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:3:

```
Ala Ile Glu Thr Asp Lys Glu Tyr Tyr Thr Val Lys Asp Asp Arg
1               5                   10                  15
```

(2) INFORMATION FOR SEQ ID NO:4:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:4:

```
Ala Val Pro Glu Gly His Glu Tyr Tyr Arg Val Arg Glu Asp Gly
1               5                   10                  15
```

(2) INFORMATION FOR SEQ ID NO:5:

(i) SEQUENCE CHARACTERISTICS:
        (A) LENGTH: 19 amino acids
        (B) TYPE: amino acid
        (D) TOPOLOGY: linear (xi) SEQUENCE DESCRIPTION: SEQ ID NO:5:

```
Asp Ser Gln Arg Lys Leu Gln Phe Tyr Glu Asp Lys His Gln Leu Pro
1               5                   10                  15
Ala Pro Lys
```

(2) INFORMATION FOR SEQ ID NO:6:

(i) SEQUENCE CHARACTERISTICS:
        (A) LENGTH: 19 amino acids
        (B) TYPE: amino acid
        (D) TOPOLOGY: linear (xi) SEQUENCE DESCRIPTION: SEQ ID NO:6:

```
Thr Leu Ile Glu Lys Glu Arg Phe Tyr Glu Ser Arg Cys Arg Pro Val
1               5                   10                  15
Thr Pro Ser
```

(2) INFORMATION FOR SEQ ID NO:7:

(i) SEQUENCE CHARACTERISTICS:
        (A) LENGTH: 19 amino acids
        (B) TYPE: amino acid
        (D) TOPOLOGY: linear (xi) SEQUENCE DESCRIPTION: SEQ ID NO:7:

-continued

```
Ser Pro Ser Glu Lys Glu His Phe Tyr Gln Arg Gln His Arg Leu Pro
 1               5                  10                  15

Glu Pro Ser (2) INFORMATION FOR SEQ ID NO:8:

(i) SEQUENCE CHARACTERISTICS:
        (A) LENGTH: 3629 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 94..3480

(xi) SEQUENCE DESCRIPTION: SEQ ID NO:8:

CGGGGGAACA AGATGTGAAC TGTTTTCCCT CCCCAGAAGA AGAGGCCCTT TTTTTCCCTC      60

CCGCGAAGGC CAATGTTCTG AAAAAAGCTC TAG ATG GGA ATG GCC TGC CTT ACA     114
                                    Met Gly Met Ala Cys Leu Thr
                                     1               5

ATG ACA GAA ATG GAG GCA ACC TCC ACA TCT CCT GTA CAT CAG AAT GGT      162
Met Thr Glu Met Glu Ala Thr Ser Thr Ser Pro Val His Gln Asn Gly
         10                  15                  20

GAT ATT CCT GGA AGT GCT AAT TCT GTG AAG CAG ATA GAG CCA GTC CTT      210
Asp Ile Pro Gly Ser Ala Asn Ser Val Lys Gln Ile Glu Pro Val Leu
     25                  30                  35

CAA GTG TAT CTG TAC CAT TCT CTT GGG CAA GCT GAA GGA GAG TAT CTG      258
Gln Val Tyr Leu Tyr His Ser Leu Gly Gln Ala Glu Gly Glu Tyr Leu
 40                  45                  50                  55

AAG TTT CCA AGT GGA GAG TAT GTT GCA GAA GAA ATT TGT GTG GCT GCT      306
Lys Phe Pro Ser Gly Glu Tyr Val Ala Glu Glu Ile Cys Val Ala Ala
                 60                  65                  70

TCT AAA GCT TGT GGT ATT ACG CCT GTG TAT CAT AAT ATG TTT GCG TTA      354
Ser Lys Ala Cys Gly Ile Thr Pro Val Tyr His Asn Met Phe Ala Leu
             75                  80                  85

ATG AGT GAA ACC GAA AGG ATC TGG TAC CCA CCC AAT CAT GTC TTC CAC      402
Met Ser Glu Thr Glu Arg Ile Trp Tyr Pro Pro Asn His Val Phe His
         90                  95                 100

ATA GAC GAG TCA ACC AGG CAT GAC ATA CTC TAC AGG ATA AGG TTC TAC      450
Ile Asp Glu Ser Thr Arg His Asp Ile Leu Tyr Arg Ile Arg Phe Tyr
    105                 110                 115

TTC CCT CAT TGG TAC TGT AGT GGC AGC AGC AGA ACC TAC AGA TAC GGA      498
Phe Pro His Trp Tyr Cys Ser Gly Ser Ser Arg Thr Tyr Arg Tyr Gly
120                 125                 130                 135

GTG TCC CGT GGG GCT GAA GCT CCT CTG CTT GAT GAC TTT GTC ATG TCT      546
Val Ser Arg Gly Ala Glu Ala Pro Leu Leu Asp Asp Phe Val Met Ser
                140                 145                 150

TAC CTT TTT GCT CAG TGG CGG CAT GAT TTT GTT CAC GGA TGG ATA AAA      594
Tyr Leu Phe Ala Gln Trp Arg His Asp Phe Val His Gly Trp Ile Lys
            155                 160                 165

GTA CCT GTG ACT CAT GAA ACT CAG GAA GAG TGT CTT GGG ATG GCG GTG      642
Val Pro Val Thr His Glu Thr Gln Glu Glu Cys Leu Gly Met Ala Val
        170                 175                 180

TTA GAC ATG ATG AGA ATA GCT AAG GAG AAA GAC CAG ACT CCA CTG GCT      690
Leu Asp Met Met Arg Ile Ala Lys Glu Lys Asp Gln Thr Pro Leu Ala
    185                 190                 195

GTC TAT AAC TCT GTC AGC TAC AAG ACA TTC TTA CCA AAG TGC GTT CGA      738
Val Tyr Asn Ser Val Ser Tyr Lys Thr Phe Leu Pro Lys Cys Val Arg
200                 205                 210                 215

GCG AAG ATC CAA GAC TAT CAC ATT TTA ACC CGG AAG CGA ATC AGG TAC      786
```

```
                    Ala Lys Ile Gln Asp Tyr His Ile Leu Thr Arg Lys Arg Ile Arg Tyr
                            220                 225                 230

AGA TTT CGC AGA TTC ATT CAG CAA TTC AGT CAA TGT AAA GCC ACT GCC         834
Arg Phe Arg Arg Phe Ile Gln Gln Phe Ser Gln Cys Lys Ala Thr Ala
            235                 240                 245

AGG AAC CTA AAA CTT AAG TAT CTT ATA AAC CTG GAA ACC CTG CAG TCT         882
Arg Asn Leu Lys Leu Lys Tyr Leu Ile Asn Leu Glu Thr Leu Gln Ser
            250                 255                 260

GCC TTC TAC ACA GAA CAG TTT GAA GTA AAA GAA TCT GCA AGA GGT CCT         930
Ala Phe Tyr Thr Glu Gln Phe Glu Val Lys Glu Ser Ala Arg Gly Pro
            265                 270                 275

TCA GGT GAG GAG ATT TTT GCA ACC ATT ATA ATA ACT GGA AAC GGT GGA         978
Ser Gly Glu Glu Ile Phe Ala Thr Ile Ile Thr Gly Asn Gly Gly
280                 285                 290                 295

ATT CAG TGG TCA AGA GGG AAA CAT AAG GAA AGT GAG ACA CTG ACA GAA        1026
Ile Gln Trp Ser Arg Gly Lys His Lys Glu Ser Glu Thr Leu Thr Glu
                300                 305                 310

CAG GAC GTA CAG TTA TAT TGT GAT TTC CCT GAT ATT ATT GAT GTC AGT        1074
Gln Asp Val Gln Leu Tyr Cys Asp Phe Pro Asp Ile Ile Asp Val Ser
            315                 320                 325

ATT AAG CAA GCA AAC CAG GAA TGC TCA AAT GAA AGT AGA ATT GTA ACT        1122
Ile Lys Gln Ala Asn Gln Glu Cys Ser Asn Glu Ser Arg Ile Val Thr
            330                 335                 340

GTC CAT AAA CAA GAT GGT AAA GTT TTG GAG ATA GAA CTT AGC TCA TTA        1170
Val His Lys Gln Asp Gly Lys Val Leu Glu Ile Glu Leu Ser Ser Leu
345                 350                 355

AAA GAA GCC TTG TCA TTC GTG TCA TTA ATT GAC GGG TAT TAC AGA CTA        1218
Lys Glu Ala Leu Ser Phe Val Ser Leu Ile Asp Gly Tyr Tyr Arg Leu
360                 365                 370                 375

ACT GCG GAT GCG CAC CAT TAC CTC TGC AAA GAG GTG GCT CCC CCA GCT        1266
Thr Ala Asp Ala His His Tyr Leu Cys Lys Glu Val Ala Pro Pro Ala
                380                 385                 390

GTG CTC GAG AAC ATA CAC AGC AAC TGC CAC GGC CCA ATA TCA ATG GAT        1314
Val Leu Glu Asn Ile His Ser Asn Cys His Gly Pro Ile Ser Met Asp
            395                 400                 405

TTT GCC ATT AGC AAA CTA AAG AAG GCG GGT AAC CAG ACT GGA CTA TAT        1362
Phe Ala Ile Ser Lys Leu Lys Lys Ala Gly Asn Gln Thr Gly Leu Tyr
            410                 415                 420

GTG CTA CGA TGC AGC CCT AAG GAC TTC AAC AAA TAC TTT CTG ACC TTT        1410
Val Leu Arg Cys Ser Pro Lys Asp Phe Asn Lys Tyr Phe Leu Thr Phe
425                 430                 435

GCT GTT GAG CGA GAA AAT GTC ATT GAA TAT AAA CAC TGT TTG ATT ACG        1458
Ala Val Glu Arg Glu Asn Val Ile Glu Tyr Lys His Cys Leu Ile Thr
440                 445                 450                 455

AAG AAT GAG AAT GGA GAA TAC AAC CTC AGC GGG ACT AAG AGG AAC TTC        1506
Lys Asn Glu Asn Gly Glu Tyr Asn Leu Ser Gly Thr Lys Arg Asn Phe
                460                 465                 470

AGT AAC CTT AAG GAC CTT TTG AAT TGC TAC CAG ATG GAA ACT GTG CGC        1554
Ser Asn Leu Lys Asp Leu Leu Asn Cys Tyr Gln Met Glu Thr Val Arg
            475                 480                 485

TCA GAC AGT ATC ATC TTC CAG TTT ACC AAA TGC TGC CCC CCA AAG CCA        1602
Ser Asp Ser Ile Ile Phe Gln Phe Thr Lys Cys Cys Pro Pro Lys Pro
            490                 495                 500

AAA GAT AAA TCA AAC CTT CTC GTC TTC AGA ACA AAT GGT ATT TCT GAT        1650
Lys Asp Lys Ser Asn Leu Leu Val Phe Arg Thr Asn Gly Ile Ser Asp
505                 510                 515

GTT CAG ATC TCA CCA ACA TTA CAG AGG CAT AAT AAT GTG AAT CAA ATG        1698
Val Gln Ile Ser Pro Thr Leu Gln Arg His Asn Asn Val Asn Gln Met
520                 525                 530                 535
```

```
GTG TTT CAC AAA ATC AGG AAT GAA GAT TTA ATA TTT AAT GAA AGT CTT      1746
Val Phe His Lys Ile Arg Asn Glu Asp Leu Ile Phe Asn Glu Ser Leu
            540                 545                 550

GGC CAA GGT ACT TTT ACA AAA ATT TTT AAA GGT GTA AGA AGA GAA GTT      1794
Gly Gln Gly Thr Phe Thr Lys Ile Phe Lys Gly Val Arg Arg Glu Val
            555                 560                 565

GGA GAT TAT GGT CAA CTG CAC AAA ACG GAA GTT CTT TTG AAA GTC CTA      1842
Gly Asp Tyr Gly Gln Leu His Lys Thr Glu Val Leu Leu Lys Val Leu
            570                 575                 580

GAT AAA GCA CAT AGG AAC TAT TCA GAG TCT TTC TTC GAA GCA GCA AGC      1890
Asp Lys Ala His Arg Asn Tyr Ser Glu Ser Phe Phe Glu Ala Ala Ser
585                 590                 595

ATG ATG AGT CAG CTT TCT CAC AAG CAT TTG GTT TTG AAT TAT GGT GTC      1938
Met Met Ser Gln Leu Ser His Lys His Leu Val Leu Asn Tyr Gly Val
600                 605                 610                 615

TGT GTC TGT GGA GAG GAG AAC ATT CTG GTT CAA GAA TTT GTA AAA TTT      1986
Cys Val Cys Gly Glu Glu Asn Ile Leu Val Gln Glu Phe Val Lys Phe
            620                 625                 630

GGA TCA CTG GAT ACA TAC CTG AAG AAG AAC AAA AAT TCC ATA AAT ATA      2034
Gly Ser Leu Asp Thr Tyr Leu Lys Lys Asn Lys Asn Ser Ile Asn Ile
            635                 640                 645

TTA TGG AAA CTT GGA GTG GCT AAG CAG TTG GCA TGG GCC ATG CAT TTT      2082
Leu Trp Lys Leu Gly Val Ala Lys Gln Leu Ala Trp Ala Met His Phe
            650                 655                 660

CTA GAA GAA AAA TCC CTT ATT CAT GGG AAT GTG TGT GCT AAA AAT ATC      2130
Leu Glu Glu Lys Ser Leu Ile His Gly Asn Val Cys Ala Lys Asn Ile
            665                 670                 675

CTG CTT ATC AGA GAA GAA GAC AGG AGA ACG GGG AAC CCA CCT TTC ATC      2178
Leu Leu Ile Arg Glu Glu Asp Arg Arg Thr Gly Asn Pro Pro Phe Ile
680                 685                 690                 695

AAA CTT AGT GAT CCT GGC ATT AGC ATT ACA GTT CTA CCG AAG GAC ATT      2226
Lys Leu Ser Asp Pro Gly Ile Ser Ile Thr Val Leu Pro Lys Asp Ile
            700                 705                 710

CTT CAG GAG AGA ATA CCA TGG GTA CCT CCT GAA TGC ATT GAG AAT CCT      2274
Leu Gln Glu Arg Ile Pro Trp Val Pro Pro Glu Cys Ile Glu Asn Pro
            715                 720                 725

AAA AAT CTC AAT CTG GCA ACA GAC AAG TGG AGC TTC GGG ACC ACT CTG      2322
Lys Asn Leu Asn Leu Ala Thr Asp Lys Trp Ser Phe Gly Thr Thr Leu
            730                 735                 740

TGG GAG ATC TGC AGT GGA GGA GAT AAG CCC CTG AGT GCT CTG GAT TCT      2370
Trp Glu Ile Cys Ser Gly Gly Asp Lys Pro Leu Ser Ala Leu Asp Ser
745                 750                 755

CAA AGA AAG CTG CAG TTC TAT GAA GAT AAG CAT CAG CTT CCT GCA CCC      2418
Gln Arg Lys Leu Gln Phe Tyr Glu Asp Lys His Gln Leu Pro Ala Pro
760                 765                 770                 775

AAG TGG ACA GAG TTA GCA AAC CTT ATA AAT AAT TGC ATG GAC TAT GAG      2466
Lys Trp Thr Glu Leu Ala Asn Leu Ile Asn Asn Cys Met Asp Tyr Glu
            780                 785                 790

CCA GAT TTC AGG CCT GCT TTC AGA GCT GTC ATC CGT GAT CTT AAC AGC      2514
Pro Asp Phe Arg Pro Ala Phe Arg Ala Val Ile Arg Asp Leu Asn Ser
            795                 800                 805

CTG TTT ACT CCA GAT TAT GAA CTA CTA ACA GAA AAT GAC ATG CTA CCA      2562
Leu Phe Thr Pro Asp Tyr Glu Leu Leu Thr Glu Asn Asp Met Leu Pro
            810                 815                 820

AAC ATG AGA ATA GGT GCC CTA GGG TTT TCT GGT GCT TTT GAA GAC AGG      2610
Asn Met Arg Ile Gly Ala Leu Gly Phe Ser Gly Ala Phe Glu Asp Arg
825                 830                 835

GAC CCT ACA CAG TTT GAA GAG AGA CAC TTG AAG TTT CTA CAG CAG CTT      2658
Asp Pro Thr Gln Phe Glu Glu Arg His Leu Lys Phe Leu Gln Gln Leu
840                 845                 850                 855
```

```
GGC AAA GGT AAC TTC GGG AGT GTG GAG ATG TGC CGC TAT GAC CCG CTG        2706
Gly Lys Gly Asn Phe Gly Ser Val Glu Met Cys Arg Tyr Asp Pro Leu
            860                 865                 870

CAG GAC AAC ACT GGC GAG GTG GTC GCT GTG AAG AAA CTC CAG CAC AGC        2754
Gln Asp Asn Thr Gly Glu Val Val Ala Val Lys Lys Leu Gln His Ser
            875                 880                 885

ACT GAA GAG CAC CTC CGA GAC TTT GAG AGG GAG ATC GAG ATC CTG AAA        2802
Thr Glu Glu His Leu Arg Asp Phe Glu Arg Glu Ile Glu Ile Leu Lys
            890                 895                 900

TCC TTG CAG CAT GAC AAC ATC GTC AAG TAC AAG GGA GTG TGC TAC AGT        2850
Ser Leu Gln His Asp Asn Ile Val Lys Tyr Lys Gly Val Cys Tyr Ser
    905                 910                 915

GCG GGT CGG CGC AAC CTA AGA TTA ATT ATG GAA TAT TTA CCA TAT GGA        2898
Ala Gly Arg Arg Asn Leu Arg Leu Ile Met Glu Tyr Leu Pro Tyr Gly
920                 925                 930                 935

AGT TTA CGA GAC TAT CTC CAA AAA CAT AAA GAA CGG ATA GAT CAC AAA        2946
Ser Leu Arg Asp Tyr Leu Gln Lys His Lys Glu Arg Ile Asp His Lys
                940                 945                 950

AAA CTT CTT CAA TAC ACA TCT CAG ATA TGC AAG GGC ATG GAA TAT CTT        2994
Lys Leu Leu Gln Tyr Thr Ser Gln Ile Cys Lys Gly Met Glu Tyr Leu
            955                 960                 965

GGT ACA AAA AGG TAT ATC CAC AGG GAC CTG GCA ACA AGG AAC ATA TTG        3042
Gly Thr Lys Arg Tyr Ile His Arg Asp Leu Ala Thr Arg Asn Ile Leu
            970                 975                 980

GTG GAA AAT GAG AAC AGG GTT AAA ATA GGA GAC TTC GGA TTA ACC AAA        3090
Val Glu Asn Glu Asn Arg Val Lys Ile Gly Asp Phe Gly Leu Thr Lys
    985                 990                 995

GTC TTG CCG CAG GAC AAA GAA TAC TAC AAA GTA AAG GAG CCA GGG GAA        3138
Val Leu Pro Gln Asp Lys Glu Tyr Tyr Lys Val Lys Glu Pro Gly Glu
1000                1005                1010                1015

AGC CCC ATA TTC TGG TAC GCA CCT GAA TCC TTG ACG GAG AGC AAG TTT        3186
Ser Pro Ile Phe Trp Tyr Ala Pro Glu Ser Leu Thr Glu Ser Lys Phe
                1020                1025                1030

TCT GTG GCC TCA GAT GTG TGG AGC TTT GGA GTG GTT CTA TAC GAA CTT        3234
Ser Val Ala Ser Asp Val Trp Ser Phe Gly Val Val Leu Tyr Glu Leu
            1035                1040                1045

TTC ACA TAC ATC GAG AAG AGT AAA AGT CCA CCC GTG GAA TTT ATG CGA        3282
Phe Thr Tyr Ile Glu Lys Ser Lys Ser Pro Pro Val Glu Phe Met Arg
            1050                1055                1060

ATG ATT GGC AAT GAT AAA CAA GGG CAA ATG ATT GTG TTC CAT TTG ATA        3330
Met Ile Gly Asn Asp Lys Gln Gly Gln Met Ile Val Phe His Leu Ile
        1065                1070                1075

GAG CTA CTG AAG AGC AAC GGA AGA TTG CCA AGG CCA GAA GGA TGC CCA        3378
Glu Leu Leu Lys Ser Asn Gly Arg Leu Pro Arg Pro Glu Gly Cys Pro
1080                1085                1090                1095

GAT GAG ATT TAT GTG ATC ATG ACA GAG TGC TGG AAC AAC AAT GTG AGC        3426
Asp Glu Ile Tyr Val Ile Met Thr Glu Cys Trp Asn Asn Asn Val Ser
                1100                1105                1110

CAG CGT CCC TCC TTC AGG GAC CTT TCG TTC GGG TGG ATC AAA TCC GGG        3474
Gln Arg Pro Ser Phe Arg Asp Leu Ser Phe Gly Trp Ile Lys Ser Gly
            1115                1120                1125

ACA GTA TAGCTGCGTG AAAGAGATGG CCTTCACTCA GAGACCAAGC AGACTTCCAG         3530
Thr Val

AACCAGAACA AAGCTCTGTA GCCTTGTGTC TACACATCCT TATCATGATG CTAGCTAGGC      3590

AGAAGAAACT GTGACGCCGT CTGCTCAAAG CTTTGCTTC                             3629

(2) INFORMATION FOR SEQ ID NO:9:
```

-continued

```
    (i) SEQUENCE CHARACTERISTICS:
         (A) LENGTH: 1129 amino acids
         (B) TYPE: amino acid
         (D) TOPOLOGY: linear (ii) MOLECULE TYPE: protein (xi) SEQUENCE DESCRIPTION: SEQ ID NO:9:

Met Gly Met Ala Cys Leu Thr Met Thr Glu Met Glu Ala Thr Ser Thr
 1               5                  10                  15

Ser Pro Val His Gln Asn Gly Asp Ile Pro Gly Ser Ala Asn Ser Val
                20                  25                  30

Lys Gln Ile Glu Pro Val Leu Gln Val Tyr Leu Tyr His Ser Leu Gly
            35                  40                  45

Gln Ala Glu Gly Glu Tyr Leu Lys Phe Pro Ser Gly Glu Tyr Val Ala
        50                  55                  60

Glu Glu Ile Cys Val Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asp Ile
               100                 105                 110

Leu Tyr Arg Ile Arg Phe Tyr Phe Pro His Trp Tyr Cys Ser Gly Ser
           115                 120                 125

Ser Arg Thr Tyr Arg Tyr Gly Val Ser Arg Gly Ala Glu Ala Pro Leu
       130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
           180                 185                 190

Lys Asp Gln Thr Pro Leu Ala Val Tyr Asn Ser Val Ser Tyr Lys Thr
       195                 200                 205

Phe Leu Pro Lys Cys Val Arg Ala Lys Ile Gln Asp Tyr His Ile Leu
   210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
                245                 250                 255

Asn Leu Glu Thr Leu Gln Ser Ala Phe Tyr Thr Glu Gln Phe Glu Val
           260                 265                 270

Lys Glu Ser Ala Arg Gly Pro Ser Gly Glu Glu Ile Phe Ala Thr Ile
       275                 280                 285

Ile Ile Thr Gly Asn Gly Gly Ile Gln Trp Ser Arg Gly Lys His Lys
   290                 295                 300

Glu Ser Glu Thr Leu Thr Glu Gln Asp Val Gln Leu Tyr Cys Asp Phe
305                 310                 315                 320

Pro Asp Ile Ile Asp Val Ser Ile Lys Gln Ala Asn Gln Glu Cys Ser
                325                 330                 335

Asn Glu Ser Arg Ile Val Thr Val His Lys Gln Asp Gly Lys Val Leu
           340                 345                 350

Glu Ile Glu Leu Ser Ser Leu Lys Glu Ala Leu Ser Phe Val Ser Leu
       355                 360                 365

Ile Asp Gly Tyr Tyr Arg Leu Thr Ala Asp Ala His His Tyr Leu Cys
```

```
          370             375             380
Lys Glu Val Ala Pro Pro Ala Val Leu Glu Asn Ile His Ser Asn Cys
385                 390                 395                 400

His Gly Pro Ile Ser Met Asp Phe Ala Ile Ser Lys Leu Lys Lys Ala
                405                 410                 415

Gly Asn Gln Thr Gly Leu Tyr Val Leu Arg Cys Ser Pro Lys Asp Phe
            420                 425                 430

Asn Lys Tyr Phe Leu Thr Phe Ala Val Glu Arg Glu Asn Val Ile Glu
                435                 440                 445

Tyr Lys His Cys Leu Ile Thr Lys Asn Glu Asn Gly Glu Tyr Asn Leu
        450                 455                 460

Ser Gly Thr Lys Arg Asn Phe Ser Asn Leu Lys Asp Leu Leu Asn Cys
465                 470                 475                 480

Tyr Gln Met Glu Thr Val Arg Ser Asp Ser Ile Ile Phe Gln Phe Thr
                485                 490                 495

Lys Cys Cys Pro Pro Lys Pro Lys Asp Lys Ser Asn Leu Leu Val Phe
            500                 505                 510

Arg Thr Asn Gly Ile Ser Asp Val Gln Ile Ser Pro Thr Leu Gln Arg
                515                 520                 525

His Asn Asn Val Asn Gln Met Val Phe His Lys Ile Arg Asn Glu Asp
    530                 535                 540

Leu Ile Phe Asn Glu Ser Leu Gly Gln Gly Thr Phe Thr Lys Ile Phe
545                 550                 555                 560

Lys Gly Val Arg Arg Glu Val Gly Asp Tyr Gly Gln Leu His Lys Thr
                565                 570                 575

Glu Val Leu Leu Lys Val Leu Asp Lys Ala His Arg Asn Tyr Ser Glu
            580                 585                 590

Ser Phe Phe Glu Ala Ala Ser Met Met Ser Gln Leu Ser His Lys His
                595                 600                 605

Leu Val Leu Asn Tyr Gly Val Cys Val Cys Gly Glu Glu Asn Ile Leu
    610                 615                 620

Val Gln Glu Phe Val Lys Phe Gly Ser Leu Asp Thr Tyr Leu Lys Lys
625                 630                 635                 640

Asn Lys Asn Ser Ile Asn Ile Leu Trp Lys Leu Gly Val Ala Lys Gln
                645                 650                 655

Leu Ala Trp Ala Met His Phe Leu Glu Glu Lys Ser Leu Ile His Gly
                660                 665                 670

Asn Val Cys Ala Lys Asn Ile Leu Leu Ile Arg Glu Glu Asp Arg Arg
            675                 680                 685

Thr Gly Asn Pro Pro Phe Ile Lys Leu Ser Asp Pro Gly Ile Ser Ile
    690                 695                 700

Thr Val Leu Pro Lys Asp Ile Leu Gln Glu Arg Ile Pro Trp Val Pro
705                 710                 715                 720

Pro Glu Cys Ile Glu Asn Pro Lys Asn Leu Asn Leu Ala Thr Asp Lys
                725                 730                 735

Trp Ser Phe Gly Thr Thr Leu Trp Glu Ile Cys Ser Gly Gly Asp Lys
            740                 745                 750

Pro Leu Ser Ala Leu Asp Ser Gln Arg Lys Leu Gln Phe Tyr Glu Asp
    755                 760                 765

Lys His Gln Leu Pro Ala Pro Lys Trp Thr Glu Leu Ala Asn Leu Ile
    770                 775                 780

Asn Asn Cys Met Asp Tyr Glu Pro Asp Phe Arg Pro Ala Phe Arg Ala
785                 790                 795                 800
```

Val Ile Arg Asp Leu Asn Ser Leu Phe Thr Pro Asp Tyr Glu Leu Leu
                805                 810                 815

Thr Glu Asn Asp Met Leu Pro Asn Met Arg Ile Gly Ala Leu Gly Phe
            820                 825                 830

Ser Gly Ala Phe Glu Asp Arg Asp Pro Thr Gln Phe Glu Glu Arg His
        835                 840                 845

Leu Lys Phe Leu Gln Gln Leu Gly Lys Gly Asn Phe Gly Ser Val Glu
    850                 855                 860

Met Cys Arg Tyr Asp Pro Leu Gln Asp Asn Thr Gly Glu Val Val Ala
865                 870                 875                 880

Val Lys Lys Leu Gln His Ser Thr Glu Glu His Leu Arg Asp Phe Glu
                885                 890                 895

Arg Glu Ile Glu Ile Leu Lys Ser Leu Gln His Asp Asn Ile Val Lys
            900                 905                 910

Tyr Lys Gly Val Cys Tyr Ser Ala Gly Arg Arg Asn Leu Arg Leu Ile
        915                 920                 925

Met Glu Tyr Leu Pro Tyr Gly Ser Leu Arg Asp Tyr Leu Gln Lys His
    930                 935                 940

Lys Glu Arg Ile Asp His Lys Lys Leu Leu Gln Tyr Thr Ser Gln Ile
945                 950                 955                 960

Cys Lys Gly Met Glu Tyr Leu Gly Thr Lys Arg Tyr Ile His Arg Asp
                965                 970                 975

Leu Ala Thr Arg Asn Ile Leu Val Glu Asn Glu Asn Arg Val Lys Ile
            980                 985                 990

Gly Asp Phe Gly Leu Thr Lys Val Leu Pro Gln Asp Lys Glu Tyr Tyr
        995                 1000                1005

Lys Val Lys Glu Pro Gly Glu Ser Pro Ile Phe Trp Tyr Ala Pro Glu
    1010                1015                1020

Ser Leu Thr Glu Ser Lys Phe Ser Val Ala Ser Asp Val Trp Ser Phe
1025                1030                1035                1040

Gly Val Val Leu Tyr Glu Leu Phe Thr Tyr Ile Glu Lys Ser Lys Ser
                1045                1050                1055

Pro Pro Val Glu Phe Met Arg Met Ile Gly Asn Asp Lys Gln Gly Gln
            1060                1065                1070

Met Ile Val Phe His Leu Ile Glu Leu Leu Lys Ser Asn Gly Arg Leu
        1075                1080                1085

Pro Arg Pro Glu Gly Cys Pro Asp Glu Ile Tyr Val Ile Met Thr Glu
    1090                1095                1100

Cys Trp Asn Asn Asn Val Ser Gln Arg Pro Ser Phe Arg Asp Leu Ser
1105                1110                1115                1120

Phe Gly Trp Ile Lys Ser Gly Thr Val
                1125

(2) INFORMATION FOR SEQ ID NO:10:

(i) SEQUENCE CHARACTERISTICS:
        (A) LENGTH: 3429 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..3426

(xi) SEQUENCE DESCRIPTION: SEQ ID NO:10:

```
ATG GCT TTC TGT GCT AAA ATG AGG AGC TCC AAG AAG ACT GAG GTG AAC        48
Met Ala Phe Cys Ala Lys Met Arg Ser Ser Lys Lys Thr Glu Val Asn
 1               5                  10                  15

CTG GAG GCC CCT GAG CCA GGG GTG GAA GTG ATC TTC TAT CTG TCG GAC        96
Leu Glu Ala Pro Glu Pro Gly Val Glu Val Ile Phe Tyr Leu Ser Asp
                 20                  25                  30

AGG GAG CCC CTC CGG CTG GGC AGT GGA GAG TAC ACA GCA GAG GAA CTG       144
Arg Glu Pro Leu Arg Leu Gly Ser Gly Glu Tyr Thr Ala Glu Glu Leu
             35                  40                  45

TGC ATC AGG GCT GCA CAG GCA TGC CGT ATC TCT CCT CTT TGT CAC AAC       192
Cys Ile Arg Ala Ala Gln Ala Cys Arg Ile Ser Pro Leu Cys His Asn
         50                  55                  60

CTC TTT GCC CTG TAT GAC GAG AAC ACC AAG CTC TGG TAT GCT CCA AAT       240
Leu Phe Ala Leu Tyr Asp Glu Asn Thr Lys Leu Trp Tyr Ala Pro Asn
 65                  70                  75                  80

CGC ACC ATC ACC GTT GAT GAC AAG ATG TCC CTC CGG CTC CAC TAC CGG       288
Arg Thr Ile Thr Val Asp Asp Lys Met Ser Leu Arg Leu His Tyr Arg
                 85                  90                  95

ATG AGG TTC TAT TTC ACC AAT TGG CAT GGA ACC AAC GAC AAT GAG CAG       336
Met Arg Phe Tyr Phe Thr Asn Trp His Gly Thr Asn Asp Asn Glu Gln
            100                 105                 110

TCA GTG TGG CGT CAT TCT CCA AAG AAG CAG AAA AAT GGC TAC GAG AAA       384
Ser Val Trp Arg His Ser Pro Lys Lys Gln Lys Asn Gly Tyr Glu Lys
        115                 120                 125

AAA AAG ATT CCA GAT GCA ACC CCT CTC CTT GAT GCC AGC TCA CTG GAG       432
Lys Lys Ile Pro Asp Ala Thr Pro Leu Leu Asp Ala Ser Ser Leu Glu
130                 135                 140

TAT CTG TTT GCT CAG GGA CAG TAT GAT TTG GTG AAA TGC CTG GCT CCT       480
Tyr Leu Phe Ala Gln Gly Gln Tyr Asp Leu Val Lys Cys Leu Ala Pro
145                 150                 155                 160

ATT CGA GAC CCC AAG ACC GAG CAG GAT GGA CAT GAT ATT GAG AAC GAG       528
Ile Arg Asp Pro Lys Thr Glu Gln Asp Gly His Asp Ile Glu Asn Glu
                165                 170                 175

TGT CTA GGG ATG GCT GTC CTG GCC ATC TCA CAC TAT GCC ATG ATG AAG       576
Cys Leu Gly Met Ala Val Leu Ala Ile Ser His Tyr Ala Met Met Lys
            180                 185                 190

AAG ATG CAG TTG CCA GAA CTG CCC AAG GAC ATC AGC TAC AAG CGA TAT       624
Lys Met Gln Leu Pro Glu Leu Pro Lys Asp Ile Ser Tyr Lys Arg Tyr
        195                 200                 205

ATT CCA GAA ACA TTG AAT AAG TCC ATC AGA CAG AGG AAC CTT CTC ACC       672
Ile Pro Glu Thr Leu Asn Lys Ser Ile Arg Gln Arg Asn Leu Leu Thr
210                 215                 220

AGG ATG CGG ATA AAT AAT GTT TTC AAG GAT TTC CTA AAG GAA TTT AAC       720
Arg Met Arg Ile Asn Asn Val Phe Lys Asp Phe Leu Lys Glu Phe Asn
225                 230                 235                 240

AAC AAG ACC ATT TGT GAC AGC AGC GTG TCC ACG CAT GAC CTG AAG GTG       768
Asn Lys Thr Ile Cys Asp Ser Ser Val Ser Thr His Asp Leu Lys Val
                245                 250                 255

AAA TAC TTG GCT ACC TTG GAA ACT TTG ACA AAA CAT TAC GGT GCT GAA       816
Lys Tyr Leu Ala Thr Leu Glu Thr Leu Thr Lys His Tyr Gly Ala Glu
            260                 265                 270

ATA TTT GAG ACT TCC ATG TTA CTG ATT TCA TCA GAA AAT GAG ATG AAT       864
Ile Phe Glu Thr Ser Met Leu Leu Ile Ser Ser Glu Asn Glu Met Asn
        275                 280                 285

TGG TTT CAT TCG AAT GAC GGT GGA AAC GTT CTC TAC TAC GAA GTG ATG       912
Trp Phe His Ser Asn Asp Gly Gly Asn Val Leu Tyr Tyr Glu Val Met
290                 295                 300

GTG ACT GGG AAT CTT GGA ATC CAG TGG AGG CAT AAA CCA AAT GTT GTT       960
Val Thr Gly Asn Leu Gly Ile Gln Trp Arg His Lys Pro Asn Val Val
305                 310                 315                 320
```

```
TCT GTT GAA AAG GAA AAA AAT AAA CTG AAG CGG AAA AAA CTG GAA AAT      1008
Ser Val Glu Lys Glu Lys Asn Lys Leu Lys Arg Lys Lys Leu Glu Asn
            325                 330                 335

AAA GAC AAG AAG GAT GAG GAG AAA AAC AAG ATC CGG GAA GAG TGG AAC      1056
Lys Asp Lys Lys Asp Glu Glu Lys Asn Lys Ile Arg Glu Glu Trp Asn
                340                 345                 350

AAT TTT TCA TTC TTC CCT GAA ATC ACT CAC ATT GTA ATA AAG GAG TCT      1104
Asn Phe Ser Phe Phe Pro Glu Ile Thr His Ile Val Ile Lys Glu Ser
            355                 360                 365

GTG GTC AGC ATT AAC AAG CAG GAC AAC AAG AAA ATG GAA CTG AAG CTC      1152
Val Val Ser Ile Asn Lys Gln Asp Asn Lys Lys Met Glu Leu Lys Leu
        370                 375                 380

TCT TCC CAC GAG GAG GCC TTG TCC TTT GTG TCC CTG GTA GAT GGC TAC      1200
Ser Ser His Glu Glu Ala Leu Ser Phe Val Ser Leu Val Asp Gly Tyr
385                 390                 395                 400

TTC CGG CTC ACA GCA GAT GCC CAT CAT TAC CTC TGC ACC GAC GTG GCC      1248
Phe Arg Leu Thr Ala Asp Ala His His Tyr Leu Cys Thr Asp Val Ala
                405                 410                 415

CCC CCG TTG ATC GTC CAC AAC ATA CAG AAT GGC TGT CAT GGT CCA ATC      1296
Pro Pro Leu Ile Val His Asn Ile Gln Asn Gly Cys His Gly Pro Ile
            420                 425                 430

TGT ACA GAA TAC GCC ATC AAT AAA TTG CGG CAA GAA GGA AGC GAG GAG      1344
Cys Thr Glu Tyr Ala Ile Asn Lys Leu Arg Gln Glu Gly Ser Glu Glu
        435                 440                 445

GGG ATG TAC GTG CTG AGG TGG AGC TGC ACC GAC TTT GAC AAC ATC CTC      1392
Gly Met Tyr Val Leu Arg Trp Ser Cys Thr Asp Phe Asp Asn Ile Leu
    450                 455                 460

ATG ACC GTC ACC TGC TTT GAG AAG TCT GAG CAG GTG CAG GGT GCC CAG      1440
Met Thr Val Thr Cys Phe Glu Lys Ser Glu Gln Val Gln Gly Ala Gln
465                 470                 475                 480

AAG CAG TTC AAG AAC TTT CAG ATC GAG GTG CAG AAG GGC CGC TAC AGT      1488
Lys Gln Phe Lys Asn Phe Gln Ile Glu Val Gln Lys Gly Arg Tyr Ser
                485                 490                 495

CTG CAC GGT TCG GAC CGC AGC TTC CCC AGC TTG GGA GAC CTC ATG AGC      1536
Leu His Gly Ser Asp Arg Ser Phe Pro Ser Leu Gly Asp Leu Met Ser
            500                 505                 510

CAC CTC AAG AAG CAG ATC CTG CGC ACG GAT AAC ATC AGC TTC ATG CTA      1584
His Leu Lys Lys Gln Ile Leu Arg Thr Asp Asn Ile Ser Phe Met Leu
        515                 520                 525

AAA CGC TGC TGC CAG CCC AAG CCC CGA GAA ATC TCC AAC CTG CTG GTG      1632
Lys Arg Cys Cys Gln Pro Lys Pro Arg Glu Ile Ser Asn Leu Leu Val
    530                 535                 540

GCT ACT AAG AAA GCC CAG GAG TGG CAG CCC GTC TAC CCC ATG AGC CAG      1680
Ala Thr Lys Lys Ala Gln Glu Trp Gln Pro Val Tyr Pro Met Ser Gln
545                 550                 555                 560

CTG AGT TTC GAT CGG ATC CTC AAG AAG GAT CTG GTG CAG GGC GAG CAC      1728
Leu Ser Phe Asp Arg Ile Leu Lys Lys Asp Leu Val Gln Gly Glu His
                565                 570                 575

CTT GGG AGA GGC ACG AGA ACA CAC ATC TAT TCT GGG ACC CTG ATG GAT      1776
Leu Gly Arg Gly Thr Arg Thr His Ile Tyr Ser Gly Thr Leu Met Asp
            580                 585                 590

TAC AAG GAT GAC GAA GGA ACT TCT GAA GAG AAG AAG ATA AAA GTG ATC      1824
Tyr Lys Asp Asp Glu Gly Thr Ser Glu Glu Lys Lys Ile Lys Val Ile
        595                 600                 605

CTC AAA GTC TTA GAC CCC AGC CAC AGG GAT ATT TCC CTG GCC TTC TTC      1872
Leu Lys Val Leu Asp Pro Ser His Arg Asp Ile Ser Leu Ala Phe Phe
    610                 615                 620

GAG GCA GCC AGC ATG ATG AGA CAG GTC TCC CAC AAA CAC ATC GTG TAC      1920
Glu Ala Ala Ser Met Met Arg Gln Val Ser His Lys His Ile Val Tyr
```

-continued

```
          625                    630                    635                    640
CTC TAT GGC GTC TGT GTC CGC GAC GTG GAG AAT ATC ATG GTG GAA GAG            1968
Leu Tyr Gly Val Cys Val Arg Asp Val Glu Asn Ile Met Val Glu Glu
                    645                    650                    655

TTT GTG GAA GGG GGT CCT CTG GAT CTC TTC ATG CAC CGG AAA AGT GAT            2016
Phe Val Glu Gly Gly Pro Leu Asp Leu Phe Met His Arg Lys Ser Asp
                660                    665                    670

GTC CTT ACC ACA CCA TGG AAA TTC AAA GTT GCC AAA CAG CTG GCC AGT            2064
Val Leu Thr Thr Pro Trp Lys Phe Lys Val Ala Lys Gln Leu Ala Ser
            675                    680                    685

GCC CTG AGC TAC TTG GAG GAT AAA GAC CTG GTC CAT GGA AAT GTG TGT            2112
Ala Leu Ser Tyr Leu Glu Asp Lys Asp Leu Val His Gly Asn Val Cys
                690                    695                    700

ACT AAA AAC CTC CTC CTG GCC CGT GAG GGA ATC GAC AGT GAG TGT GGC            2160
Thr Lys Asn Leu Leu Leu Ala Arg Glu Gly Ile Asp Ser Glu Cys Gly
705                    710                    715                    720

CCA TTC ATC AAG CTC AGT GAC CCC GGC ATC CCC ATT ACG GTG CTG TCT            2208
Pro Phe Ile Lys Leu Ser Asp Pro Gly Ile Pro Ile Thr Val Leu Ser
                    725                    730                    735

AGG CAA GAA TGC ATT GAA CGA ATC CCA TGG ATT GCT CCT GAG TGT GTT            2256
Arg Gln Glu Cys Ile Glu Arg Ile Pro Trp Ile Ala Pro Glu Cys Val
                740                    745                    750

GAG GAC TCC AAG AAC CTG AGT GTG GCT GCT GAC AAG TGG AGC TTT GGA            2304
Glu Asp Ser Lys Asn Leu Ser Val Ala Ala Asp Lys Trp Ser Phe Gly
            755                    760                    765

ACC ACG CTC TGG GAA ATC TGC TAC AAT GGC GAG ATC CCC TTG AAA GAC            2352
Thr Thr Leu Trp Glu Ile Cys Tyr Asn Gly Glu Ile Pro Leu Lys Asp
        770                    775                    780

AAG ACG CTG ATT GAG AAA GAG AGA TTC TAT GAA AGC CGG TGC AGG CCA            2400
Lys Thr Leu Ile Glu Lys Glu Arg Phe Tyr Glu Ser Arg Cys Arg Pro
785                    790                    795                    800

GTG ACA CCA TCA TGT AAG GAG CTG GCT GAC CTC ATG ACC CGC TGC ATG            2448
Val Thr Pro Ser Cys Lys Glu Leu Ala Asp Leu Met Thr Arg Cys Met
                    805                    810                    815

AAC TAT GAC CCC AAT CAG AGG CCT TTC TTC CGA GCC ATC ATG AGA GAC            2496
Asn Tyr Asp Pro Asn Gln Arg Pro Phe Phe Arg Ala Ile Met Arg Asp
                820                    825                    830

ATT AAT AAG CTT GAA GAG CAG AAT CCA GAT ATT GTT TCC AGA AAA AAA            2544
Ile Asn Lys Leu Glu Glu Gln Asn Pro Asp Ile Val Ser Arg Lys Lys
            835                    840                    845

AAC CAG CCA ACT GAA GTG GAC CCC ACA CAT TTT GAG AAG CGC TTC CTA            2592
Asn Gln Pro Thr Glu Val Asp Pro Thr His Phe Glu Lys Arg Phe Leu
        850                    855                    860

AAG AGG ATC CGT GAC TTG GGA GAG GGC CAC TTT GGG AAG GTT GAG CTC            2640
Lys Arg Ile Arg Asp Leu Gly Glu Gly His Phe Gly Lys Val Glu Leu
865                    870                    875                    880

TGC AGG TAT GAC CCC GAA GAC AAT ACA GGG GAG CAG GTG GCT GTT AAA            2688
Cys Arg Tyr Asp Pro Glu Asp Asn Thr Gly Glu Gln Val Ala Val Lys
                    885                    890                    895

TCT CTG AAG CCT GAG AGT GGA GGT AAC CAC ATA GCT GAT CTG AAA AAG            2736
Ser Leu Lys Pro Glu Ser Gly Gly Asn His Ile Ala Asp Leu Lys Lys
                900                    905                    910

GAA ATC GAG ATC TTA AGG AAC CTC TAT CAT GAG AAC ATT GTG AAG TAC            2784
Glu Ile Glu Ile Leu Arg Asn Leu Tyr His Glu Asn Ile Val Lys Tyr
            915                    920                    925

AAA GGA ATC TGC ACA GAA GAC GGA GGA AAT GGT ATT AAG CTC ATC ATG            2832
Lys Gly Ile Cys Thr Glu Asp Gly Gly Asn Gly Ile Lys Leu Ile Met
        930                    935                    940

GAA TTT CTG CCT TCG GGA AGC CTT AAG GAA TAT CTT CCA AAG AAT AAG            2880
```

```
Glu Phe Leu Pro Ser Gly Ser Leu Lys Glu Tyr Leu Pro Lys Asn Lys
945                 950                 955                 960

AAC AAA ATA AAC CTC AAA CAG CAG CTA AAA TAT GCC GTT CAG ATT TGT     2928
Asn Lys Ile Asn Leu Lys Gln Gln Leu Lys Tyr Ala Val Gln Ile Cys
                965                 970                 975

AAG GGG ATG GAC TAT TTG GGT TCT CGG CAA TAC GTT CAC CGG GAC TTG     2976
Lys Gly Met Asp Tyr Leu Gly Ser Arg Gln Tyr Val His Arg Asp Leu
            980                 985                 990

GCA GCA AGA AAT GTC CTT GTT GAG AGT GAA CAC CAA GTG AAA ATT GGA     3024
Ala Ala Arg Asn Val Leu Val Glu Ser Glu His Gln Val Lys Ile Gly
            995                 1000                1005

GAC TTC GGT TTA ACC AAA GCA ATT GAA ACC GAT AAG GAG TAT TAC ACC     3072
Asp Phe Gly Leu Thr Lys Ala Ile Glu Thr Asp Lys Glu Tyr Tyr Thr
        1010                1015                1020

GTC AAG GAT GAC CGG GAC AGC CCT GTG TTT TGG TAT GCT CCA GAA TGT     3120
Val Lys Asp Asp Arg Asp Ser Pro Val Phe Trp Tyr Ala Pro Glu Cys
1025                1030                1035                1040

TTA ATG CAA TCT AAA TTT TAT ATT GCC TCT GAC GTC TGG TCT TTT GGA     3168
Leu Met Gln Ser Lys Phe Tyr Ile Ala Ser Asp Val Trp Ser Phe Gly
                1045                1050                1055

GTC ACT CTG CAT GAG CTG CTG ACT TAC TGT GAT TCA GAT TCT AGT CCC     3216
Val Thr Leu His Glu Leu Leu Thr Tyr Cys Asp Ser Asp Ser Ser Pro
            1060                1065                1070

ATG GCT TTG TTC CTG AAA ATG ATA GGC CCA ACC CAT GGC CAG ATG ACA     3264
Met Ala Leu Phe Leu Lys Met Ile Gly Pro Thr His Gly Gln Met Thr
        1075                1080                1085

GTC ACA AGA CTT GTG AAT ACG TTA AAA GAA GGA AAA CGC CTG CCG TGC     3312
Val Thr Arg Leu Val Asn Thr Leu Lys Glu Gly Lys Arg Leu Pro Cys
    1090                1095                1100

CCA CCT AAC TGT CCA GAT GAG GTT TAT CAG CTT ATG AGA AAA TGC TGG     3360
Pro Pro Asn Cys Pro Asp Glu Val Tyr Gln Leu Met Arg Lys Cys Trp
1105                1110                1115                1120

GAA TTC CAA CCA TCC AAT CGG ACA AGC TTT CAG AAC CTT ATT GAA GGA     3408
Glu Phe Gln Pro Ser Asn Arg Thr Ser Phe Gln Asn Leu Ile Glu Gly
                1125                1130                1135

TTT GAA GCA CTT TTA AAA TAA                                         3429
Phe Glu Ala Leu Leu Lys
            1140

(2) INFORMATION FOR SEQ ID NO:11:

(i) SEQUENCE CHARACTERISTICS:
        (A) LENGTH: 1142 amino acids
        (B) TYPE: amino acid
        (D) TOPOLOGY: linear (ii) MOLECULE TYPE: protein (xi) SEQUENCE DESCRIPTION: SEQ ID NO:11:

Met Ala Phe Cys Ala Lys Met Arg Ser Ser Lys Lys Thr Glu Val Asn
1               5                   10                  15

Leu Glu Ala Pro Glu Pro Gly Val Glu Val Ile Phe Tyr Leu Ser Asp
            20                  25                  30

Arg Glu Pro Leu Arg Leu Gly Ser Gly Glu Tyr Thr Ala Glu Glu Leu
        35                  40                  45

Cys Ile Arg Ala Ala Gln Ala Cys Arg Ile Ser Pro Leu Cys His Asn
    50                  55                  60

Leu Phe Ala Leu Tyr Asp Glu Asn Thr Lys Leu Trp Tyr Ala Pro Asn
65                  70                  75                  80

Arg Thr Ile Thr Val Asp Asp Lys Met Ser Leu Arg Leu His Tyr Arg
```

-continued

```
                    85                    90                    95
Met Arg Phe Tyr Phe Thr Asn Trp His Gly Thr Asn Asp Asn Glu Gln
                100                   105                   110
Ser Val Trp Arg His Ser Pro Lys Lys Gln Lys Asn Gly Tyr Glu Lys
                115                   120                   125
Lys Lys Ile Pro Asp Ala Thr Pro Leu Leu Asp Ala Ser Ser Leu Glu
            130                   135                   140
Tyr Leu Phe Ala Gln Gly Gln Tyr Asp Leu Val Lys Cys Leu Ala Pro
145                   150                   155                   160
Ile Arg Asp Pro Lys Thr Glu Gln Asp Gly His Asp Ile Glu Asn Glu
                    165                   170                   175
Cys Leu Gly Met Ala Val Leu Ala Ile Ser His Tyr Ala Met Met Lys
                180                   185                   190
Lys Met Gln Leu Pro Glu Leu Pro Lys Asp Ile Ser Tyr Lys Arg Tyr
                195                   200                   205
Ile Pro Glu Thr Leu Asn Lys Ser Ile Arg Gln Arg Asn Leu Leu Thr
            210                   215                   220
Arg Met Arg Ile Asn Asn Val Phe Lys Asp Phe Leu Lys Glu Phe Asn
225                   230                   235                   240
Asn Lys Thr Ile Cys Asp Ser Ser Val Ser Thr His Asp Leu Lys Val
                    245                   250                   255
Lys Tyr Leu Ala Thr Leu Glu Thr Leu Thr Lys His Tyr Gly Ala Glu
                260                   265                   270
Ile Phe Glu Thr Ser Met Leu Leu Ile Ser Ser Glu Asn Glu Met Asn
                275                   280                   285
Trp Phe His Ser Asn Asp Gly Gly Asn Val Leu Tyr Tyr Glu Val Met
            290                   295                   300
Val Thr Gly Asn Leu Gly Ile Gln Trp Arg His Lys Pro Asn Val Val
305                   310                   315                   320
Ser Val Glu Lys Glu Lys Asn Lys Leu Lys Arg Lys Lys Leu Glu Asn
                    325                   330                   335
Lys Asp Lys Lys Asp Glu Glu Lys Lys Ile Arg Glu Glu Trp Asn
                340                   345                   350
Asn Phe Ser Phe Phe Pro Glu Ile Thr His Ile Val Ile Lys Glu Ser
                355                   360                   365
Val Val Ser Ile Asn Lys Gln Asp Asn Lys Lys Met Glu Leu Lys Leu
            370                   375                   380
Ser Ser His Glu Glu Ala Leu Ser Phe Val Ser Leu Val Asp Gly Tyr
385                   390                   395                   400
Phe Arg Leu Thr Ala Asp Ala His His Tyr Leu Cys Thr Asp Val Ala
                    405                   410                   415
Pro Pro Leu Ile Val His Asn Ile Gln Asn Gly Cys His Gly Pro Ile
                420                   425                   430
Cys Thr Glu Tyr Ala Ile Asn Lys Leu Arg Gln Glu Gly Ser Glu Glu
            435                   440                   445
Gly Met Tyr Val Leu Arg Trp Ser Cys Thr Asp Phe Asp Asn Ile Leu
450                   455                   460
Met Thr Val Thr Cys Phe Glu Lys Ser Glu Gln Val Gln Gly Ala Gln
465                   470                   475                   480
Lys Gln Phe Lys Asn Phe Gln Ile Glu Val Gln Lys Gly Arg Tyr Ser
                    485                   490                   495
Leu His Gly Ser Asp Arg Ser Phe Pro Ser Leu Gly Asp Leu Met Ser
                500                   505                   510
```

```
His Leu Lys Lys Gln Ile Leu Arg Thr Asp Asn Ile Ser Phe Met Leu
            515                 520                 525

Lys Arg Cys Cys Gln Pro Lys Pro Arg Glu Ile Ser Asn Leu Leu Val
530                 535                 540

Ala Thr Lys Lys Ala Gln Glu Trp Gln Pro Val Tyr Pro Met Ser Gln
545                 550                 555                 560

Leu Ser Phe Asp Arg Ile Leu Lys Lys Asp Leu Val Gln Gly Glu His
                565                 570                 575

Leu Gly Arg Gly Thr Arg Thr His Ile Tyr Ser Gly Thr Leu Met Asp
            580                 585                 590

Tyr Lys Asp Asp Glu Gly Thr Ser Glu Glu Lys Lys Ile Lys Val Ile
        595                 600                 605

Leu Lys Val Leu Asp Pro Ser His Arg Asp Ile Ser Leu Ala Phe Phe
610                 615                 620

Glu Ala Ala Ser Met Met Arg Gln Val Ser His Lys His Ile Val Tyr
625                 630                 635                 640

Leu Tyr Gly Val Cys Val Arg Asp Val Glu Asn Ile Met Val Glu Glu
                645                 650                 655

Phe Val Glu Gly Gly Pro Leu Asp Leu Phe Met His Arg Lys Ser Asp
            660                 665                 670

Val Leu Thr Thr Pro Trp Lys Phe Lys Val Ala Lys Gln Leu Ala Ser
        675                 680                 685

Ala Leu Ser Tyr Leu Glu Asp Lys Asp Leu Val His Gly Asn Val Cys
    690                 695                 700

Thr Lys Asn Leu Leu Leu Ala Arg Glu Gly Ile Asp Ser Glu Cys Gly
705                 710                 715                 720

Pro Phe Ile Lys Leu Ser Asp Pro Gly Ile Pro Ile Thr Val Leu Ser
                725                 730                 735

Arg Gln Glu Cys Ile Glu Arg Ile Pro Trp Ile Ala Pro Glu Cys Val
            740                 745                 750

Glu Asp Ser Lys Asn Leu Ser Val Ala Ala Asp Lys Trp Ser Phe Gly
        755                 760                 765

Thr Thr Leu Trp Glu Ile Cys Tyr Asn Gly Glu Ile Pro Leu Lys Asp
770                 775                 780

Lys Thr Leu Ile Glu Lys Glu Arg Phe Tyr Glu Ser Arg Cys Arg Pro
785                 790                 795                 800

Val Thr Pro Ser Cys Lys Glu Leu Ala Asp Leu Met Thr Arg Cys Met
                805                 810                 815

Asn Tyr Asp Pro Asn Gln Arg Pro Phe Phe Arg Ala Ile Met Arg Asp
            820                 825                 830

Ile Asn Lys Leu Glu Glu Gln Asn Pro Asp Ile Val Ser Arg Lys Lys
        835                 840                 845

Asn Gln Pro Thr Glu Val Asp Pro Thr His Phe Glu Lys Arg Phe Leu
850                 855                 860

Lys Arg Ile Arg Asp Leu Gly Glu Gly His Phe Gly Lys Val Glu Leu
865                 870                 875                 880

Cys Arg Tyr Asp Pro Glu Asp Asn Thr Gly Glu Gln Val Ala Val Lys
                885                 890                 895

Ser Leu Lys Pro Glu Ser Gly Gly Asn His Ile Ala Asp Leu Lys Lys
            900                 905                 910

Glu Ile Glu Ile Leu Arg Asn Leu Tyr His Glu Asn Ile Val Lys Tyr
        915                 920                 925
```

```
Lys Gly Ile Cys Thr Glu Asp Gly Asn Gly Ile Lys Leu Ile Met
    930                 935                 940

Glu Phe Leu Pro Ser Gly Ser Leu Lys Glu Tyr Leu Pro Lys Asn Lys
945                 950                 955                 960

Asn Lys Ile Asn Leu Lys Gln Gln Leu Lys Tyr Ala Val Gln Ile Cys
                965                 970                 975

Lys Gly Met Asp Tyr Leu Gly Ser Arg Gln Tyr Val His Arg Asp Leu
            980                 985                 990

Ala Ala Arg Asn Val Leu Val Glu Ser Glu His Gln Val Lys Ile Gly
            995                1000                1005

Asp Phe Gly Leu Thr Lys Ala Ile Glu Thr Asp Lys Glu Tyr Tyr Thr
        1010                1015                1020

Val Lys Asp Asp Arg Asp Ser Pro Val Phe Trp Tyr Ala Pro Glu Cys
1025                1030                1035                1040

Leu Met Gln Ser Lys Phe Tyr Ile Ala Ser Asp Val Trp Ser Phe Gly
                1045                1050                1055

Val Thr Leu His Glu Leu Leu Thr Tyr Cys Asp Ser Asp Ser Ser Pro
            1060                1065                1070

Met Ala Leu Phe Leu Lys Met Ile Gly Pro Thr His Gly Gln Met Thr
            1075                1080                1085

Val Thr Arg Leu Val Asn Thr Leu Lys Glu Gly Lys Arg Leu Pro Cys
            1090                1095                1100

Pro Pro Asn Cys Pro Asp Glu Val Tyr Gln Leu Met Arg Lys Cys Trp
1105                1110                1115                1120

Glu Phe Gln Pro Ser Asn Arg Thr Ser Phe Gln Asn Leu Ile Glu Gly
                1125                1130                1135

Phe Glu Ala Leu Leu Lys
            1140

(2) INFORMATION FOR SEQ ID NO:12:

(i) SEQUENCE CHARACTERISTICS:
        (A) LENGTH: 3561 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..3561

(xi) SEQUENCE DESCRIPTION: SEQ ID NO:12:

ATG CCT CTG CGC CAC TGG GGG ATG GCC AGG GGC AGT AAG CCC GTT GGG      48
Met Pro Leu Arg His Trp Gly Met Ala Arg Gly Ser Lys Pro Val Gly
1               5                  10                  15

GAT GGA GCC CAG CCC ATG GCT GCC ATG GGA GGC CTG AAG GTG CTT CTG      96
Asp Gly Ala Gln Pro Met Ala Ala Met Gly Gly Leu Lys Val Leu Leu
            20                  25                  30

CAC TGG GCT GGT CCA GGC GGC GGG GAG CCC TGG GTC ACT TTC AGT GAG     144
His Trp Ala Gly Pro Gly Gly Gly Glu Pro Trp Val Thr Phe Ser Glu
        35                  40                  45

TCA TCG CTG ACA GCT GAG GAA GTC TGC ATC CAC ATT GCA CAT AAA GTT     192
Ser Ser Leu Thr Ala Glu Glu Val Cys Ile His Ile Ala His Lys Val
    50                  55                  60

GGT ATC ACT CCT CCT TGC TTC AAT CTC TTT GCC CTC TTC GAT GCT CAG     240
Gly Ile Thr Pro Pro Cys Phe Asn Leu Phe Ala Leu Phe Asp Ala Gln
65                  70                  75                  80

GCC CAA GTC TGG TTG CCC CCA AAC CAC ATC CTA GAG ATC CCC AGA GAT     288
Ala Gln Val Trp Leu Pro Pro Asn His Ile Leu Glu Ile Pro Arg Asp
                85                  90                  95
```

|  |  |
|---|---|
| GCA AGC CTG ATG CTA TAT TTC CGC ATA AGG TTT TAT TTC CGG AAC TGG<br>Ala Ser Leu Met Leu Tyr Phe Arg Ile Arg Phe Tyr Phe Arg Asn Trp<br>        100             105             110 | 336 |
| CAT GGC ATG AAT CCT CGG GAA CCG GCT GTG TAC CGT TGT GGG CCC CCA<br>His Gly Met Asn Pro Arg Glu Pro Ala Val Tyr Arg Cys Gly Pro Pro<br>    115             120             125 | 384 |
| GGA ACC GAG GCA TCC TCA GAT CAG ACA GCA CAG GGG ATG CAA CTC CTG<br>Gly Thr Glu Ala Ser Ser Asp Gln Thr Ala Gln Gly Met Gln Leu Leu<br>130             135             140 | 432 |
| GAC CCA GCC TCA TTT GAG TAC CTC TTT GAG CAG GGC AAG CAT GAG TTT<br>Asp Pro Ala Ser Phe Glu Tyr Leu Phe Glu Gln Gly Lys His Glu Phe<br>145             150             155             160 | 480 |
| GTG AAT GAC GTG GCA TCA CTG TGG GAG CTG TCG ACC GAG GAG GAG ATC<br>Val Asn Asp Val Ala Ser Leu Trp Glu Leu Ser Thr Glu Glu Glu Ile<br>            165             170             175 | 528 |
| CAC CAC TTT AAG AAT GAG AGC CTG GGC ATG GCC TTT CTG CAC CTC TGT<br>His His Phe Lys Asn Glu Ser Leu Gly Met Ala Phe Leu His Leu Cys<br>        180             185             190 | 576 |
| CAC CTC GCT CTC CGC CAT GGC ATC CCC CTG GAG GAG GTG GCC AAG AAG<br>His Leu Ala Leu Arg His Gly Ile Pro Leu Glu Glu Val Ala Lys Lys<br>    195             200             205 | 624 |
| ACC AGC TTC AAG GAC TGC ATC CCG CGC TCC TTC CGC CGG CAT ATC CGG<br>Thr Ser Phe Lys Asp Cys Ile Pro Arg Ser Phe Arg Arg His Ile Arg<br>210             215             220 | 672 |
| CAG CAC AGC GCC CTG ACC CGG CTG CGC CTT CGG AAC GTC TTC CGC AGG<br>Gln His Ser Ala Leu Thr Arg Leu Arg Leu Arg Asn Val Phe Arg Arg<br>225             230             235             240 | 720 |
| TTC CTG CGG GAC TTC CAG CCG GGC CGA CTC TCC CAG CAG ATG GTC ATG<br>Phe Leu Arg Asp Phe Gln Pro Gly Arg Leu Ser Gln Gln Met Val Met<br>            245             250             255 | 768 |
| GTC AAA TAC CTA GCC ACA CTC GAG CGG CTG GCA CCC CGC TTC GGC ACA<br>Val Lys Tyr Leu Ala Thr Leu Glu Arg Leu Ala Pro Arg Phe Gly Thr<br>        260             265             270 | 816 |
| GAG CGT GTG CCC GTG TGC CAC CTG AGG CTG CTG GCC CAG GCC GAG GGG<br>Glu Arg Val Pro Val Cys His Leu Arg Leu Leu Ala Gln Ala Glu Gly<br>    275             280             285 | 864 |
| GAG CCC TGC TAC ATC CGG GAC AGT GGG GTG GCC CCT ACA GAC CCT GGC<br>Glu Pro Cys Tyr Ile Arg Asp Ser Gly Val Ala Pro Thr Asp Pro Gly<br>290             295             300 | 912 |
| CCT GAG TCT GCT GCT GGG CCC CCA ACC CAC GAG GTG CTG GTG ACA GGC<br>Pro Glu Ser Ala Ala Gly Pro Pro Thr His Glu Val Leu Val Thr Gly<br>305             310             315             320 | 960 |
| ACT GGT GGC ATC CAG TGG TGG CCA GTA GAG GAG GAG GTG AAC AAG GAG<br>Thr Gly Gly Ile Gln Trp Trp Pro Val Glu Glu Glu Val Asn Lys Glu<br>            325             330             335 | 1008 |
| GAG GGT TCT AGT GGC AGC AGT GGC AGG AAC CCC CAA GCC AGC CTG TTT<br>Glu Gly Ser Ser Gly Ser Ser Gly Arg Asn Pro Gln Ala Ser Leu Phe<br>        340             345             350 | 1056 |
| GGG AAG AAG GCC AAG GCT CAC AAG GCA TTC GGC CAG CCG GCA GAC AGG<br>Gly Lys Lys Ala Lys Ala His Lys Ala Phe Gly Gln Pro Ala Asp Arg<br>    355             360             365 | 1104 |
| CCG CGG GAG CCA CTG TGG GCC TAC TTC TGT GAC TTC CGG GAC ATC ACC<br>Pro Arg Glu Pro Leu Trp Ala Tyr Phe Cys Asp Phe Arg Asp Ile Thr<br>370             375             380 | 1152 |
| CAC GTG GTG CTG AAA GAG CAC TGT GTC AGC ATC CAC CGG CAG GAC AAC<br>His Val Val Leu Lys Glu His Cys Val Ser Ile His Arg Gln Asp Asn<br>385             390             395             400 | 1200 |
| AAG TGC CTG GAG CTG AGC TTG CCT TCC CGG GCT GCG GCG CTG TCC TTC | 1248 |

```
                    Lys Cys Leu Glu Leu Ser Leu Pro Ser Arg Ala Ala Leu Ser Phe
                                    405                 410                 415

GTG TCG CTG GTG GAC GGC TAT TTC CGC CTG ACG GCC GAC TCC AGC CAC             1296
Val Ser Leu Val Asp Gly Tyr Phe Arg Leu Thr Ala Asp Ser Ser His
            420                 425                 430

TAC CTG TGC CAC GAG GTG GCT CCC CCA CGG CTG GTG ATG AGC ATC CGG             1344
Tyr Leu Cys His Glu Val Ala Pro Pro Arg Leu Val Met Ser Ile Arg
        435                 440                 445

GAT GGG ATC CAC GGA CCC CTG CTG GAG CCA TTT GTG CAG GCC AAG CTG             1392
Asp Gly Ile His Gly Pro Leu Leu Glu Pro Phe Val Gln Ala Lys Leu
    450                 455                 460

CGG CCC GAG GAC GGC CTG TAC CTC ATT CAC TGG AGC ACC AGC CAC CCC             1440
Arg Pro Glu Asp Gly Leu Tyr Leu Ile His Trp Ser Thr Ser His Pro
465                 470                 475                 480

TAC CGC CTG ATC CTC ACA GTG GCC CAG CGT AGC CAG GCA CCA GAC GGC             1488
Tyr Arg Leu Ile Leu Thr Val Ala Gln Arg Ser Gln Ala Pro Asp Gly
                485                 490                 495

ATG CAG AGC TTG CGG CTC CGA AAG TTC CCC ATT GAG CAG CAG GAC GGG             1536
Met Gln Ser Leu Arg Leu Arg Lys Phe Pro Ile Glu Gln Gln Asp Gly
            500                 505                 510

GCC TTC GTG CTG GAG GGC TGG GGC CGG TCC TTC CCC AGC GTT CGG GAA             1584
Ala Phe Val Leu Glu Gly Trp Gly Arg Ser Phe Pro Ser Val Arg Glu
        515                 520                 525

CTT GGG GCT GCC TTG CAG GGC TGC TTG CTG AGG GCC GGG GAT GAC TGC             1632
Leu Gly Ala Ala Leu Gln Gly Cys Leu Leu Arg Ala Gly Asp Asp Cys
    530                 535                 540

TTC TCT CTG CGT CGC TGT TGC CTG CCC CAA CCA GGA GAA ACC TCC AAT             1680
Phe Ser Leu Arg Arg Cys Cys Leu Pro Gln Pro Gly Glu Thr Ser Asn
545                 550                 555                 560

CTC ATC ATC ATG CGG GGG GCT CGG GCC AGC CCC AGG ACA CTC AAC CTC             1728
Leu Ile Ile Met Arg Gly Ala Arg Ala Ser Pro Arg Thr Leu Asn Leu
                565                 570                 575

AGC CAG CTC AGC TTC CAC CGG GTT GAC CAG AAG GAG ATC ACC CAG CTG             1776
Ser Gln Leu Ser Phe His Arg Val Asp Gln Lys Glu Ile Thr Gln Leu
            580                 585                 590

TCC CAC TTG GGC CAG GGC ACA AGG ACC AAC GTG TAT GAG GGC CGC CTG             1824
Ser His Leu Gly Gln Gly Thr Arg Thr Asn Val Tyr Glu Gly Arg Leu
        595                 600                 605

CGA GTG GAG GGC AGC GGG GAC CCT GAG GAG GGC AAG ATG GAT GAC GAG             1872
Arg Val Glu Gly Ser Gly Asp Pro Glu Glu Gly Lys Met Asp Asp Glu
    610                 615                 620

GAC CCC CTC GTG CCT GGC AGG GAC CGT GGG CAG GAG CTA CGA GTG GTG             1920
Asp Pro Leu Val Pro Gly Arg Asp Arg Gly Gln Glu Leu Arg Val Val
625                 630                 635                 640

CTC AAA GTG CTG GAC CCT AGT CAC CAT GAC ATC GCC CTG GCC TTC TAC             1968
Leu Lys Val Leu Asp Pro Ser His His Asp Ile Ala Leu Ala Phe Tyr
                645                 650                 655

GAG ACA GCC AGC CTC ATG AGC CAG GTC TCC CAC ACG CAC CTG GCC TTC             2016
Glu Thr Ala Ser Leu Met Ser Gln Val Ser His Thr His Leu Ala Phe
            660                 665                 670

GTG CAT GGC GTC TGT GTG CGC GGC CCT GAA AAT AGC ATG GTG ACA GAG             2064
Val His Gly Val Cys Val Arg Gly Pro Glu Asn Ser Met Val Thr Glu
        675                 680                 685

TAC GTG GAG CAC GGA CCC CTG GAT GTG TGG CTG CGG AGG GAG CGG GGC             2112
Tyr Val Glu His Gly Pro Leu Asp Val Trp Leu Arg Arg Glu Arg Gly
    690                 695                 700

CAT GTG CCC ATG GCT TGG AAG ATG GTG GTG GCC CAG CAG CTG GCC AGC             2160
His Val Pro Met Ala Trp Lys Met Val Val Ala Gln Gln Leu Ala Ser
705                 710                 715                 720
```

-continued

| | |
|---|---|
| GCC CTC AGC TAC CTG GAG AAC AAG AAC CTG GTT CAT GGT AAT GTG TGT<br>Ala Leu Ser Tyr Leu Glu Asn Lys Asn Leu Val His Gly Asn Val Cys<br>                    725                    730                    735 | 2208 |
| GGC CGG AAC ATC CTG CTG GCC CGG CTG GGG TTG GCA GAG GGC ACC AGC<br>Gly Arg Asn Ile Leu Leu Ala Arg Leu Gly Leu Ala Glu Gly Thr Ser<br>                    740                    745                    750 | 2256 |
| CCC TTC ATC AAG CTG AGT GAT CCT GGC GTG GGC CTG GGC GCC CTC TCC<br>Pro Phe Ile Lys Leu Ser Asp Pro Gly Val Gly Leu Gly Ala Leu Ser<br>                    755                    760                    765 | 2304 |
| AGG GAG GAG CGG GTG GAG AGG ATC CCC TGG CTG GCC CCC GAA TGC CTA<br>Arg Glu Glu Arg Val Glu Arg Ile Pro Trp Leu Ala Pro Glu Cys Leu<br>        770                    775                    780 | 2352 |
| CCA GGT GGG GCC AAC AGC CTA AGC ACC GCC ATG GAC AAG TGG GGG TTT<br>Pro Gly Gly Ala Asn Ser Leu Ser Thr Ala Met Asp Lys Trp Gly Phe<br>785                    790                    795                    800 | 2400 |
| GGC GCC ACC CTC CTG GAG ATC TGC TTT GAC GGA GAG GCC CCT CTG CAG<br>Gly Ala Thr Leu Leu Glu Ile Cys Phe Asp Gly Glu Ala Pro Leu Gln<br>                    805                    810                    815 | 2448 |
| AGC CGC AGT CCC TCC GAG AAG GAG CAT TTC TAC CAG AGG CAG CAC CGG<br>Ser Arg Ser Pro Ser Glu Lys Glu His Phe Tyr Gln Arg Gln His Arg<br>        820                    825                    830 | 2496 |
| CTG CCC GAG CCC TCC TGC CCA CAG CTG GCC ACA CTC ACC AGC CAG TGT<br>Leu Pro Glu Pro Ser Cys Pro Gln Leu Ala Thr Leu Thr Ser Gln Cys<br>                    835                    840                    845 | 2544 |
| CTG ACC TAT GAG CCA ACC CAG AGG CCA TCA TTC CGC ACC ATC CTG CGT<br>Leu Thr Tyr Glu Pro Thr Gln Arg Pro Ser Phe Arg Thr Ile Leu Arg<br>        850                    855                    860 | 2592 |
| GAC CTC ACC CGC GTG CAG CCC CAC AAT CTT GCT GAC GTC TTG ACT GTG<br>Asp Leu Thr Arg Val Gln Pro His Asn Leu Ala Asp Val Leu Thr Val<br>865                    870                    875                    880 | 2640 |
| AAC CGG GAC TCA CCG GCC GTC GGA CCT ACT ACT TTC CAC AAG CGC TAT<br>Asn Arg Asp Ser Pro Ala Val Gly Pro Thr Thr Phe His Lys Arg Tyr<br>                    885                    890                    895 | 2688 |
| TTG AAA AAG ATC CGA GAT CTG GGC GAG GGT CAC TTC GGC AAG GTC AGC<br>Leu Lys Lys Ile Arg Asp Leu Gly Glu Gly His Phe Gly Lys Val Ser<br>        900                    905                    910 | 2736 |
| TTG TAC TGC TAC GAT CCG ACC AAC GAC GGC ACT GGC GAG ATG GTG GCG<br>Leu Tyr Cys Tyr Asp Pro Thr Asn Asp Gly Thr Gly Glu Met Val Ala<br>                    915                    920                    925 | 2784 |
| GTG AAA GCC CTC AAG GCA GAC TGC GGC CCC CAG CAC CGC TCG GGC TGG<br>Val Lys Ala Leu Lys Ala Asp Cys Gly Pro Gln His Arg Ser Gly Trp<br>930                    935                    940 | 2832 |
| AAG CAG GAG ATT GAC ATT CTG CGC ACG CTC TAC CAC GAG CAC ATC ATC<br>Lys Gln Glu Ile Asp Ile Leu Arg Thr Leu Tyr His Glu His Ile Ile<br>945                    950                    955                    960 | 2880 |
| AAG TAC AAG GGC TGC TGC GAG GAC CAA GGC GAG AAG TCG CTG CAG CTG<br>Lys Tyr Lys Gly Cys Cys Glu Asp Gln Gly Glu Lys Ser Leu Gln Leu<br>                    965                    970                    975 | 2928 |
| GTC ATG GAG TAC GTG CCC CTG GGC AGC CTC CGA GAC TAC CTG CCC CGG<br>Val Met Glu Tyr Val Pro Leu Gly Ser Leu Arg Asp Tyr Leu Pro Arg<br>        980                    985                    990 | 2976 |
| CAC AGC ATC GGG CTG GCC CAG CTG CTG CTC TTC GCC CAG CAG ATC TGC<br>His Ser Ile Gly Leu Ala Gln Leu Leu Leu Phe Ala Gln Gln Ile Cys<br>                    995                   1000                 1005 | 3024 |
| GAG GGC ATG GCC TAT CTG CAC GCG CAC GAC TAC ATC CAC CGA GAC CTA<br>Glu Gly Met Ala Tyr Leu His Ala His Asp Tyr Ile His Arg Asp Leu<br>        1010                   1015                 1020 | 3072 |
| GCC GCG CGC AAC GTG CTG CTG GAC AAC GAC AGG CTG GTC AAG ATC GGG<br>Ala Ala Arg Asn Val Leu Leu Asp Asn Asp Arg Leu Val Lys Ile Gly<br>1025                   1030                 1035                 1040 | 3120 |

```
GAC TTT GGC CTA GCC AAG GCC GTG CCC GAA GGC CAC GAG TAC TAC CGC      3168
Asp Phe Gly Leu Ala Lys Ala Val Pro Glu Gly His Glu Tyr Tyr Arg
                    1045                1050                1055

GTG CGC GAG GAT GGG GAC AGC CCC GTG TTC TGG TAT GCC CCA GAG TGC      3216
Val Arg Glu Asp Gly Asp Ser Pro Val Phe Trp Tyr Ala Pro Glu Cys
                    1060                1065                1070

CTG AAG GAG TAT AAG TTC TAC TAT GCG TCA GAT GTC TGG TCC TTC GGG      3264
Leu Lys Glu Tyr Lys Phe Tyr Tyr Ala Ser Asp Val Trp Ser Phe Gly
                1075                1080                1085

GTG ACC CTG TAT GAG CTG CTG ACG CAC TGT GAC TCC AGC CAG AGC CCC      3312
Val Thr Leu Tyr Glu Leu Leu Thr His Cys Asp Ser Ser Gln Ser Pro
                1090                1095                1100

CCC ACG AAA TTC CTT GAG CTC ATA GGC ATT GCT CAG GGT CAG ATG ACA      3360
Pro Thr Lys Phe Leu Glu Leu Ile Gly Ile Ala Gln Gly Gln Met Thr
1105                1110                1115                1120

GTT CTG AGA CTC ACT GAG TTG CTG GAA CGA GGG GAG AGG CTG CCA CGG      3408
Val Leu Arg Leu Thr Glu Leu Leu Glu Arg Gly Glu Arg Leu Pro Arg
                    1125                1130                1135

CCC GAC AAA TGT CCC TGT GAG GTC TAT CAT CTC ATG AAG AAC TGC TGG      3456
Pro Asp Lys Cys Pro Cys Glu Val Tyr His Leu Met Lys Asn Cys Trp
                    1140                1145                1150

GAG ACA GAG GCG TCC TTT CGC CCA ACC TTC GAG AAC CTC ATA CCC ATT      3504
Glu Thr Glu Ala Ser Phe Arg Pro Thr Phe Glu Asn Leu Ile Pro Ile
                1155                1160                1165

CTG AAG ACA GTC CAT GAG AAG TAC CAA GGC CAG GCC CCT TCA GTG TTC      3552
Leu Lys Thr Val His Glu Lys Tyr Gln Gly Gln Ala Pro Ser Val Phe
                1170                1175                1180

AGC GTG TGC                                                           3561
Ser Val Cys
1185

(2) INFORMATION FOR SEQ ID NO:13:

(i) SEQUENCE CHARACTERISTICS:
        (A) LENGTH: 1187 amino acids
        (B) TYPE: amino acid
        (D) TOPOLOGY: linear (ii) MOLECULE TYPE: protein (xi) SEQUENCE DESCRIPTION: SEQ ID NO:13:

Met Pro Leu Arg His Trp Gly Met Ala Arg Gly Ser Lys Pro Val Gly
 1               5                  10                  15

Asp Gly Ala Gln Pro Met Ala Ala Met Gly Gly Leu Lys Val Leu Leu
                20                  25                  30

His Trp Ala Gly Pro Gly Gly Gly Glu Pro Trp Val Thr Phe Ser Glu
            35                  40                  45

Ser Ser Leu Thr Ala Glu Glu Val Cys Ile His Ile Ala His Lys Val
        50                  55                  60

Gly Ile Thr Pro Pro Cys Phe Asn Leu Phe Ala Leu Phe Asp Ala Gln
65                  70                  75                  80

Ala Gln Val Trp Leu Pro Pro Asn His Ile Leu Glu Ile Pro Arg Asp
                85                  90                  95

Ala Ser Leu Met Leu Tyr Phe Arg Ile Arg Phe Tyr Phe Arg Asn Trp
                100                 105                 110

His Gly Met Asn Pro Arg Glu Pro Ala Val Tyr Arg Cys Gly Pro Pro
            115                 120                 125

Gly Thr Glu Ala Ser Ser Asp Gln Thr Ala Gln Gly Met Gln Leu Leu
        130                 135                 140
```

-continued

```
Asp Pro Ala Ser Phe Glu Tyr Leu Phe Glu Gln Gly Lys His Glu Phe
145                 150                 155                 160

Val Asn Asp Val Ala Ser Leu Trp Glu Leu Ser Thr Glu Glu Glu Ile
            165                 170                 175

His His Phe Lys Asn Glu Ser Leu Gly Met Ala Phe Leu His Leu Cys
        180                 185                 190

His Leu Ala Leu Arg His Gly Ile Pro Leu Glu Glu Val Ala Lys Lys
    195                 200                 205

Thr Ser Phe Lys Asp Cys Ile Pro Arg Ser Phe Arg Arg His Ile Arg
210                 215                 220

Gln His Ser Ala Leu Thr Arg Leu Arg Leu Arg Asn Val Phe Arg Arg
225                 230                 235                 240

Phe Leu Arg Asp Phe Gln Pro Gly Arg Leu Ser Gln Gln Met Val Met
                245                 250                 255

Val Lys Tyr Leu Ala Thr Leu Glu Arg Leu Ala Pro Arg Phe Gly Thr
            260                 265                 270

Glu Arg Val Pro Val Cys His Leu Arg Leu Leu Ala Gln Ala Glu Gly
        275                 280                 285

Glu Pro Cys Tyr Ile Arg Asp Ser Gly Val Ala Pro Thr Asp Pro Gly
290                 295                 300

Pro Glu Ser Ala Ala Gly Pro Pro Thr His Glu Val Leu Val Thr Gly
305                 310                 315                 320

Thr Gly Gly Ile Gln Trp Trp Pro Val Glu Glu Val Asn Lys Glu
                325                 330                 335

Glu Gly Ser Ser Gly Ser Ser Gly Arg Asn Pro Gln Ala Ser Leu Phe
            340                 345                 350

Gly Lys Lys Ala Lys Ala His Lys Ala Phe Gly Gln Pro Ala Asp Arg
        355                 360                 365

Pro Arg Glu Pro Leu Trp Ala Tyr Phe Cys Asp Phe Arg Asp Ile Thr
370                 375                 380

His Val Val Leu Lys Glu His Cys Val Ser Ile His Arg Gln Asp Asn
385                 390                 395                 400

Lys Cys Leu Glu Leu Ser Leu Pro Ser Arg Ala Ala Leu Ser Phe
                405                 410                 415

Val Ser Leu Val Asp Gly Tyr Phe Arg Leu Thr Ala Asp Ser Ser His
            420                 425                 430

Tyr Leu Cys His Glu Val Ala Pro Pro Arg Leu Val Met Ser Ile Arg
        435                 440                 445

Asp Gly Ile His Gly Pro Leu Leu Glu Pro Phe Val Gln Ala Lys Leu
450                 455                 460

Arg Pro Glu Asp Gly Leu Tyr Leu Ile His Trp Ser Thr Ser His Pro
465                 470                 475                 480

Tyr Arg Leu Ile Leu Thr Val Ala Gln Arg Ser Gln Ala Pro Asp Gly
                485                 490                 495

Met Gln Ser Leu Arg Leu Arg Lys Phe Pro Ile Glu Gln Gln Asp Gly
            500                 505                 510

Ala Phe Val Leu Glu Gly Trp Gly Arg Ser Phe Pro Ser Val Arg Glu
        515                 520                 525

Leu Gly Ala Ala Leu Gln Gly Cys Leu Leu Arg Ala Gly Asp Asp Cys
530                 535                 540

Phe Ser Leu Arg Arg Cys Cys Leu Pro Gln Pro Gly Glu Thr Ser Asn
545                 550                 555                 560
```

-continued

```
Leu Ile Ile Met Arg Gly Ala Arg Ala Ser Pro Arg Thr Leu Asn Leu
                565                 570                 575

Ser Gln Leu Ser Phe His Arg Val Asp Gln Lys Glu Ile Thr Gln Leu
            580                 585                 590

Ser His Leu Gly Gln Gly Thr Arg Thr Asn Val Tyr Glu Gly Arg Leu
        595                 600                 605

Arg Val Glu Gly Ser Gly Asp Pro Glu Glu Gly Lys Met Asp Asp Glu
    610                 615                 620

Asp Pro Leu Val Pro Gly Arg Asp Arg Gly Gln Glu Leu Arg Val Val
625                 630                 635                 640

Leu Lys Val Leu Asp Pro Ser His His Asp Ile Ala Leu Ala Phe Tyr
                645                 650                 655

Glu Thr Ala Ser Leu Met Ser Gln Val Ser His Thr His Leu Ala Phe
                660                 665                 670

Val His Gly Val Cys Val Arg Gly Pro Glu Asn Ser Met Val Thr Glu
            675                 680                 685

Tyr Val Glu His Gly Pro Leu Asp Val Trp Leu Arg Arg Glu Arg Gly
        690                 695                 700

His Val Pro Met Ala Trp Lys Met Val Val Ala Gln Gln Leu Ala Ser
705                 710                 715                 720

Ala Leu Ser Tyr Leu Glu Asn Lys Asn Leu Val His Gly Asn Val Cys
                725                 730                 735

Gly Arg Asn Ile Leu Leu Ala Arg Leu Gly Leu Ala Glu Gly Thr Ser
            740                 745                 750

Pro Phe Ile Lys Leu Ser Asp Pro Gly Val Gly Leu Gly Ala Leu Ser
        755                 760                 765

Arg Glu Glu Arg Val Glu Arg Ile Pro Trp Leu Ala Pro Glu Cys Leu
    770                 775                 780

Pro Gly Gly Ala Asn Ser Leu Ser Thr Ala Met Asp Lys Trp Gly Phe
785                 790                 795                 800

Gly Ala Thr Leu Leu Glu Ile Cys Phe Asp Gly Glu Ala Pro Leu Gln
                805                 810                 815

Ser Arg Ser Pro Ser Glu Lys Glu His Phe Tyr Gln Arg Gln His Arg
            820                 825                 830

Leu Pro Glu Pro Ser Cys Pro Gln Leu Ala Thr Leu Thr Ser Gln Cys
        835                 840                 845

Leu Thr Tyr Glu Pro Thr Gln Arg Pro Ser Phe Arg Thr Ile Leu Arg
    850                 855                 860

Asp Leu Thr Arg Val Gln Pro His Asn Leu Ala Asp Val Leu Thr Val
865                 870                 875                 880

Asn Arg Asp Ser Pro Ala Val Gly Pro Thr Thr Phe His Lys Arg Tyr
                885                 890                 895

Leu Lys Lys Ile Arg Asp Leu Gly Glu Gly His Phe Gly Lys Val Ser
            900                 905                 910

Leu Tyr Cys Tyr Asp Pro Thr Asn Asp Gly Thr Gly Glu Met Val Ala
        915                 920                 925

Val Lys Ala Leu Lys Ala Asp Cys Gly Pro Gln His Arg Ser Gly Trp
    930                 935                 940

Lys Gln Glu Ile Asp Ile Leu Arg Thr Leu Tyr His Glu His Ile Ile
945                 950                 955                 960

Lys Tyr Lys Gly Cys Cys Glu Asp Gln Gly Glu Lys Ser Leu Gln Leu
                965                 970                 975

Val Met Glu Tyr Val Pro Leu Gly Ser Leu Arg Asp Tyr Leu Pro Arg
```

-continued

```
                    980                 985                 990
His Ser Ile Gly Leu Ala Gln Leu Leu Leu Phe Ala Gln Gln Ile Cys
            995                 1000                1005
Glu Gly Met Ala Tyr Leu His Ala His Asp Tyr Ile His Arg Asp Leu
    1010                1015                1020
Ala Ala Arg Asn Val Leu Leu Asp Asn Asp Arg Leu Val Lys Ile Gly
1025                1030                1035                1040
Asp Phe Gly Leu Ala Lys Ala Val Pro Glu Gly His Glu Tyr Tyr Arg
                1045                1050                1055
Val Arg Glu Asp Gly Asp Ser Pro Val Phe Trp Tyr Ala Pro Glu Cys
            1060                1065                1070
Leu Lys Glu Tyr Lys Phe Tyr Tyr Ala Ser Asp Val Trp Ser Phe Gly
            1075                1080                1085
Val Thr Leu Tyr Glu Leu Leu Thr His Cys Asp Ser Ser Gln Ser Pro
    1090                1095                1100
Pro Thr Lys Phe Leu Glu Leu Ile Gly Ile Ala Gln Gly Gln Met Thr
1105                1110                1115                1120
Val Leu Arg Leu Thr Glu Leu Leu Glu Arg Gly Glu Arg Leu Pro Arg
                1125                1130                1135
Pro Asp Lys Cys Pro Cys Glu Val Tyr His Leu Met Lys Asn Cys Trp
            1140                1145                1150
Glu Thr Glu Ala Ser Phe Arg Pro Thr Phe Glu Asn Leu Ile Pro Ile
            1155                1160                1165
Leu Lys Thr Val His Glu Lys Tyr Gln Gly Gln Ala Pro Ser Val Phe
            1170                1175                1180
Ser Val Cys
1185

(2) INFORMATION FOR SEQ ID NO:14:

(i) SEQUENCE CHARACTERISTICS:
        (A) LENGTH: 1153 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:14:

Met Gln Tyr Leu Asn Ile Lys Glu Asp Cys Asn Ala Met Ala Phe Cys
1               5                   10                  15
Ala Lys Met Arg Ser Phe Lys Lys Thr Glu Val Lys Gln Val Val Pro
            20                  25                  30
Glu Pro Gly Val Glu Val Thr Phe Tyr Leu Ser Asp Arg Glu Pro Leu
        35                  40                  45
Arg Leu Gly Ser Gly Glu Tyr Thr Ala Glu Glu Leu Cys Ile Arg Ala
50                  55                  60
Ala Gln Glu Cys Ser Ile Ser Pro Leu Cys His Asn Leu Phe Ala Leu
65                  70                  75                  80
Tyr Asp Glu Ser Thr Lys Leu Trp Tyr Ala Pro Asn Arg Ile Ile Thr
                85                  90                  95
Val Asp Asp Lys Thr Ser Leu Arg Leu His Tyr Arg Met Arg Phe Tyr
            100                 105                 110
Phe Thr Asn Trp His Gly Thr Asn Asp Asn Glu Gln Ser Val Trp Arg
            115                 120                 125
His Ser Pro Lys Lys Gln Lys Asn Gly Tyr Glu Lys Lys Arg Val Pro
```

-continued

```
            130                 135                 140
Glu Ala Thr Pro Leu Leu Asp Ala Ser Ser Leu Glu Tyr Leu Phe Ala
145                 150                 155                 160
Gln Gly Gln Tyr Asp Leu Ile Lys Phe Leu Ala Pro Ile Arg Asp Pro
                165                 170                 175
Lys Thr Glu Gln Asp Gly His Asp Ile Glu Asn Glu Cys Leu Gly Met
                180                 185                 190
Ala Val Leu Ala Ile Ser His Tyr Ala Met Met Lys Lys Met Gln Leu
            195                 200                 205
Pro Glu Leu Pro Lys Asp Ile Ser Tyr Lys Arg Tyr Ile Pro Glu Thr
            210                 215                 220
Leu Asn Lys Ser Ile Arg Gln Arg Asn Leu Leu Thr Arg Met Arg Ile
225                 230                 235                 240
Asn Asn Val Phe Lys Asp Phe Leu Lys Glu Phe Asn Asn Lys Thr Ile
                245                 250                 255
Cys Asp Ser Ser Val Ser Thr His Asp Leu Lys Val Lys Tyr Leu Ala
                260                 265                 270
Thr Leu Glu Thr Leu Thr Lys His Tyr Gly Ala Glu Ile Phe Glu Thr
            275                 280                 285
Ser Met Leu Leu Ile Ser Ser Glu Asn Glu Leu Ser Arg Cys His Ser
            290                 295                 300
Asn Asp Ser Gly Asn Val Leu Tyr Glu Val Met Val Thr Gly Asn Leu
305                 310                 315                 320
Gly Ile Gln Trp Arg Gln Lys Pro Asn Val Pro Val Glu Lys Glu
                325                 330                 335
Lys Asn Lys Leu Lys Arg Lys Leu Glu Tyr Asn Lys His Lys Lys
                340                 345                 350
Asp Asp Glu Arg Asn Lys Leu Arg Glu Glu Trp Asn Asn Phe Ser Tyr
            355                 360                 365
Phe Pro Glu Ile Thr His Ile Val Ile Lys Glu Ser Val Val Ser Ile
            370                 375                 380
Asn Lys Gln Asp Asn Lys Asn Met Glu Leu Lys Leu Ser Ser Arg Glu
385                 390                 395                 400
Glu Ala Leu Ser Phe Val Ser Leu Val Asp Gly Tyr Phe Arg Leu Thr
                405                 410                 415
Ala Asp Ala His His Tyr Leu Cys Thr Asp Val Ala Pro Pro Leu Ile
                420                 425                 430
Val His Asn Ile Gln Asn Gly Cys His Gly Pro Ile Cys Thr Glu Tyr
            435                 440                 445
Ala Ile Asn Lys Leu Arg Gln Glu Gly Ser Glu Glu Gly Met Tyr Val
            450                 455                 460
Leu Arg Trp Ser Cys Thr Asp Phe Asp Asn Ile Leu Met Thr Val Thr
465                 470                 475                 480
Cys Phe Glu Lys Ser Glu Val Leu Gly Gly Gln Lys Gln Phe Lys Asn
                485                 490                 495
Phe Gln Ile Glu Val Gln Lys Gly Arg Tyr Ser Leu His Gly Ser Met
                500                 505                 510
Asp His Phe Pro Ser Leu Arg Asp Leu Met Asn His Leu Lys Lys Gln
            515                 520                 525
Ile Leu Arg Thr Asp Asn Ile Ser Phe Val Leu Lys Arg Cys Cys Gln
            530                 535                 540
Pro Lys Pro Arg Glu Ile Ser Asn Leu Leu Val Ala Thr Lys Lys Ala
545                 550                 555                 560
```

-continued

```
Gln Glu Trp Gln Pro Val Tyr Ser Met Ser Gln Leu Ser Phe Asp Arg
            565                 570                 575
Ile Leu Lys Lys Asp Ile Ile Gln Gly Glu His Leu Gly Arg Gly Thr
            580                 585                 590
Arg Thr His Ile Tyr Ser Gly Thr Leu Leu Asp Tyr Lys Asp Glu Glu
            595                 600                 605
Gly Ile Ala Glu Glu Lys Lys Ile Lys Val Ile Leu Lys Val Leu Asp
            610                 615                 620
Pro Ser His Arg Asp Ile Ser Leu Ala Phe Phe Glu Ala Ala Ser Met
625                 630                 635                 640
Met Arg Gln Val Ser His Lys His Ile Val Tyr Leu Tyr Gly Val Cys
                    645                 650                 655
Val Arg Asp Val Glu Asn Ile Met Val Glu Glu Phe Val Glu Gly Gly
                    660                 665                 670
Pro Leu Asp Leu Phe Met His Arg Lys Ser Asp Ala Leu Thr Thr Pro
            675                 680                 685
Trp Lys Phe Lys Val Ala Lys Gln Leu Ala Ser Ala Leu Ser Tyr Leu
            690                 695                 700
Glu Asp Lys Asp Leu Val His Gly Asn Val Cys Thr Lys Asn Leu Leu
705                 710                 715                 720
Leu Ala Arg Glu Gly Ile Asp Ser Asp Ile Gly Pro Phe Ile Lys Leu
                    725                 730                 735
Ser Asp Pro Gly Ile Pro Val Ser Val Leu Thr Arg Gln Glu Cys Ile
                    740                 745                 750
Glu Arg Ile Pro Trp Ile Ala Pro Glu Cys Val Glu Asp Ser Lys Asn
            755                 760                 765
Leu Ser Val Ala Ala Asp Lys Trp Ser Phe Gly Thr Thr Leu Trp Glu
770                 775                 780
Ile Cys Tyr Asn Gly Glu Ile Pro Leu Lys Asp Lys Thr Leu Ile Glu
785                 790                 795                 800
Lys Glu Arg Phe Tyr Glu Ser Arg Cys Arg Pro Val Thr Pro Ser Cys
                    805                 810                 815
Lys Glu Leu Ala Asp Leu Met Thr Arg Cys Met Asn Tyr Asp Pro Asn
            820                 825                 830
Gln Arg Pro Phe Phe Arg Ala Ile Met Arg Asp Ile Asn Lys Leu Glu
            835                 840                 845
Glu Gln Asn Pro Asp Ile Val Ser Glu Lys Gln Pro Thr Thr Glu Val
            850                 855                 860
Asp Pro Thr His Phe Glu Lys Arg Phe Leu Lys Arg Ile Arg Asp Leu
865                 870                 875                 880
Gly Glu Gly His Phe Gly Lys Val Glu Leu Cys Arg Tyr Asp Pro Glu
                    885                 890                 895
Gly Asp Asn Thr Gly Glu Gln Val Ala Val Lys Ser Leu Lys Pro Glu
                    900                 905                 910
Ser Gly Gly Asn His Ile Ala Asp Leu Lys Lys Glu Ile Glu Ile Leu
            915                 920                 925
Arg Asn Leu Tyr His Glu Asn Ile Val Lys Tyr Lys Gly Ile Cys Met
            930                 935                 940
Glu Asp Gly Gly Asn Gly Ile Lys Leu Ile Met Glu Phe Leu Pro Ser
945                 950                 955                 960
Gly Ser Leu Lys Glu Tyr Leu Pro Lys Asn Lys Asn Lys Ile Asn Leu
                    965                 970                 975
```

-continued

```
Lys Gln Gln Leu Lys Tyr Ala Ile Gln Ile Cys Lys Gly Met Asp Tyr
            980                 985                 990

Leu Gly Ser Arg Gln Tyr Val His Arg Asp Leu Ala Ala Arg Asn Val
        995                1000                1005

Leu Val Glu Ser Glu His Gln Val Lys Ile Gly Asp Phe Gly Leu Thr
   1010                1015                1020

Lys Ala Ile Glu Thr Asp Lys Glu Tyr Tyr Thr Val Lys Asp Asp Arg
1025                1030                1035                1040

Asp Ser Pro Val Phe Trp Tyr Ala Pro Glu Cys Leu Ile Gln Cys Lys
                1045                1050                1055

Phe Tyr Ile Ala Ser Asp Val Trp Ser Phe Gly Val Thr Leu His Glu
                1060                1065                1070

Leu Leu Thr Tyr Cys Asp Ser Asp Ser Phe Pro Met Ala Leu Phe Leu
            1075                1080                1085

Lys Met Ile Gly Pro Thr His Gly Gln Met Thr Val Thr Arg Leu Val
        1090                1095                1100

Asn Thr Leu Lys Glu Gly Lys Arg Leu Pro Cys Pro Pro Asn Cys Pro
1105                1110                1115                1120

Asp Glu Val Tyr Gln Leu Met Arg Lys Cys Trp Glu Phe Gln Pro Ser
                1125                1130                1135

Asn Arg Thr Thr Phe Gln Asn Leu Ile Glu Gly Phe Glu Ala Leu Leu
            1140                1145                1150

Lys (2) INFORMATION FOR SEQ ID NO:15:

(i) SEQUENCE CHARACTERISTICS:
        (A) LENGTH: 17 amino acids
        (B) TYPE: amino acid
        (D) TOPOLOGY: linear (xi) SEQUENCE DESCRIPTION: SEQ ID NO:15:

Ala Lys Leu Leu Pro Leu Asp Lys Asp Tyr Tyr Val Val Arg Glu Pro
1               5                  10                  15
Gly (2) INFORMATION FOR SEQ ID NO:16:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO:16:

Met Gln Tyr Leu Asn Ile Lys Glu Asp Cys Asn Ala
1               5                  10

(2) INFORMATION FOR SEQ ID NO:17:

(i) SEQUENCE CHARACTERISTICS:
        (A) LENGTH: 1098 amino acids
        (B) TYPE: amino acid
        (D) TOPOLOGY: linear (xi) SEQUENCE DESCRIPTION: SEQ ID NO:17:

Met Ala Pro Pro Ser Glu Glu Thr Pro Leu Ile Pro Gln Arg Ser Cys
1               5                  10                  15

Ser Leu Ser Ser Ser Glu Ala Gly Ala Leu His Val Leu Leu Pro Pro
            20                  25                  30
```

-continued

```
Arg Gly Pro Gly Pro Gln Arg Leu Ser Phe Ser Phe Gly Asp Tyr
         35                  40                  45

Leu Ala Glu Asp Leu Cys Val Arg Ala Ala Lys Ala Cys Gly Ile Leu
     50                  55                  60

Pro Val Tyr His Ser Leu Phe Ala Leu Ala Thr Glu Asp Phe Ser Cys
 65                  70                  75                  80

Trp Phe Pro Pro Ser His Ile Phe Cys Ile Glu Asp Val Asp Thr Gln
                 85                  90                  95

Val Leu Val Tyr Arg Leu Arg Phe Tyr Phe Pro Asp Trp Phe Gly Leu
                100                 105                 110

Glu Thr Cys His Arg Phe Gly Leu Arg Lys Asp Leu Thr Ser Ala Ile
             115                 120                 125

Leu Asp Leu His Val Leu Glu His Leu Phe Ala Gln His Arg Ser Asp
     130                 135                 140

Leu Val Ser Gly Arg Leu Pro Val Gly Leu Ser Met Lys Glu Gln Gly
145                 150                 155                 160

Glu Phe Leu Ser Leu Ala Val Leu Asp Leu Ala Gln Met Ala Arg Glu
                165                 170                 175

Gln Ala Gln Arg Pro Gly Glu Leu Leu Lys Thr Val Ser Tyr Lys Ala
             180                 185                 190

Cys Leu Pro Pro Ser Leu Arg Asp Val Ile Gln Gly Gln Asn Phe Val
     195                 200                 205

Thr Arg Arg Arg Ile Arg Arg Thr Val Val Leu Ala Leu Leu Pro Cys
     210                 215                 220

Gly Pro Leu Pro Gly Arg Pro Tyr Ala Leu Met Ala Lys Tyr Ile Leu
225                 230                 235                 240

Asp Leu Glu Arg Leu His Pro Ala Ala Thr Thr Glu Thr Phe Arg Val
                245                 250                 255

Gly Leu Pro Gly Ala Gln Glu Glu Pro Gly Leu Leu Arg Val Ala Gly
             260                 265                 270

Asp Asn Gly Ile Pro Trp Ser Ser Asn Asp Glu Leu Phe Gln Thr Phe
     275                 280                 285

Cys Asp Phe Pro Glu Ile Val Asp Val Ser Ile Asn Gln Ala Pro Arg
 290                 295                 300

Val Gly Pro Ala Gly Glu His Arg Leu Val Thr Val Thr Arg Met Asp
305                 310                 315                 320

Gly His Ile Leu Glu Ala Glu Phe Pro Gly Leu Pro Glu Ala Leu Ser
                325                 330                 335

Phe Val Ala Leu Val Asp Gly Tyr Phe Arg Leu Ile Cys Asp Ser Arg
             340                 345                 350

His Tyr Phe Cys Lys Glu Val Ala Pro Pro Arg Leu Leu Glu Glu Glu
     355                 360                 365

Ala Asp Val Cys His Gly Pro Ile Thr Leu Asp Phe Ala Ile His Lys
 370                 375                 380

Leu Lys Ala Ala Gly Ser Leu Pro Gly Thr Tyr Ile Leu Arg Arg Ser
385                 390                 395                 400

Pro Gln Asp Tyr Asp Ser Phe Leu Leu Thr Ala Cys Val Gln Thr Pro
                405                 410                 415

Leu Gly Pro Asp Tyr Lys Gly Cys Leu Ile Arg Gln Asp Pro Ser Gly
             420                 425                 430

Ala Phe Ser Leu Val Gly Leu Ser Gln Pro His Arg Ser Leu Arg Glu
 435                 440                 445

Leu Leu Ala Ala Cys Trp Asn Ser Gly Leu Arg Val Asp Gly Ala Ala
```

-continued

```
            450                 455                 460
Leu Tyr Leu Thr Ser Cys Cys Ala Pro Arg Pro Lys Glu Lys Ser Asn
465                 470                 475                 480
Leu Ile Val Val Arg Arg Gly Cys Asn Pro Ala Pro Ala Pro Gly Cys
                    485                 490                 495
Ser Pro Ser Cys Cys Ala Leu Thr Gln Leu Ser Phe His Thr Ile Pro
                500                 505                 510
Thr Asp Ser Leu Glu Trp His Glu Asn Leu Gly His Gly Ser Phe Thr
                515                 520                 525
Lys Ile Phe Arg Gly Ser Arg Arg Glu Val Val Asp Gly Glu Thr His
                530                 535                 540
Asp Ser Glu Val Leu Leu Lys Val Met Asp Ser Arg His Arg Asn Cys
545                 550                 555                 560
Met Glu Ser Phe Leu Glu Ala Ala Ser Leu Met Ser Gln Val Ser Tyr
                565                 570                 575
Pro His Leu Val Leu Leu His Gly Val Cys Met Ala Gly Asp Ser Ile
                580                 585                 590
Met Val Gln Glu Phe Val Tyr Leu Gly Ala Ile Asp Met Tyr Leu Arg
                595                 600                 605
Lys Arg Gly His Leu Val Ser Ala Ser Trp Lys Leu Gln Val Thr Lys
                610                 615                 620
Gln Leu Ala Tyr Ala Leu Asn Tyr Leu Glu Asp Lys Gly Leu Pro His
625                 630                 635                 640
Gly Asn Val Ser Ala Arg Lys Val Leu Leu Ala Arg Glu Gly Gly Asp
                    645                 650                 655
Gly Asn Pro Pro Phe Ile Lys Leu Ser Asp Pro Gly Val Ser Pro Thr
                660                 665                 670
Val Leu Ser Leu Glu Met Leu Thr Asp Arg Ile Pro Trp Val Ala Pro
                675                 680                 685
Glu Cys Leu Gln Glu Ala Gln Thr Leu Cys Leu Glu Ala Asp Lys Trp
                690                 695                 700
Gly Phe Gly Ala Thr Thr Trp Glu Val Phe Ser Arg Gly Pro Ala His
705                 710                 715                 720
Ile Thr Ser Leu Glu Pro Ala Lys Lys Leu Lys Phe Tyr Glu Asp Gln
                    725                 730                 735
Gly Gln Leu Pro Ala Leu Lys Trp Thr Glu Leu Ala Gly Leu Ile Thr
                740                 745                 750
Gln Cys Met Ala Tyr Asp Pro Gly Arg Arg Pro Ser Phe Arg Ala Ile
                755                 760                 765
Leu Arg Asp Leu Asn Gly Leu Ile Thr Ser Asp Tyr Glu Leu Leu Ser
                770                 775                 780
Asp Pro Thr Pro Gly Ile Pro Ser Pro Arg Asp Glu Leu Cys Val Ala
785                 790                 795                 800
Ala Gln Leu Tyr Ala Cys Gln Asp Pro Ala Ile Phe Glu Glu Arg His
                805                 810                 815
Leu Lys Tyr Ile Ser Leu Leu Gly Lys Gly Asn Phe Gly Ser Val Glu
                820                 825                 830
Leu Cys Arg Tyr Asp Pro Leu Gly Asp Asn Thr Gly Pro Leu Val Ala
                835                 840                 845
Val Lys Gln Leu Gln His Ser Val Pro Asp Gln Gln Arg Asp Phe Gln
                850                 855                 860
Arg Glu Ile Gln Ile Leu Lys Ala Leu His Ser Asp Phe Ile Val Lys
865                 870                 875                 880
```

-continued

```
Tyr Arg Gly Val Ser Tyr Gly Pro Gly Arg Gln Ser Leu Arg Leu Val
            885                 890                 895

Met Glu Tyr Leu Pro Ser Gly Cys Leu Arg Asp Phe Leu Gln Arg His
        900                 905                 910

Arg Gly Leu His Thr Asp Arg Leu Leu Leu Phe Ala Trp Gln Ile Cys
        915                 920                 925

Lys Gly Met Glu Tyr Leu Gly Ala Arg Arg Cys Val His Arg Asp Leu
    930                 935                 940

Ala Ala Arg Asn Ile Leu Val Glu Ser Glu Ala His Val Lys Ile Ala
945                 950                 955                 960

Asp Phe Gly Leu Ala Lys Leu Leu Pro Leu Gly Lys Asp Tyr Tyr Val
            965                 970                 975

Val Arg Glu Pro Gly Gln Ser Pro Ile Phe Trp Tyr Ala Pro Glu Ser
            980                 985                 990

Leu Ser Asp Asn Ile Phe Ser Arg Gln Ser Asp Val Trp Ser Phe Gly
            995                 1000                1005

Val Val Leu Tyr Glu Leu Phe Thr Tyr Cys Asp Lys Ser Cys Ser Pro
        1010                1015                1020

Ser Ala Glu Phe Leu Arg Met Met Gly Pro Glu Arg Glu Gly Pro Pro
1025                1030                1035                1040

Leu Cys Arg Leu Leu Glu Leu Leu Ala Glu Gly Arg Arg Leu Pro Pro
                1045                1050                1055

Pro Pro Thr Cys Pro Thr Glu Val Gln Glu Leu Met Gln Leu Cys Trp
            1060                1065                1070

Ala Pro Glu Pro His Asp Arg Pro Ala Phe Ala Thr Leu Ser Pro Gln
        1075                1080                1085

Leu Asp Pro Leu Trp Arg Gly Arg Pro Gly
1090                1095
```